US012264171B2

(12) United States Patent
Sebhat et al.

(10) Patent No.: US 12,264,171 B2
(45) Date of Patent: Apr. 1, 2025

(54) GPR40 AGONISTS

(71) Applicant: Kallyope, Inc., New York, NY (US)

(72) Inventors: Iyassu Sebhat, Jersey City, NJ (US); Shuwen He, Fanwood, NJ (US)

(73) Assignee: KALLYOPE, INC., New York, NY (US)

( * ) Notice: Subject to any disclaimer, the term of this patent is extended or adjusted under 35 U.S.C. 154(b) by 0 days.

(21) Appl. No.: 17/745,126

(22) Filed: May 16, 2022

(65) Prior Publication Data

US 2022/0289772 A1    Sep. 15, 2022

Related U.S. Application Data

(63) Continuation of application No. PCT/US2021/019975, filed on Feb. 26, 2021.

(60) Provisional application No. 63/147,980, filed on Feb. 10, 2021, provisional application No. 63/117,074, filed on Nov. 23, 2020, provisional application No. 63/076,113, filed on Sep. 9, 2020, provisional application No. 62/983,438, filed on Feb. 28, 2020.

(51) Int. Cl.
| | | |
|---|---|---|
| *C07F 9/38* | (2006.01) | |
| *A61K 31/10* | (2006.01) | |
| *A61K 31/662* | (2006.01) | |
| *A61K 31/675* | (2006.01) | |
| *C07C 309/24* | (2006.01) | |
| *C07F 9/30* | (2006.01) | |
| *C07F 9/58* | (2006.01) | |
| *C07F 9/59* | (2006.01) | |

(52) U.S. Cl.
CPC ............ *C07F 9/3808* (2013.01); *A61K 31/10* (2013.01); *A61K 31/662* (2013.01); *A61K 31/675* (2013.01); *C07C 309/24* (2013.01); *C07F 9/301* (2013.01); *C07F 9/58* (2013.01); *C07F 9/59* (2013.01)

(58) Field of Classification Search
CPC .... A61K 31/10; A61K 31/185; A61K 31/662; A61K 31/675; A61K 45/06; C07C 309/24; C07F 9/301; C07F 9/3808; C07F 9/383; C07F 9/568; C07F 9/58; C07F 9/59; C07F 9/65583; A61P 1/06; A61P 3/00
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 7,750,048 B2 | 7/2010 | Kuo et al. | |
| 8,013,015 B2 | 9/2011 | Harran et al. | |
| 8,153,635 B2 | 4/2012 | Alper et al. | |
| 9,340,578 B2 | 5/2016 | Hougland | |
| 10,428,055 B2 | 10/2019 | Yang et al. | |
| 11,186,565 B2 | 11/2021 | Miwatashi et al. | |
| 11,512,065 B2 | 12/2022 | Sebhat et al. | |
| 2006/0177438 A1 | 8/2006 | Kopin et al. | |
| 2007/0142384 A1* | 6/2007 | Akerman .................. A61P 7/10 514/249 |
| 2009/0137561 A1 | 5/2009 | Brown et al. | |
| 2012/0053180 A1 | 3/2012 | Kang et al. | |
| 2013/0131042 A1 | 5/2013 | Duffy et al. | |
| 2013/0184240 A1 | 7/2013 | Tonogaki et al. | |
| 2015/0018422 A1 | 1/2015 | Miwatashi et al. | |
| 2015/0274664 A1 | 10/2015 | Acton et al. | |
| 2016/0009622 A1 | 1/2016 | Taarning et al. | |
| 2016/0009662 A1 | 1/2016 | Meegalla et al. | |
| 2016/0096862 A1 | 4/2016 | Pellicciari | |
| 2016/0332968 A1 | 11/2016 | Chobanian et al. | |
| 2017/0029405 A1 | 2/2017 | Schwink et al. | |
| 2017/0044146 A1 | 2/2017 | Huang et al. | |
| 2017/0056373 A1 | 3/2017 | Hougland | |
| 2020/0039957 A1* | 2/2020 | Miwatashi ........... C07D 413/10 |
| 2022/0152164 A1 | 5/2022 | Thornberry et al. | |
| 2022/0153719 A1 | 5/2022 | Sebhat et al. | |
| 2022/0226298 A1 | 7/2022 | Sebhat et al. | |
| 2023/0041621 A1 | 2/2023 | Sebhat et al. | |
| 2023/0050965 A1 | 2/2023 | Sebhat et al. | |
| 2023/0061736 A1 | 3/2023 | Sebhat et al. | |
| 2023/0113609 A1 | 4/2023 | Sebhat et al. | |
| 2023/0151037 A1 | 5/2023 | Sebhat et al. | |
| 2024/0217983 A1 | 7/2024 | Moyes | |

FOREIGN PATENT DOCUMENTS

| | | |
|---|---|---|
| CN | 1946666 A | 4/2007 |
| CN | 102131778 A | 7/2011 |
| CN | 107074838 A | 8/2017 |

(Continued)

OTHER PUBLICATIONS

Ballatore et al. ChemMedChem 2013, Mar. 8, (3), pp. 385-395. (Year: 2013).*
Berge et al. Pharmaceutical Salts. Journal of Pharmaceutical Sciences 66(1):1-19 (Jan. 1977).
Bundgard, H. Design of Prodrugs. 1985; pp. 7-9, 21-24 (Elsevier, Amsterdam).

(Continued)

*Primary Examiner* — Kara R. McMillian
(74) *Attorney, Agent, or Firm* — WILSON SONSINI GOODRICH & ROSATI

(57) ABSTRACT

This disclosure is directed, at least in part, to GPR40 agonists useful for the treatment of conditions or disorders involving the gut-brain axis. In some embodiments, the GPR40 agonists are gut-restricted compounds. In some embodiments, the GPR40 agonists are full agonists or partial agonists. In some embodiments, the condition or disorder is a metabolic disorder, such as diabetes, obesity, nonalcoholic steatohepatitis (NASH), or a nutritional disorder such as short bowel syndrome.

6 Claims, No Drawings

(56) References Cited

FOREIGN PATENT DOCUMENTS

| | | |
|---|---|---|
| CN | 110719903 A | 1/2020 |
| EP | 0697403 A1 | 2/1996 |
| EP | 2399914 A1 | 12/2011 |
| GB | 2498968 A | 8/2013 |
| GB | 2498976 A | 8/2013 |
| KR | 101726819 B1 | 4/2017 |
| WO | WO-9314066 A1 | 7/1993 |
| WO | WO-9316982 A1 | 9/1993 |
| WO | WO-9424151 A1 | 10/1994 |
| WO | WO-9528391 A1 | 10/1995 |
| WO | WO-9528399 A1 | 10/1995 |
| WO | WO-9528419 A1 | 10/1995 |
| WO | WO-9611691 A1 | 4/1996 |
| WO | WO-9611940 A1 | 4/1996 |
| WO | WO-9632414 A1 | 10/1996 |
| WO | WO-9739031 A1 | 10/1997 |
| WO | WO-9851686 A1 | 11/1998 |
| WO | WO-9915525 A1 | 4/1999 |
| WO | WO-0068209 A2 | 11/2000 |
| WO | WO-0177108 A1 | 10/2001 |
| WO | WO-0234743 A1 | 5/2002 |
| WO | WO-0244150 A1 | 6/2002 |
| WO | WO-02066511 A2 | 8/2002 |
| WO | WO-03104816 A1 | 12/2003 |
| WO | WO-2004041813 A1 | 5/2004 |
| WO | WO-2005035793 A2 | 4/2005 |
| WO | WO-2005051890 A1 | 6/2005 |
| WO | WO-2005067368 A2 | 7/2005 |
| WO | WO-2005086661 A2 | 9/2005 |
| WO | WO-2005095338 A1 | 10/2005 |
| WO | WO-2005116034 A1 | 12/2005 |
| WO | WO-2006011615 A1 | 2/2006 |
| WO | WO-2006083612 A1 | 8/2006 |
| WO | WO-2006083781 A1 | 8/2006 |
| WO | WO-2006117565 A2 | 11/2006 |
| WO | WO-2006128803 A1 | 12/2006 |
| WO | WO-2007003962 A2 | 1/2007 |
| WO | WO-2007067828 A2 | 6/2007 |
| WO | WO-2007088857 A1 | 8/2007 |
| WO | WO-2007120655 A2 | 10/2007 |
| WO | WO-2007120688 A2 | 10/2007 |
| WO | WO-2007120689 A2 | 10/2007 |
| WO | WO-2007120702 A2 | 10/2007 |
| WO | WO-2007123225 A1 | 11/2007 |
| WO | WO-2007136572 A2 | 11/2007 |
| WO | WO-2008022771 A1 | 2/2008 |
| WO | WO-2008025798 A1 | 3/2008 |
| WO | WO-2008028117 A2 | 3/2008 |
| WO | WO-2008054674 A2 | 5/2008 |
| WO | WO-2008054675 A2 | 5/2008 |
| WO | WO-2008056155 A1 | 5/2008 |
| WO | WO-2008063768 A2 | 5/2008 |
| WO | WO-2008067219 A2 | 6/2008 |
| WO | WO-2008067222 A1 | 6/2008 |
| WO | WO-2008070692 A2 | 6/2008 |
| WO | WO-2008083238 A2 | 7/2008 |
| WO | WO-2008091540 A2 | 7/2008 |
| WO | WO-2008091631 A1 | 7/2008 |
| WO | WO-2008097428 A2 | 8/2008 |
| WO | WO-2008097976 A1 | 8/2008 |
| WO | WO-2008109702 A1 | 9/2008 |
| WO | WO-2008137435 A1 | 11/2008 |
| WO | WO-2008137436 A1 | 11/2008 |
| WO | WO-2009012275 A1 | 1/2009 |
| WO | WO-2009026241 A1 | 2/2009 |
| WO | WO-2009034388 A1 | 3/2009 |
| WO | WO-2009039942 A1 | 4/2009 |
| WO | WO-2009039943 A1 | 4/2009 |
| WO | WO-2009050309 A1 | 4/2009 |
| WO | WO-2009054390 A1 | 4/2009 |
| WO | WO-2009054423 A1 | 4/2009 |
| WO | WO-2009054468 A1 | 4/2009 |
| WO | WO-2009054479 A1 | 4/2009 |
| WO | WO-2009058237 A1 | 5/2009 |
| WO | WO-2009105715 A1 | 8/2009 |
| WO | WO-2009105717 A1 | 8/2009 |
| WO | WO-2009105722 A1 | 8/2009 |
| WO | WO-2009106561 A1 | 9/2009 |
| WO | WO-2009106565 A1 | 9/2009 |
| WO | WO-2009117421 A2 | 9/2009 |
| WO | WO-2009119733 A1 | 10/2009 |
| WO | WO-2009123992 A1 | 10/2009 |
| WO | WO-2009126535 A1 | 10/2009 |
| WO | WO-2009141238 A1 | 11/2009 |
| WO | WO-2009143049 A1 | 11/2009 |
| WO | WO-2010004343 A1 | 1/2010 |
| WO | WO-2010004347 A1 | 1/2010 |
| WO | WO-2010006191 A1 | 1/2010 |
| WO | WO-2010008739 A2 | 1/2010 |
| WO | WO-2010008851 A1 | 1/2010 |
| WO | WO-2010009183 A1 | 1/2010 |
| WO | WO-2010013849 A1 | 2/2010 |
| WO | WO-2010014739 A2 | 2/2010 |
| WO | WO-2010014836 A2 | 2/2010 |
| WO | WO-2010016846 A1 | 2/2010 |
| WO | WO-2010036613 A1 | 4/2010 |
| WO | WO-2010039461 A2 | 4/2010 |
| WO | WO-2010042145 A1 | 4/2010 |
| WO | WO-2010048149 A2 | 4/2010 |
| WO | WO-2010056717 A1 | 5/2010 |
| WO | WO-2010059853 A1 | 5/2010 |
| WO | WO-2010059859 A1 | 5/2010 |
| WO | WO-2010067233 A1 | 6/2010 |
| WO | WO-2010085522 A1 | 7/2010 |
| WO | WO-2010085525 A1 | 7/2010 |
| WO | WO-2010085528 A1 | 7/2010 |
| WO | WO-2010091176 A1 | 8/2010 |
| WO | WO-2010093845 A2 | 8/2010 |
| WO | WO-2010123016 A1 | 10/2010 |
| WO | WO-2010123017 A1 | 10/2010 |
| WO | WO-2010128414 A1 | 11/2010 |
| WO | WO-2010143733 A1 | 12/2010 |
| WO | WO-2011008663 A1 | 1/2011 |
| WO | WO-2011025006 A1 | 3/2011 |
| WO | WO-2011030139 A1 | 3/2011 |
| WO | WO-2011041154 A1 | 4/2011 |
| WO | WO-2011044001 A1 | 4/2011 |
| WO | WO-2011046851 A1 | 4/2011 |
| WO | WO-2011050174 A1 | 4/2011 |
| WO | WO-2011052756 A1 | 5/2011 |
| WO | WO-2011061679 A1 | 5/2011 |
| WO | WO-2011066183 A1 | 6/2011 |
| WO | WO-2011071565 A1 | 6/2011 |
| WO | WO-2011078371 A1 | 6/2011 |
| WO | WO-2011113947 A1 | 9/2011 |
| WO | WO-2011127106 A1 | 10/2011 |
| WO | WO-2011138427 A2 | 11/2011 |
| WO | WO-2011140160 A1 | 11/2011 |
| WO | WO-2011140161 A1 | 11/2011 |
| WO | WO-2011146324 A1 | 11/2011 |
| WO | WO-2011146335 A1 | 11/2011 |
| WO | WO-2011147951 A1 | 12/2011 |
| WO | WO-2011150067 A1 | 12/2011 |
| WO | WO-2011153435 A1 | 12/2011 |
| WO | WO-2011161030 A1 | 12/2011 |
| WO | WO-2011163090 A1 | 12/2011 |
| WO | WO-2012004269 A1 | 1/2012 |
| WO | WO-2012004270 A1 | 1/2012 |
| WO | WO-2012010413 A1 | 1/2012 |
| WO | WO-2012011125 A1 | 1/2012 |
| WO | WO-2012024183 A1 | 2/2012 |
| WO | WO-2012025811 A1 | 3/2012 |
| WO | WO-2012028602 A1 | 3/2012 |
| WO | WO-2012037393 A1 | 3/2012 |
| WO | WO-2012046249 A1 | 4/2012 |
| WO | WO-2012046792 A1 | 4/2012 |
| WO | WO-2012046869 A1 | 4/2012 |
| WO | WO-2012070554 A1 | 5/2012 |
| WO | WO-2012072691 A1 | 6/2012 |
| WO | WO-2012077655 A1 | 6/2012 |
| WO | WO-2012080476 A1 | 6/2012 |
| WO | WO-2012082947 A1 | 6/2012 |
| WO | WO-2012098217 A1 | 7/2012 |

(56) References Cited

FOREIGN PATENT DOCUMENTS

| | | |
|---|---|---|
| WO | WO-2012103806 A1 | 8/2012 |
| WO | WO-2012111849 A1 | 8/2012 |
| WO | WO-2012117996 A1 | 9/2012 |
| WO | WO-2012138845 A1 | 10/2012 |
| WO | WO-2012138919 A2 | 10/2012 |
| WO | WO-2012145361 A1 | 10/2012 |
| WO | WO-2012145603 A1 | 10/2012 |
| WO | WO-2012145604 A1 | 10/2012 |
| WO | WO-2012147518 A1 | 11/2012 |
| WO | WO-2012149236 A1 | 11/2012 |
| WO | WO-2012170702 A1 | 12/2012 |
| WO | WO-2012173917 A1 | 12/2012 |
| WO | WO-2013025424 A1 | 2/2013 |
| WO | WO-2013040093 A2 | 3/2013 |
| WO | WO-2013054338 A1 | 4/2013 |
| WO | WO-2013055910 A1 | 4/2013 |
| WO | WO-2013057743 A1 | 4/2013 |
| WO | WO-2013066869 A1 | 5/2013 |
| WO | WO-2013074388 A1 | 5/2013 |
| WO | WO-2013096771 A1 | 6/2013 |
| WO | WO-2013104257 A1 | 7/2013 |
| WO | WO-2013122028 A1 | 8/2013 |
| WO | WO-2013122029 A1 | 8/2013 |
| WO | WO-2013122821 A1 | 8/2013 |
| WO | WO-2013125732 A1 | 8/2013 |
| WO | WO-2013128378 A1 | 9/2013 |
| WO | WO-2013144097 A1 | 10/2013 |
| WO | WO-2013154163 A1 | 10/2013 |
| WO | WO-2013164292 A1 | 11/2013 |
| WO | WO-2013164484 A1 | 11/2013 |
| WO | WO-2013167514 A1 | 11/2013 |
| WO | WO-2013173198 A1 | 11/2013 |
| WO | WO-2013178575 A1 | 12/2013 |
| WO | WO-2014019186 A1 | 2/2014 |
| WO | WO-2014052619 A1 | 4/2014 |
| WO | WO-2014056938 A1 | 4/2014 |
| WO | WO-2014066819 A1 | 5/2014 |
| WO | WO-2014073904 A1 | 5/2014 |
| WO | WO-2014074668 A1 | 5/2014 |
| WO | WO-2014082918 A1 | 6/2014 |
| WO | WO-2014085474 A1 | 6/2014 |
| WO | WO-2014086712 A1 | 6/2014 |
| WO | WO-2014096440 A2 | 6/2014 |
| WO | WO-2014100021 A1 | 6/2014 |
| WO | WO-2014100025 A1 | 6/2014 |
| WO | WO-2014122067 A1 | 8/2014 |
| WO | WO-2014130608 A1 | 8/2014 |
| WO | WO-2014146604 A1 | 9/2014 |
| WO | WO-2014169817 A1 | 10/2014 |
| WO | WO-2014170842 A2 | 10/2014 |
| WO | WO-2014187343 A1 | 11/2014 |
| WO | WO-2014200349 A1 | 12/2014 |
| WO | WO-2015000412 A1 | 1/2015 |
| WO | WO-2015010655 A1 | 1/2015 |
| WO | WO-2015017710 A1 | 2/2015 |
| WO | WO-2015020184 A1 | 2/2015 |
| WO | WO-2015024448 A1 | 2/2015 |
| WO | WO-2015024526 A1 | 2/2015 |
| WO | WO-2015028960 A1 | 3/2015 |
| WO | WO-2015032328 A1 | 3/2015 |
| WO | WO-2015044073 A1 | 4/2015 |
| WO | WO-2015051496 A1 | 4/2015 |
| WO | WO-2015052910 A1 | 4/2015 |
| WO | WO-2015062486 A1 | 5/2015 |
| WO | WO-2015073281 A1 | 5/2015 |
| WO | WO-2015073342 A1 | 5/2015 |
| WO | WO-2015078802 A1 | 6/2015 |
| WO | WO-2015080446 A1 | 6/2015 |
| WO | WO-2015084692 A1 | 6/2015 |
| WO | WO-2015088868 A1 | 6/2015 |
| WO | WO-2015089809 A1 | 6/2015 |
| WO | WO-2015097713 A1 | 7/2015 |
| WO | WO-2015105779 A1 | 7/2015 |
| WO | WO-2015105786 A1 | 7/2015 |
| WO | WO-2015119899 A1 | 8/2015 |
| WO | WO-2015150563 A1 | 10/2015 |
| WO | WO-2015150564 A1 | 10/2015 |
| WO | WO-2015150565 A1 | 10/2015 |
| WO | WO-2015160772 A1 | 10/2015 |
| WO | WO-2015176267 A1 | 11/2015 |
| WO | WO-2015181275 A1 | 12/2015 |
| WO | WO-2015183794 A1 | 12/2015 |
| WO | WO-2015198199 A1 | 12/2015 |
| WO | WO-2016000771 A1 | 1/2016 |
| WO | WO-2016019587 A1 | 2/2016 |
| WO | WO-2016022446 A1 | 2/2016 |
| WO | WO-2016022448 A1 | 2/2016 |
| WO | WO-2016022742 A1 | 2/2016 |
| WO | WO-2016032120 A1 | 3/2016 |
| WO | WO-2016044467 A1 | 3/2016 |
| WO | WO-2016054208 A1 | 4/2016 |
| WO | WO-2016057731 A1 | 4/2016 |
| WO | WO-2016066818 A1 | 5/2016 |
| WO | WO-2016068453 A1 | 5/2016 |
| WO | WO-2016073767 A1 | 5/2016 |
| WO | WO-2016086115 A1 | 6/2016 |
| WO | WO-2016130809 A1 | 8/2016 |
| WO | WO-2016161003 A1 | 10/2016 |
| WO | WO-2016168222 A1 | 10/2016 |
| WO | WO-2016168225 A1 | 10/2016 |
| WO | WO-2016205032 A1 | 12/2016 |
| WO | WO-2016205475 A2 | 12/2016 |
| WO | WO-2017002786 A1 | 1/2017 |
| WO | WO-2017005765 A1 | 1/2017 |
| WO | WO-2017025368 A1 | 2/2017 |
| WO | WO-2017027309 A1 | 2/2017 |
| WO | WO-2017027310 A1 | 2/2017 |
| WO | WO-2017027312 A1 | 2/2017 |
| WO | WO-2017027396 A1 | 2/2017 |
| WO | WO-2017042121 A1 | 3/2017 |
| WO | WO-2017053826 A1 | 3/2017 |
| WO | WO-2017079062 A1 | 5/2017 |
| WO | WO-2017106112 A1 | 6/2017 |
| WO | WO-2017106818 A1 | 6/2017 |
| WO | WO-2017147137 A1 | 8/2017 |
| WO | WO-2017147159 A1 | 8/2017 |
| WO | WO-2017147174 A1 | 8/2017 |
| WO | WO-2017147742 A1 | 9/2017 |
| WO | WO-2017172505 A1 | 10/2017 |
| WO | WO-2017175066 A1 | 10/2017 |
| WO | WO-2017175068 A1 | 10/2017 |
| WO | WO-2017180571 A1 | 10/2017 |
| WO | WO-2017180577 A1 | 10/2017 |
| WO | WO-2017222713 A1 | 12/2017 |
| WO | WO-2018005794 A2 | 1/2018 |
| WO | WO-2018005801 A2 | 1/2018 |
| WO | WO-2018009778 A1 | 1/2018 |
| WO | WO-2018024602 A1 | 2/2018 |
| WO | WO-2018024653 A1 | 2/2018 |
| WO | WO-2018026890 A1 | 2/2018 |
| WO | WO-2018035079 A1 | 2/2018 |
| WO | WO-2018064441 A1 | 4/2018 |
| WO | WO-2018071493 A1 | 4/2018 |
| WO | WO-2018077699 A1 | 5/2018 |
| WO | WO-2018081047 A1 | 5/2018 |
| WO | WO-2018095877 A1 | 5/2018 |
| WO | WO-2018103868 A1 | 6/2018 |
| WO | WO-2018104558 A1 | 6/2018 |
| WO | WO-2018104559 A1 | 6/2018 |
| WO | WO-2018104560 A1 | 6/2018 |
| WO | WO-2018104561 A1 | 6/2018 |
| WO | WO-2018106518 A1 | 6/2018 |
| WO | WO-2018111012 A1 | 6/2018 |
| WO | WO-2018118670 A1 | 6/2018 |
| WO | WO-2018138026 A1 | 8/2018 |
| WO | WO-2018138027 A1 | 8/2018 |
| WO | WO-2018138028 A1 | 8/2018 |
| WO | WO-2018138029 A1 | 8/2018 |
| WO | WO-2018138030 A1 | 8/2018 |
| WO | WO-2018142363 A1 | 8/2018 |
| WO | WO-2018146008 A1 | 8/2018 |
| WO | WO-2018153849 A1 | 8/2018 |
| WO | WO-2018172727 A1 | 9/2018 |
| WO | WO-2018181847 A1 * | 10/2018 ........... A61K 31/192 |

(56) References Cited

FOREIGN PATENT DOCUMENTS

| WO | WO-2018182050 A1 | 10/2018 |
|---|---|---|
| WO | WO-2018219204 A1 | 12/2018 |
| WO | WO-2018222701 A1 | 12/2018 |
| WO | WO-2018226724 A1 | 12/2018 |
| WO | WO-2018229252 A1 | 12/2018 |
| WO | WO-2018237350 A1 | 12/2018 |
| WO | WO-2019040399 A1 | 2/2019 |
| WO | WO-2019086559 A1 | 5/2019 |
| WO | WO-2019090209 A1 | 5/2019 |
| WO | WO-2019099315 A1 | 5/2019 |
| WO | WO-2019134984 A1 | 7/2019 |
| WO | WO-2019149657 A1 | 8/2019 |
| WO | WO-2019149658 A1 | 8/2019 |
| WO | WO-2019149659 A1 | 8/2019 |
| WO | WO-2019149660 A1 | 8/2019 |
| WO | WO-2019149959 A1 | 8/2019 |
| WO | WO-2019152889 A1 | 8/2019 |
| WO | WO-2020197926 A1 | 10/2020 |
| WO | WO-2020242943 A1 | 12/2020 |
| WO | WO-2021071837 A1 | 4/2021 |
| WO | WO-2021113362 A1 | 6/2021 |
| WO | WO-2021113363 A1 | 6/2021 |
| WO | WO-2021113368 A1 | 6/2021 |
| WO | WO-2021174046 A1 | 9/2021 |
| WO | WO-2021174048 A1 | 9/2021 |
| WO | WO-2022216709 A1 | 10/2022 |
| WO | WO-2023097187 A1 | 6/2023 |
| WO | WO-2023250323 A1 | 12/2023 |

OTHER PUBLICATIONS

Evans. Synthesis of radiolabeled compounds. J Radioanal Chem 64(1-2):9-32 (1981).

Jurica et al., Discovery of pyrrolidine-containing GPR40 agonists: stereochemistry effects a change in binding mode. Journal of Medicinal Chemistry 60(4):1417-1431 (2017).

Kabalka et al. The Synthesis of Radiolabeled Compounds via Organometallic Intermediates. Tetrahedron 45(21):6601-6621 (1989).

Meegalla et al., Discovery of a novel potent GPR40 full agonist. Bioorganic and Medicinal Chemistry Letters 28(4):720-726 (2018).

PCT/US2020/034226 International Search Report and Written Opinion dated Aug. 27, 2020.

PCT/US2021/019973 International Search Report and Written Opinion dated Jun. 14, 2021.

PCT/US2021/019975 International Search Report and Written Opinion dated Jun. 15, 2021.

Wang et al., Discovery and optimization of potent GPR40 full agonists containing tricyclic spirocycles. ACS Med Chem. Lett 4(6):551-555 (2013).

Boltromeyuk. General Chemistry. Minsk, Higher School, p. 65 (2012).

Ekberg et al., GPR119, a major enteroendocrine sensor of dietary triglyceride metabolites coacting in synergy with FFA1 (GPR40). Endocrinology 157(12):4561-4569 (2016).

Hauge et al., Gq and Gs signaling acting in synergy to control GLP-1 secretion. Molecular and Cellular Endocrinology 449:64-73 (2017).

Liu et al., Optimization of preclinical metabolism for somatostatin receptor subtype 5-selective antagonists. ACS Med Chem Lett. 9(11):1088-1093 (2018).

PCT/US2020/023611 International Search Report and Written Opinion dated Jul. 16, 2020.

PCT/US2020/023611 Invitation to Pay Additional Fees dated May 15, 2020.

PCT/US2020/054403 International Search Report and Written Opinion dated Jan. 22, 2021.

PCT/US2022/023481 International Search Report and Written Opinion dated Jul. 25, 2022.

PCT/US2022/080260 International Search Report and Written Opinion dated Feb. 16, 2023.

PCT/US2023/068729 International Search Report and Written Opinion dated Aug. 21, 2023.

Pols et al., Targeting the TGR5-GLP-1 pathway to combat type 2 diabetes and non-alcoholic fatty liver disease. Gastroenterol. Clin. Biol. 34(4-5):270-273 (2010).

Richards et al., The gut-brain axis: Identifying new therapeutic approaches for type 2 diabetes, obesity, and related disorders. Molecular Metabolism 46:101175 (2021).

Sato et al. Chapter 19: Primary mouse small intestinal epithelial cell cultures. Methods Mol Biol 945:319-28 (2013).

Zhu et al. Discovery of phenyl acetamides as potent and selective GPR119 agonists. Bioorg Med Chem Lett. 27(5):1124-1128 (2017).

Co-Pending U.S. Appl. No. 18/387,170, inventor Pinto, Shirly, filed on Nov. 6, 2023.

RN 2094855-09-9. CAS May 3, 2017.

* cited by examiner

GPR40 AGONISTS

CROSS-REFERENCE TO RELATED APPLICATIONS

This application is a continuation of International Application No. PCT/US2021/019975, filed Feb. 26, 2012, which claims the benefit of U.S. Provisional Application No. 62/983,438 filed on Feb. 28, 2020, U.S. Provisional Application No. 63/076,113 filed on Sep. 9, 2020, U.S. Provisional Application No. 63/117,074 filed on Nov. 23, 2020, and U.S. Provisional Application No. 63/147,980 filed on Feb. 10, 2021, each of which is incorporated herein by reference in its entirety.

BRIEF SUMMARY OF THE INVENTION

Disclosed herein, in certain embodiments, are free fatty acid receptor 1 (GPR40) agonists useful for the treatment of conditions or disorders involving the gut-brain axis. In some embodiments, the GPR40 agonists are gut-restricted or selectively modulate GPR40 located in the gut. In some embodiments, the condition is selected from the group consisting of: central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis and celiac disease; necrotizing enterocolitis; gastrointestinal injury resulting from toxic insults such as radiation or chemotherapy; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

Disclosed herein, in certain embodiments, is a compound of Formula (I):

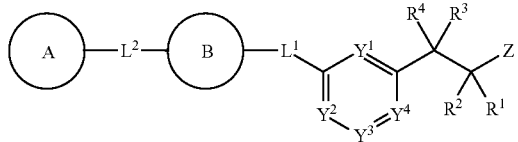

Formula (I)

or a pharmaceutically acceptable salt, solvate, stereoisomer, or prodrug thereof, wherein:

Z is $-P(=O)(H)OR^6$, $-P(=O)(R^5)OR^6$, $-P(=O)(OR^6)_2$, $-S(=O)(OR^6)$, $-SO_2OR^6$, $-C(=O)NHSO_2R^5$, $-C(=O)NHSO_2N(R^6)_2$, $-N(R^6)SO_2N(R^6)_2$, $-N(R^6)C(=O)NHSO_2(R^5)$, $-N(R^6)C(=O)NHSO_2N(R^6)_2$, $-N(R^6)C(=NH)NH_2$, $-C(=O)NHNHC(=O)N(R^6)_2$, or $-B(OR^6)_2$;

$R^5$ is $C_1$-$C_6$ alkyl, $C_3$-$C_6$ cycloalkyl, phenyl, or $-(C_1$-$C_6$ alkyl)-phenyl; wherein each alkyl, cycloalkyl, and phenyl is independently unsubstituted or substituted with 1, 2, or 3 substituents selected from the group consisting of halogen, $-CN$, $-OH$, $-O-(C_1$-$C_6$ alkyl), $C_1$-$C_6$ alkyl, $C_1$-$C_6$ fluoroalkyl, $C_1$-$C_6$ hydroxyalkyl, $-O-(C_1$-$C_6$ fluoroalkyl), $C_3$-$C_6$ cycloalkyl, and 3- to 6-membered heterocycloalkyl;

each $R^6$ is independently hydrogen, $C_1$-$C_6$ alkyl, $C_3$-$C_6$ cycloalkyl, phenyl, or $-(C_1$-$C_6$ alkyl)-phenyl; wherein each alkyl, cycloalkyl, and phenyl is independently unsubstituted or substituted with 1, 2, or 3 substituents selected from the group consisting of halogen, $-CN$, $-OH$, $-O-(C_1$-$C_6$ alkyl), $C_1$-$C_6$ alkyl, $C_1$-$C_6$ fluoroalkyl, $C_1$-$C_6$ hydroxyalkyl, $-O-(C_1$-$C_6$ fluoroalkyl), $C_3$-$C_6$ cycloalkyl, and 3- to 6-membered heterocycloalkyl;

$R^1$, $R^2$, and $R^3$ are each independently hydrogen, halogen, $-OH$, $-O-(C_1$-$C_6$ alkyl), $C_1$-$C_6$ alkyl, $C_3$-$C_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, $-CN$, $-OH$, $-O-(C_1$-$C_6$ alkyl), and $C_1$-$C_6$ alkyl;

$R^4$ is $C_1$-$C_6$ alkyl, $C_3$-$C_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, $-CN$, $-OH$, $-O-(C_1$-$C_6$ alkyl), and $C_1$-$C_6$ alkyl;

$Y^1$, $Y^2$, $Y^3$, and $Y^4$ are each independently N, CH, or $C-R^Y$;

each $R^Y$ is independently halogen, $-CN$, $-OH$, $-O(C_1$-$C_6$ alkyl), $-NH_2$, $-NH-(C_1$-$C_6$ alkyl), $-N(C_1$-$C_6$ alkyl)$_2$, $C_1$-$C_6$ alkyl, $C_3$-$C_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, $-CN$, $-OH$, $-O-(C_1$-$C_6$ alkyl), and $C_1$-$C_6$ alkyl;

$L^1$ is $-O-$, $-NR^7-$, $*-O-CH_2-$, $*-CH_2-O-$, $*-NR^7-CH_2-$, $*-CH_2-NR^7-$, $*-NR^7-C(O)-$, $*-C(O)-NR^7-$, or $*-C(O)-CH_2-$; wherein * represents the connection to Ring B;

$R^7$ is hydrogen, $C_1$-$C_6$ alkyl, or $C_3$-$C_6$ cycloalkyl;

Ring B is cycloalkylene or heterocycloalkylene; wherein the cycloalkylene or heterocycloalkylene is unsubstituted or substituted with 1, 2, 3, or 4 $R^B$ substituents;

Ring A is carbocycle or heterocycle; wherein the carbocycle or heterocycle is unsubstituted or substituted with 1, 2, 3, 4, or 5 $R^A$ substituents;

$L^2$ is a bond, $C_1$-$C_6$ alkylene, or $-(C_1$-$C_6$ alkylene)-O$-$; wherein the alkylene is unsubstituted or substituted with 1, 2, or 3 substituents selected from the group consisting of halogen, $-CN$, $-OH$, $C_1$-$C_6$ alkyl, and $-O-(C_1$-$C_6$ alkyl);

each $R^A$ is independently halogen, $C_1$-$C_{10}$ alkyl, $C_2$-$C_{10}$ alkenyl, $C_2$-$C_{10}$ alkynyl, $C_1$-$C_{10}$ fluoroalkyl, $-L^A$-CN, $-L^A$-OH, $-L^A$-OR$^{10}$, $-L^A$-NR$^{11}$R$^{11}$, $-L^A$-C(=O)R$^{10}$, $-L^A$-C(=O)OR$^{11}$, $-L^A$-OC(=O)R$^{11}$, $-L^A$-C(=O)NR$^{11}$R$^{11}$, $-L^A$-NR$^{11}$C(=O)R$^{11}$, $-L^A$-NR$^{11}$C(=O)

$NR^{11}R^{11}$, -$L^A$-OC(=O)$NR^{11}R^{11}$, -$L^A$-$NR^{11}$C(=O)$OR^{11}$, -$L^A$-OC(=O)$OR^{10}$, -$L^A$-aryl, -$L^A$-heteroaryl, -$L^A$-($C_3$-$C_{10}$ cycloalkyl), or -$L^A$-(3- to 10-membered heterocycloalkyl); wherein each alkyl, alkenyl, alkynyl, fluoroalkyl, aryl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

each $R^B$ is independently halogen, $C_1$-$C_{10}$ alkyl, $C_2$-$C_{10}$ alkenyl, $C_2$-$C_{10}$ alkynyl, $C_1$-$C_{10}$ fluoroalkyl, -$L^B$-CN, -$L^B$-OH, -$L^B$-$OR^{10}$, -$L^B$-$NR^{11}R^{11}$, -$L^B$-C(=O)$R^{10}$, -$L^B$-C(=O)$OR^{11}$, -$L^B$-OC(=O)$R^{11}$, -$L^B$-C(=O)$NR^{11}R^{11}$, -$L^B$-$NR^{11}$C(=O)$R^{11}$, -$L^B$-$NR^{11}$C(=O)$NR^{11}R^{11}$, -$L^B$-OC(=O)$NR^{11}R^{11}$, -$L^B$-$NR^{11}$C(=O)$OR^{10}$, -$L^B$-OC(=O)$OR^{10}$, -$L^B$-aryl, -$L^B$-heteroaryl, -$L^B$-($C_3$-$C_{10}$ cycloalkyl), or -$L^B$-(3- to 10-membered heterocycloalkyl); wherein each alkyl, alkenyl, alkynyl, fluoroalkyl, aryl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

each $L^A$ and $L^B$ is independently a bond or $C_1$-$C_6$ alkylene; wherein the alkylene is unsubstituted or substituted with 1, 2, or 3 substituents selected from the group consisting of halogen, —CN, —OH, —O—($C_1$-$C_6$ alkyl), and $C_1$-$C_6$ alkyl;

each $R^{10}$ is independently $C_1$-$C_{10}$ alkyl, $C_2$-$C_{10}$ alkenyl, $C_2$-$C_{10}$ alkynyl, $C_3$-$C_{10}$ cycloalkyl, 3- to 10-membered heterocycloalkyl, phenyl, or monocyclic heteroaryl; wherein each alkyl, alkenyl, alkynyl, phenyl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl); and each $R^{11}$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, 3- to 10-membered heterocycloalkyl, phenyl, or monocyclic heteroaryl; wherein each alkyl, alkenyl, alkynyl, phenyl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —($C_1$-$C_6$ fluoroalkyl);

or two $R^{11}$ on the same nitrogen atom are taken together with the nitrogen to which they are attached to form a 3- to 10-membered N-heterocycloalkyl; wherein the heterocycloalkyl is unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl).

Any combination of the groups described above or below for the various variables is contemplated herein. Throughout the specification, groups and substituents thereof are chosen by one skilled in the field to provide stable moieties and compounds.

In some embodiments, the compound is a compound of Formula (II):

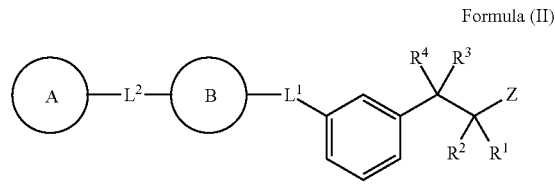

Formula (II)

or a pharmaceutically acceptable salt, solvate, stereoisomer, or prodrug thereof.

In some embodiments, the compound is a compound of Formula (III):

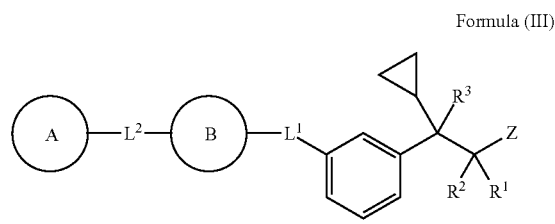

Formula (III)

or a pharmaceutically acceptable salt, solvate, stereoisomer, or prodrug thereof, wherein $R^1$, $R^2$, and $R^3$ are each independently hydrogen, —F, —Cl, or $C_1$-$C_4$ alkyl.

In some embodiments, the compound is a compound of Formula (IV):

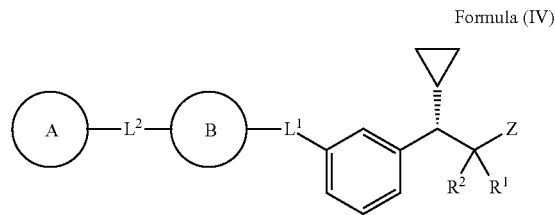

Formula (IV)

or a pharmaceutically acceptable salt, solvate, stereoisomer, or prodrug thereof, wherein $R^1$ and $R^2$ are each independently hydrogen, —F, or methyl.

In some embodiments, the compound is a compound of Formula (IVa) or Formula (IVb):

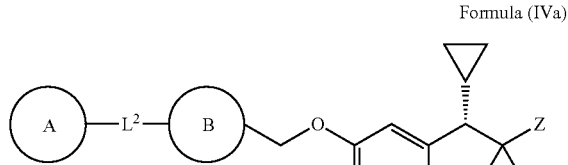

Formula (IVa)

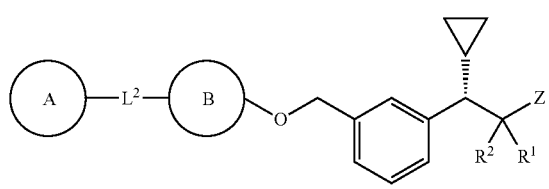

Formula (IVb)

or a pharmaceutically acceptable salt, solvate, stereoisomer, or prodrug thereof.

In some embodiments, the compound is a compound of Formula (V):

Formula (V)

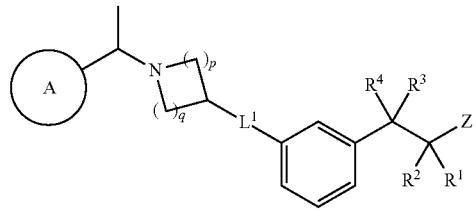

or a pharmaceutically acceptable salt, solvate, stereoisomer, or prodrug thereof; wherein p and q are each independently 1 or 2.

In some embodiments, the compound is a compound of Formula (Va) or Formula (Vb):

Formula (Va)

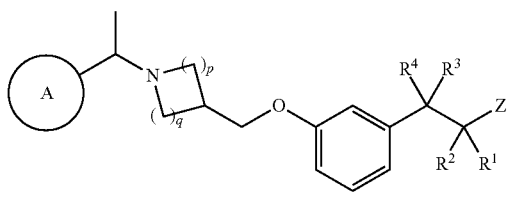

Formula (Vb)

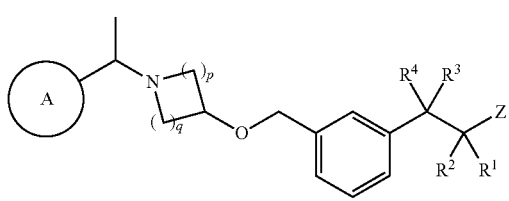

or a pharmaceutically acceptable salt, solvate, stereoisomer, or prodrug thereof.

In some embodiments, the compound is a compound of Formula (VI):

Formula (VI)

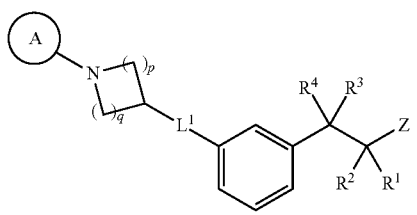

or a pharmaceutically acceptable salt, solvate, stereoisomer, or prodrug thereof; wherein p and q are each independently 1 or 2.

In some embodiments, the compound is a compound of Formula (VIa) or Formula (VIb):

Formula (VIa)

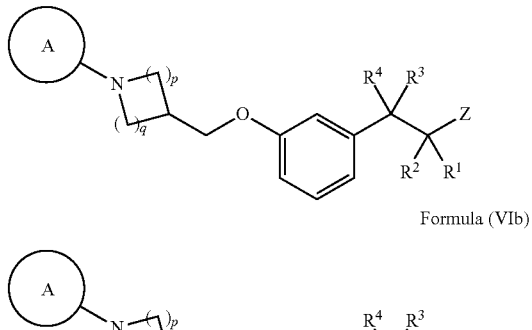

Formula (VIb)

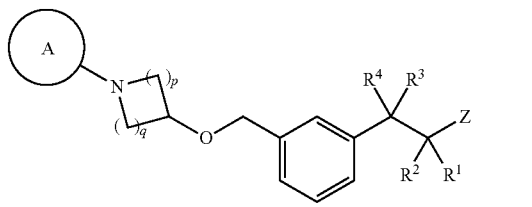

or a pharmaceutically acceptable salt, solvate, stereoisomer, or prodrug thereof.

In some embodiments, the compound is a compound of Formula (VIa-i) or Formula (VIb-i):

Formula (VIa-i)

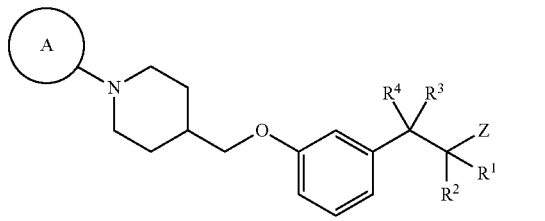

Formula (VIb-i)

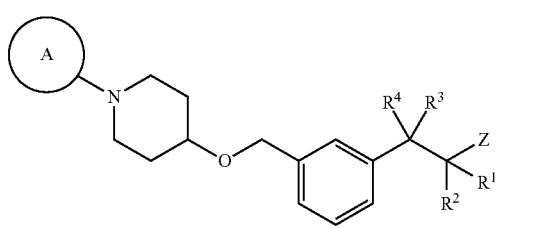

or a pharmaceutically acceptable salt, solvate, stereoisomer, or prodrug thereof.

In some embodiments, the compound is a compound of Formula (XV):

Formula (XV)

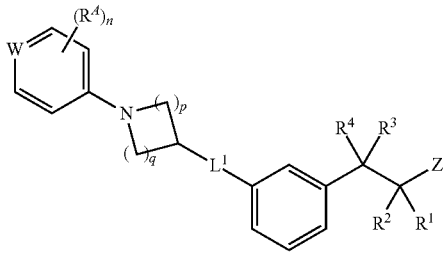

or a pharmaceutically acceptable salt, solvate, stereoisomer, or prodrug thereof; wherein: W is N, CH, or CR$^A$; each R$^A$ is independently —F, —Cl, C$_1$-C$_7$ alkyl, C$_1$-C$_4$ fluoroalkyl, —OH, or —OR$^{10}$; and n is 0, 1, or 2.

In some embodiments, the compound is a compound of Formula (XVa-i):

Formula (XVa-i)

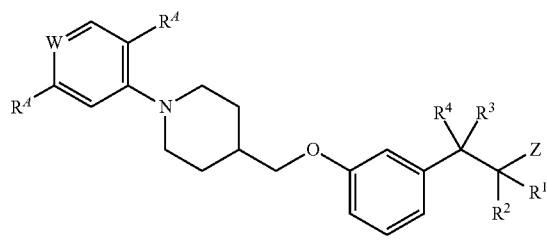

or a pharmaceutically acceptable salt, solvate, stereoisomer, or prodrug thereof.

In some embodiments, the compound is a compound of Formula (VII):

Formula (VII)

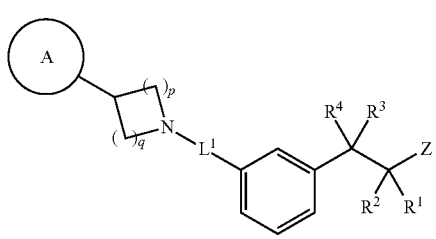

or a pharmaceutically acceptable salt, solvate, stereoisomer, or prodrug thereof; wherein p and q are each independently 1 or 2.

In some embodiments, the compound is a compound of Formula (VIIa) or Formula (VIIb):

Formula (VIIa)

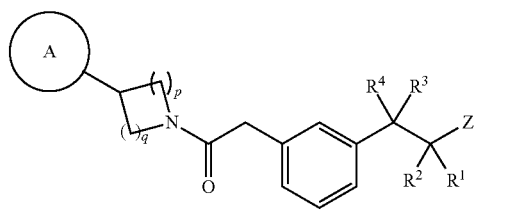

Formula (VIIb)

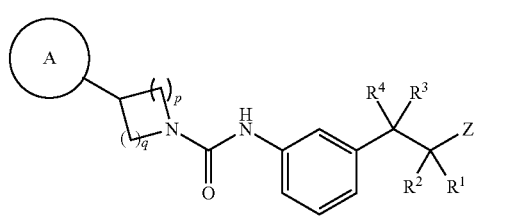

or a pharmaceutically acceptable salt, solvate, stereoisomer, or prodrug thereof.

In some embodiments, the compound is a compound of Formula (VIII):

Formula (VIII)

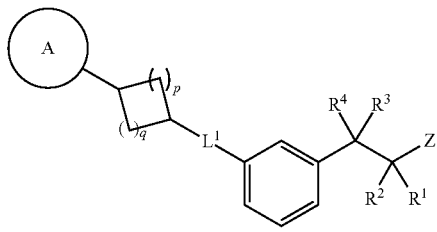

or a pharmaceutically acceptable salt, solvate, stereoisomer, or prodrug thereof; wherein p and q are each independently 1 or 2.

In some embodiments, the compound is a compound of Formula (VIIIa) or Formula (VIIIb):

Formula (VIIIa)

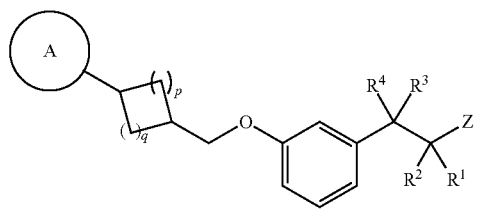

Formula (VIIIb)

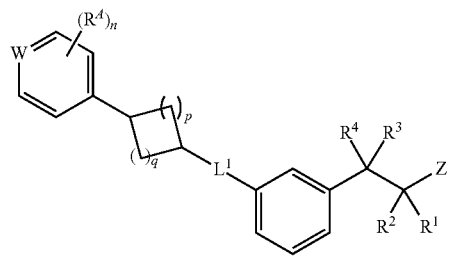

or a pharmaceutically acceptable salt, solvate, stereoisomer, or prodrug thereof.

In some embodiments, the compound is a compound of Formula (XIV):

Formula (XIV)

or a pharmaceutically acceptable salt, solvate, stereoisomer, or prodrug thereof; wherein: W is N, CH, or CR$^A$; each R$^A$ is independently —F, —Cl, C$_1$-C$_7$ alkyl, C$_1$-C$_4$ fluoroalkyl, —OH, or —OR$^{10}$; and n is 0, 1, or 2.

In some embodiments, the compound is a compound of Formula (XIVa-i):

Formula (XIVa-i)

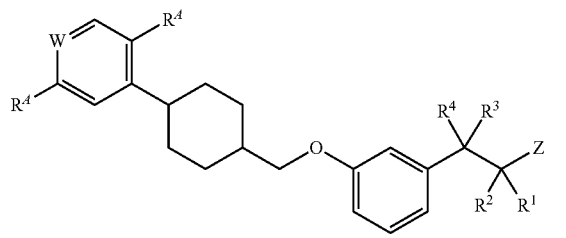

or a pharmaceutically acceptable salt, solvate, stereoisomer, or prodrug thereof.

Disclosed herein, in certain embodiments, are pharmaceutical compositions comprising a compound disclosed herein, or a pharmaceutically acceptable salt, solvate, stereoisomer, or prodrug thereof, and at least one pharmaceutically acceptable excipient.

Disclosed herein, in certain embodiments, are methods of treating a condition or disorder involving the gut-brain axis in a subject in need thereof, the method comprising administering to the subject a therapeutically effective amount of a compound disclosed herein, or a pharmaceutically acceptable salt, solvate, stereoisomer, or prodrug thereof. In some embodiments, the condition or disorder is associated with GPR40 activity. In some embodiments, the condition or disorder is a metabolic disorder. In some embodiments, the condition or disorder is type 2 diabetes, hyperglycemia, metabolic syndrome, obesity, hypercholesterolemia, nonalcoholic steatohepatitis, or hypertension. In some embodiments, the condition or disorder is a nutritional disorder. In some embodiments, the condition or disorder is short bowel syndrome, intestinal failure, or intestinal insufficiency. In some embodiments, the compound disclosed herein is gut-restricted. In some embodiments, the compound disclosed herein has low systemic exposure.

In some embodiments, the methods disclosed herein further comprise administering one or more additional therapeutic agents to the subject. In some embodiments, the one or more additional therapeutic agents are selected from a TGR5 agonist, a GPR119 agonist, an SSTR5 antagonist, an SSTR5 inverse agonist, a CCK1 agonist, a PDE4 inhibitor, a DPP-4 inhibitor, a GLP-1 receptor agonist, a GOAT inhibitor, metformin, or combinations thereof. In some embodiments, the TGR5 agonist, GPR119 agonist, SSTR5 antagonist, SSTR5 inverse agonist or CCK1 agonist is gut-restricted.

DETAILED DESCRIPTION OF THE INVENTION

This disclosure is directed, at least in part, to GPR40 agonists useful for the treatment of conditions or disorders involving the gut-brain axis. In some embodiments, the GPR40 agonists are gut-restricted compounds. In some embodiments, the GPR40 agonists are full agonists or partial agonists.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulas, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below:

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

"Alkyl" refers to an optionally substituted straight-chain, or optionally substituted branched-chain saturated hydrocarbon monoradical having from one to about ten carbon atoms, or more preferably, from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^a$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an $sp^2$-hybridized carbon or an $sp^3$-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl (—C(CH$_3$)═CH$_2$), butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. Unless stated otherwise specifically in the specification, an alkenyl group is optionally substituted as described below by one or more of the following substituents: halo, cyano, nitro, oxo, thioxo, imino, oximo, trimethylsilanyl, —OR$^a$, —SR$^a$, —OC(O)—R$^f$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms, wherein an sp-hybridized carbon or an $sp^3$-hybridized carbon of the alkynyl residue is attached to the rest of the molecule by a single bond. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. Unless stated otherwise specifically in the specification, an alkylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R)S(O)$_t$R$^f$ (where t is 1 or 2), —S(O)$_t$OR$^a$ (where t is 1 or 2), —S(O)$_t$R$^f$ (where t is 1 or 2) and —S(O)XN(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. Unless stated otherwise specifically in the specification, an alkenylene group is optionally substituted as described below by one or more of the following substituents: halo, cyano, nitro, oxo, thioxo, imino, oximo, trimethylsilanyl, —OR$^a$, —SR$^a$, —OC(O)—R$^f$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. Unless stated otherwise specifically in the specification, an alkynylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkoxy" or "alkoxyl" refers to a radical bonded through an oxygen atom of the formula —O-alkyl, where alkyl is an alkyl chain as defined above.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms unless otherwise specified (i.e., from 6 to 18 carbon atoms), where at least one of the rings in the ring system is fully unsaturated, (i.e., it contains a cyclic, delocalized (4n+2) π-electron system in accordance with the Hückel theory). The ring system from which aryl groups are derived include, but are not limited to, groups such as benzene, fluorene, indane, indene, tetralin and naphthalene. In some embodiments, the aryl is a $C_6$-$C_{10}$ aryl. In some embodiments, the aryl is a phenyl. Unless stated otherwise specifically in the specification, the term "aryl" or the prefix "ar-" (such as in "aralkyl") is meant to include aryl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—SR$^a$, —R$^b$—OC(O)—R$^a$, —R$^b$—OC(O)—OR$^f$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^f$, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, R$^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

An "arylene" refers to a divalent radical derived from an "aryl" group as described above linking the rest of the molecule to a radical group. The arylene is attached to the rest of the molecule through a single bond and to the radical group through a single bond. In some embodiments, the arylene is a phenylene. Unless stated otherwise specifically in the specification, an arylene group is optionally substituted as described above for an aryl group.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[1.1.1]pentyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, 7,7-dimethyl-bicyclo[2.2.1]heptanyl, and the like. Unless otherwise stated specifically in the specification, the term "cycloalkyl" is meant to include cycloalkyl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—SR$^a$, —R$^b$—OC(O)—R$^a$, —R$^b$—OC(O)—OR$^f$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, R$^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

A "cycloalkylene" refers to a divalent radical derived from a "cycloalkyl" group as described above linking the rest of the molecule to a radical group. The cycloalkylene is attached to the rest of the molecule through a single bond and to the radical group through a single bond. Unless stated otherwise specifically in the specification, a cycloalkylene group is optionally substituted as described above for a cycloalkyl group.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more hydroxy radicals, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like.

"Haloalkoxy" or "haloalkoxyl" refers to an alkoxyl radical, as defined above, that is substituted by one or more halo radicals, as defined above.

"Fluoroalkoxy" or "fluoroalkoxyl" refers to an alkoxy radical, as defined above, that is substituted by one or more fluoro radicals, as defined above, for example, trifluoromethoxy, difluoromethoxy, fluoromethoxy, and the like.

"Hydroxyalkyl" refers to an alkyl radical, as defined above, that is substituted by one or more halo radicals, as defined above, e.g., hydroxymethyl, 1-hydroxyethyl, 2-hydroxyethyl, 2-hydroxypropyl, 3-hydroxypropyl, 1,2-dihydroxyethyl, 2,3-dihydroxypropyl, 2,3,4,5,6-pentahydroxyhexyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 8-membered heterocycloalkyl. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. More preferably, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-SR^a$, $-R^b-OC(O)-R^a$, $-R^b-OC(O)-OR^f$, $-R^b-OC(O)-N(R^a)_2$, $-R^b-N(R^a)_2$, $-R^b-N^+(R^a)_3$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^f$, $-R^b-N(R^a)C(O)R^a$, $-R^b-N(R^a)S(O)_tR^f$ (where t is 1 or 2), $-R^b-S(O)_tOR^a$ (where t is 1 or 2), $-R^b-S(O)_tR^f$ (where t is 1 or 2) and $-R^b-S(O)_tN(R^a)_2$ (where t is 1 or 2), where each R is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals.

"C-heterocycloalkyl" refers to a heterocycloalkyl radical as defined above and where the point of attachment of the heterocycloalkyl radical to the rest of the molecule is through a carbon atom in the heterocycloalkyl radical. A C-heterocycloalkyl radical is optionally substituted as described above for heterocycloalkyl radicals.

A "heterocycloalkylene" refers to a divalent radical derived from a "heterocycloalkyl" group as described above linking the rest of the molecule to a radical group. The heterocycloalkylene is attached to the rest of the molecule through a single bond and to the radical group through a single bond. Unless stated otherwise specifically in the specification, a heterocycloalkylene group is optionally substituted as described above for a heterocycloalkyl group.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. In some embodiments, the heteroaryl is a 5- to 10-membered heteroaryl. In some embodiments, the heteroaryl is a monocyclic heteroaryl, or a monocyclic 5- or 6-membered heteroaryl. In some embodiments, the heteroaryl is a 6,5-fused bicyclic heteroaryl. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-SR^a$, $-R^b-OC(O)-R^a$, $-R^b-OC(O)-OR^f$, $-R^b-OC(O)-N(R^a)_2$, $-R^b-N(R^a)_2$, $-R^b-N^+(R^a)_3$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^f$, $-R^b-N(R^a)C(O)R^a$, $-R^b-N(R^a)S(O)_tR^f$ (where t is 1 or 2), $-R^b-S(O)_tOR^a$ (where t is 1 or 2), $-R^b-S(O)_tR^f$ (where t is 1 or 2) and $-R^b-S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "heteroarylene" refers to a divalent radical derived from a "heteroaryl" group as described above linking the rest of the molecule to a radical group. The heteroarylene is attached to the rest of the molecule through a single bond and to the radical group through a single bond. Unless stated otherwise specifically in the specification, a heteroarylene group is optionally substituted as described above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be unsubstituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

The term "modulate" or "modulating" or "modulation" refers to an increase or decrease in the amount, quality, or effect of a particular activity, function or molecule. By way of illustration and not limitation, agonists, partial agonists, inverse agonists, antagonists, and allosteric modulators of a G protein-coupled receptor are modulators of the receptor.

The term "agonism" as used herein refers to the activation of a receptor or enzyme by a modulator, or agonist, to produce a biological response.

The term "agonist" as used herein refers to a modulator that binds to a receptor or target enzyme and activates the receptor or enzyme to produce a biological response. By way of example, "GPR40 agonist" can be used to refer to a compound that exhibits an EC$_{50}$ with respect to GPR40 activity of no more than about 100 μM, as measured in the as measured in the inositol phosphate accumulation assay. In some embodiments, the term "agonist" includes full agonists or partial agonists.

The term "full agonist" refers to a modulator that binds to and activates a receptor or target enzyme with the maximum response that an agonist can elicit at the receptor or enzyme.

The term "partial agonist" refers to a modulator that binds to and activates a receptor or target enzyme, but has partial efficacy, that is, less than the maximal response, at the receptor or enzyme relative to a full agonist.

The term "positive allosteric modulator" refers to a modulator that binds to a site distinct from the orthosteric binding site and enhances or amplifies the effect of an agonist.

The term "antagonism" as used herein refers to the inactivation of a receptor or target enzyme by a modulator, or antagonist. Antagonism of a receptor, for example, is when a molecule binds to the receptor or target enzyme and does not allow activity to occur.

The term "antagonist" or "neutral antagonist" as used herein refers to a modulator that binds to a receptor or target enzyme and blocks a biological response. By way of example, "SSTR5 antagonist" can be used to refer to a compound that exhibits an IC$_{50}$ with respect to SSTR5 activity of no more than about 100 μM, as measured in the as measured in the inositol phosphate accumulation assay. An antagonist has no activity in the absence of an agonist or inverse agonist but can block the activity of either, causing no change in the biological response.

The term "inverse agonist" refers to a modulator that binds to the same receptor or target enzyme as an agonist but induces a pharmacological response opposite to that agonist, i.e., a decrease in biological response.

The term "negative allosteric modulator" refers to a modulator that binds to a site distinct from the orthosteric binding site and reduces or dampens the effect of an agonist.

As used herein, "EC$_{50}$" is intended to refer to the concentration of a substance (e.g., a compound or a drug) that is required for 50% activation or enhancement of a biological process. In some instances, EC$_{50}$ refers to the concentration of agonist that provokes a response halfway between the baseline and maximum response in an in vitro assay. In some embodiments as used herein, EC$_{50}$ refers to the concentration of an agonist (e.g., a GPR40 agonist) that is required for 50% activation of a receptor or target enzyme (e.g., GPR40).

As used herein, "IC$_{50}$" is intended to refer to the concentration of a substance (e.g., a compound or a drug) that is required for 50% inhibition of a biological process. For example, IC$_{50}$ refers to the half maximal (50%) inhibitory concentration (IC) of a substance as determined in a suitable assay. In some instances, an IC$_{50}$ is determined in an in vitro assay system. In some embodiments as used herein, IC$_{50}$ refers to the concentration of a modulator (e.g., an SSTR5 antagonist) that is required for 50% inhibition of a receptor or a target enzyme (e.g., SSTR5).

The terms "subject," "individual," and "patient" are used interchangeably. These terms encompass mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The term "gut-restricted" as used herein refers to a compound, e.g., a GPR40 agonist, that is predominantly active in the gastrointestinal system. In some embodiments, the biological activity of the gut-restricted compound, e.g., a gut-restricted GPR40 agonist, is restricted to the gastrointestinal system. In some embodiments, gastrointestinal concentration of a gut-restricted modulator, e.g., a gut-restricted GPR40 agonist, is higher than the IC$_{50}$ value or the EC$_{50}$ value of the gut-restricted modulator against its receptor or target enzyme, e.g., GPR40, while the plasma levels of said gut-restricted modulator, e.g., gut-restricted GPR40 agonist, are lower than the IC$_{50}$ value or the EC$_{50}$ value of the gut-restricted modulator against its receptor or target enzyme, e.g., GPR40. In some embodiments, the gut-restricted compound, e.g., a gut-restricted GPR40 agonist, is non-systemic. In some embodiments, the gut-restricted compound, e.g., a gut-restricted GPR40 agonist, is a non-absorbed compound. In other embodiments, the gut-restricted compound, e.g., a gut-restricted GPR40 agonist, is absorbed, but is rapidly metabolized to metabolites that are significantly less active than the modulator itself toward the target receptor or enzyme, i.e., a "soft drug." In other embodiments, the gut-restricted compound, e.g., a gut-restricted GPR40 agonist, is minimally absorbed and rapidly metabolized to metabolites that are significantly less active than the modulator itself toward the target receptor or enzyme.

In some embodiments, the gut-restricted modulator, e.g., a gut-restricted GPR40 agonist, is non-systemic but is instead localized to the gastrointestinal system. For example, the modulator, e.g., a gut-restricted GPR40 agonist, may be present in high levels in the gut, but low levels in serum. In some embodiments, the systemic exposure of a gut-restricted modulator, e.g., a gut-restricted GPR40 agonist, is, for example, less than 100, less than 50, less than 20, less than 10, or less than 5 nM, bound or unbound, in blood serum. In some embodiments, the intestinal exposure of a gut-restricted modulator, e.g., a gut-restricted GPR40 agonist, is, for example, greater than 1000, 5000, 10000, 50000, 100000, or 500000 nM. In some embodiments, a modulator, e.g., a GPR40 agonist, is gut-restricted due to poor absorption of the modulator itself, or because of absorption of the modulator which is rapidly metabolized in serum resulting in low systemic circulation, or due to both poor absorption and rapid metabolism in the serum. In some embodiments, a modulator, e.g., a GPR40 agonist, is covalently bonded to a kinetophore, optionally through a linker, which changes the pharmacokinetic profile of the modulator.

In particular embodiments, the gut-restricted GPR40 agonist is a soft drug. The term "soft drug" as used herein refers to a compound that is biologically active but is rapidly metabolized to metabolites that are significantly less active than the compound itself toward the target receptor. In some embodiments, the gut-restricted GPR40 agonist is a soft drug that is rapidly metabolized in the blood to significantly less active metabolites. In some embodiments, the gut-restricted GPR40 agonist is a soft drug that is rapidly metabolized in the liver to significantly less active metabolites. In some embodiments, the gut-restricted GPR40 agonist is a soft drug that is rapidly metabolized in the blood and the liver to significantly less active metabolites. In some embodiments, the gut-restricted GPR40 agonist is a soft drug that has low systemic exposure. In some embodiments, the biological activity of the metabolite(s) is/are 10-fold, 20-fold, 50-fold, 100-fold, 500-fold, or 1000-fold lower than the biological activity of the soft drug gut-restricted GPR40 agonist.

The term "kinetophore" as used herein refers to a structural unit tethered to a small molecule modulator, e.g., a GPR40 agonist, optionally through a linker, which makes the whole molecule larger and increases the polar surface area while maintaining biological activity of the small molecule modulator. The kinetophore influences the pharmacokinetic properties, for example solubility, absorption, distribution, rate of elimination, and the like, of the small molecule modulator, e.g., a GPR40 agonist, and has minimal changes to the binding to or association with a receptor or target enzyme. The defining feature of a kinetophore is not its interaction with the target, for example a receptor, but rather its effect on specific physiochemical characteristics of the modulator to which it is attached, e.g., a GPR40 agonist. In some instances, kinetophores are used to restrict a modulator, e.g., a GPR40 agonist, to the gut.

The term "linked" as used herein refers to a covalent linkage between a modulator, e.g., a GPR40 agonist, and a kinetophore. The linkage can be through a covalent bond, or through a "linker." As used herein, "linker" refers to one or more bifunctional molecules which can be used to covalently bond to the modulator, e.g., a GPR40 agonist, and kinetophore. In some embodiments, the linker is attached to any part of the modulator, e.g., a GPR40 agonist, so long as the point of attachment does not interfere with the binding of the modulator to its receptor or target enzyme. In some embodiments, the linker is non-cleavable. In some embodiments, the linker is cleavable. In some embodiments, the linker is cleavable in the gut. In some embodiments, cleaving the linker releases the biologically active modulator, e.g., a GPR40 agonist, in the gut.

The term "gastrointestinal system" (GI system) or "gastrointestinal tract" (GI tract) as used herein, refers to the organs and systems involved in the process of digestion. The gastrointestinal tract includes the esophagus, stomach, small intestine, which includes the duodenum, jejunum, and ileum, and large intestine, which includes the cecum, colon, and rectum. In some embodiments herein, the GI system refers to the "gut," meaning the stomach, small intestines, and large intestines or to the small and large intestines, including, for example, the duodenum, jejunum, and/or colon.

Gut-Brain Axis

The gut-brain axis refers to the bidirectional biochemical signaling that connects the gastrointestinal tract (GI tract) with the central nervous system (CNS) through the peripheral nervous system (PNS) and endocrine, immune, and metabolic pathways.

In some instances, the gut-brain axis comprises the GI tract; the PNS including the dorsal root ganglia (DRG) and the sympathetic and parasympathetic arms of the autonomic nervous system including the enteric nervous system and the vagus nerve; the CNS; and the neuroendocrine and neuroimmune systems including the hypothalamic-pituitary-adrenal axis (HPA axis). The gut-brain axis is important for maintaining homeostasis of the body and is regulated and modulates physiology through the central and peripheral nervous systems and endocrine, immune, and metabolic pathways.

The gut-brain axis modulates several important aspects of physiology and behavior. Modulation by the gut-brain axis occurs via hormonal and neural circuits. Key components of these hormonal and neural circuits of the gut-brain axis include highly specialized, secretory intestinal cells that release hormones (enteroendocrine cells or EECs), the autonomic nervous system (including the vagus nerve and enteric nervous system), and the central nervous system. These systems work together in a highly coordinated fashion to modulate physiology and behavior.

Defects in the gut-brain axis are linked to a number of diseases, including those of high unmet need. Diseases and conditions affected by the gut-brain axis, include central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis, celiac disease, and enteritis, including chemotherapy-induced enteritis or radiation-induced enteritis; necrotizing enterocolitis; gastrointestinal injury resulting from toxic insults such as radiation or chemotherapy; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

GPR40 in the Gut-Brain Axis

Free fatty acid receptor 1 (FFA1, FFAR1), also known as GPR40, is a class A G-protein coupled receptor. This membrane protein binds free fatty acids, acting as a nutrient sensor for regulating energy homeostasis. In some instances, GPR40 is expressed in enteroendocrine cells and pancreatic islet β cells. In some instances, GPR40 is expressed in enteroendocrine cells. Several naturally-occurring medium to long-chain fatty acids act as ligands for GPR40. GPR40 agonists or partial agonists may be useful in the treatment of metabolic diseases such as obesity, diabetes, and NASH, and other diseases involving the gut-brain axis.

In some instances, modulators of GPR40, for example, GPR40 agonists or partial agonists, induce insulin secretion. In some instances, modulators of GPR40, for example, GPR40 agonists or partial agonists, induce an increase in cytosolic $Ca^{2+}$. In some instances, modulators of GPR40, for example, GPR40 agonists or partial agonists, induce higher levels of intracellular cAMP. In some instances, GPR40 modulation is in enteroendocrine cells. In some instances, modulators of GPR40, for example, GPR40 agonists or partial agonists, induce the secretion of GLP-1, GLP-2, GIP, PYY, CCK, or other hormones. In some instances, modulators of GPR40, for example, GPR40 agonists, induce the secretion of GLP-1, GIP, CCK or PYY. In some instances, modulators of GPR40, for example, GPR40 agonists, induce the secretion of GLP-1.

Described herein is a method of treating a condition or disorder involving the gut-brain axis in an individual in need thereof, the method comprising administering to the individual a GPR40 receptor modulator. In some embodiments, the GPR40 receptor modulator is a GPR40 agonist or partial agonist. In some embodiments, the GPR40 receptor modulator is a GPR40 agonist. In some embodiments, the GPR40 receptor modulator is a GPR40 partial agonist. In some embodiments, the GPR40 receptor modulator is a GPR40 positive allosteric modulator. In some embodiments, the GPR40 modulator is a gut-restricted GPR40 modulator. In some embodiments, the GPR40 modulator is a soft drug.

In some embodiments, the condition or disorder involving the gut-brain axis is selected from the group consisting of: central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis, celiac disease, and enteritis, including chemotherapy-induced enteritis or radiation-induced enteritis; necrotizing enterocolitis; gastrointestinal injury resulting from toxic insults such as radiation or chemotherapy; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, other conditions involving the gut-brain axis. In some embodiments, the condition is a metabolic disorder. In some embodiments, the metabolic disorder is type 2 diabetes, hyperglycemia, metabolic syndrome, obesity, hypercholesterolemia, nonalcoholic steatohepatitis, or hypertension. In some embodiments, the metabolic disorder is diabetes. In other embodiments, the metabolic disorder is obesity. In other embodiments, the metabolic disorder is nonalcoholic steatohepatitis. In some embodiments, the condition involving the gut-brain axis is a nutritional disorder. In some embodiments, the nutritional disorder is short bowel syndrome, intestinal failure, or intestinal insufficiency. In some embodiments, the nutritional disorder is short bowel syndrome. In some embodiments, the condition involving the gut-brain axis is enteritis. In some embodiments, the condition involving the gut-brain axis is chemotherapy-induced enteritis or radiation-induced enteritis. In some embodiments, the condition involving the gut-brain axis is weight loss or preventing weight gain or weight regain. In some embodiments, the condition involving the gut-brain axis is weight loss or preventing weight gain or weight regain post-bariatric surgery. In some embodiments, the condition involving the gut-brain axis is weight loss or preventing weight gain or weight regain, wherein the subject has had bariatric surgery.

Gut-Restricted Modulators

In some instances, differentiation of systemic effects of a GPR40 agonist from beneficial, gut-driven effects would be critical for the development of a GPR40 agonist for the treatment of disease.

In some instances, activation of GPR40 by a GPR40 agonist recapitulates the lipotoxicity of free fatty acids on pancreatic beta-cells. In some instances, activation of GPR40 by a GPR40 agonist leads to beta-cell degeneration, islet insulin depletion, glucose intolerance and hyperglycemia In some instances, the detrimental effects on beta-cells by a GPR40 agonist may be mediated through ER stress and NF-kB signaling pathways. In some instances, differentiation of deleterious systemic effects of a GPR40 agonist on beta-cell function and viability from beneficial, gut-driven effects would be critical for the development of a GPR40 agonist for the treatment of disease.

In some embodiments, the GPR40 agonist is gut-restricted. In some embodiments, the GPR40 agonist is designed to be substantially non-permeable or substantially non-bioavailable in the blood stream. In some embodiments, the GPR40 agonist is designed to activate GPR40 activity in the gut and is substantially non-systemic. In some embodiments, the GPR40 agonist has low systemic exposure.

In some embodiments, a gut-restricted GPR40 agonist has low oral bioavailability. In some embodiments, a gut-restricted GPR40 agonist has <40% oral bioavailability, <30% oral bioavailability, <20% oral bioavailability, <10% oral bioavailability, <8% oral bioavailability, <5% oral bioavailability, <3% oral bioavailability, or <2% oral bioavailability.

In some embodiments, the unbound plasma levels of a gut-restricted GPR40 agonist are lower than the $EC_{50}$ value of the GPR40 agonist against GPR40. In some embodiments, the unbound plasma levels of a gut-restricted GPR40 agonist are significantly lower than the $EC_{50}$ value of the gut-restricted GPR40 agonist against GPR40. In some embodiments, the unbound plasma levels of the GPR40 agonist are 2-fold, 10-fold, 20-fold, 30-fold, 40-fold, 50-fold, or 100-fold lower than the $EC_{50}$ value of the gut-restricted GPR40 agonist against GPR40. In some embodiments, the unbound plasma levels of the GPR40 agonist are greater than 2-fold, greater than 10-fold, greater than 20-fold, greater than 30-fold, greater than 40-fold, greater than 50-fold, or greater than 100-fold lower than the $EC_{50}$ value of the gut-restricted GPR40 agonist against GPR40.

In some embodiments, a gut-restricted GPR40 agonist has low systemic exposure. In some embodiments, the systemic exposure of a gut-restricted GPR40 agonist is, for example, less than 500, less than 200, less than 100, less than 50, less than 20, less than 10, or less than 5 nM, bound or unbound, in blood serum. In some embodiments, the systemic exposure of a gut-restricted GPR40 agonist is, for example, less than 500, less than 200, less than 100, less than 50, less than 20, less than 10, or less than 5 ng/mL, bound or unbound, in blood serum.

In some embodiments, a gut-restricted GPR40 agonist has low pancreatic exposure. In some embodiments, the pancreatic exposure of a gut-restricted GPR40 agonist is, for example, less than 500, less than 200, less than 100, less than 50, less than 20, less than 10, or less than 5 nM in the pancreas. In some embodiments, the pancreatic exposure of a gut-restricted GPR40 agonist is, for example, less than 500, less than 200, less than 100, less than 50, less than 20, less than 10, or less than 5 ng/mL in the pancreas.

In some embodiments, a gut-restricted GPR40 agonist has low permeability. In some embodiments, a gut-restricted GPR40 agonist has low intestinal permeability. In some embodiments, the permeability of a gut-restricted GPR40 agonist is, for example, less than $5.0 \times 10^{-6}$ cm/s, less than $2.0 \times 10^{-6}$ cm/s, less than $1.5 \times 10^{-6}$ cm/s, less than $1.0 \times 10^{-6}$ cm/s, less than $0.75 \times 10^{-6}$ cm/s, less than $0.50 \times 10^{-6}$ cm/s, less than $0.25 \times 10^{-6}$ cm/s, less than $0.10 \times 10^{-6}$ cm/s, or less than $0.05 \times 10^{-6}$ cm/s.

In some embodiments, a gut-restricted GPR40 agonist has low absorption. In some embodiments, the absorption of a gut-restricted GPR40 agonist is less than less than 40%, less than 30%, less than 20%, or less than 10%, less than 5%, or less than 1%.

In some embodiments, a gut-restricted GPR40 agonist has high plasma clearance. In some embodiments, a gut-restricted GPR40 agonist is undetectable in plasma in less than 8 hours, less than 6 hours, less than 4 hours, less than 3 hours, less than 120 min, less than 90 min, less than 60 min, less than 45 min, less than 30 min, or less than 15 min.

In some embodiments, a gut-restricted GPR40 agonist is rapidly metabolized upon administration. In some embodiments, the internal ester of the compounds described herein is rapidly cleaved upon administration. In some embodiments, a gut-restricted GPR40 agonist has a short half-life. In some embodiments, the half-life of a gut-restricted GPR40 agonist is less than less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted GPR40 agonist have rapid clearance. In some embodiments, the metabolites of a gut-restricted GPR40 agonist are undetectable in less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted GPR40 agonist have low bioactivity. In some embodiments, the $EC_{50}$ value of the metabolites of a gut-restricted GPR40 agonist is 10-fold, 20-fold, 30-fold, 40-fold, 50-fold, 100-fold, 500-fold, or 1000-fold higher than the $EC_{50}$ value of the gut-restricted GPR40 agonist against GPR40. In some embodiments, the metabolites of a gut-restricted GPR40 agonist have rapid clearance and low bioactivity.

In some embodiments of the methods described herein, the GPR40 modulator is gut-restricted. In some embodiments, the GPR40 modulator is a gut-restricted GPR40 agonist. In some embodiments, the GPR40 agonist is a gut-restricted GPR40 full agonist. In some embodiments, the GPR40 agonist is a gut-restricted GPR40 partial agonist. In some embodiments, the GPR40 agonist is covalently bonded to a kinetophore. In some embodiments, the GPR40 agonist is covalently bonded to a kinetophore through a linker.

Compounds

Disclosed herein, in certain embodiments, is a compound of Formula (I):

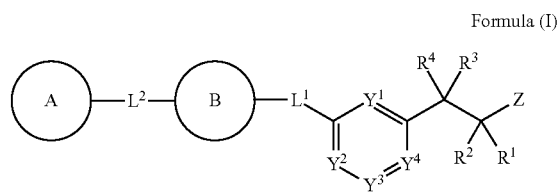

Formula (I)

or a pharmaceutically acceptable salt, solvate, stereoisomer, or prodrug thereof, wherein:

Z is —P(=O)(H)OR$^6$, —P(=O)(R$^5$)OR$^6$, —P(=O)(OR$^6$)$_2$, —S(=O)(OR$^6$), —SO$_2$OR$^6$, —C(=O)NHSO$_2$R$^3$, —C(=O)NHSO$_2$N(R$^6$)$_2$, —N(R$^6$)SO$_2$N(R$^6$)$_2$, —N(R$^6$)C(=O)NHSO$_2$(R$^6$), —N(R$^6$)C(=O)NHSO$_2$N(R$^6$)$_2$, —N(R$^6$)C(=NH)NH$_2$, —C(=O)NHNHC(=O)N(R$^6$)$_2$, or —B(OR$^6$)$_2$;

R$^5$ is C$_1$-C$_6$ alkyl, C$_3$-C$_6$ cycloalkyl, phenyl, or —(C$_1$-C$_6$ alkyl)-phenyl; wherein each alkyl, cycloalkyl, and phenyl is independently unsubstituted or substituted with 1, 2, or 3 substituents selected from the group consisting of halogen, —CN, —OH, —O—(C$_1$-C$_6$ alkyl), C$_1$-C$_6$ alkyl, C$_1$-C$_6$ fluoroalkyl, C$_1$-C$_6$ hydroxyalkyl, —O—(C$_1$-C$_6$ fluoroalkyl), C$_3$-C$_6$ cycloalkyl, and 3- to 6-membered heterocycloalkyl;

each R$^6$ is independently hydrogen, C$_1$-C$_6$ alkyl, C$_3$-C$_6$ cycloalkyl, phenyl, or —(C$_1$-C$_6$ alkyl)-phenyl; wherein each alkyl, cycloalkyl, and phenyl is independently unsubstituted or substituted with 1, 2, or 3 substituents selected from the group consisting of halogen, —CN, —OH, —O—(C$_1$-C$_6$ alkyl), C$_1$-C$_6$ alkyl, C$_1$-C$_6$ fluoroalkyl, C$_1$-C$_6$ hydroxyalkyl, —O—(C$_1$-C$_6$ fluoroalkyl), C$_3$-C$_6$ cycloalkyl, and 3- to 6-membered heterocycloalkyl;

R$^1$, R$^2$, and R$^3$ are each independently hydrogen, halogen, —OH, —O—(C$_1$-C$_6$ alkyl), C$_1$-C$_6$ alkyl, C$_3$-C$_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, —CN, —OH, —O—(C$_1$-C$_6$ alkyl), and C$_1$-C$_6$ alkyl;

R$^4$ is C$_1$-C$_6$ alkyl, C$_3$-C$_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, —CN, —OH, —O—(C$_1$-C$_6$ alkyl), and C$_1$-C$_6$ alkyl;

Y$^1$, Y$^2$, Y$^3$, and Y$^4$ are each independently N, CH, or C—R$^Y$;

each R$^Y$ is independently halogen, —CN, —OH, —O(C$_1$-C$_6$ alkyl), —NH$_2$, —NH—(C$_1$-C$_6$ alkyl), —N(C$_1$-C$_6$ alkyl)$_2$, C$_1$-C$_6$ alkyl, C$_3$-C$_6$ cycloalkyl, or 3- to 6-membered heterocycloalkyl; wherein each alkyl, cycloalkyl, and heterocycloalkyl is independently unsubstituted or substituted with 1, 2, or 3 substituents selected from the group consisting of halogen, —CN, —OH, —O—($C_1$-$C_6$ alkyl), and $C_1$-$C_6$ alkyl;

$L^1$ is —O—, —$NR^7$—, *—O—$CH_2$—, *—$CH_2$—O—, *—$NR^7$—$CH_2$—, *—$CH_2$—$NR^7$—, *—$NR^7$—C(O)—, *—C(O)—$NR^7$—, or *—C(O)—$CH_2$—; wherein * represents the connection to Ring B;

$R^7$ is hydrogen, $C_1$-$C_6$ alkyl, or $C_3$-$C_6$ cycloalkyl;

Ring B is cycloalkylene or heterocycloalkylene; wherein the cycloalkylene or heterocycloalkylene is unsubstituted or substituted with 1, 2, 3, or 4 $R^B$ substituents;

Ring A is carbocycle or heterocycle; wherein the carbocycle or heterocycle is unsubstituted or substituted with 1, 2, 3, 4, or 5 $R^A$ substituents;

$L^2$ is a bond, $C_1$-$C_6$ alkylene, or —($C_1$-$C_6$ alkylene)-O—; wherein the alkylene is unsubstituted or substituted with 1, 2, or 3 substituents selected from the group consisting of halogen, —CN, —OH, $C_1$-$C_6$ alkyl, and —O—($C_1$-$C_6$ alkyl);

each $R^A$ is independently halogen, $C_1$-$C_{10}$ alkyl, $C_2$-$C_{10}$ alkenyl, $C_2$-$C_{10}$ alkynyl, $C_1$-$C_{10}$ fluoroalkyl, -$L^A$-CN, -$L^A$-OK-$L^A$-$OR^{10}$, -$L^A$-$NR^{11}R^{11}$, -$L^A$-C(=O)$R^{10}$, -$L^A$-C(=O)$OR^{11}$, -$L^A$-OC(=O)$R^{11}$, -$L^A$-C(=O)$NR^{11}R^{11}$, -$L^A$-$NR^{11}$C(=O)$R^{11}$, -$L^A$-$NR^{11}$C(=O)$NR^{11}R^{11}$, -$L^A$-OC(=O)$NR^{11}R^{11}$, -$L^A$-$NR^{11}$C(=O)$OR^{11}$, -$L^A$-OC(=O)$OR^{10}$, -$L^A$-aryl, -$L^A$-heteroaryl, -$L^A$-($C_3$-$C_{10}$ cycloalkyl), or -$L^A$-(3- to 10-membered heterocycloalkyl); wherein each alkyl, alkenyl, alkynyl, fluoroalkyl, aryl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

each $R^B$ is independently halogen, $C_1$-$C_{10}$ alkyl, $C_2$-$C_{10}$ alkenyl, $C_2$-$C_{10}$ alkynyl, $C_1$-$C_{10}$ fluoroalkyl, -$L^B$-CN, -$L^B$-OH, -$L^B$-$OR^{10}$, -$L^B$-$NR^{11}R^{11}$, -$L^B$-C(=O)$R^{10}$, -$L^B$-C(=O)$OR^{11}$, -$L^B$-OC(=O)$R^{11}$, -$L^B$-C(=O)$NR^{11}R^{11}$, -$L^B$-$NR^{11}$C(=O)$R^{11}$, -$L^B$-$NR^{11}$C(=O)$NR^{11}R^{11}$, -$L^B$-OC(=O)$NR^{11}R^{11}$, -$L^B$-$NR^{11}$C(=O)$OR^{11}$, -$L^B$-OC(=O)$OR^{10}$, -$L^B$-aryl, -$L^B$-heteroaryl, -$L^B$-($C_3$-$C_{10}$ cycloalkyl), or -$L^B$-(3- to 10-membered heterocycloalkyl); wherein each alkyl, alkenyl, alkynyl, fluoroalkyl, aryl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

each $L^A$ and $L^B$ is independently a bond or $C_1$-$C_6$ alkylene; wherein the alkylene is unsubstituted or substituted with 1, 2, or 3 substituents selected from the group consisting of halogen, —CN, —OH, —O—($C_1$-$C_6$ alkyl), and $C_1$-$C_6$ alkyl;

each $R^{10}$ is independently $C_1$-$C_{10}$ alkyl, $C_2$-$C_{10}$ alkenyl, $C_2$-$C_{10}$ alkynyl, $C_3$-$C_{10}$ cycloalkyl, 3- to 10-membered heterocycloalkyl, phenyl, or monocyclic heteroaryl; wherein each alkyl, alkenyl, alkynyl, phenyl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl); and each $R^{11}$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, 3- to 10-membered heterocycloalkyl, phenyl, or monocyclic heteroaryl; wherein each alkyl, alkenyl, alkynyl, phenyl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

or two $R^{11}$ on the same nitrogen atom are taken together with the nitrogen to which they are attached to form a 3- to 10-membered N-heterocycloalkyl; wherein the heterocycloalkyl is unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl).

In some embodiments of a compound of Formula (I), or a pharmaceutically acceptable salt, solvate, stereoisomer, or prodrug thereof, $Y^1$, $Y^2$, $Y^3$, and $Y^4$ are each independently N, CH, or C—$R^Y$; wherein one or two of $Y^1$, $Y^2$, $Y^3$, and $Y^4$ is N. In some embodiments, one of $Y^1$, $Y^2$, $Y^3$, and $Y^4$ is N. In some embodiments, $Y^1$ is N, and $Y^2$, $Y^3$, and $Y^4$ are each independently CH, or C—$R^Y$. In some embodiments, $Y^2$ is N, and $Y^1$, $Y^3$, and $Y^4$ are each independently CH, or C—$R^Y$. In some embodiments, $Y^3$ is N, and $Y^1$, $Y^2$, and $Y^4$ are each independently CH, or C—$R^Y$. In some embodiments, $Y^4$ is N, and $Y^1$, $Y^2$, and $Y^3$ are each independently CH, or C—$R^Y$.

In some embodiments of a compound of Formula (I), or a pharmaceutically acceptable salt, solvate, stereoisomer, or prodrug thereof, $Y^1$, $Y^2$, $Y^3$, and $Y^4$ are each independently CH, or C—$R^Y$.

In some embodiments of a compound of Formula (I), or a pharmaceutically acceptable salt, solvate, stereoisomer, or prodrug thereof, each $R^Y$ is independently F, Cl, Br, —CN, —OH, —O—($C_1$-$C_6$ alkyl), $C_1$-$C_6$ alkyl. In some embodiments, each $R^Y$ is independently F, Cl, Br, —CN, —OH, —$OCH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In some embodiments, each $R^Y$ is F.

In some embodiments of a compound of Formula (I), or a pharmaceutically acceptable salt, solvate, stereoisomer, or prodrug thereof, $Y^1$, $Y^2$, $Y^3$, and $Y^4$ are each independently N, CH, or C—$R^Y$; and each $R^Y$ is independently F, Cl, Br, —CN, —OH, —O—($C_1$-$C_6$ alkyl), $C_1$-$C_6$ alkyl. In some embodiments, $Y^1$, $Y^2$, $Y^3$, and $Y^4$ are each independently N or CH.

In some embodiments of a compound of Formula (I), or a pharmaceutically acceptable salt, solvate, stereoisomer, or prodrug thereof, $Y^1$, $Y^2$, $Y^3$, and $Y^4$ are each independently N, CH, or CF. In some embodiments, $Y^1$, $Y^2$, $Y^3$, and $Y^4$ are each independently N or CH. In some embodiments, $Y^1$ is N, and $Y^2$, $Y^3$, and $Y^4$ are each independently CH. In some embodiments, $Y^2$ is N, and $Y^1$, $Y^3$, and $Y^4$ are each independently CH. In some embodiments, $Y^3$ is N, and $Y^1$, $Y^2$, and $Y^4$ are each independently CH. In some embodiments, $Y^1$, $Y^2$, $Y^3$, and $Y^4$ are each CH.

In some embodiments, the compound of Formula (I), or a pharmaceutically acceptable salt, solvate, stereoisomer, or prodrug thereof, is a compound of Formula 2:

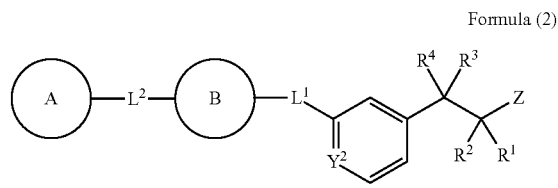

Formula (2)

or a pharmaceutically acceptable salt, solvate, stereoisomer, or prodrug thereof. In some embodiments, $Y^2$ is CH or N. In some embodiments, $Y^2$ is N. In some embodiments, $Y^2$ is CH.

In some embodiments, the compound of Formula (I), or a pharmaceutically acceptable salt, solvate, stereoisomer, or prodrug thereof, is a compound of Formula (II):

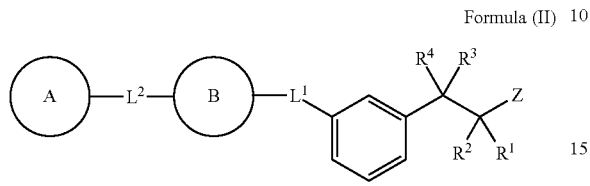

Formula (II)

or a pharmaceutically acceptable salt, solvate, stereoisomer, or prodrug thereof.

In some embodiments of a compound of Formula (I) or (II), or a pharmaceutically acceptable salt, solvate, stereoisomer, or prodrug thereof, $R^1$, $R^2$, and $R^3$ are each independently hydrogen, halogen, or $C_1$-$C_6$ alkyl. In some embodiments, $R^1$, $R^2$, and $R^3$ are each independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In some embodiments, $R^1$, $R^2$, and $R^3$ are each independently hydrogen, —F, —Cl, or $C_1$-$C_4$ alkyl. In some embodiments, $R^1$, $R^2$, and $R^3$ are each independently hydrogen, F, or —$CH_3$.

In some embodiments of a compound of Formula (I) or (II), or a pharmaceutically acceptable salt, solvate, stereoisomer, or prodrug thereof, $R^4$ is $C_1$-$C_6$ alkyl or $C_3$-$C_6$ cycloalkyl. In some embodiments, $R^4$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, cyclopropyl, cyclobutyl, cyclopentyl, or cyclohexyl. In some embodiments, $R^4$ is —$CH_3$, —$CH_2CH_3$, cyclopropyl, or cyclobutyl. In some embodiments, $R^4$ is —$CH_2CH_3$. In some embodiments, $R^4$ is cyclopropyl.

In some embodiments of a compound of Formula (I) or (II), or a pharmaceutically acceptable salt, solvate, stereoisomer, or prodrug thereof, $R^1$, $R^2$, and $R^3$ are each independently hydrogen, halogen, or $C_1$-$C_6$ alkyl; and $R^4$ is $C_1$-$C_6$ alkyl or $C_3$-$C_6$ cycloalkyl. In some embodiments, $R^1$, $R^2$, and $R^3$ are each independently hydrogen, halogen, or $C_1$-$C_4$ alkyl; and $R^4$ is unsubstituted $C_3$-$C_6$ cycloalkyl.

In some embodiments, the compound of Formula (I) or (2), or a pharmaceutically acceptable salt, solvate, stereoisomer, or prodrug thereof, is a compound of Formula (3):

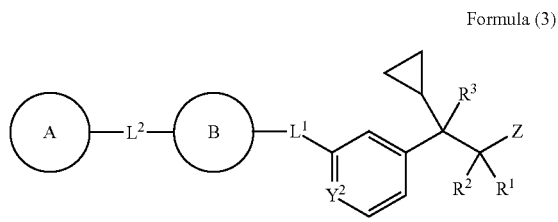

Formula (3)

or a pharmaceutically acceptable salt, solvate, stereoisomer, or prodrug thereof, wherein $Y^2$ is CH or N; and $R^1$, $R^2$, and $R^3$ are each independently hydrogen, —F, —Cl, or $C_1$-$C_4$ alkyl. In some embodiments, $Y^2$ is N. In some embodiments, $Y^2$ is CH.

In some embodiments, the compound of Formula (I) or (II), or a pharmaceutically acceptable salt, solvate, stereoisomer, or prodrug thereof, is a compound of Formula (III):

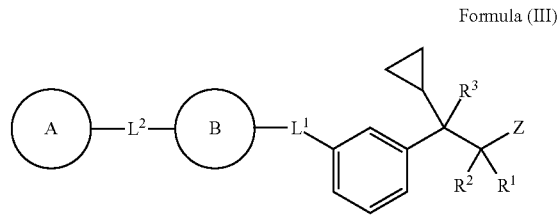

Formula (III)

or a pharmaceutically acceptable salt, solvate, stereoisomer, or prodrug thereof, wherein $R^1$, $R^2$, and $R^3$ are each independently hydrogen, —F, —Cl, or $C_1$-$C_4$ alkyl.

In some embodiments of a compound of Formula (I), (II), or (III), or a pharmaceutically acceptable salt, solvate, stereoisomer, or prodrug thereof, $R^1$, $R^2$, and $R^3$ are each independently hydrogen, —F, or methyl. In some embodiments, $R^3$ is hydrogen; and $R^1$ and $R^2$ are each independently hydrogen, —F, or methyl.

In some embodiments, the compound of Formula (I), (2), or (3), or a pharmaceutically acceptable salt, solvate, stereoisomer, or prodrug thereof, is a compound of Formula (4):

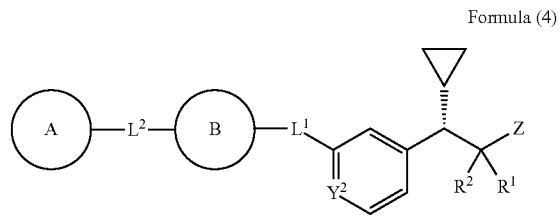

Formula (4)

or a pharmaceutically acceptable salt, solvate, stereoisomer, or prodrug thereof, wherein $Y^2$ is CH or N; and $R^1$ and $R^2$ are each independently hydrogen, —F, or methyl. In some embodiments, $Y^2$ is N. In some embodiments, $Y^2$ is CH.

In some embodiments, the compound of Formula (I), (II), or (III), or a pharmaceutically acceptable salt, solvate, stereoisomer, or prodrug thereof, is a compound of Formula (IV):

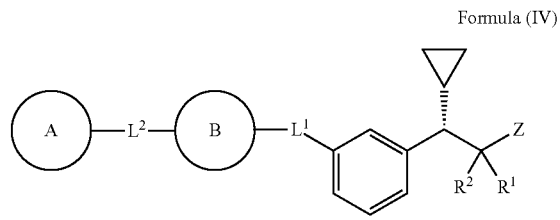

Formula (IV)

or a pharmaceutically acceptable salt, solvate, stereoisomer, or prodrug thereof, wherein $R^1$ and $R^2$ are each independently hydrogen, —F, or methyl.

In some embodiments of a compound of Formula (I), (II), (III), or (IV), or a pharmaceutically acceptable salt, solvate, stereoisomer, or prodrug thereof, $L^1$ is *—O—$CH_2$—, *—$CH_2$—O—, *—NR7-$CH_2$—, *—$NR^7$—C(O)—, *—C(O)—$NR^7$—, or *—C(O)—$CH_2$—; wherein * represents the connection to Ring B. In some embodiments, L¹ is *—NR⁷—CH₂—; wherein * represents the connection to Ring B. In some embodiments, L¹ is *—NR⁷—C(O)— or *—C(O)—NR⁷—; wherein * represents the connection to Ring B. In some embodiments, L¹ is *—C(O)—CH₂—; wherein * represents the connection to Ring B. In some embodiments, L¹ is *—O—CH₂— or *—CH₂—O—; wherein * represents the connection to Ring B. In some embodiments, L¹ is *—O—CH₂—; wherein * represents the connection to Ring B. In some embodiments, L¹ is *—CH₂—O—; wherein * represents the connection to Ring B. In some embodiments, R⁷ is hydrogen or $C_1$-$C_6$ alkyl. In some embodiments, R⁷ is hydrogen, —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, or —C(CH₃)₃. In some embodiments, R⁷ is hydrogen or methyl. In some embodiments, R⁷ is hydrogen.

In some embodiments, the compound of Formula (I), (II), (III), or (IV), or a pharmaceutically acceptable salt, solvate, stereoisomer, or prodrug thereof, is a compound of Formula (IVa) or Formula (IVb):

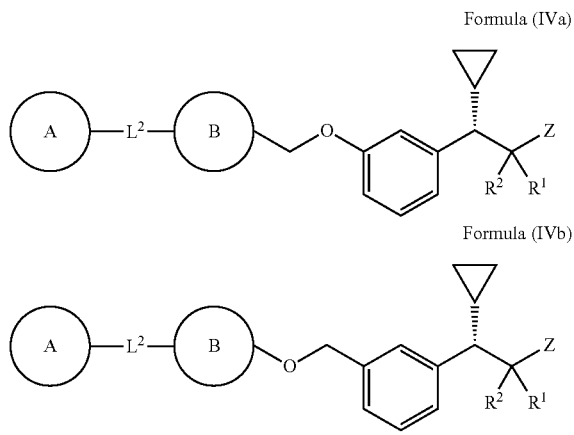

Formula (IVa)

Formula (IVb)

or a pharmaceutically acceptable salt, solvate, stereoisomer, or prodrug thereof.

In some embodiments, the compound of Formula (I), (II), (III), or (IV), or a pharmaceutically acceptable salt, solvate, stereoisomer, or prodrug thereof, is a compound of Formula (IVa), or a pharmaceutically acceptable salt, solvate, stereoisomer, or prodrug thereof. In some embodiments, the compound is a compound of Formula (IVb), or a pharmaceutically acceptable salt, solvate, stereoisomer, or prodrug thereof.

In some embodiments of a compound of Formula (I), (II), (III), (IV), (IVa), or (IVb), or a pharmaceutically acceptable salt, solvate, stereoisomer, or prodrug thereof, Ring B is $C_3$-$C_{10}$ cycloalkylene or 3- to 10-membered heterocycloalkylene. In some embodiments, Ring B is $C_3$-$C_{10}$ cycloalkylene or 3- to 10-membered heterocycloalkylene; wherein the cycloalkylene or heterocycloalkylene is unsubstituted or substituted with 1, 2, 3, or 4 $R^B$ substituents.

In some embodiments of a compound of Formula (I), (II), (III), (IV), (IVa), or (IVb), or a pharmaceutically acceptable salt, solvate, stereoisomer, or prodrug thereof, Ring B is bicyclic carbocycle or bicyclic heterocycle. In some embodiments of a compound of Formula (I), (II), (III), (IV), (IVa), or (b), or a pharmaceutically acceptable salt, solvate, stereoisomer, or prodrug thereof, Ring B is bicyclic carbocycle or bicyclic heterocycle; wherein the carbocycle or heterocycle is unsubstituted or substituted with 1, 2, 3, or 4 $R^B$ substituents. In some embodiments of a compound of Formula (I), (II), (III), (IV), (IVa), or (IVb), or a pharmaceutically acceptable salt, solvate, stereoisomer, or prodrug thereof, Ring B is bicyclic heterocycle; wherein the bicyclic heterocycle is unsubstituted or substituted with 1, 2, 3, or 4 $R^B$ substituents. In some embodiments of a compound of Formula (I), (II), (III), (IV), (IVa), or (IVb), or a pharmaceutically acceptable salt, solvate, stereoisomer, or prodrug thereof, Ring B is bicyclic carbocycle; wherein the bicyclic carbocycle is unsubstituted or substituted with 1, 2, 3, or 4 $R^B$ substituents.

In some embodiments of a compound of Formula (I), (II), (III), (IV), (IVa), or (IVb), or a pharmaceutically acceptable salt, solvate, stereoisomer, or prodrug thereof, Ring A is aryl, heteroaryl, $C_3$-$C_{10}$ cycloalkyl, or 3- to 10-membered heterocycloalkyl. In some embodiments, Ring A is aryl, heteroaryl, $C_3$-$C_{10}$ cycloalkyl, or 3- to 10-membered heterocycloalkyl; wherein the aryl, heteroaryl, cycloalkyl, or heterocycloalkyl is unsubstituted or substituted with 1, 2, 3, 4, or 5 $R^A$ substituents.

In some embodiments of a compound of Formula (I), (II), (III), (IV), (IVa), or (IVb), or a pharmaceutically acceptable salt, solvate, stereoisomer, or prodrug thereof, Ring B is $C_3$-$C_{10}$ cycloalkylene, or 3- to 10-membered heterocycloalkylene; wherein the cycloalkylene or heterocycloalkylene is unsubstituted or substituted with 1, 2, 3, or 4 $R^B$ substituents; and Ring A is aryl, heteroaryl, $C_3$-$C_{10}$ cycloalkyl, or 3- to 10-membered heterocycloalkyl; wherein the aryl, heteroaryl, cycloalkyl, or heterocycloalkyl is unsubstituted or substituted with 1, 2, 3, 4, or 5 $R^A$ substituents.

In some embodiments of a compound of Formula (I), (II), (III), (IV), (IVa), or (IVb), or a pharmaceutically acceptable salt, solvate, stereoisomer, or prodrug thereof, Ring B is 3- to 6-membered heterocycloalkylene; wherein the heterocycloalkylene is unsubstituted or substituted with 1, 2, 3, or 4 $R^B$ substituents. In some embodiments, Ring B is 3- to 6-membered heterocycloalkylene; wherein the heterocycloalkylene is unsubstituted or substituted with 1, 2, 3, or 4 $R^B$ substituents; each $R^B$ is independently halogen, $C_1$-$C_6$ alkyl, or $C_1$-$C_6$ fluoroalkyl. In some embodiments, Ring B is azetidinylene, pyrrolidinylene, or piperidinylene; wherein the heterocycloalkylene is unsubstituted or substituted with 1, 2, 3, or 4 $R^B$ substituents; each $R^B$ is independently halogen, $C_1$-$C_6$ alkyl, or $C_1$-$C_6$ fluoroalkyl. In some embodiments, Ring B is unsubstituted 3- to 6-membered heterocycloalkylene. In some embodiments, Ring B is unsubstituted piperidinylene. In some embodiments, Ring B is unsubstituted pyrrolidinylene. In some embodiments, Ring B is unsubstituted azetidinylene.

In some embodiments of a compound of Formula (I), (II), (III), (IV), (IVa), or (IVb), or a pharmaceutically acceptable salt, solvate, stereoisomer, or prodrug thereof, Ring B is $C_3$-$C_6$ cycloalkylene; wherein the cycloalkylene is unsubstituted or substituted with 1, 2, 3, or 4 $R^B$ substituents. In some embodiments, Ring B is $C_3$-$C_6$ cycloalkylene; wherein the cycloalkylene is unsubstituted or substituted with 1, 2, 3, or 4 $R^B$ substituents; each $R^B$ is independently halogen, $C_1$-$C_6$ alkyl, or $C_1$-$C_6$ fluoroalkyl. In some embodiments, Ring B is unsubstituted $C_3$-$C_6$ cycloalkylene. In some embodiments, Ring B is cyclohexylene; wherein the cyclohexylene is unsubstituted or substituted with 1, 2, 3, or 4 $R^B$ substituents; each $R^B$ is independently halogen, $C_1$-$C_6$ alkyl, or $C_1$-$C_6$ fluoroalkyl. In some embodiments, Ring B is unsubstituted cyclohexylene.

In some embodiments of a compound of Formula (I), (II), (III), (IV), (IVa), or (IVb), or a pharmaceutically acceptable salt, solvate, stereoisomer, or prodrug thereof, each $R^B$ is independently halogen, $C_1$-$C_6$ alkyl, or $C_1$-$C_6$ fluoroalkyl. In some embodiments, each $R^B$ is independently F, Cl, Br, —$CF_3$, —$CHF_2$, —$CH_2F$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$.

In some embodiments of a compound of Formula (I), (II), (III), (IV), (IVa), or (IVb), or a pharmaceutically acceptable salt, solvate, stereoisomer, or prodrug thereof, Ring A is aryl or heteroaryl; wherein the aryl or heteroaryl is unsubstituted or substituted with 1, 2, or 3 $R^A$ substituents.

In some embodiments of a compound of Formula (I), (II), (III), (IV), (IVa), or (IVb), or a pharmaceutically acceptable salt, solvate, stereoisomer, or prodrug thereof, $L^2$ is a bond or $C_1$-$C_6$ alkylene. In some embodiments, $L^2$ is a bond or $C_1$-$C_6$ alkylene; wherein the alkylene is unsubstituted or substituted with 1, 2, or 3 substituents selected from the group consisting of —OH, $C_1$-$C_6$ alkyl, and —O—($C_1$-$C_6$ alkyl).

In some embodiments of a compound of Formula (I), (II), (III), (IV), (IVa), or (IVb), or a pharmaceutically acceptable salt, solvate, stereoisomer, or prodrug thereof, Ring B is 3- to 6-membered heterocycloalkylene; wherein the heterocycloalkylene is unsubstituted or substituted with 1, 2, 3, or 4 $R^B$ substituents; each $R^B$ is independently halogen, $C_1$-$C_6$ alkyl, or $C_1$-$C_6$ fluoroalkyl; $L^2$ is a bond or $C_1$-$C_6$ alkylene; wherein the alkylene is unsubstituted or substituted with 1, 2, or 3 substituents selected from the group consisting of —OH, $C_1$-$C_6$ alkyl, and —O—($C_1$-$C_6$ alkyl); and Ring A is aryl or heteroaryl; wherein the aryl or heteroaryl is unsubstituted or substituted with 1, 2, or 3 $R^A$ substituents.

In some embodiments, the compound of Formula (I), (2), (3), or (4), or a pharmaceutically acceptable salt, solvate, stereoisomer, or prodrug thereof, is a compound of Formula (5):

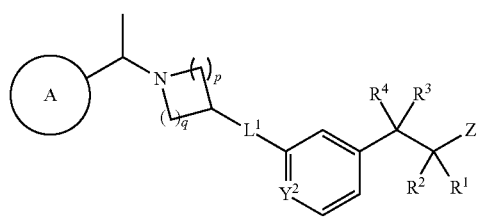

Formula (5)

or a pharmaceutically acceptable salt, solvate, stereoisomer, or prodrug thereof; wherein $Y^2$ is CH or N; and p and q are each independently 1 or 2. In some embodiments, $Y^2$ is N. In some embodiments, $Y^2$ is CH. In some embodiments, p is 1 and q is 1. In some embodiments, p is 1 and q is 2. In some embodiments, p is 2 and q is 2.

In some embodiments, the compound of Formula (I), (II), (III), or (IV), or a pharmaceutically acceptable salt, solvate, stereoisomer, or prodrug thereof, is a compound of Formula (V):

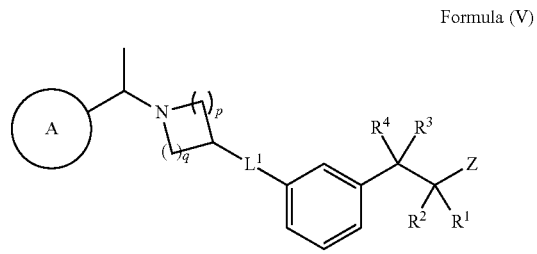

Formula (V)

or a pharmaceutically acceptable salt, solvate, stereoisomer, or prodrug thereof; wherein p and q are each independently 1 or 2. In some embodiments, p is 1 and q is 1. In some embodiments, p is 1 and q is 2. In some embodiments, p is 2 and q is 2.

In some embodiments of a compound of Formula (V), or a pharmaceutically acceptable salt, solvate, stereoisomer, or prodrug thereof, is a compound of Formula (V-i):

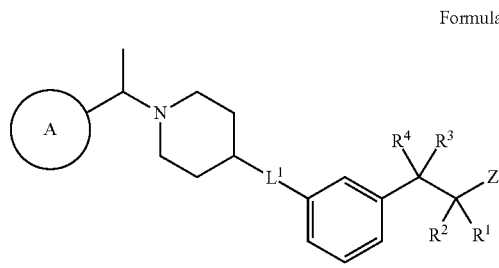

Formula (V-i)

or a pharmaceutically acceptable salt, solvate, stereoisomer, or prodrug thereof.

In some embodiments of a compound of Formula (V), or a pharmaceutically acceptable salt, solvate, stereoisomer, or prodrug thereof, is a compound of Formula (V-ii):

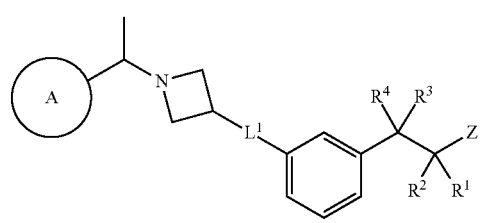

Formula (V-ii)

or a pharmaceutically acceptable salt, solvate, stereoisomer, or prodrug thereof.

In some embodiments of a compound of Formula (V), or a pharmaceutically acceptable salt, solvate, stereoisomer, or prodrug thereof, $L^1$ is *—O—$CH_2$—, *—$CH_2$—O—, *—$NR^7$—$CH_2$—, *—$NR^7$—C(O)—, *—C(O)—$NR^7$—, or *—C(O)$H_2$—; wherein * represents the connection to Ring B. In some embodiments, $L^1$ is *—$NR^7$—$CH_2$—; wherein * represents the connection to Ring B. In some embodiments, $L^1$ is *—NR—C(O)— or *—C(O)—$NR^7$—; wherein * represents the connection to Ring B. In some embodiments, $L^1$ is *—C(O)—$CH_2$—; wherein * represents the connection to Ring B. In some embodiments, $L^1$ is *—O—$CH_2$— or *—$CH_2$—O—; wherein * represents the connection to Ring B. In some embodiments, $L^1$ is *—O—$CH_2$—; wherein * represents the connection to Ring B. In some embodiments, $L^1$ is *—$CH_2$—O—; wherein * represents the connection to Ring B. In some embodiments, $R^7$ is hydrogen or $C_1$-$C_6$ alkyl. In some embodiments, $R^7$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, or —$C(CH_3)_3$. In some embodiments, $R^7$ is hydrogen or methyl. In some embodiments, $R^7$ is hydrogen.

In some embodiments, the compound of Formula (I), (II), (III), (IV), or (V), or a pharmaceutically acceptable salt, solvate, stereoisomer, or prodrug thereof, is a compound of Formula (Va) or Formula (Vb):

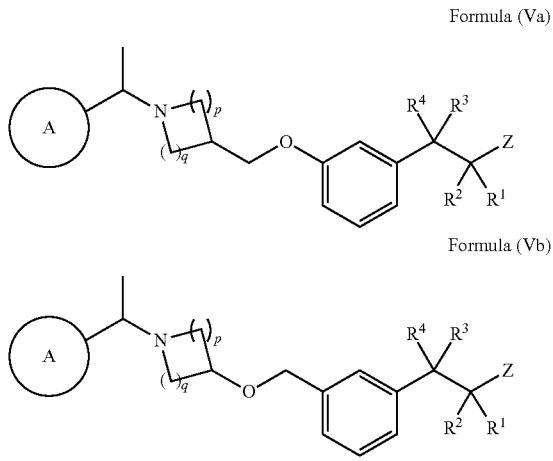

Formula (Va)

Formula (Vb)

or a pharmaceutically acceptable salt, solvate, stereoisomer, or prodrug thereof. In some embodiments, p and q are each independently 1 or 2. In some embodiments, p is 1 and q is 1. In some embodiments, p is 1 and q is 2. In some embodiments, p is 2 and q is 2.

In some embodiments, the compound of Formula (I), (II), (III), (IV), or (V), or a pharmaceutically acceptable salt, solvate, stereoisomer, or prodrug thereof, is a compound of Formula (Va), or a pharmaceutically acceptable salt, solvate, stereoisomer, or prodrug thereof. In some embodiments, the compound is a compound of Formula (Vb), or a pharmaceutically acceptable salt, solvate, stereoisomer, or prodrug thereof.

In some embodiments of a compound of Formula (Va), or a pharmaceutically acceptable salt, solvate, stereoisomer, or prodrug thereof, is a compound of Formula (Va-i):

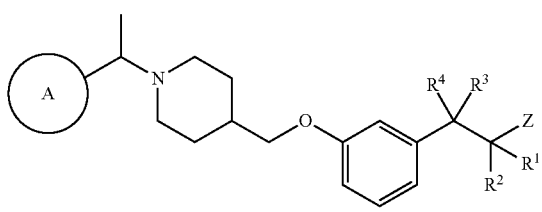

Formula (Va-i)

or a pharmaceutically acceptable salt, solvate, stereoisomer, or prodrug thereof.

In some embodiments of a compound of Formula (Vb), or a pharmaceutically acceptable salt, solvate, stereoisomer, or prodrug thereof, is a compound of Formula (Vb-i):

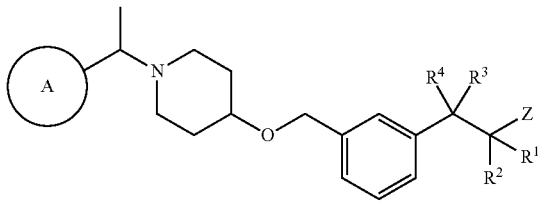

Formula (Vb-i)

or a pharmaceutically acceptable salt, solvate, stereoisomer, or prodrug thereof.

In some embodiments of a compound of Formula (Va), or a pharmaceutically acceptable salt, solvate, stereoisomer, or prodrug thereof, is a compound of Formula (Va-ii):

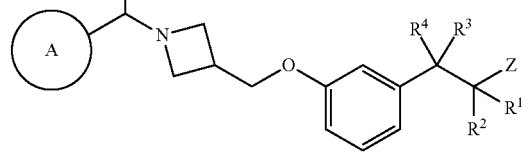

Formula (Va-ii)

or a pharmaceutically acceptable salt, solvate, stereoisomer, or prodrug thereof.

In some embodiments of a compound of Formula (Vb), or a pharmaceutically acceptable salt, solvate, stereoisomer, or prodrug thereof, is a compound of Formula (Vb-ii):

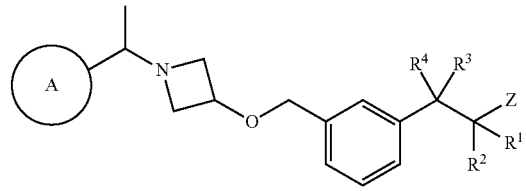

Formula (Vb-ii)

or a pharmaceutically acceptable salt, solvate, stereoisomer, or prodrug thereof.

In some embodiments, the compound of Formula (I), (2), (3), or (4), or a pharmaceutically acceptable salt, solvate, stereoisomer, or prodrug thereof, is a compound of Formula (6):

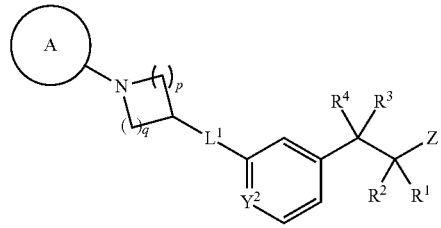

Formula (6)

or a pharmaceutically acceptable salt, solvate, stereoisomer, or prodrug thereof; wherein $Y^2$ is CH or N; and p and q are each independently 1 or 2. In some embodiments, $Y^2$ is N. In some embodiments, $Y^2$ is CH. In some embodiments, p is 1 and q is 1. In some embodiments, p is 1 and q is 2. In some embodiments, p is 2 and q is 2.

In some embodiments, the compound of Formula (I), (II), (III), or (IV), or a pharmaceutically acceptable salt, solvate, stereoisomer, or prodrug thereof, is a compound of Formula (VI):

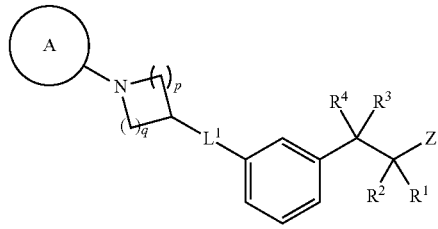

Formula (VI)

or a pharmaceutically acceptable salt, solvate, stereoisomer, or prodrug thereof; wherein p and q are each independently 1 or 2. In some embodiments, p is 1 and q is 1. In some embodiments, p is 1 and q is 2. In some embodiments, p is 2 and q is 2.

In some embodiments of a compound of Formula (VI), or a pharmaceutically acceptable salt, solvate, stereoisomer, or prodrug thereof, is a compound of Formula (VI-i):

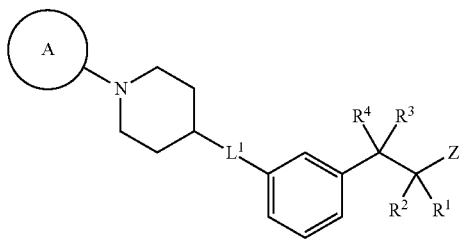

Formula (VI-i)

or a pharmaceutically acceptable salt, solvate, stereoisomer, or prodrug thereof.

In some embodiments of a compound of Formula (VI), or a pharmaceutically acceptable salt, solvate, stereoisomer, or prodrug thereof, is a compound of Formula (VI-ii):

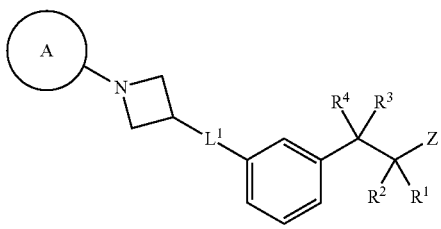

Formula (VI-ii)

or a pharmaceutically acceptable salt, solvate, stereoisomer, or prodrug thereof.

In some embodiments of a compound of Formula (VI), or a pharmaceutically acceptable salt, solvate, stereoisomer, or prodrug thereof, $L^1$ is *—O—$CH_2$—, *—$CH_2$—O—, *—$NR^7$—$CH_2$—, *—$NR^7$—C(O)—, *—C(O)—$NR^7$—, or *—C(O)$H_2$—; wherein * represents the connection to Ring B. In some embodiments, $L^1$ is *—$NR^7$—$CH_2$—; wherein * represents the connection to Ring B. In some embodiments, $L^1$ is *—$NR^7$—C(O)— or *—C(O)—$NR^7$—; wherein * represents the connection to Ring B. In some embodiments, $L^1$ is *—C(O)—$CH_2$—; wherein * represents the connection to Ring B. In some embodiments, $L^1$ is *—O—$CH_2$— or *—$CH_2$—O—; wherein * represents the connection to Ring B. In some embodiments, $L^1$ is *—O—$CH_2$—; wherein * represents the connection to Ring B. In some embodiments, $L^1$ is *—$CH_2$—O—; wherein * represents the connection to Ring B. In some embodiments, $R^7$ is hydrogen or $C_1$-$C_6$ alkyl. In some embodiments, $R^7$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In some embodiments, $R^7$ is hydrogen or methyl. In some embodiments, $R^7$ is hydrogen.

In some embodiments of a compound of Formula (I), (II), (III), (IV), or (VI), or a pharmaceutically acceptable salt, solvate, stereoisomer, or prodrug thereof, is a compound of Formula (VIa) or Formula (VIb):

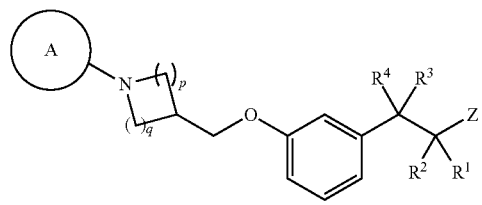

Formula (VIa)

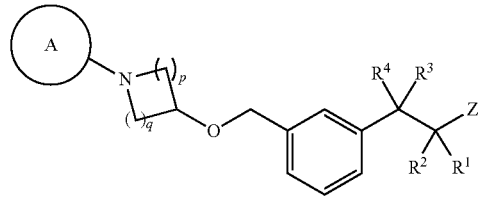

Formula (VIb)

or a pharmaceutically acceptable salt, solvate, stereoisomer, or prodrug thereof. In some embodiments, p and q are each independently 1 or 2. In some embodiments, p is 1 and q is 1. In some embodiments, p is 1 and q is 2. In some embodiments, p is 2 and q is 2.

In some embodiments, the compound of Formula (I), (II), (III), (IV), or (VI), or a pharmaceutically acceptable salt, solvate, stereoisomer, or prodrug thereof, is a compound of Formula (VIa), or a pharmaceutically acceptable salt, solvate, stereoisomer, or prodrug thereof. In some embodiments, the compound is a compound of Formula (VIb), or a pharmaceutically acceptable salt, solvate, stereoisomer, or prodrug thereof.

In some embodiments of a compound of Formula (VIa), or a pharmaceutically acceptable salt, solvate, stereoisomer, or prodrug thereof, is a compound of Formula (VIa-i):

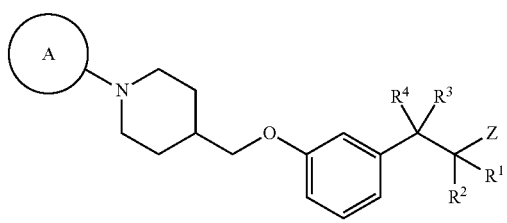

Formula (VIa-i)

or a pharmaceutically acceptable salt, solvate, stereoisomer, or prodrug thereof.

In some embodiments of a compound of Formula (VIb), or a pharmaceutically acceptable salt, solvate, stereoisomer, or prodrug thereof, is a compound of Formula (VIb-i):

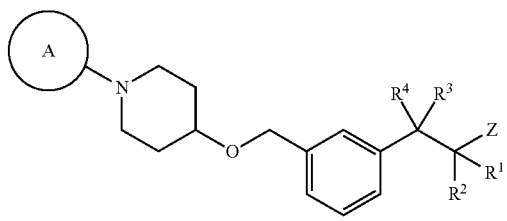

Formula (VIb-i)

or a pharmaceutically acceptable salt, solvate, stereoisomer, or prodrug thereof.

In some embodiments of a compound of Formula (VIa), or a pharmaceutically acceptable salt, solvate, stereoisomer, or prodrug thereof, is a compound of Formula (VIa-ii):

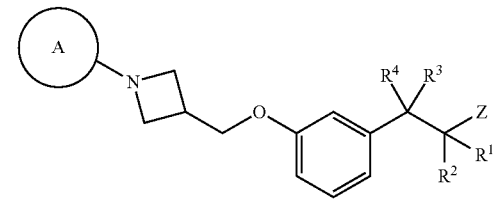

Formula (VIa-ii)

or a pharmaceutically acceptable salt, solvate, stereoisomer, or prodrug thereof.

In some embodiments of a compound of Formula (VIb), or a pharmaceutically acceptable salt, solvate, stereoisomer, or prodrug thereof, is a compound of Formula (VIb-ii):

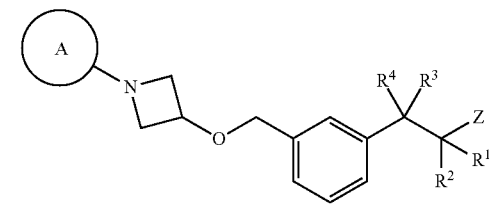

Formula (VIb-ii)

or a pharmaceutically acceptable salt, solvate, stereoisomer, or prodrug thereof.

In some embodiments, the compound of Formula (I), (2), (3), or (4), or a pharmaceutically acceptable salt, solvate, stereoisomer, or prodrug thereof, is a compound of Formula (7):

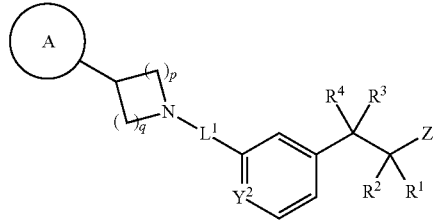

Formula (7)

or a pharmaceutically acceptable salt, solvate, stereoisomer, or prodrug thereof; wherein $Y^2$ is CH or N; and p and q are each independently 1 or 2. In some embodiments, $Y^2$ is N. In some embodiments, $Y^2$ is CH. In some embodiments, p is 1 and q is 1. In some embodiments, p is 1 and q is 2. In some embodiments, p is 2 and q is 2.

In some embodiments, the compound of Formula (I), (II), (III), or (IV), or a pharmaceutically acceptable salt, solvate, stereoisomer, or prodrug thereof, is a compound of Formula (VII):

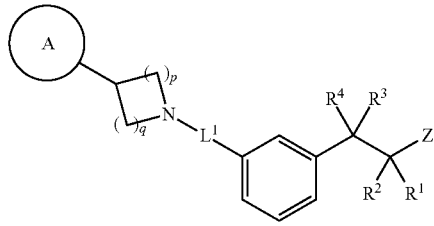

Formula (VII)

or a pharmaceutically acceptable salt, solvate, stereoisomer, or prodrug thereof; wherein p and q are each independently 1 or 2. In some embodiments, p is 1 and q is 1. In some embodiments, p is 1 and q is 2. In some embodiments, p is 2 and q is 2.

In some embodiments of a compound of Formula (VII), or a pharmaceutically acceptable salt, solvate, stereoisomer, or prodrug thereof, is a compound of Formula (VII-i):

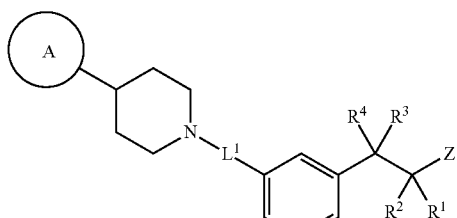

Formula (VII-i)

or a pharmaceutically acceptable salt, solvate, stereoisomer, or prodrug thereof.

In some embodiments of a compound of Formula (VII), or a pharmaceutically acceptable salt, solvate, stereoisomer, or prodrug thereof, is a compound of Formula (VII-ii):

Formula (VII-ii)

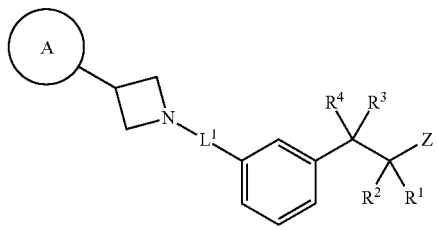

or a pharmaceutically acceptable salt, solvate, stereoisomer, or prodrug thereof.

In some embodiments of a compound of Formula (VII), or a pharmaceutically acceptable salt, solvate, stereoisomer, or prodrug thereof, $L^1$ is *—C(O)—$NR^7$—, or *—C(O)—$CH_2$—; wherein * represents the connection to Ring B. In some embodiments, $L^1$ is *—C(O)—$NR^7$—; wherein * represents the connection to Ring B. In some embodiments, $L^1$ is *—C(O)—$CH_2$—; wherein * represents the connection to Ring B. In some embodiments, $R^7$ is hydrogen or $C_1$-$C_6$ alkyl. In some embodiments, $R^7$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In some embodiments, $R^7$ is hydrogen or methyl. In some embodiments, $R^7$ is hydrogen.

In some embodiments of a compound of Formula (I), (II), (III), (IV), or (VII), or a pharmaceutically acceptable salt, solvate, stereoisomer, or prodrug thereof, is a compound of Formula (VIIa) or Formula (VIIb):

Formula (VIIa)

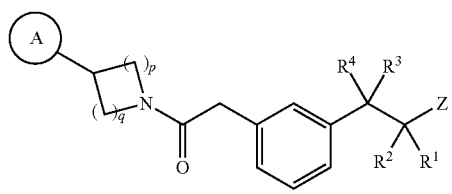

Formula (VIIb)

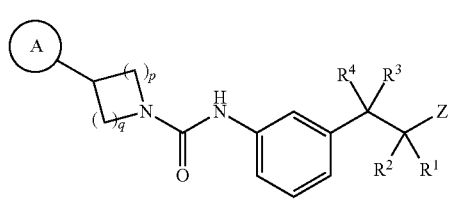

or a pharmaceutically acceptable salt, solvate, stereoisomer, or prodrug thereof. In some embodiments, p and q are each independently 1 or 2. In some embodiments, p is 1 and q is 1. In some embodiments, p is 1 and q is 2. In some embodiments, p is 2 and q is 2.

In some embodiments, the compound of Formula (I), (II), (III), (IV), or (VII), or a pharmaceutically acceptable salt, solvate, stereoisomer, or prodrug thereof, is a compound of Formula (VIIa), or a pharmaceutically acceptable salt, solvate, stereoisomer, or prodrug thereof. In some embodiments, the compound is a compound of Formula (VIIb), or a pharmaceutically acceptable salt, solvate, stereoisomer, or prodrug thereof.

In some embodiments of a compound of Formula (VIIa), or a pharmaceutically acceptable salt, solvate, stereoisomer, or prodrug thereof, is a compound of Formula (VIIa-i):

Formula (VIIa-i)

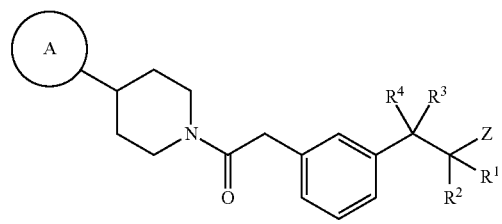

or a pharmaceutically acceptable salt, solvate, stereoisomer, or prodrug thereof.

In some embodiments of a compound of Formula (VIIb), or a pharmaceutically acceptable salt, solvate, stereoisomer, or prodrug thereof, is a compound of Formula (VIIb-i):

Formula (VIIb-i)

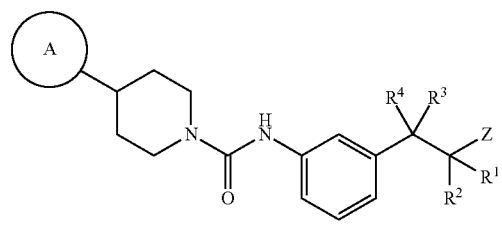

or a pharmaceutically acceptable salt, solvate, stereoisomer, or prodrug thereof.

In some embodiments of a compound of Formula (VIIa), or a pharmaceutically acceptable salt, solvate, stereoisomer, or prodrug thereof, is a compound of Formula (VIIa-ii):

Formula (VIIa-ii)

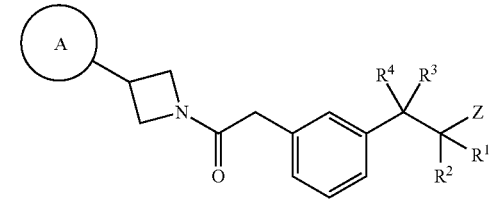

or a pharmaceutically acceptable salt, solvate, stereoisomer, or prodrug thereof.

In some embodiments of a compound of Formula (VIIb), or a pharmaceutically acceptable salt, solvate, stereoisomer, or prodrug thereof, is a compound of Formula (VIIb-ii):

Formula (VIIb-ii)

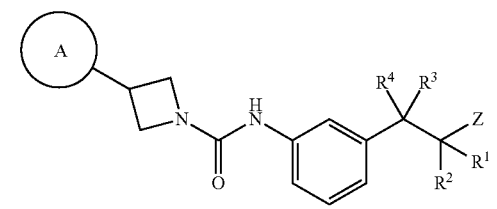

or a pharmaceutically acceptable salt, solvate, stereoisomer, or prodrug thereof.

In some embodiments of a compound of Formula (I), (II), (III), (IV), (IVa), or (IVb), or a pharmaceutically acceptable salt, solvate, stereoisomer, or prodrug thereof, Ring B is $C_3$-$C_6$ cycloalkylene; wherein the cycloalkylene is unsubstituted or substituted with 1, 2, 3, or 4 $R^B$ substituents; each $R^B$ is independently halogen, $C_1$-$C_6$ alkyl, or $C_1$-$C_6$ fluoroalkyl; $L^2$ is a bond or $C_1$-$C_6$ alkylene; wherein the alkylene is unsubstituted or substituted with 1, 2, or 3 substituents selected from the group consisting of —OH, $C_1$-$C_6$ alkyl, and —O—($C_1$-$C_6$ alkyl); and Ring A is aryl or heteroaryl; wherein the aryl or heteroaryl is unsubstituted or substituted with 1, 2, or 3 $R^A$ substituents.

In some embodiments, the compound of Formula (I), (2), (3), or (4), or a pharmaceutically acceptable salt, solvate, stereoisomer, or prodrug thereof, is a compound of Formula (8):

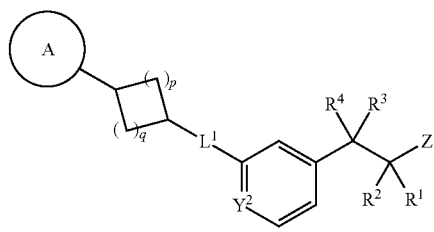

Formula (8)

or a pharmaceutically acceptable salt, solvate, stereoisomer, or prodrug thereof; wherein $Y^2$ is CH or N; and p and q are each independently 1 or 2. In some embodiments, $Y^2$ is N. In some embodiments, $Y^2$ is CH. In some embodiments, p is 1 and q is 1. In some embodiments, p is 1 and q is 2. In some embodiments, p is 2 and q is 2.

In some embodiments, the compound of Formula (I), (II), (III), or (IV), or a pharmaceutically acceptable salt, solvate, stereoisomer, or prodrug thereof, is a compound of Formula (VIII):

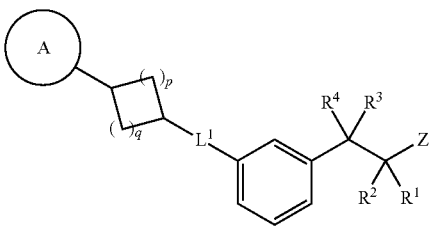

Formula (VIII)

or a pharmaceutically acceptable salt, solvate, stereoisomer, or prodrug thereof; wherein p and q are each independently 1 or 2. In some embodiments, p is 1 and q is 1. In some embodiments, p is 1 and q is 2. In some embodiments, p is 2 and q is 2.

In some embodiments of a compound of Formula (VIII), or a pharmaceutically acceptable salt, solvate, stereoisomer, or prodrug thereof, is a compound of Formula (VIII-i):

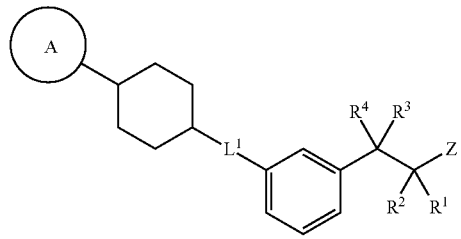

Formula (VIII-i)

or a pharmaceutically acceptable salt, solvate, stereoisomer, or prodrug thereof.

In some embodiments of a compound of Formula (VIII), or a pharmaceutically acceptable salt, solvate, stereoisomer, or prodrug thereof, is a compound of Formula (VIII-ii):

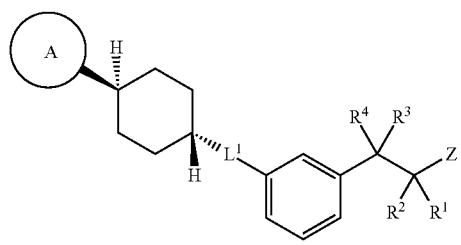

Formula (VIII-ii)

or a pharmaceutically acceptable salt, solvate, stereoisomer, or prodrug thereof.

In some embodiments of a compound of Formula (VIII), or a pharmaceutically acceptable salt, solvate, stereoisomer, or prodrug thereof, is a compound of Formula (VIII-iii):

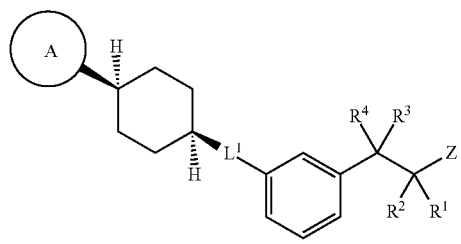

Formula (VIII-iii)

or a pharmaceutically acceptable salt, solvate, stereoisomer, or prodrug thereof.

In some embodiments of a compound of Formula (VIII), or a pharmaceutically acceptable salt, solvate, stereoisomer, or prodrug thereof, $L^1$ is *—O—$CH_2$—, *—$CH_2$—O—, *—$NR^7$—$CH_2$—, *—$NR^7$—C(O)—, *—C(O)—$NR^7$—, or *—C(O)$H_2$—; wherein * represents the connection to Ring B. In some embodiments, $L^1$ is *—$NR^7$—$CH_2$—; wherein * represents the connection to Ring B. In some embodiments, $L^1$ is *—$NR^7$—C(O)— or *—C(O)—$NR^7$—; wherein * represents the connection to Ring B. In some embodiments, $L^1$ is *—C(O)—$CH_2$—; wherein * represents the connection to Ring B. In some embodiments, $L^1$ is *—O—$CH_2$— or *—$CH_2$—O—; wherein * represents the connection to Ring B. In some embodiments, $L^1$ is *—O—$CH_2$—; wherein * represents the connection to Ring B. In some embodiments, L¹ is *—CH₂—O—; wherein * represents the connection to Ring B. In some embodiments, R⁷ is hydrogen or C₁-C₆ alkyl. In some embodiments, R⁷ is hydrogen, —CH₃, —CH₂CH₃, —CH₂CH₂CH₃, —CH(CH₃)₂, —CH₂CH₂CH₂CH₃, —CH₂CH(CH₃)₂, —CH(CH₃) CH₂CH₃, or —C(CH₃)₃. In some embodiments, R⁷ is hydrogen or methyl. In some embodiments, R⁷ is hydrogen.

In some embodiments of a compound of Formula (I), (II), (III), (IV), or (VIII), or a pharmaceutically acceptable salt, solvate, stereoisomer, or prodrug thereof, is a compound of Formula (VIIIa) or Formula (VIIIb):

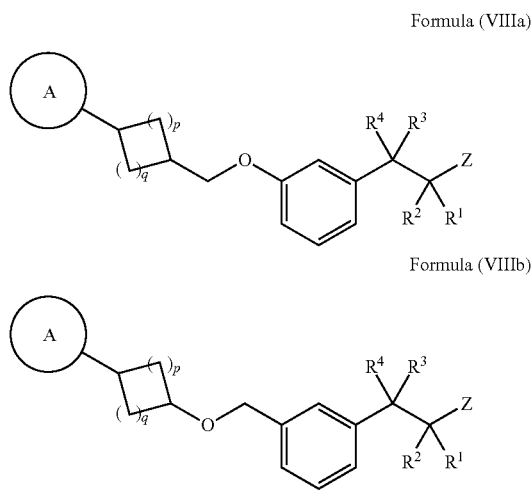

Formula (VIIIa)

Formula (VIIIb)

or a pharmaceutically acceptable salt, solvate, stereoisomer, or prodrug thereof. In some embodiments, p and q are each independently 1 or 2. In some embodiments, p is 1 and q is 1. In some embodiments, p is 1 and q is 2. In some embodiments, p is 2 and q is 2.

In some embodiments, the compound of Formula (I), (II), (III), (IV), or (VIII), or a pharmaceutically acceptable salt, solvate, stereoisomer, or prodrug thereof, is a compound of Formula (VIIIa), or a pharmaceutically acceptable salt, solvate, stereoisomer, or prodrug thereof. In some embodiments, the compound is a compound of Formula (VIIIb), or a pharmaceutically acceptable salt, solvate, stereoisomer, or prodrug thereof.

In some embodiments of a compound of Formula (VIIIa), or a pharmaceutically acceptable salt, solvate, stereoisomer, or prodrug thereof, is a compound of Formula (VIIIa-i):

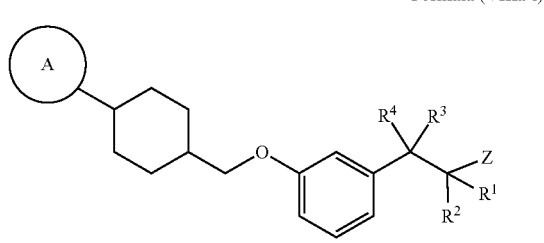

Formula (VIIIa-i)

or a pharmaceutically acceptable salt, solvate, stereoisomer, or prodrug thereof.

In some embodiments of a compound of Formula (VIIIa), or a pharmaceutically acceptable salt, solvate, stereoisomer, or prodrug thereof, is a compound of Formula (VIIIa-ii):

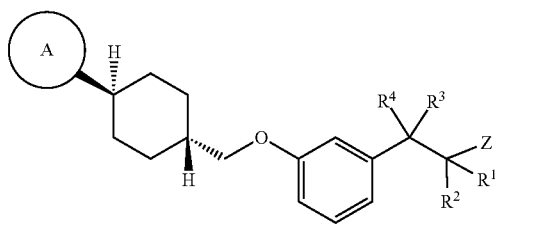

Formula (VIIIa-ii)

or a pharmaceutically acceptable salt, solvate, stereoisomer, or prodrug thereof.

In some embodiments of a compound of Formula (VIIIa), or a pharmaceutically acceptable salt, solvate, stereoisomer, or prodrug thereof, is a compound of Formula (VIIIa-iii):

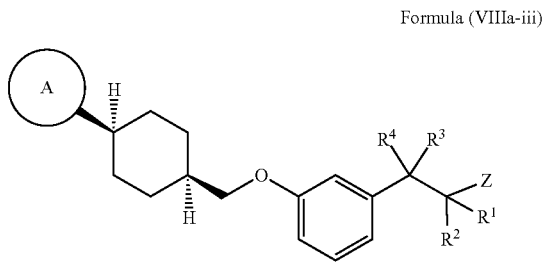

Formula (VIIIa-iii)

or a pharmaceutically acceptable salt, solvate, stereoisomer, or prodrug thereof.

In some embodiments of a compound of Formula (VIIIb), or a pharmaceutically acceptable salt, solvate, stereoisomer, or prodrug thereof, is a compound of Formula (VIIIb-i):

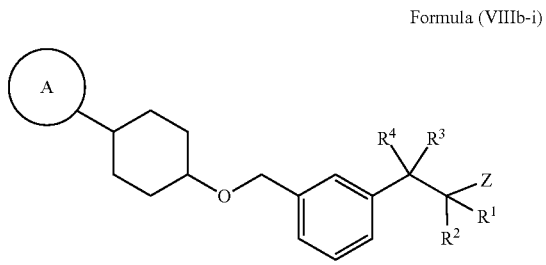

Formula (VIIIb-i)

or a pharmaceutically acceptable salt, solvate, stereoisomer, or prodrug thereof.

In some embodiments of a compound of Formula (VIIIb), or a pharmaceutically acceptable salt, solvate, stereoisomer, or prodrug thereof, is a compound of Formula (VIIIb-ii):

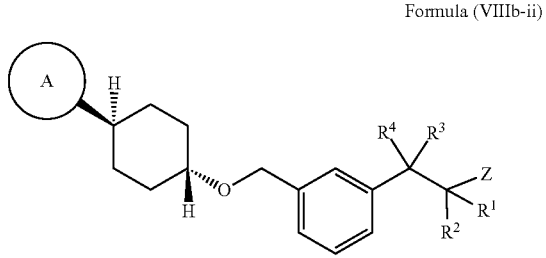

Formula (VIIIb-ii)

or a pharmaceutically acceptable salt, solvate, stereoisomer, or prodrug thereof.

In some embodiments of a compound of Formula (VIIIb), or a pharmaceutically acceptable salt, solvate, stereoisomer, or prodrug thereof, is a compound of Formula (VIIIb-iii):

Formula (VIIIb-iii)

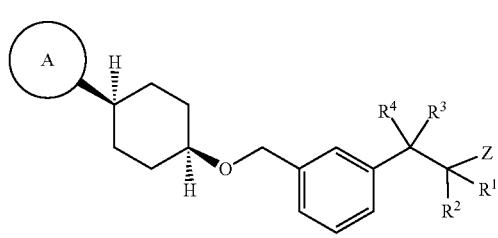

or a pharmaceutically acceptable salt, solvate, stereoisomer, or prodrug thereof.

In some embodiments, the compound of Formula (I), (2), (3), (4), or (8), or a pharmaceutically acceptable salt, solvate, stereoisomer, or prodrug thereof, is a compound of Formula (14):

Formula (14)

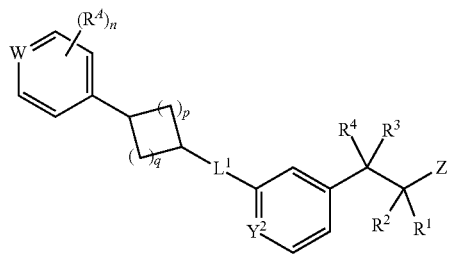

or a pharmaceutically acceptable salt, solvate, stereoisomer, or prodrug thereof; wherein $Y^2$ is CH or N; p and q are each independently 1 or 2; W is N, CH, or $CR^A$; and n is 0, 1, or 2. In some embodiments, $Y^2$ is N. In some embodiments, $Y^2$ is CH. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is $CR^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2. In some embodiments, W is CH and $Y^2$ is N. In some embodiments, W is N and $Y^2$ is N.

In some embodiments, the compound of Formula (I), (II), (III), (IV), or (VIII), or a pharmaceutically acceptable salt, solvate, stereoisomer, or prodrug thereof, is a compound of Formula (XIV):

Formula (XIV)

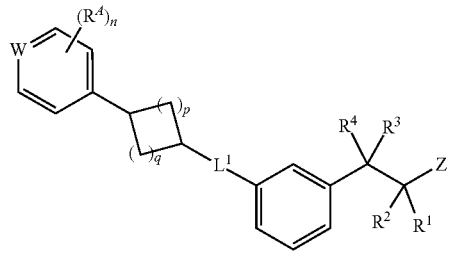

or a pharmaceutically acceptable salt, solvate, stereoisomer, or prodrug thereof; wherein p and q are each independently 1 or 2; W is N, CH, or $CR^A$; and n is 0, 1, or 2. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is $CR^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2.

In some embodiments of a compound of Formula (XIV), or a pharmaceutically acceptable salt, solvate, stereoisomer, or prodrug thereof, is a compound of Formula (XIV-i):

Formula (XIV-i)

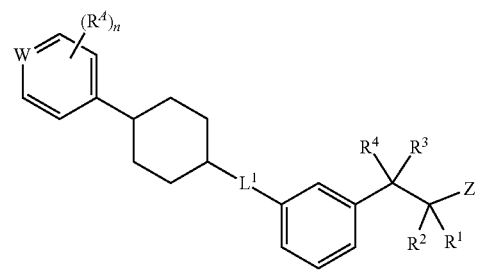

or a pharmaceutically acceptable salt, solvate, stereoisomer, or prodrug thereof.

In some embodiments of a compound of Formula (XIV), or a pharmaceutically acceptable salt, solvate, stereoisomer, or prodrug thereof, is a compound of Formula (XIV-ii):

Formula (XIV-ii)

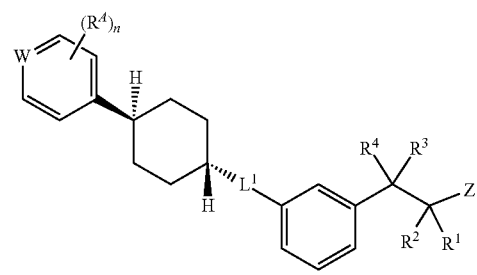

or a pharmaceutically acceptable salt, solvate, stereoisomer, or prodrug thereof.

In some embodiments of a compound of Formula (XIV), or a pharmaceutically acceptable salt, solvate, stereoisomer, or prodrug thereof, is a compound of Formula (XIV-iii):

Formula (XIV-iii)

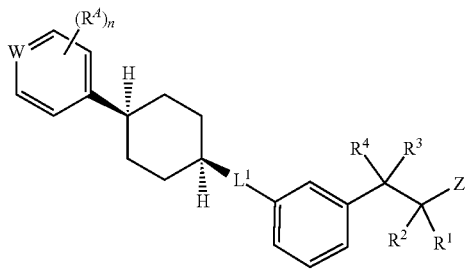

or a pharmaceutically acceptable salt, solvate, stereoisomer, or prodrug thereof.

In some embodiments of a compound of Formula (XIV), or a pharmaceutically acceptable salt, solvate, stereoisomer, or prodrug thereof, $L^1$ is *—O—$CH_2$—, *—$CH_2$—O—, *—$NR^7$—$CH_2$—, *—$NR^7$—C(O)—, *—C(O)—$NR^7$—, or *—C(O)$H_2$—; wherein * represents the connection to Ring B. In some embodiments, $L^1$ is *—$NR^7$—$CH_2$—; wherein * represents the connection to Ring B. In some embodiments, $L^1$ is *—$NR^7$—C(O)— or *—C(O)—$NR^7$—; wherein * represents the connection to Ring B. In some embodiments, $L^1$ is *—C(O)—$CH_2$—; wherein * represents the connection to Ring B. In some embodiments, $L^1$ is *—O—$CH_2$— or *—$CH_2$—O—; wherein * represents the Connection to Ring B. In some embodiments, $L^1$ is *—O—$CH_2$—; wherein * represents the connection to Ring B. In some embodiments, $L^1$ is *—$CH_2$—O—; wherein * represents the connection to Ring B. In some embodiments, $R^7$ is hydrogen or $C_1$-$C_6$ alkyl. In some embodiments, $R^7$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, or —$C(CH_3)_3$. In some embodiments, $R^7$ is hydrogen or methyl. In some embodiments, $R^7$ is hydrogen.

In some embodiments of a compound of Formula (I), (II), (III), (IV), (VIII), or (XIV), or a pharmaceutically acceptable salt, solvate, stereoisomer, or prodrug thereof, is a compound of Formula (XIVa) or Formula (XIVb):

Formula (XIVa)

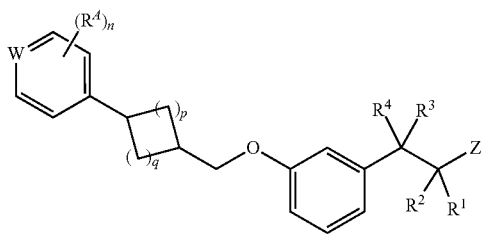

-continued

Formula (XIVb)

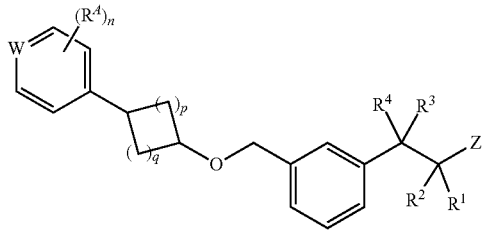

or a pharmaceutically acceptable salt, solvate, stereoisomer, or prodrug thereof; wherein p and q are each independently 1 or 2; W is N, CH, or $CR^A$; and n is 0, 1, or 2. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is $CR^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2.

In some embodiments of a compound of Formula (I), (II), (III), (IV), (VIII), or (XIV), or a pharmaceutically acceptable salt, solvate, stereoisomer, or prodrug thereof, is a compound of Formula (XIVa), or a pharmaceutically acceptable salt, solvate, stereoisomer, or prodrug thereof. In some embodiments, the compound is a compound of Formula (XIVb), or a pharmaceutically acceptable salt, solvate, stereoisomer, or prodrug thereof.

In some embodiments of a compound of Formula (XIVa), or a pharmaceutically acceptable salt, solvate, stereoisomer, or prodrug thereof, is a compound of Formula (XIVa-i):

Formula (XIVa-i)

or a pharmaceutically acceptable salt, solvate, stereoisomer, or prodrug thereof. In some embodiments, W is N, CH, or $CR^A$. In some embodiments, each $R^A$ is independently —F, —Cl, $C_1$-$C_7$ alkyl, $C_1$-$C_4$ fluoroalkyl, —OH, or —$OR^{10}$. In some embodiments, each $R^A$ is independently —F, —Cl, $C_1$-$C_4$ alkyl, $C_1$-$C_4$ fluoroalkyl, —OH, or —$OR^{10}$. In some embodiments, each $R^A$ is independently —F, —Cl, $C_1$-$C_7$ alkyl, $C_1$-$C_4$ fluoroalkyl, or —$OR^{10}$. In some embodiments, each $R^A$ is independently —F, —Cl, $C_1$-$C_4$ alkyl, $C_1$-$C_4$ fluoroalkyl, or —$OR^{10}$. In some embodiments, each $R^A$ is independently —F, —Cl, —Br, —$CH_3$, —$CH_2CH_3$, —$CH_2CH_2CH_3$, —$CH(CH_3)_2$, —$CH_2CH_2CH_3$, —$CH_2CH(CH_3)_2$, —$CH(CH_3)(CH_2CH_3)$, —$C(CH_3)_3$, —$CH_2CH_2CH_2CH_2CH_3$, —$CH_2CH_2CH(CH_3)_2$, —$CH_2C(CH_3)_3$, —$CH_2CH_2CH_2CH_2CH_2CH_3$, —$CH_2CH_2CH_2CH(CH_3)_2$, —$CH_2CH_2C(CH_3)_3$, —CH$_2$CH$_2$CH$_2$CH$_2$CH$_2$CH$_2$CH$_3$, —CH$_2$CH$_2$CH$_2$CH$_2$CH(CH$_3$)$_2$, —CH$_2$CH$_2$CH$_2$C(CH$_3$)$_3$, —CH$_2$F, —CHF$_2$, —CF$_3$, —OH, —OCH$_3$, —OCH$_2$CH$_3$, —OCH(CH$_3$)$_2$, or —OCF$_3$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$F, —CHF$_2$, —CF$_3$, —OH, —OCH$_3$, —OCH$_2$CH$_3$, —OCH(CH$_3$)$_2$, or —OCF$_3$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$CH$_2$CH$_2$CH$_3$, —CH$_2$CH$_2$CH(CH$_3$)$_2$, —CH$_2$C(CH$_3$)$_3$, —CH$_2$CH$_2$CH$_2$CH$_2$CH$_2$CH$_3$, —CH$_2$CH$_2$CH$_2$CH(CH$_3$)$_2$, —CH$_2$CH$_2$C(CH$_3$)$_3$, —CH$_2$CH$_2$CH$_2$CH$_2$CH$_2$CH$_2$CH$_3$, —CH$_2$CH$_2$CH$_2$CH$_2$CH(CH$_3$)$_2$, —CH$_2$CH$_2$CH$_2$C(CH$_3$)$_3$, —CH$_2$F, —CHF$_2$, —CF$_3$, —OCH$_3$, —OCH$_2$CH$_3$, —OCH(CH$_3$)$_2$, or —OCF$_3$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$F, —CHF$_2$, —CF$_3$, —OCH$_3$, —OCH$_2$CH$_3$, —OCH(CH$_3$)$_2$, or —OCF$_3$. In some embodiments, each R$^A$ is independently halogen, C$_1$-C$_7$ alkyl, —OH, or —OR$^{10}$; wherein each R$^{10}$ is independently C$_1$-C$_{10}$ alkyl. In some embodiments, each R$^A$ is independently halogen, —OH, or —OR$^{10}$; wherein each R$^{10}$ is independently C$_1$-C$_{10}$ alkyl. In some embodiments, each R$^A$ is independently halogen, C$_1$-C$_7$ alkyl, or —OR$^{10}$; wherein each R$^{10}$ is independently C$_1$-C$_{10}$ alkyl. In some embodiments, each R$^A$ is independently halogen or —OR$^{10}$; wherein each R$^{10}$ is independently C$_1$-C$_{10}$ alkyl.

In some embodiments of a compound of Formula (XIVa), or a pharmaceutically acceptable salt, solvate, stereoisomer, or prodrug thereof, is a compound of Formula (XIVa-ii):

Formula (XIVa-ii)

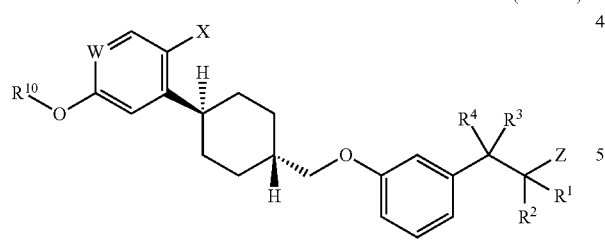

or a pharmaceutically acceptable salt, solvate, stereoisomer, or prodrug thereof; wherein W is N or CH; X is halogen; and R$^{10}$ is C$_1$-C$_{10}$ alkyl.

In some embodiments, the compound of Formula (I), (2), (3), (4), or (8), or a pharmaceutically acceptable salt, solvate, stereoisomer, or prodrug thereof, is a compound of Formula (15):

Formula (15)

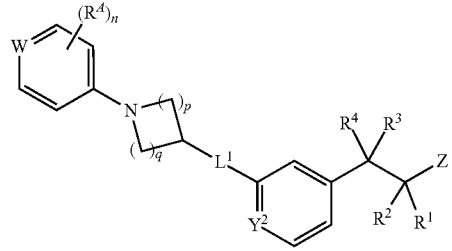

or a pharmaceutically acceptable salt, solvate, stereoisomer, or prodrug thereof; wherein Y$^2$ is CH or N; p and q are each independently 1 or 2; W is N, CH, or CR$^A$; and n is 0, 1, or 2. In some embodiments, Y$^2$ is N. In some embodiments, Y$^2$ is CH. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is CR$^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2. In some embodiments, W is CH and Y$^2$ is N. In some embodiments, W is N and Y$^2$ is N.

In some embodiments, the compound of Formula (I), (II), (III), (IV), or (VIII), or a pharmaceutically acceptable salt, solvate, stereoisomer, or prodrug thereof, is a compound of Formula (XV):

Formula (XV)

or a pharmaceutically acceptable salt, solvate, stereoisomer, or prodrug thereof; wherein p and q are each independently 1 or 2; W is N, CH, or CR$^A$; and n is 0, 1, or 2. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is CR$^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2.

In some embodiments of a compound of Formula (XV), or a pharmaceutically acceptable salt, solvate, stereoisomer, or prodrug thereof, is a compound of Formula (XV-i):

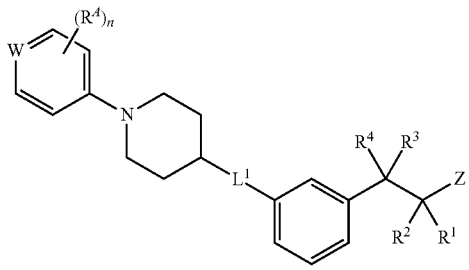

Formula (XV-i)

or a pharmaceutically acceptable salt, solvate, stereoisomer, or prodrug thereof.

In some embodiments of a compound of Formula (XV), or a pharmaceutically acceptable salt, solvate, stereoisomer, or prodrug thereof, $L^1$ is *—O—CH$_2$—, *—CH$_2$—O—, *—NR$^7$—CH$_2$—, *—NR$^7$—C(O)—, *—C(O)—NR$^7$—, or *—C(OCH$_2$—; wherein * represents the connection to Ring B. In some embodiments, $L^1$ is *—NR$^7$—CH$_2$—; wherein * represents the connection to Ring B. In some embodiments, $L^1$ is *—NR$^7$—C(O)— or *—C(O)—NR$^7$—; wherein * represents the connection to Ring B. In some embodiments, $L^1$ is *—C(O)—CH$_2$—; wherein * represents the connection to Ring B. In some embodiments, L is *—O—CH$_2$— or *—CH$_2$—O—; wherein * represents the connection to Ring B. In some embodiments, L is *—O—CH$_2$—; wherein * represents the connection to Ring B. In some embodiments, $L^1$ is *—CH$_2$—O—; wherein * represents the connection to Ring B. In some embodiments, $R^7$ is hydrogen or $C_1$-$C_6$ alkyl. In some embodiments, $R^7$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, or —C(CH$_3$)$_3$. In some embodiments, $R^7$ is hydrogen or methyl. In some embodiments, $R^7$ is hydrogen.

In some embodiments of a compound of Formula (I), (II), (III), (IV), (VIII), or (XV), or a pharmaceutically acceptable salt, solvate, stereoisomer, or prodrug thereof, is a compound of Formula (XVa) or Formula (XVb):

Formula (XVa)

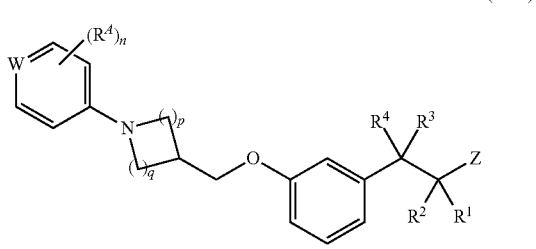

Formula (XVb)

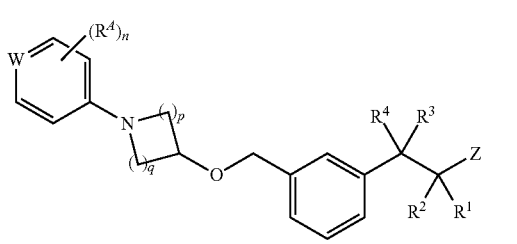

or a pharmaceutically acceptable salt, solvate, stereoisomer, or prodrug thereof; wherein p and q are each independently 1 or 2; W is N, CH, or CR$^A$; and n is 0, 1, or 2. In some embodiments, p is 1 and q is 1. In some embodiments, p is 1 and q is 2. In some embodiments, p is 2 and q is 2. In some embodiments, n is 1 or 2. In some embodiments, n is 1. In some embodiments, n is 2. In some embodiments W is N. In some embodiments, W is CH. In some embodiments, W is CR$^A$. In some embodiments, W is N; n is 1 or 2; p is 1 or 2; and q is 1 or 2. In some embodiments, W is N; n is 2; p is 2; and q is 2. In some embodiments, W is CH; n is 1 or 2; p is 1 or 2; and q is 1 or 2. In some embodiments, W is CH; n is 2; p is 2; and q is 2.

In some embodiments of a compound of Formula (I), (II), (III), (IV), (VIII), or (XV), or a pharmaceutically acceptable salt, solvate, stereoisomer, or prodrug thereof, is a compound of Formula (XVa), or a pharmaceutically acceptable salt, solvate, stereoisomer, or prodrug thereof. In some embodiments, the compound is a compound of Formula (XVb), or a pharmaceutically acceptable salt, solvate, stereoisomer, or prodrug thereof.

In some embodiments of a compound of Formula (XVa), or a pharmaceutically acceptable salt, solvate, stereoisomer, or prodrug thereof, is a compound of Formula (XVa-i):

Formula (XVa-i)

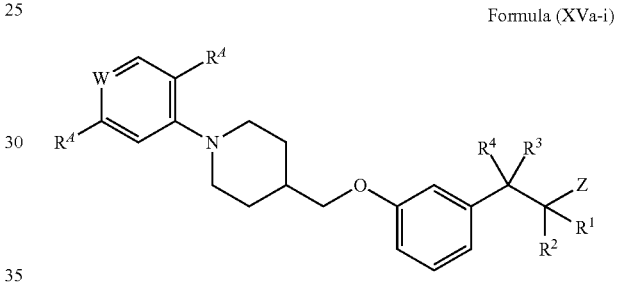

or a pharmaceutically acceptable salt, solvate, stereoisomer, or prodrug thereof. In some embodiments, W is N, CH, or CR$^A$. In some embodiments, each R$^A$ is independently —F, —Cl, $C_1$-$C_7$ alkyl, $C_1$-$C_4$ fluoroalkyl, —OH, or —OR$^{10}$. In some embodiments, each R$^A$ is independently —F, —Cl, $C_1$-$C_4$ alkyl, $C_1$-$C_4$ fluoroalkyl, —OH, or —OR$^{10}$. In some embodiments, each R$^A$ is independently —F, —Cl, $C_1$-$C_7$ alkyl, $C_1$-$C_4$ fluoroalkyl, or —OR$^{10}$. In some embodiments, each R$^A$ is independently —F, —Cl, $C_1$-$C_4$ alkyl, $C_1$-$C_4$ fluoroalkyl, or —OR$^{10}$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$CH$_2$CH$_2$CH$_3$, —CH$_2$CH$_2$CH(CH$_3$)$_2$, —CH$_2$C(CH$_3$)$_3$, —CH$_2$CH$_2$CH$_2$CH$_2$CH$_2$CH$_3$, —CH$_2$CH$_2$CH$_2$CH(CH$_3$)$_2$, —CH$_2$CH$_2$C(CH$_3$)$_3$, —CH$_2$CH$_2$CH$_2$CH$_2$CH$_2$CH$_2$CH$_3$, —CH$_2$CH$_2$CH$_2$CH$_2$CH(CH$_3$)$_2$, —CH$_2$CH$_2$CH$_2$C(CH$_3$)$_3$, —CH$_2$F, —CHF$_2$, —CF$_3$, —OH, —OCH$_3$, —OCH$_2$CH$_3$, —OCH(CH$_3$)$_2$, or —OCF$_3$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$F, —CHF$_2$, —CF$_3$, —OH, —OCH$_3$, —OCH$_2$CH$_3$, —OCH(CH$_3$)$_2$, or —OCF$_3$. In some embodiments, each R$^A$ is independently —F, —Cl, —Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$CH$_2$CH$_2$CH$_3$, —CH$_2$CH$_2$CH(CH$_3$)$_2$, —CH$_2$C(CH$_3$)$_3$, —CH$_2$CH$_2$CH$_2$CH$_2$CH$_2$CH$_3$, —CH$_2$CH$_2$CH$_2$CH(CH$_3$)$_2$, —CH$_2$CH$_2$C(CH$_3$)$_3$, —CH$_2$CH$_2$CH$_2$CH$_2$CH$_2$CH$_2$CH$_3$, —CH₂CH₂CH₂CH₂CH(CH₃)₂, —CH₂CH₂CH₂C(CH₃)₃, —CH₂F, —CHF₂, —CF₃, —OCH₃, —OCH₂CH₃, —OCH(CH₃)₂, or —OCF₃. In some embodiments, each $R^A$ is independently —F, —Cl, —Br, —CH₃, —CH₂CH₃, —CH₂CH₂CH₃, —CH(CH₃)₂, —CH₂CH₂CH₂CH₃, —CH₂CH(CH₃)₂, —CH(CH₃)(CH₂CH₃), —C(CH₃)₃, —CH₂F, —CHF₂, —CF₃, —OCH₃, —OCH₂CH₃, —OCH(CH₃)₂, or —OCF₃. In some embodiments, each $R^A$ is independently halogen, $C_1$-$C_7$ alkyl, —OH, or —OR¹⁰; wherein each $R^{10}$ is independently $C_1$-$C_{10}$ alkyl. In some embodiments, each $R^A$ is independently $C_1$-$C_7$ alkyl, —OH, or —OR¹⁰; wherein each $R^{10}$ is independently $C_1$-$C_{10}$ alkyl. In some embodiments, each $R^A$ is independently halogen, $C_1$-$C_7$ alkyl, or —OR¹⁰; wherein each $R^{10}$ is independently $C_1$-$C_{10}$ alkyl. In some embodiments, each $R^A$ is independently $C_1$-$C_7$ alkyl or —OR¹⁰; wherein each $R^{10}$ is independently $C_1$-$C_{10}$ alkyl.

In some embodiments of a compound of Formula (XVa), or a pharmaceutically acceptable salt, solvate, stereoisomer, or prodrug thereof, is a compound of Formula (XVa-ii):

Formula (XVa-ii)

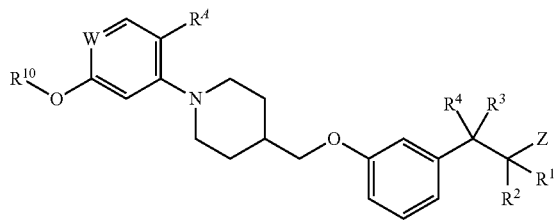

or a pharmaceutically acceptable salt, solvate, stereoisomer, or prodrug thereof; wherein W is N or CH; $R^A$ is $C_1$-$C_7$ alkyl; and $R^{10}$ is $C_1$-$C_{10}$ alkyl.

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, Z is —P(=O)(H)OR⁶, —P(=O)(R⁵)OR⁶, —P(=O)(OR⁶)₂, —S(=O)(OR⁶), —SO₂OR⁶, —C(=O)NHSO₂R⁵. In some embodiments, Z is —P(=O)(H)OR⁶, —P(=O)(R⁵)OR⁶, —P(=O)(OR⁶)₂, —S(=O)(OR⁶), or —SO₂OR⁶. In some embodiments, Z is —P(=O)(H)OR⁶, —P(=O)(R⁵)OR⁶, —P(=O)(OR⁶)₂, or —SO₂OR⁶.

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, $R^5$ is $C_1$-$C_6$ alkyl, $C_3$-$C_6$ cycloalkyl, phenyl, or —($C_1$-$C_6$ alkyl)-phenyl; wherein each alkyl, cycloalkyl, and phenyl is independently unsubstituted or substituted with one, two, or three substituents selected from —F, —Cl, —OH, —O—($C_1$-$C_6$ alkyl), $C_1$-$C_6$ alkyl, and $C_1$-$C_6$ hydroxyalkyl. In some embodiments, $R^5$ is $C_1$-$C_6$ alkyl. In some embodiments, $R^5$ is —CH₃, —CH₂CH₃, —CH₂CH₂CH₃, —CH(CH₃)₂, —CH₂CH₂CH₂CH₃, —CH₂CH(CH₃)₂, or —CH(CH₃)(CH₂CH₃).

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, each $R^6$ is independently hydrogen, $C_1$-$C_6$ alkyl, $C_3$-$C_6$ cycloalkyl, phenyl, or —($C_1$-$C_6$ alkyl)-phenyl; wherein each alkyl, cycloalkyl, and phenyl is independently unsubstituted or substituted with one, two, or three substituents selected from —F, —Cl, —OH, —O—($C_1$-$C_6$ alkyl), $C_1$-$C_6$ alkyl, and $C_1$-$C_6$ hydroxyalkyl. In some embodiments, each $R^6$ is independently hydrogen or $C_1$-$C_6$ alkyl. In some embodiments, each $R^6$ is independently hydrogen, —CH₃, —CH₂CH₃, —CH₂CH₂CH₃, —CH(CH₃)₂, —CH₂CH₂CH₂CH₃, —CH₂CH(CH₃)₂, or —CH(CH₃)(CH₂CH₃).

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, Z is —P(=O)(H)OR⁶, —P(=O)(R⁵)OR⁶, —P(=O)(OR⁶)₂, —S(=O)(OR⁶), —SO₂OR⁶, —C(=O)NHSO₂R⁵; $R^5$ is $C_1$-$C_6$ alkyl, $C_3$-$C_6$ cycloalkyl, phenyl, or —($C_1$-$C_6$ alkyl)-phenyl; wherein each alkyl, cycloalkyl, and phenyl is independently unsubstituted or substituted with one, two, or three substituents selected from —F, —Cl, —OH, —O—($C_1$-$C_6$ alkyl), $C_1$-$C_6$ alkyl, and $C_1$-$C_6$ hydroxyalkyl; and each $R^6$ is independently hydrogen, $C_1$-$C_6$ alkyl, $C_3$-$C_6$ cycloalkyl, phenyl, or —($C_1$-$C_6$ alkyl)-phenyl; wherein each alkyl, cycloalkyl, and phenyl is independently unsubstituted or substituted with one, two, or three substituents selected from —F, —Cl, —OH, —O—($C_1$-$C_6$ alkyl), $C_1$-$C_6$ alkyl, and $C_1$-$C_6$ hydroxyalkyl.

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, Z is —P(=O)(H)OR⁶, —P(=O)(R⁵)OR⁶, —P(=O)(OR⁶)₂, —S(=O)(OR⁶), or —SO₂OR⁶; $R^5$ is $C_1$-$C_6$ alkyl; and each $R^6$ is independently hydrogen or $C_1$-$C_6$ alkyl.

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, Z is —P(=O)(H)OR⁶, —P(=O)(R⁵)OR⁶, —P(=O)(OR⁶)₂, or —SO₂OR⁶; $R^5$ is —CH₃, —CH₂CH₃, —CH₂CH₂CH₃, —CH(CH₃)₂, —CH₂CH₂CH₂CH₃, —CH₂CH(CH₃)₂, or —CH(CH₃)(CH₂CH₃); and each $R^6$ is independently hydrogen, —CH₃, —CH₂CH₃, —CH₂CH₂CH₃, —CH(CH₃)₂, —CH₂CH₂CH₂CH₃, —CH₂CH(CH₃)₂, or —CH(CH₃)(CH₂CH₃).

In some embodiments of a compound of Formula (I), (II), (III), (IV), (IVa), (IVb), (V), (Va), (Vb), (VI), (VIa), (VIb), (VII), (VIIa), (VIIb), (VIII), (VIIIa), (VIIIb), (XIV), (XIVa), (XIVb), (XV), (XVa), or (XVb), or a pharmaceutically acceptable salt, solvate, stereoisomer, or prodrug thereof, Z is —P(=O)(H)OH, —P(=O)(CH₃)OH, —P(=O)(CH₂CH₃)OH, —PO₃H₂, —P(=O)(OCH₃)(OH), —S(=O)OH, —SO₂OH, or —C(=O)NHSO₂CH₃. In some embodiments, Z is —P(=O)(CH₃)OH, or —SO₂OH. In some embodiments, Z is —P(=O)(CH₃)OH. In some embodiments, Z is —P(=O)(H)OH. In some embodiments, Z is —P(=O)(CH₂CH₃)OH. In some embodiments, Z is —PO₃H₂. In some embodiments, —P(=O)(OCH₃)(OH). In some embodiments, Z is —S(=O)OH. In some embodiments, Z is —SO₂OH. In some embodiments, Z is —C(=O)NHSO₂CH₃.

In some embodiments, each $R^{10}$ is independently $C_1$-$C_6$ alkyl; wherein each alkyl is independently unsubstituted or substituted with 1, 2, 3, 4, or 5 substituents selected from the group consisting of halogen, —OH, $C_1$-$C_6$ alkyl and $C_1$-$C_6$ hydroxyalkyl. In some embodiments, each $R^{10}$ is independently $C_1$-$C_{10}$ alkyl. In some embodiments, each $R^{10}$ is independently $C_1$-$C_6$ alkyl.

In some embodiments, each $R^{11}$ is independently hydrogen, $C_1$-$C_6$ alkyl, or monocyclic heteroaryl; wherein each alkyl and heteroaryl is independently unsubstituted or substituted with 1, 2, 3, 4, or 5 substituents selected from the group consisting of halogen, —OH, $C_1$-$C_6$ alkyl and $C_1$-$C_6$ hydroxyalkyl. In some embodiments, each $R^{11}$ is independently hydrogen or $C_1$-$C_6$ alkyl; wherein each alkyl is independently unsubstituted or substituted with 1, 2, 3, 4, or 5 substituents selected from the group consisting of halogen, —OH, $C_1$-$C_6$ alkyl and $C_1$-$C_6$ hydroxyalkyl. In some embodiments, each $R^{11}$ is independently hydrogen or $C_1$-$C_{10}$ alkyl. In some embodiments, each $R^{11}$ is independently hydrogen or $C_1$-$C_6$ alkyl.

In some embodiments, two $R^{11}$ on the same nitrogen atom are taken together with the nitrogen to which they are attached to form a 3- to 6-membered N-heterocycloalkyl; wherein the heterocycloalkyl is unsubstituted or substituted with 1, 2, 3, 4, or 5 substituents selected from the group consisting of halogen, —OH, $C_1$-$C_6$ alkyl, and $C_1$-$C_6$ hydroxyalkyl. In some embodiments, two $R^{11}$ on the same nitrogen atom are taken together with the nitrogen to which they are attached to form a 3- to 6-membered N-heterocycloalkyl.

In some embodiments, each $R^{10}$ is independently $C_1$-$C_6$ alkyl; wherein each alkyl is independently unsubstituted or substituted with 1, 2, 3, 4, or 5 substituents selected from the group consisting of halogen, —OH, $C_1$-$C_6$ alkyl and $C_1$-$C_6$ hydroxyalkyl; and each $R^{11}$ is independently hydrogen, $C_1$-$C_6$ alkyl, or monocyclic heteroaryl; wherein each alkyl and heteroaryl is independently unsubstituted or substituted with 1, 2, 3, 4, or 5 substituents selected from the group consisting of halogen, —OH, $C_1$-$C_6$ alkyl and $C_1$-$C_6$ hydroxyalkyl; or two $R^{11}$ on the same nitrogen atom are taken together with the nitrogen to which they are attached to form a 3- to 6-membered N-heterocycloalkyl; wherein the heterocycloalkyl is unsubstituted or substituted with 1, 2, 3, 4, or 5 substituents selected from the group consisting of halogen, —OH, $C_1$-$C_6$ alkyl, and $C_1$-$C_6$ hydroxyalkyl.

Any combination of the groups described above for the various variables is contemplated herein. Throughout the specification, groups and substituents thereof are chosen by one skilled in the field to provide stable moieties and compounds.

In some embodiments, the compound of Formula (I) or a pharmaceutically acceptable salt, solvate, stereoisomer, or prodrug thereof, is a compound selected from:

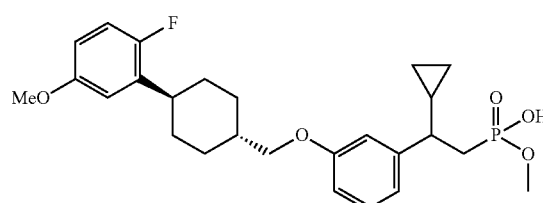

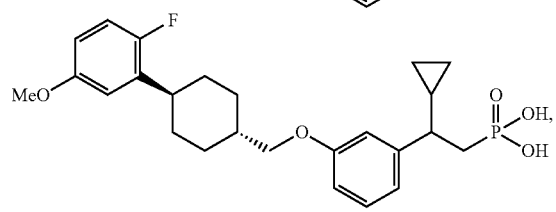

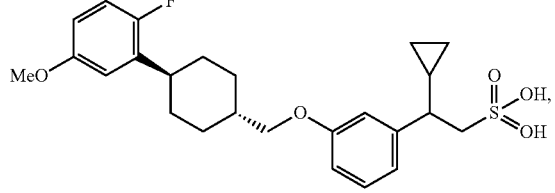

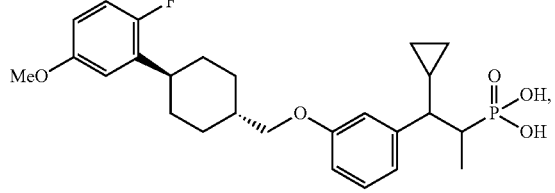

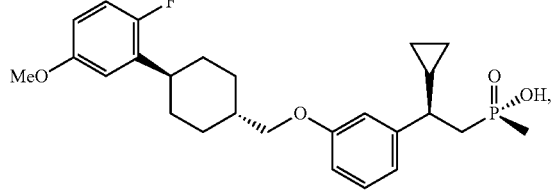

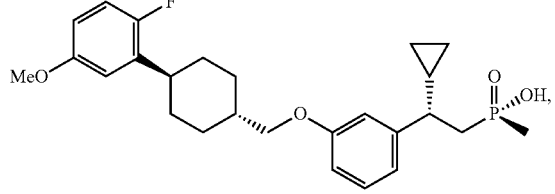

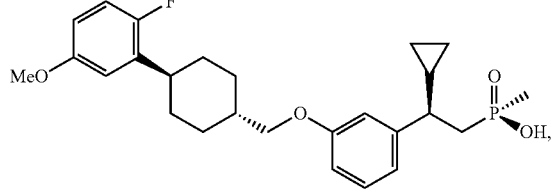

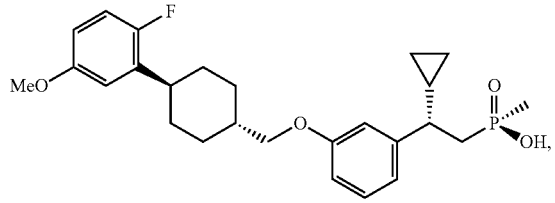

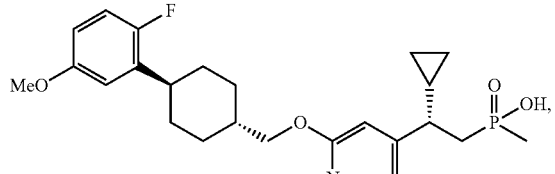

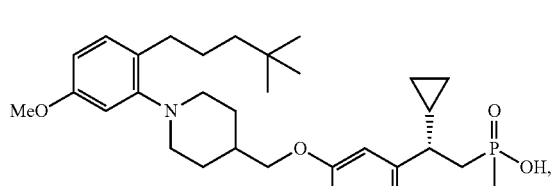

-continued
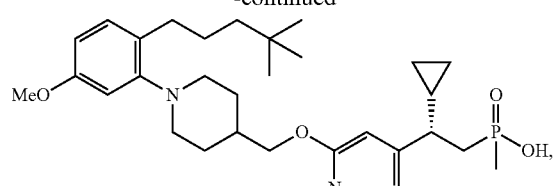
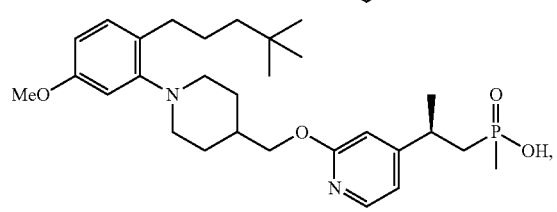
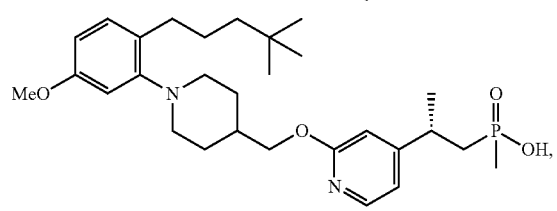
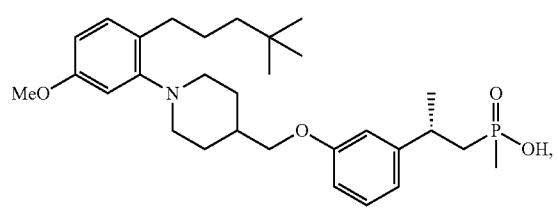
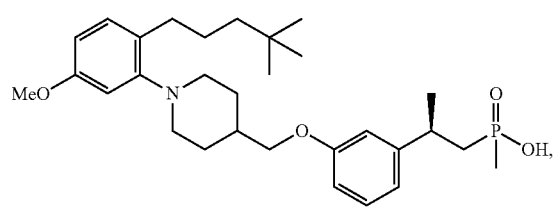
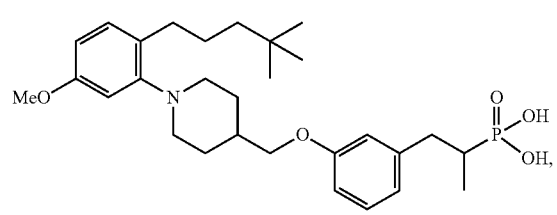
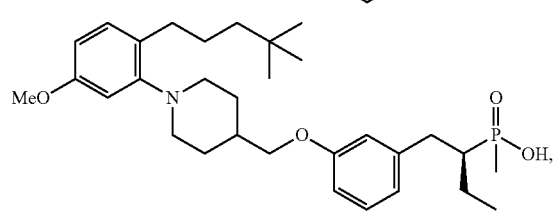
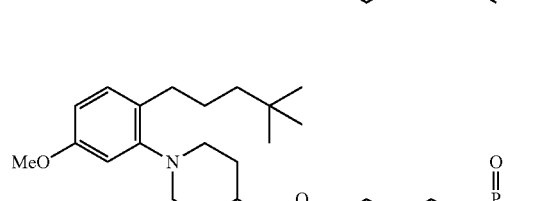
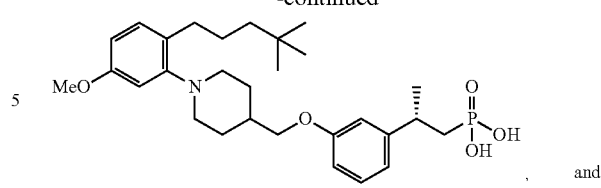
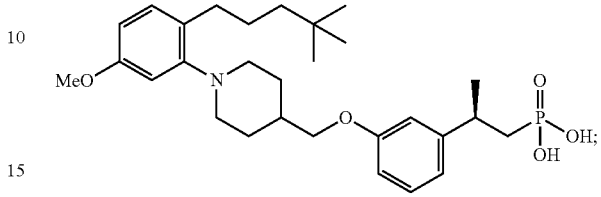
, and
or a pharmaceutically acceptable salt, solvate, stereoisomer, or prodrug thereof.
In some embodiments, the compound of Formula (I) or a pharmaceutically acceptable salt, solvate, stereoisomer, or prodrug thereof, is a compound selected from:
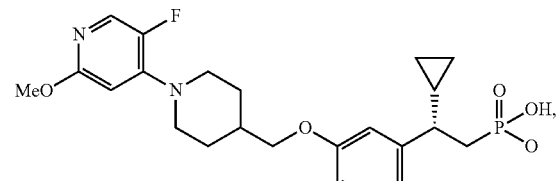
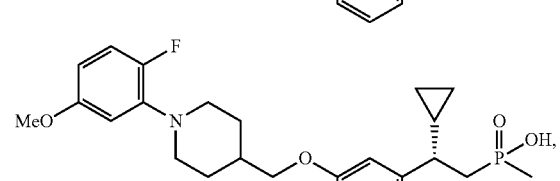
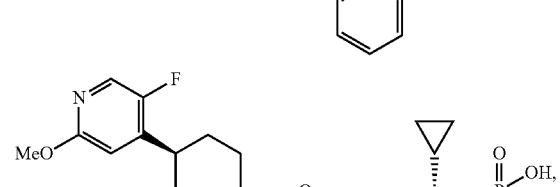
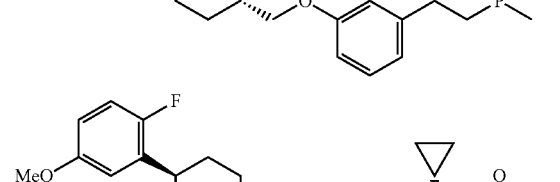
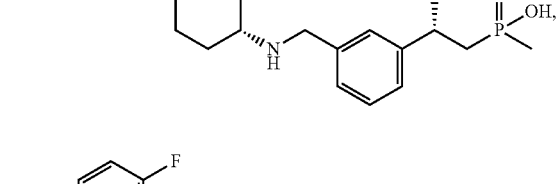
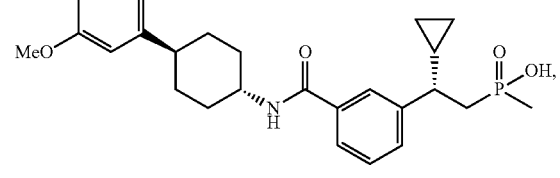

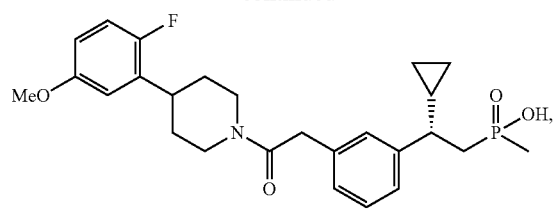
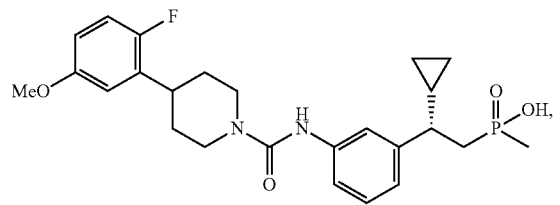
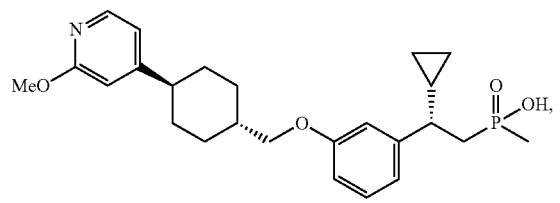
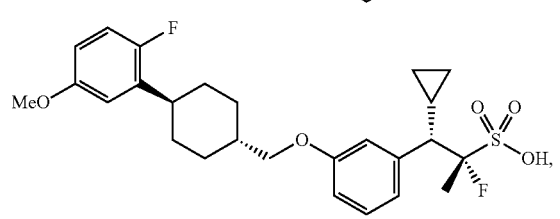
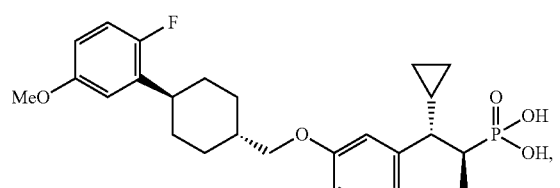
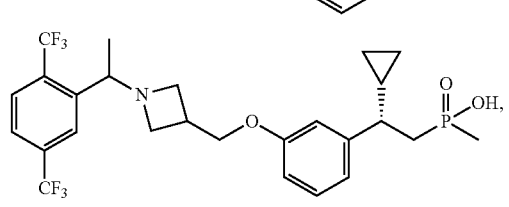
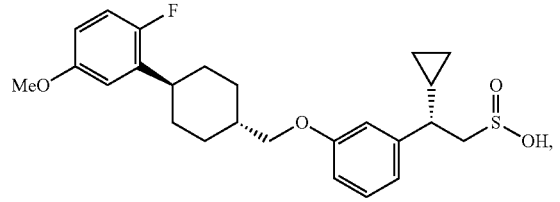
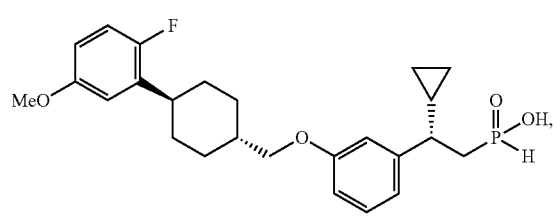

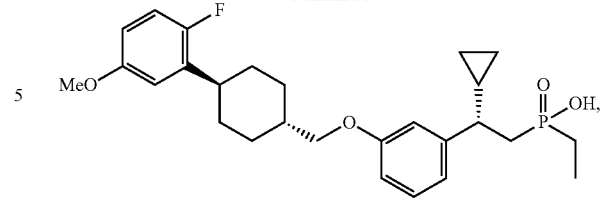
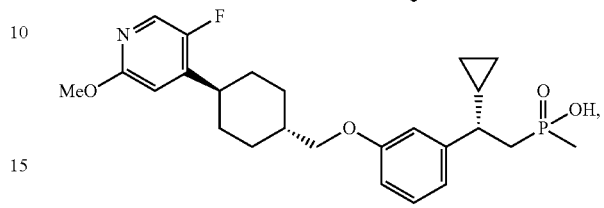
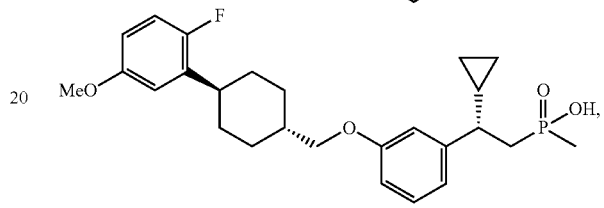
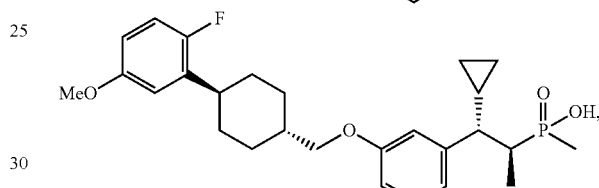
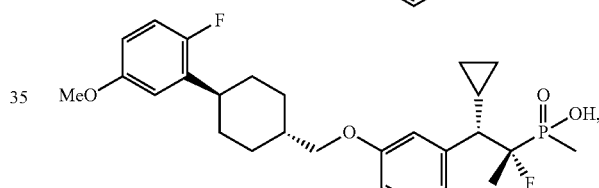
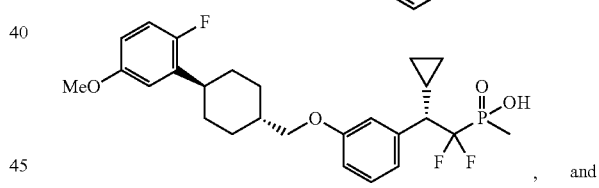
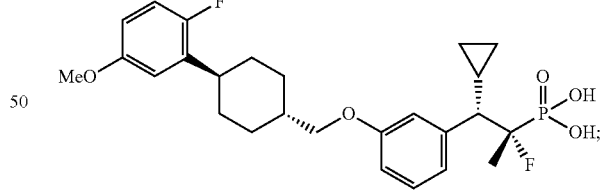

or a pharmaceutically acceptable salt, solvate, stereoisomer, or prodrug thereof.

Further Forms of Compounds

Furthermore, in some embodiments, the compounds described herein exist as "geometric isomers." In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

of compounds described herein, as well as active metabolites of these compounds having the same type of activity.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the com-

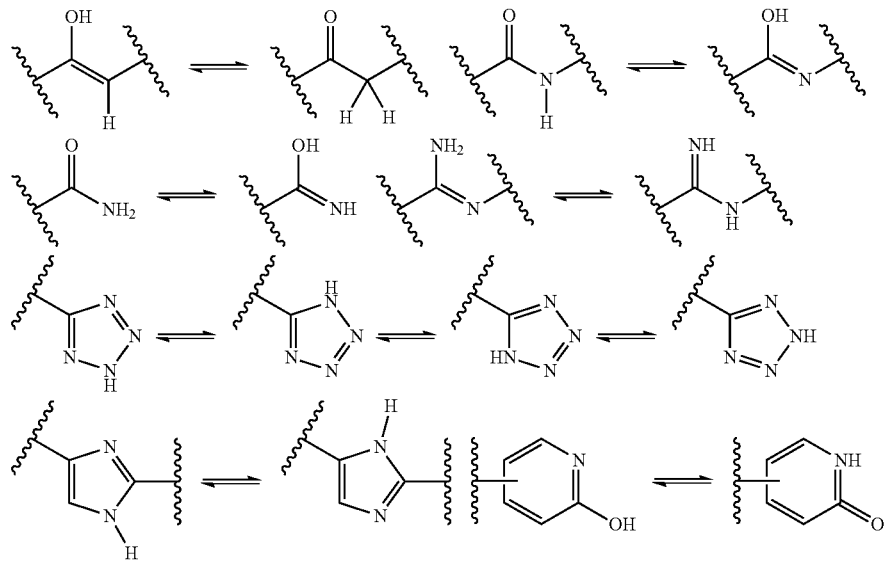

In some situations, the compounds described herein possess one or more chiral centers and each center exists in the (R)-configuration or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "positional isomer" refers to structural isomers around a central ring, such as ortho-, meta-, and para-isomers around a benzene ring.

The methods and formulations described herein include the use of N-oxides (if appropriate), crystalline forms (also known as polymorphs), or pharmaceutically acceptable salts pounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to an active compound described herein. Thus, the term prodrug refers to a precursor of an active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see. e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, carboxy, or mercapto group is bonded to any group that, when the prodrug of the active compound is administered to a mammalian subject, cleaves to form a free hydroxy, free amino, free carboxy, or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or nonstoichiometric amounts of a solvent, and are formed during the process of making with pharmaceutically acceptable solvents such as water, ethanol, and the like. "Hydrates" are formed when the solvent is water, or "alcoholates" are formed when the solvent is alcohol. Solvates of compounds described herein are conveniently prepared or formed during the processes described herein. The compounds provided herein optionally exist in either unsolvated as well as solvated forms.

The compounds disclosed herein, in some embodiments, are used in different enriched isotopic forms, e.g., enriched in the content of $^{2}H$, $^{3}H$, $^{11}C$, $^{13}C$ and/or $^{14}C$. In some embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{3}H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

In certain embodiments, the compounds described herein, or a pharmaceutically acceptable salt, solvate, stereoisomer, or prodrug thereof, as described herein are substantially pure, in that it contains less than about 5%, or less than about 1%, or less than about 0.1%, of other organic small molecules, such as contaminating intermediates or by-products that are created, for example, in one or more of the steps of a synthesis method.

Preparation of the Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described as outlined in the Examples.

Pharmaceutical Compositions

In some embodiments, disclosed herein is a pharmaceutical composition comprising a GPR40 agonist described herein, or a pharmaceutically acceptable salt, solvate, stereoisomer, or prodrug thereof, and a pharmaceutically acceptable excipient. In some embodiments, the GPR40 agonist is combined with a pharmaceutically suitable (or acceptable) carrier (also referred to herein as a pharmaceutically suitable (or acceptable) excipient, physiologically suitable (or acceptable) excipient, or physiologically suitable (or acceptable) carrier) selected on the basis of a chosen route of administration, e.g., oral administration, and standard pharmaceutical practice as described, for example, in *Remington: The Science and Practice of Pharmacy* (Gennaro, 21$^{st}$ Ed. Mack Pub. Co., Easton, PA (2005)).

Accordingly, provided herein is a pharmaceutical composition comprising a compound described herein, or a pharmaceutically acceptable salt or solvate thereof, together with a pharmaceutically acceptable excipient.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Combination Therapies

In certain embodiments, it is appropriate to administer at least one compound described herein, or a pharmaceutically acceptable salt, solvate, stereoisomer, or prodrug thereof, in combination with one or more other therapeutic agents. In some embodiments, a compound described herein, or a pharmaceutically acceptable salt, solvate, stereoisomer, or prodrug thereof, is administered in combination with a TGR5 agonist, a GPR119 agonist, an SSTR5 antagonist, an SSTR5 inverse agonist, a CCK1 agonist, a PDE4 inhibitor, a DPP-4 inhibitor, a GLP-1 receptor agonist, a ghrelin O-acyltransferase (GOAT) inhibitor, metformin, or combinations thereof. In certain embodiments, the pharmaceutical composition further comprises one or more anti-diabetic agents. In certain embodiments, the pharmaceutical composition further comprises one or more anti-obesity agents. In certain embodiments, the pharmaceutical composition further comprises one or more agents to treat nutritional disorders.

Examples of a TGR5 agonist to be used in combination with a compound described herein, or a pharmaceutically acceptable salt, solvate, stereoisomer, or prodrug thereof, include: INT-777, XL-475, SRX-1374, RDX-8940, RDX-98940, SB-756050, and those disclosed in WO-2008091540, WO-2010059853, WO-2011071565, WO-2018005801, WO-2010014739, WO-2018005794, WO-2016054208, WO-2015160772, WO-2013096771, WO-2008067222, WO-2008067219, WO-2009026241, WO-2010016846, WO-2012082947, WO-2012149236, WO-2008097976, WO-2016205475, WO-2015183794, WO-2013054338, WO-2010059859, WO-2010014836, WO-2016086115, WO-2017147159, WO-2017147174, WO-2017106818, WO-2016161003, WO-2014100025, WO-2014100021, WO-2016073767, WO-2016130809, WO-2018226724, WO-2018237350, WO-2010093845, WO-2017147137, WO-2015181275, WO-2017027396, WO-2018222701, WO-2018064441, WO-2017053826, WO-2014066819, WO-2017079062, WO-2014200349, WO-2017180577, WO-2014085474.

Examples of a GPR119 agonist to be used in combination with a compound described herein, or a pharmaceutically acceptable salt, solvate, stereoisomer, or prodrug thereof, include: DS-8500a, HD-2355, LC34AD3, PSN-491, HM-47000, PSN-821, MBX-2982, GSK-1292263, APD597, DA-1241, and those described in WO-2009141238, WO-2010008739, WO-2011008663, WO-2010013849, WO-2012046792, WO-2012117996, WO-2010128414, WO-2011025006, WO-2012046249, WO-2009106565, WO-2011147951, WO-2011127106, WO-2012025811, WO-2011138427, WO-2011140161, WO-2011061679, WO-2017175066, WO-2017175068, WO-2015080446, WO-2013173198, US-20120053180, WO-2011044001, WO-2010009183, WO-2012037393, WO-2009105715, WO-2013074388, WO-2013066869, WO-2009117421, WO-201008851, WO-2012077655, WO-2009106561, WO-2008109702, WO-2011140160, WO-2009126535, WO-2009105717, WO-2013122821, WO-2010006191, WO-2009012275, WO-2010048149, WO-2009105722, WO-2012103806, WO-2008025798, WO-2008097428, WO-2011146335, WO-2012080476, WO-2017106112, WO-2012145361, WO-2012098217, WO-2008137435, WO-2008137436, WO-2009143049, WO-2014074668, WO-2014052619, WO-2013055910, WO-2012170702, WO-2012145604, WO-2012145603, WO-2011030139, WO-2018153849, WO-2017222713, WO-2015150565, WO-2015150563, WO-2015150564, WO-2014056938, WO-2007120689, WO-2016068453, WO-2007120702, WO-2013167514, WO-2011113947, WO-2007003962, WO-2011153435, WO-2018026890, WO-2011163090, WO-2011041154, WO-2008083238, WO-2008070692, WO-2011150067, and WO-2009123992.

Examples of a SSTR5 antagonist or inverse agonist to be used in combination with a compound described herein, or a pharmaceutically acceptable salt, solvate, stereoisomer, or prodrug thereof, include those described in: WO-03104816, WO-2009050309, WO-2015052910, WO-2011146324, WO-2006128803, WO-2010056717, WO-2012024183, and WO-2016205032.

Examples of a CCK1 agonist to be used in combination with a compound described herein, or a pharmaceutically acceptable salt, solvate, stereoisomer, or prodrug thereof, include: A-70874, A-71378, A-71623, A-74498, CE-326597, GI-248573, GSKI-181771X, NN-9056, PD-149164, PD-134308, PD-135158, PD-170292, PF-04756956, SR-146131, SSR-125180, and those described in EP-00697403, US-20060177438, WO-2000068209, WO-2000177108, WO-2000234743, WO-2000244150, WO-2009119733, WO-2009314066, WO-2009316982, WO-2009424151, WO-2009528391, WO-2009528399, WO-2009528419, WO-2009611691, WO-2009611940, WO-2009851686, WO-2009915525, WO-2005035793, WO-2005116034, WO-2007120655, WO-2007120688, WO-2008091631, WO-2010067233, WO-2012070554, and WO-2017005765.

Examples of a PDE4 inhibitor to be used in combination with a compound described herein, or a pharmaceutically acceptable salt, solvate, stereoisomer, or prodrug thereof, include: apremilast, cilomilast, crisaborole, diazepam, luteolin, piclamilast, and roflumilast.

Examples of a DPP-4 inhibitor to be used in combination with a compound described herein, or a pharmaceutically acceptable salt, solvate, stereoisomer, or prodrug thereof, include: sitagliptin, vildagliptin, saxagliptin, linagliptin, gemigliptin, teneligliptin, alogliptin, trelagliptin, omarigliptin, evogliptin, gosogliptin, and dutogliptin.

Examples of a GLP-1 receptor agonist to be used in combination with a compound described herein, or a pharmaceutically acceptable salt, solvate, stereoisomer, or prodrug thereof, include: albiglutide, dulaglutide, exenatide, extended-release exenatide, liraglutide, lixisenatide, and semaglutide.

Examples of a GOAT inhibitors to be used in combination with a compound described herein, or a pharmaceutically acceptable salt, solvate, stereoisomer, or prodrug thereof, include: T-3525770 (RM-852), GLWL-01, BOS-704, and those described in U.S. Ser. No. 08/013,015, U.S. Ser. No. 09/340,578, WO-2019149959, US-20170056373, WO-2018035079, WO-2016044467, WO-2010039461, WO-2018024653, WO-2019149660, WO-2019149659, WO-2015073281, WO-2019149658, WO-2016168225, WO-2016168222, WO-2019149657, WO-2013125732, and WO-2019152889.

Examples of anti-diabetic agents to be used in combination with a compound described herein, or a pharmaceutically acceptable salt, solvate, stereoisomer, or prodrug thereof, include: GLP-1 receptor agonists such as exenatide, liraglutide, taspoglutide, lixisenatide, albiglutide, dulaglutide, semaglutide, OWL833 and ORMD 0901; SGLT2 inhibitors such as dapagliflozin, canagliflozin, empagliflozin, ertugliflozin, ipragliflozin, luseogliflozin, remogliflozin, sergliflozin, sotagliflozin, and tofogliflozin; biguinides such as metformin; insulin and insulin analogs.

Examples of anti-obesity agents to be used in combination with a compound described herein, or a pharmaceutically acceptable salt, solvate, stereoisomer, or prodrug thereof, include: GLP-1 receptor agonists such as liraglutide, semaglutide; SGLT1/2 inhibitors such as LIK066, pramlintide and other amylin analogs such as AM-833, AC2307, and BI 473494; PYY analogs such as NN-9747, NN-9748, AC-162352, AC-163954, GT-001, GT-002, GT-003, and RHS-08; GIP receptor agonists such as APD-668 and APD-597; GLP-1/GIP co-agonists such as tirzepatide (LY329176), BHM-089, LBT-6030, CT-868, SCO-094, NNC-0090-2746, RG-7685, NN-9709, and SAR-438335; GLP-1/glucagon co-agonist such as cotadutide (MEDI0382), BI 456906, TT-401, G-49, H&D-001A, ZP-2929, and HM-12525A; GLP-1/GIP/glucagon triple agonist such as SAR-441255, HM-15211, and NN-9423; GLP-1/secretin co-agonists such as GUB06-046; leptin analogs such as metreleptin; GDF15 modulators such as those described in WO2012138919, WO2015017710, WO2015198199, WO-2017147742 and WO-2018071493; FGF21 receptor modulators such as NN9499, NGM386, NGM313, BFKB8488A (RG7992), AKR-001, LLF-580, CVX-343, LY-2405319, BI089-100, and BMS-986036; MC4 agonists such as setmelanotide; MetAP2 inhibitors such as ZGN-1061; ghrelin receptor modulators such as HM04 and AZP-531; and oxytocin analogs such as carbetocin.

Examples of agents for nutritional disorders to be used in combination with a compound described herein, or a pharmaceutically acceptable salt, solvate, stereoisomer, or prodrug thereof, include: GLP-2 receptor agonists such as tedaglutide, glepaglutide (ZP1848), elsiglutide (ZP1846), apraglutide (FE 203799), HM-15912, NB-1002, GX-G8, PE-0503, SAN-134, and those described in WO-2011050174, WO-2012028602, WO-2013164484, WO-2019040399, WO-2018142363, WO-2019090209, WO-2006117565, WO-2019086559, WO-2017002786, WO-2010042145, WO-2008056155, WO-2007067828, WO-2018229252, WO-2013040093, WO-2002066511, WO-2005067368, WO-2009739031, WO-2009632414, and WO2008028117; and GLP-1/GLP-2 receptor co-agonists such as ZP-GG-72 and those described in WO-2018104561, WO-2018104558, WO-2018103868, WO-2018104560, WO-2018104559, WO-2018009778, WO-2016066818, and WO-2014096440.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt, solvate, stereoisomer, or prodrug thereof, is co-administered with one or more additional therapeutic agents, wherein the compound described herein, or a pharmaceutically acceptable salt, solvate, stereoisomer, or prodrug thereof, and the additional therapeutic agent(s) modulate different aspects of the disease, disorder or condition being treated, thereby providing a greater overall benefit than administration of either therapeutic agent alone. In some embodiments, the additional therapeutic agent(s) is a TGR5 agonist, a GPR119 agonist, an SSTR5 antagonist, an SSTR5 inverse agonist, a CCK1 agonist, a PDE4 inhibitor, a DPP-4 inhibitor, a GOAT inhibitor, a GLP-1 receptor agonist, metformin, or combinations thereof. In some embodiments, the additional therapeutic agent is an anti-diabetic agent. In some embodiments, the additional therapeutic agent is an anti-obesity agent. In some embodiments, the additional therapeutic agent is an agent to treat nutritional disorders.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or pharmaceutically acceptable salts, solvates, stereoisomers, or prodrugs thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease.

In some embodiments, a compound described herein, or a pharmaceutically acceptable salt thereof, is administered in combination with anti-inflammatory agent, anti-cancer agent, immunosuppressive agent, steroid, non-steroidal anti-inflammatory agent, antihistamine, analgesic, hormone blocking therapy, radiation therapy, monoclonal antibodies, or combinations thereof.

EXAMPLES

List of Abbreviations

As used above, and throughout the description of the invention, the following abbreviations, unless otherwise indicated, shall be understood to have the following meanings:

ACN or MeCN acetonitrile
AIBN azobisisobutyronitrile
BINAP 2,2'-bis(diphenylphosphino)-1,1'-binaphthyl
BPO benzoyl peroxide
Boc or BOC tert-butyloxycarbonyl
Bn benzyl
BnBr benzyl bromide
DCC N,N'-dicyclohexylcarbodiimide
DCM dichloromethane ($CH_2Cl_2$)
DEA diethylamine
DIAD diisopropyl azodicarboxylate
DIBAL-H diisobutylaluminum hydride
DIPEA or DIEA diisopropylethylamine
DMAP 4-dimethylaminopyridine
DME 1,2-dimethoxyethane
DMF dimethylformamide
DMP Dess-Martin periodinane
DMSO dimethylsulfoxide
EDCI 1-ethyl-3-(3-dimethylaminopropyl)carbodiimide
eq equivalent(s)
Et ethyl
EtOH ethanol
EA ethyl acetate
EtOAc ethyl acetate
FA formic acid
h, hr(s) hour(s)
HATU 1-[bis(dimethylamino)methylene]-1H-1,2,3-triazolo[4,5-b]pyridinium 3-oxide hexafluorophosphate
HPLC high performance liquid chromatography
IPA isopropanol
LDA lithium diisopropylamide
LCMS liquid chromatography-mass spectrometry
Me methyl
MeOH methanol
MS mass spectroscopy
Ms methanesulfonyl (mesyl)
MsCl methanesulfonyl chloride (mesyl chloride)
NBS N-bromosuccinimide
NMR nuclear magnetic resonance
PE petroleum ether
Py pyridine
Rt or RT room temperature
SFC supercritical fluid chromatography
TEA triethylamine
Tf trifluoromethylsulfonyl (triflyl)
TFA trifluoroacetic acid
THF tetrahydrofuran
TLC thin layer chromatography
TMAD tetramethylazodicarboxamide
TMS trimethylsilyl
Tol or tol toluene
tR retention time
Xantphos 4,5-bis(diphenylphosphino)-9,9-dimethylxanthene I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Preparation of ethyl ((S)-2-cyclopropyl-2-(3-hydroxyphenyl)ethyl)(methyl)phosphinate (Int-A

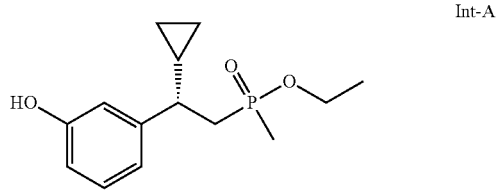 [SMILES: CCOP(C)(=O)C[C@H](c1cccc(O)c1)C1CC1]

Step 1:
(3-(benzyloxy)phenyl)(cyclopropyl)methanol (A-1

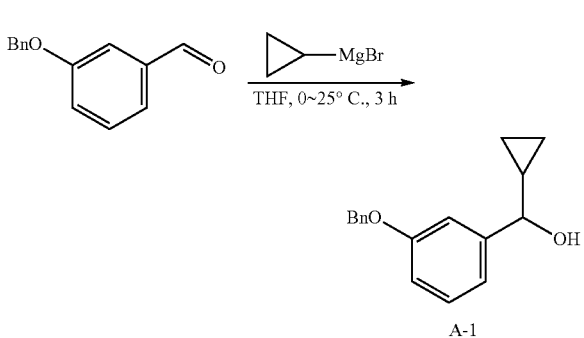

To a solution of 3-(benzyloxy)benzaldehyde (25 g, 0.12 mol, 1 eq) in THF (450 mL) was added cyclopropylmagnesium bromide (0.50 M in THF, 0.71 L, 3 eq) at 0° C. The mixture was stirred at 25° C. for 3 hours. The reaction mixture was quenched by addition water (300 mL) at 0° C., then diluted with ethyl acetate (300 mL) and extracted with ethyl acetate (300 mL×3). The combined organic layers were washed with saturated brine (100 mL×3), dried over $Na_2SO_4$, filtered and concentrated under reduced pressure to give a residue. The residue was purified by column chromatography ($SiO_2$, Petroleum ether:Ethyl acetate=10:1 to 0:1) to give A-1 (23 g, 68% yield, 89% purity) as a yellow oil. $^1$H-NMR (DMSO-$d_6$, 400 MHz): δ=7.49-7.42 (m, 2H), 7.39 (t, J=7.2 Hz, 2H), 7.33 (d, J=7.2 Hz, 1H), 7.22 (t, J=7.6 Hz, 1H), 7.03 (s, 1H), 6.96 (d, J=7.6 Hz, 1H), 6.87 (dd, $J_1$=2.4 Hz, $J_2$=8 Hz, 1H), 5.14 (d, J=4.4 Hz, 1H), 5.09 (s, 2H), 3.96-3.90 (m, 1H), 1.16-0.95 (m, 1H), 0.48-0.28 (d, J=7.2 Hz, 4H).

Step 2:
(3-(benzyloxy)phenyl)(cyclopropyl)methanone (A-2

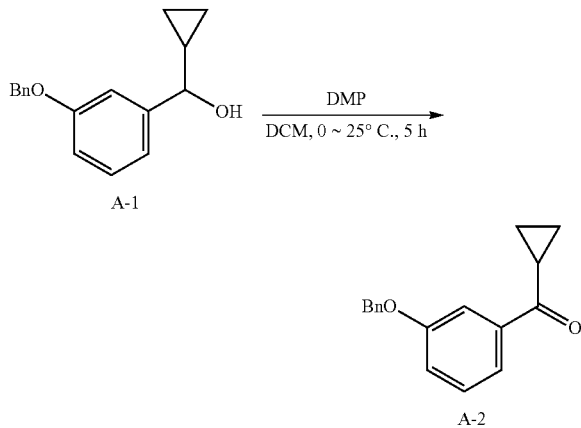

To a solution of A-1 (23 g, 90 mmol, 1 eq) in DCM (0.23 L) was added DMP (58 g, 0.14 mol, 42 mL, 1.5 eq) at 0° C. The mixture was stirred at 25° C. for 5 hours. The reaction mixture diluted with H$_2$O (100 mL) and extracted with DCM (100 mL×2). The combined organic layers were washed with saturated brine (100 mL×2), dried over Na$_2$SO$_4$, filtered and concentrated under reduced pressure to give a residue. The residue was purified by column chromatography (SiO$_2$, Petroleum ether:Ethyl acetate=20:1 to 5:1) to give A-2 (16 g, 68.02% yield, 97% purity) as a yellow oil. $^1$H-NMR (CDCl$_3$, 400 MHz): δ=7.50-7.45 (m, 3H), 7.45-7.38 (m, 4H), 7.37 (d, J=7.2 Hz, 1H), 7.21 (m, 1H), 5.14 (s, 2H), 2.67 (tt, J$_1$=4.8 Hz, J$_2$=8.0 Hz, 1H), 1.32-1.23 (m, 3H), 1.06 (dd, J$_1$=3.6 Hz, J$_2$=8.0 Hz, 2H).

Step 3:
1-(benzyloxy)-3-(1-cyclopropylvinyl)benzene (A-3

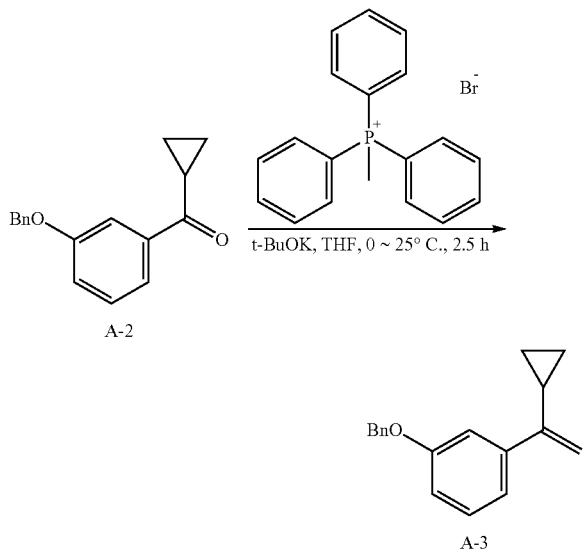

To a solution of methyltriphenylphosphonium bromide (45 g, 0.13 mol, 2 eq) in THF (0.16 L) was added t-BuOK (1 M in THF, 0.13 L, 2 eq) at 0° C., and the reaction was stirred at 0° C. for 30 min. Then A-2 (16 g, 63 mmol, 1 eq) was added at 0° C., and the reaction was stirred at 25° C. for 2 hours. The mixture was quenched with water (50 mL) and extracted with ethyl acetate (300 mL×2). The combined organic phase was washed with saturated brine (100 mL×2), dried with anhydrous Na$_2$SO$_4$, filtered and concentrated in vacuum. The residue was purified by column chromatography (SiO$_2$, Petroleum ether:Ethyl acetate=100:1 to 10:1) to give A-3 (14 g, 71% yield, 80% purity) as a yellow oil. $^1$H-NMR (CDCl$_3$, 400 MHz): δ=7.38-7.32 (m, 2H), 7.27 (s, 2H), 7.25-7.19 (m, 1H), 7.18-7.09 (m, 3H), 6.83-6.78 (m, 1H), 5.17 (d, J=0.8 Hz, 1H), 4.99 (s, 2H), 4.83 (t, J=1.2 Hz, 1H), 1.58-1.46 (m, 1H), 0.77-0.67 (m, 2H), 0.53-0.43 (m, 2H).

Step 4:
2-(3-(benzyloxy)phenyl)-2-cyclopropylethanol (A-4

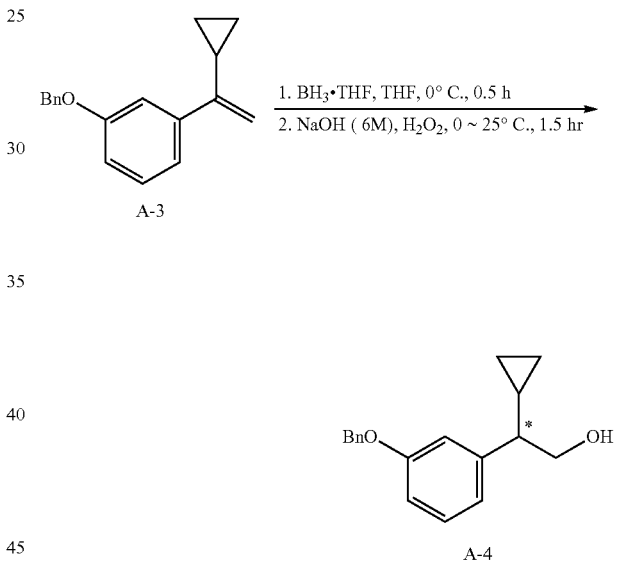

To a solution of A-3 (14 g, 56 mmol, 1 eq) in THF (150 mL) was added BH$_3$·THF (1 M, 0.17 L, 3 eq) at 0° C. for 30 min. Then aqueous NaOH (6 M, 56 mL, 6 eq) and H$_2$O$_2$ (130 g, 1.1 mol, 107 mL, 30% purity, 20 eq) were added at 0° C., and the mixture was stirred at 25° C. for 1.5 hours. The mixture was quenched with water (50 mL) and extracted with ethyl acetate (200 mL×2). The combined organic phase was washed with saturated brine (50 mL×2), dried with anhydrous Na$_2$SO$_4$, filtered and concentrated in vacuum. The residue was purified by column chromatography (SiO$_2$, Petroleum ether:Ethyl acetate=20:1 to 3:1) to give A-4 (11 g, 70% yield, 94% purity) as a colorless oil. $^1$H-NMR (CDCl$_3$, 400 MHz): δ=7.35-7.30 (m, 2H), 7.27 (s, 2H), 7.24-7.18 (m, 1H), 7.14 (t, J=8 Hz, 1H), 6.81-6.78 (m, 1H), 6.77-6.73 (m, 2H), 4.94 (s, 2H), 3.86-3.63 (m, 2H), 1.91-1.84 (m, 1H), 1.44 (s, 1H), 0.93-0.82 (m, 1H), 0.56-0.45 (m, 1H), 0.38-0.28 (m, 1H), 0.22-0.15 (m, 1H), 0.02-0.05 (m, 1H).

Step 5: (S)-2-(3-(benzyloxy)phenyl)-2-cyclopropyl-ethanol (A-5

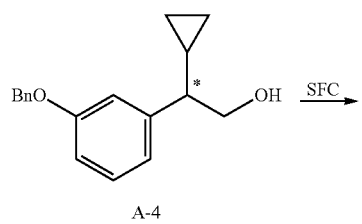

A-4

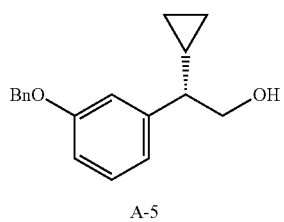

A-5

Compound A-4 (9.1 g) was separated by SFC (column: DAICEL CHIRALPAK AD (250 mm×50 mm, 10 um); mobile phase: [A: $CO_2$, B: 0.1% $NH_4OH$ in MeOH]; B %: 45%-45%) to give A-5 (4.2 g, 45% yield) as a colourless oil. tR=1.767 min on SFC.

Step 6: (S)-1-(benzyloxy)-3-(1-cyclopropyl-2-iodo-ethyl)benzene (A-6

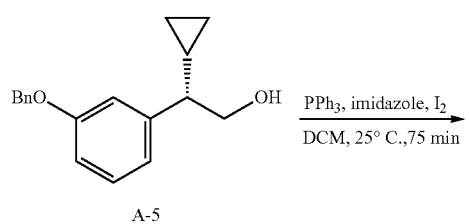

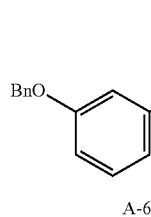

A-6

$PPh_3$ (7.6 g, 29 mmol, 1.5 eq) and imidazole (2.0 g, 29 mmol, 1.5 eq) were dissolved in DCM (50 mL), and the solution was stirred for 5 minutes. Then $I_2$ (7.4 g, 29 mmol, 5.9 mL, 1.5 eq) was added, and the mixture was stirred for 10 minutes. A DCM (170 mL) solution of A-5 (5.2 g, 19 mmol, 1 eq) was added dropwise, and the mixture was stirred at 25° C. for 1 hour. The mixture was poured into water (50 mL) and extracted with dichloromethane (100 mL×2). The combine organic layers were washed with saturated brine (50 mL×2) and concentrated in vacuo. The residue was purified by column chromatography ($SiO_2$, Petroleum ether:Ethyl acetate=1:0 to 100:1) to give A-6 (6.5 g, 89% yield) as a white solid. $^1$H-NMR ($CDCl_3$, 400 MHz): δ=7.27 (s, 2H), 7.25-7.19 (m, 2H), 7.18-7.13 (m, 1H), 7.11-7.03 (m, 1H), 6.73-6.65 (m, 3H), 4.90 (s, 2H), 3.41-3.37 (m, 1H), 3.31-3.27 (m, 1H), 1.94-1.88 (m, 1H), 0.93-0.90 (m, 1H), 0.52-0.40 (m, 1H), 0.34-0.12 (m, 2H), 0.03-0.05 (m, 1H).

Step 7: ethyl ((S)-2-(3-(benzyloxy)phenyl)-2-cyclopropylethyl)(methyl)phosphinate (A-7

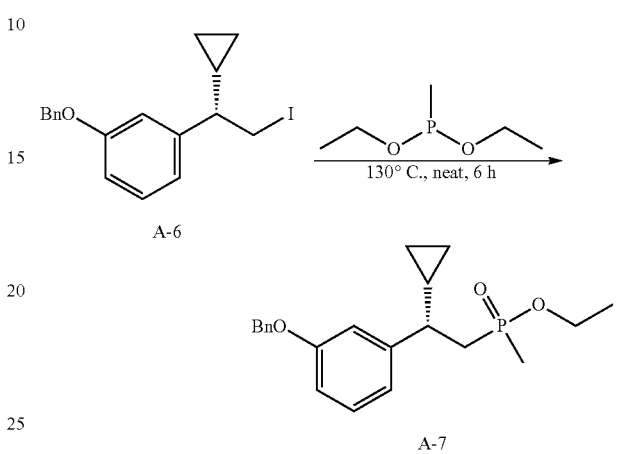

A mixture of A-6 (1.0 g, 2.6 mmol, 1 eq) in diethyl methylphosphonite (7.2 g, 52 mmol, 20 eq) was stirred at 130° C. for 6 hours. The mixture was purified by reversed-phase HPLC (column: Phenomenex luna C18 250×50 mm×10 um; mobile phase: A: water (0.1% FA, v/v), B: ACN; B %: 45%-75% gradient over 30 min) to give A-7 (0.53 g, 59% yield) as a white oil. LCMS: ($ES^+$) m/z $(M+H)^+$=359.2.

Step 8: ethyl ((S)-2-cyclopropyl-2-(3-hydroxyphenyl)ethyl)(methyl)phosphinate (Int-A

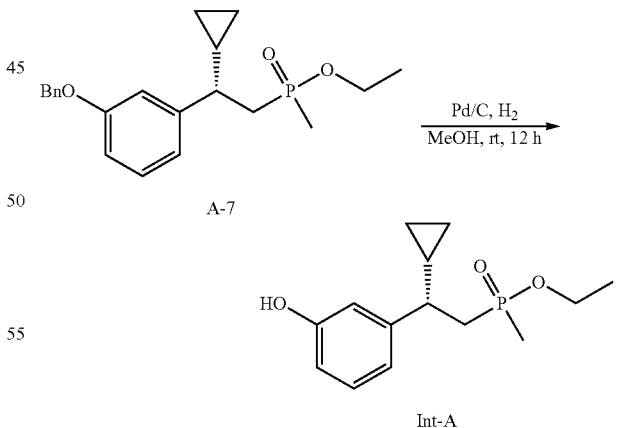

To a solution of A-7 (0.53 g, 1.5 mmol, 1 eq) in MeOH (4.0 ML) was added 5% Pd/C (0.53 g) under $N_2$. The suspension was degassed under vacuum and purged with $H_2$ several times. The mixture was stirred under $H_2$ (50 psi) at 25° C. for 12 hours. The reaction mixture was filtered, and the filtrate was concentrated to give Int-A (0.33 g, crude) as a white oil. LCMS: ($ES^+$) m/z $(M+H)^+$=269.2.

Example 1a: Preparation of ethyl (2-cyclopropyl-2-(3-hydroxyphenyl)ethyl)(methyl)phosphinate (R,S-Int-A Racemic R,S-Int-A was prepared following the procedures outlined in Example 1 Steps 6 to 8 starting from A-4.

Example 2: Preparation of ethyl ((S)-2-cyclopropyl-2-(2-hydroxypyridin-4-yl)ethyl)(methyl)phosphinate (Int-B

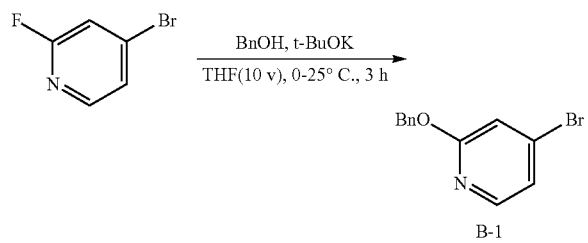

Int-B

Step 1: 2-(benzyloxy)-4-bromopyridine (B-1

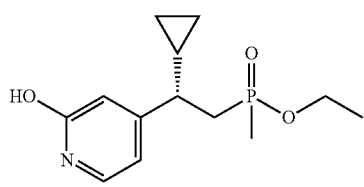

B-1

To a solution of 4-bromo-2-fluoropyridine (0.10 kg, 0.57 mol) and BnOH (61 g, 0.57 mol) in THF (1000 mL) was added t-BuOK (64 g, 0.57 mol) at 0° C. The mixture was stirred at 25° C. for 3 hours. The reaction mixture was quenched by addition of water (500 mL), then diluted with ethyl acetate (500 mL) and extracted with ethyl acetate (200 mL). The organic layer was washed with saturated brine (200 mL), dried over $Na_2SO_4$, filtered and concentrated under reduced pressure to give a residue. The residue was purified by MPLC ($SiO_2$, Petroleum ether: Ethyl acetate=1:0 to 10:1) to give B-1 (0.12 kg, 80% yield) as a yellow oil. $^1$H NMR (400 MHz, $CDCl_3$): δ 7.91-7.81 (m, 1H), 7.35-7.29 (m, 2H), 7.28-7.23 (m, 2H), 7.22-7.17 (m, 1H), 6.96-6.84 (m, 2H), 5.26 (s, 2H).

Step 2: 2-(1-cyclopropylvinyl)-4,4,5,5-tetramethyl-1,3,2-dioxaborolane (B-2

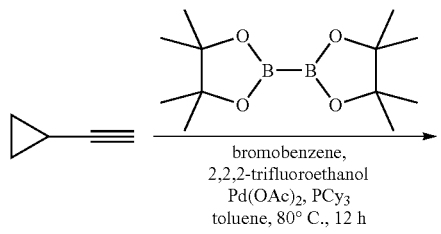

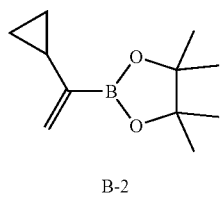

B-2

To a solution of ethynylcyclopropane (50 g, 0.76 mol) and 4,4,4',4',5,5,5',5'-octamethyl-2,2'-bi(1,3,2-dioxaborolane) (0.21 kg, 0.83 mmol) in toluene (1500 mL) was added $Pd(OAc)_2$ (8.5 g, 38 mmol), 2,2,2-trifluoroethanol (0.15 kg, 1.5 mol), $PCy_3$ (21 g, 76 mmol) and bromobenzene (0.12 kg, 0.76 mol). The mixture was stirred at 80° C. for 12 hours. The reaction mixture was concentrated under reduced pressure to give a residue. The residue was purified by column chromatography ($SiO_2$, Petroleum ether:Ethyl acetate=1:0 to 1:1) to give B-2 (72 g, 0.37 mol, 49% yield) as a yellow oil. $^1$H NMR (400 MHz, $CDCl_3$): δ 5.57 (d, J=3.2 Hz, 1H), 5.42 (s, 1H), 1.29-1.26 (m, 1H), 1.19 (s, 11H), 0.64-0.58 (m, 2H), 0.54-0.48 (m, 2H).

Step 3: 2-(benzyloxy)-4-(1-cyclopropylvinyl)pyridine (B-3

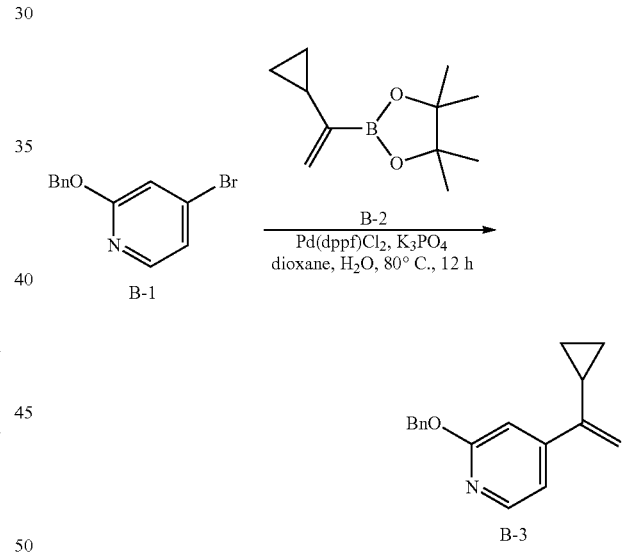

B-3

To a solution of B-1 (0.14 kg, 0.53 mol) and B-2 (0.13 kg, 0.69 mol) in dioxane (1200 mL) and $H_2O$ (400 mL) was added $K_3PO_4$ (0.34 kg, 1.6 mol) and $Pd(dppf)Cl_2$ (39 g, 53 mmol) under $N_2$. The mixture was stirred at 80° C. for 12 hours. The reaction mixture was filtered and concentrated under reduced pressure to give a residue. The reaction mixture was quenched by addition of water (500 mL), then diluted with ethyl acetate (300 mL) and extracted with ethyl acetate (200 mL×3). The combined organic layers were washed with saturated brine (200 mL), dried over $Na_2SO_4$, filtered and concentrated under reduced pressure to give a residue. The residue was purified by MPLC ($SiO_2$, Petroleum ether:Ethyl acetate=1:0 to 10:1) to give B-3 (0.12 kg, 84% yield) as a yellow oil. LCMS: ($ES^+$) m/z $(M+H)^+$=252.2

Step 4: 2-(2-(benzyloxy)pyridin-4-yl)-2-cyclopropylethanol (B-4)

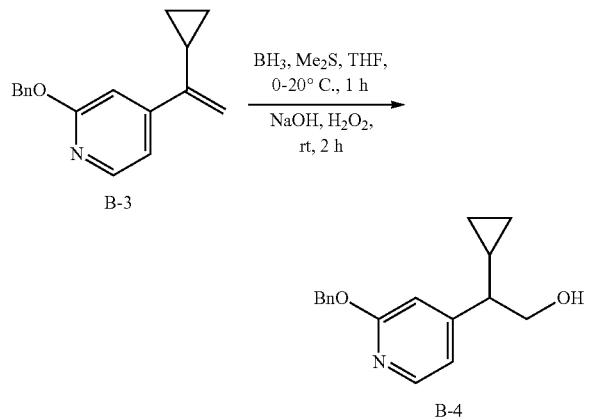

To a solution of B-3 (60 g, 0.24 mol) in THF (500 mL) was added BH$_3$Me$_2$S (10 M in dimethylsulfide, 72 mL) at 0° C. The mixture was stirred at 25° C. for 0.5 hour. NaOH (6 M, 0.24 L) was added to the mixture at 0° C., and then H$_2$O$_2$ (0.27 kg, 2.4 mol, 0.23 L, 30% purity) was added to the mixture at 0° C. The mixture was stirred at 25° C. for 2 hours. The reaction mixture was added to cold saturated Na$_2$SO$_3$. The solution was filtered, then diluted with ethyl acetate (300 mL) and extracted with ethyl acetate (200 mL×3). The combined organic layers were washed with saturated brine (200 mL), dried over Na$_2$SO$_4$, filtered and concentrated under reduced pressure to give a residue. The residue was purified by MPLC (SiO$_2$, Petroleum ether:Ethyl acetate=1:0 to 1:1) to give B-4 (76 g, 59% yield) as a yellow oil. LCMS: (ES$^+$) m/z (M+H)$^+$=270.3.

Step 5: (S)-2-(2-(benzyloxy)pyridin-4-yl)-2-cyclopropylethanol (B-5)

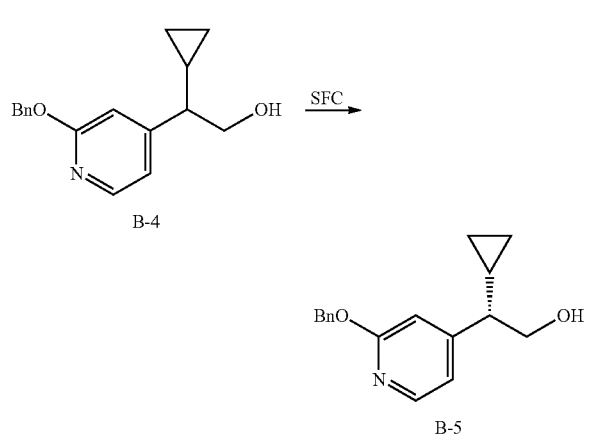

Compound B-4 (38 g) was purified by SFC (column: DAICEL CHIRALPAK AY (250 mm×50 mm, 10 um); mobile phase: [A: CO$_2$, B: 0.1% NH$_4$OH in IPA]; B %: 20%) to give B-5 (16 g, 42% yield) as a yellow oil. tR=1.797 min on SFC.

Step 6: (S)-2-(benzyloxy)-4-(1-cyclopropyl-2-iodoethyl)pyridine (B-6)

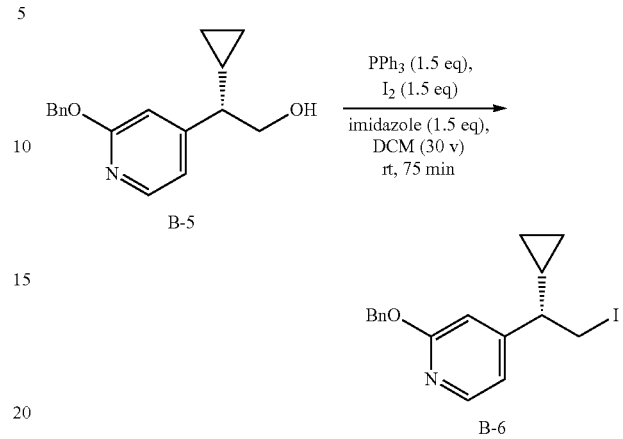

PPh$_3$ (24 g, 91 mmol) and imidazole (6.2 g, 91 mmol) were dissolved in DCM (300 mL), and the solution was stirred for 5 min. Then I$_2$ (23 g, 91 mmol) was added, and the mixture was stirred for 10 min. A DCM (50 mL) solution of B-5 (16 g, 61 mmol) was added dropwise, and the mixture was stirred at 25° C. for 1 hour. The reaction mixture was quenched by addition of water (100 mL), then diluted with DCM (60 mL) and extracted with ethyl acetate (200 mL×1). The combined organic layers were washed with saturated brine (200 mL), dried over Na$_2$SO$_4$, filtered and concentrated under reduced pressure to give a residue. The residue was purified by column chromatography (SiO$_2$, Petroleum ether:Ethyl acetate=1:0 to 1:1) to give B-6 (16 g, 70% yield) as a yellow oil. LCMS: (ES$^+$) m/z (M+H)$^+$=380.0.

Step 7: ethyl ((S)-2-(2-(benzyloxy)pyridin-4-yl)-2-cyclopropylethyl)(methyl)phosphinate (B-7)

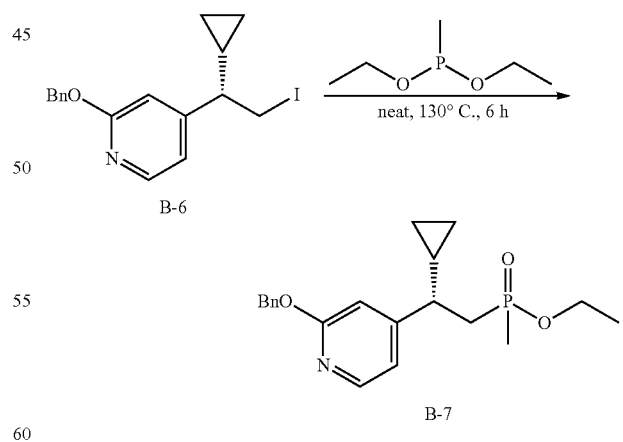

A solution of B-6 (4.0 g, 11 mmol) in diethyl methylphosphonite (29 g, 0.21 mol) was stirred at 130° C. for 6 hours. The reaction mixture was concentrated under reduced pressure to give a residue. The residue was purified by reversed-phase HPLC (column: Phenomenex luna C18 250×50 mm×10 um; mobile phase: A: water (0.1% FA, v/v), B:

ACN; B %: 30%-60% gradient over 50 min) to give B-7 (1.5 g, 40% yield) as a yellow oil. LCMS: (ES+) m/z (M+H)+ =360.2.

Step 8: ethyl ((S)-2-cyclopropyl-2-(2-hydroxypyridin-4-yl)ethyl)(methyl)phosphinate (Int-B

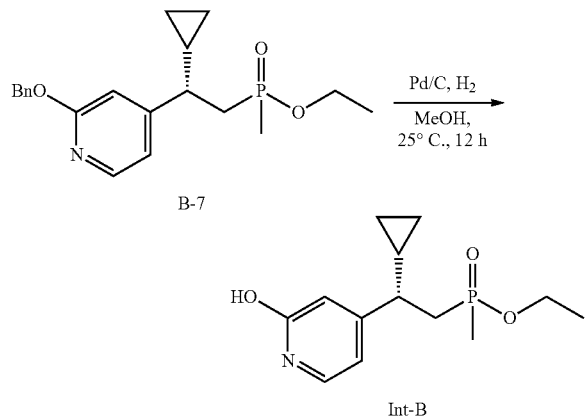

To a solution of B-7 (11 g, 32 mmol) in MeOH (100 mL) was added 5% Pd/C (3.0 g). The mixture was stirred at 25° C. for 12 hours under H$_2$ at 15 psi. The reaction mixture was filtered, and the filtrate was concentrated under reduced pressure to give a residue. The residue was purified by column chromatography (SiO$_2$, Ethyl acetate:EtOH=1:0 to 5:1) to give Int-B (2.2 g, 8.0 mmol, 25% yield) as a yellow oil. LCMS: (ES+) m/z (M+H)+=270.1.

Example 3: Preparation of ethyl (2-(3-hydroxyphenyl)propyl)(methyl)phosphinate (Int-C

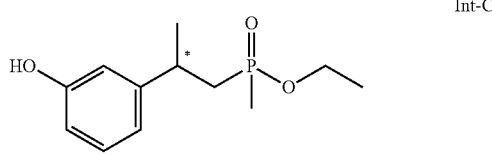 [SMILES: CCOP(C)(=O)CC(C)c1cccc(O)c1]

Step 1: 1-(benzyloxy)-3-(prop-1-en-2-yl)benzene (C-1

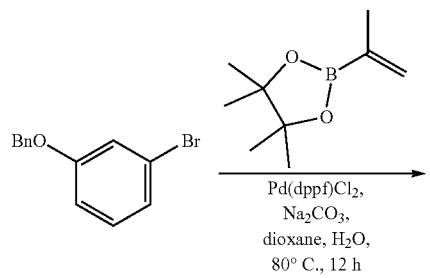

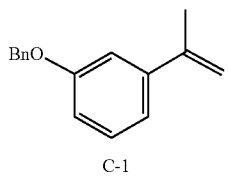

To a solution of 1-benzyloxy-3-bromo-benzene (10 g, 38 mmol, 1 eq), 2-isopropenyl-4,4,5,5-tetramethyl-1,3,2-dioxaborolane (13 g, 76 mmol, 2 eq) in dioxane (100 mL) and H$_2$O (20 mL) was added Pd(dppf)Cl$_2$·CH$_2$Cl$_2$ (0.62 g, 0.76 mmol, 0.02 eq) and Na$_2$CO$_3$ (12 g, 0.11 mol, 3 eq) under N$_2$. The mixture was stirred at 80° C. for 12 hours. The reaction mixture was diluted with water (200 mL) and extracted with ethyl acetate (200 mL×2). The combined organic layers were washed with saturated brine (200 mL×2), dried over Na$_2$SO$_4$, filtered and concentrated under reduced pressure to give a residue. The residue was purified by column chromatography (SiO$_2$, Petroleum ether:Ethyl acetate=100:0 to 100:1) to give C-1 (6.8 g, 80% yield) as a yellow oil. $^1$H NMR (400 MHz, CDCl$_3$) δ 7.65-7.51 (m, 5H), 7.50-7.39 (m, 2H), 7.27-7.24 (m, 1H), 7.11-7.03 (m, 1H), 5.53 (d, J=0.4 Hz, 1H), 5.26 (m, 3H), 2.31 (s, 3H).

Step 2: 2-(3-(benzyloxy)phenyl)propan-1-ol (C-2

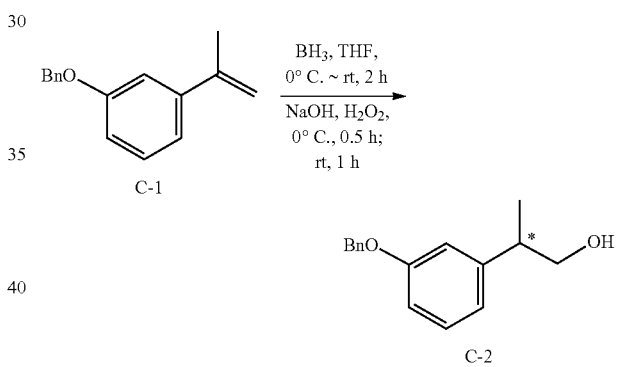

To a solution of C-1 (0.5 g, 2.2 mmol, 1 eq) in THF (10 mL) was added BH$_3$·Me$_2$S (10 M, 0.67 mL, 3 eq) at 0° C. The mixture was stirred at 0° C. for 30 min, and at 25° C. for 2 hours. Then NaOH (6 M, 2.2 mL, 6 eq) was added at 0° C. and stirred for 30 min, H$_2$O$_2$ (1.7 g, 18 mmol, 1.4 mL, 36% purity, 7.9 eq) was added. The mixture was stirred at 25° C. for 1 hour. The reaction mixture was quenched by addition saturated Na$_2$SO$_3$ solution (10 mL), and extracted with ethyl acetate (20 mL×2). The combined organic layers were washed with saturated brine (20 mL×2), dried over Na$_2$SO$_4$, filtered and concentrated under reduced pressure to give a residue. The residue was purified by column chromatography (SiO$_2$, Petroleum ether:Ethyl acetate=95:5 to 90:10) to give a C-2 as a mix of enantiomers (0.40 g, 73% yield) as a yellow oil. $^1$H NMR (400 MHz, CDCl$_3$) δ 7.49-7.29 (m, 5H), 7.27 (s, 1H), 6.92-6.80 (m, 3H), 5.07 (s, 2H), 3.70 (t, J=6.4 Hz, 2H), 3.08-2.83 (m, 1H), 1.27 (d, J=7.2 Hz, 3H). An enantiomeric mixture of C-2 (2.5 g, 10 mmol, 1 eq) was further purified by SFC (column: DAICEL CHIRALPAKAS (250 mm×30 mm, 5 um); mobile phase: [0.1% NH$_3$H$_2$O in MeOH]; B %: 40%-40%, 5.1 min; 55 min). The solution was concentrated under reduced pressure to give C-2(1) (1.2 g, 49% yield, tR=1.45 min) and C-2(2)

(1.2 g, 49% yield, tR=2.04 min) as yellow oil, corresponding to (R)-2-(3-(benzyloxy)phenyl)propan-1-ol and (S)-2-(3-(benzyloxy)phenyl)propan-1-ol (stereochemistry not assigned).

Step 3: 1-(benzyloxy)-3-(1-iodopropan-2-yl)benzene (C-3

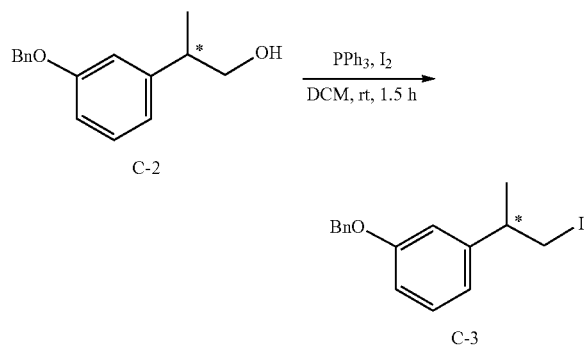

A solution of PPh₃ (2.0 g, 7.4 mmol, 1.5 eq) and imidazole (0.51 g, 7.4 mmol, 1.5 eq) in DCM (10 mL) was stirred at 25° C. for 5 min. Then I2 (1.9 g, 7.4 mmol, 1.5 eq) was added. The mixture was stirred at 25° C. for 25 min. A solution of C-2 (specifically C-2(1), 1.2 g, 5.0 mmol, 1 eq) in DCM (10 mL) was added dropwise. The mixture was stirred at 25° C. for another 1 hour. The reaction solution was diluted with water (50 mL) and extracted with ethyl acetate (50 mL×2). The combined organic layers were washed with saturated brine (40 mL×2), dried over Na₂SO₄, filtered and concentrated under reduced pressure to give a residue. The residue was purified by column chromatography (SiO₂, Petroleum ether:Ethyl acetate=100:0 to 98:2) to give C-3(1) (1.5 g, 85% yield) as a white solid. The corresponding enantiomer C-3(2) (1.0 g, 56% yield) was prepared from C-2(2) according to same procedure.

Step 4: ethyl (2-(3-(benzyloxy)phenyl)propyl)(methyl)phosphinate (C-4

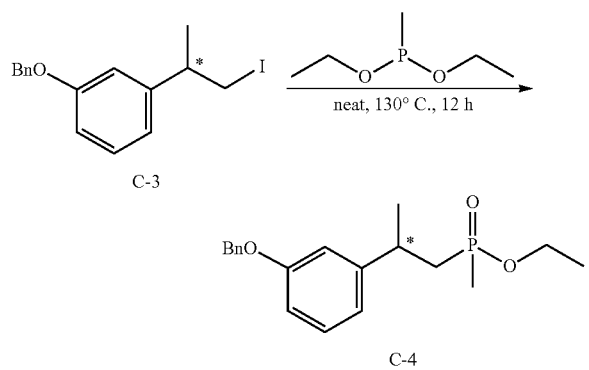

A mixture of C-3(1) (1.5 g, 4.3 mmol, 1 eq) and diethyl methylphosphonite (12 g, 85 mmol, 20 eq) was stirred at 130° C. for 12 hours. The reaction solution was purified by reversed-phase HPLC (column: Phenomenex luna C18 250× 50 mm×10 um, 100 Å; Flow rate: 200 mL/min; mobile phase: A: water (0.1% FA, v/v), B: ACN; B %: 40%-70% gradient over 30 min) to give C-4(1) (0.90 g, 64% yield) as a colourless oil. ¹H NMR (400 MHz, CD₃OD) δ 7.47-7.40 (m, 2H), 7.39-7.26 (m, 3H), 7.22 (m, 1H), 6.97-6.80 (m, 3H), 5.10 (s, 2H), 3.99-3.83 (m, 2H), 3.12 (m, 1H), 2.23-2.06 (m, 2H), 1.39-1.33 (m, 3H), 1.22 (t, J=7.2 Hz, 3H), 1.20-1.08 (m, 3H). C-4(2) (0.9 g, 95% yield) was prepared from C-3(2) according to same procedure. ¹H NMR (400 MHz, CD₃OD) δ 7.47-7.27 (m, 5H), 7.22 (m, 1H), 6.95-6.81 (m, 3H), 5.10 (s, 2H), 4.02-3.80 (m, 2H), 3.13 (m, 1H), 2.27-2.04 (m, 2H), 1.36 (m, 3H), 1.25-1.20 (m, 3H), 1.20-1.09 (m, 3H).

Step 5: ethyl (2-(3-hydroxyphenyl)propyl)(methyl)phosphinate (Int-C

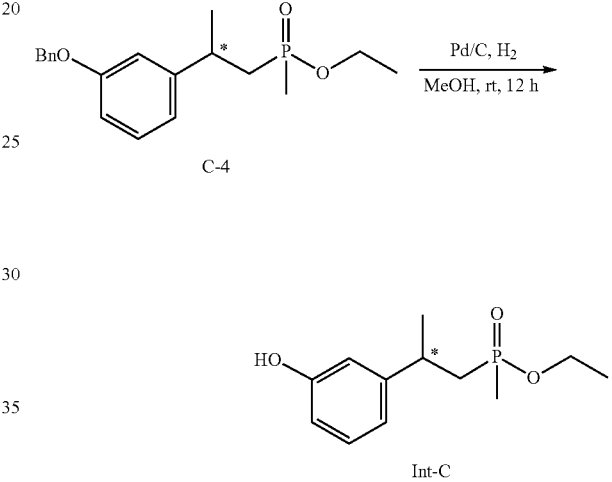

To a solution of C-4(1) (0.90 g, 4.3 mmol, 1 eq) in MeOH (4 mL) was added Pd/C (0.45 g, 10% purity) under N₂. The suspension was degassed under vacuum and purged with H₂ several times. The mixture was stirred under H₂ (15 psi) at 25° C. for 12 hours. The reaction mixture was filtered and concentrated under reduced pressure to give Int-C(1) (0.60 g, crude) as a colourless oil. LCMS: tR=0.458, (ES+) m/z (M+H)⁺=243.4. Int-C(2) (0.57 g, crude) was prepared from C-4(2) according to same procedure. LCMS: tR=0.462, (ES+) m/z (M+H)⁺=243.4. Int-C(1) and Int-C(2) correspond to ethyl ((R)-2-(3-hydroxyphenyl)propyl)(methyl)phosphinate and ethyl ((S)-2-(3-hydroxyphenyl)propyl)(methyl) phosphinate, respectively.

Example 4: Preparation of ethyl (2-(2-hydroxypyridin-4-yl)propyl)(methyl)phosphinate (Int-D

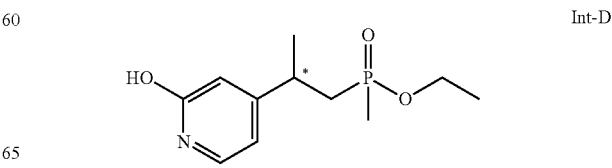

Step 1: 2-(benzyloxy)-4-bromopyridine (D-1

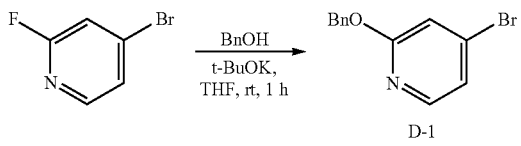

To a solution of 4-bromo-2-fluoro-pyridine (10 g, 57 mmol, 1 eq) and phenylmethanol (6.1 g, 57 mmol, 5.9 mL, 1 eq) in THF (100 mL) was added at t-BuOK (7.0 g, 63 mmol, 1.1 eq) at 0° C. The mixture was stirred at 25° C. for 1 hr. The solution was diluted with H₂O (100 mL) and extracted with EA (100 mL×2). The combined organic layers were washed with saturated brine (50 mL), concentrated under reduced pressure to give a residue. The residue was purified by column chromatography (SiO₂, Petroleum ether:Ethyl acetate=99:1 to 95:5) to give D-1 (9.1 g, 60% yield) as a yellow oil. LCMS: tR=0.768 min., (ES+) m/z (M+H)⁺=264.1.

Step 2: 2-(benzyloxy)-4-(prop-1-en-2-yl)pyridine (D-2

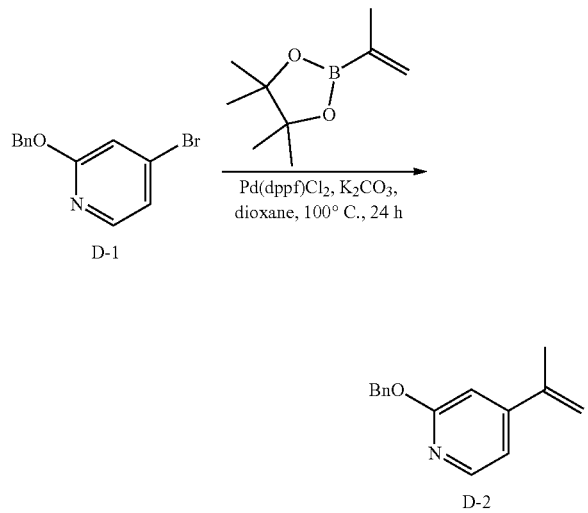

To a solution of D-1 (9.1 g, 34 mmol, 1 eq) and 2-isopropenyl-4,4,5,5-tetramethyl-1,3,2-dioxaborolane (7.0 g, 41 mmol, 1.2 eq) in dioxane (100 mL) and H₂O (20 mL) was added K₂CO₃ (9.5 g, 69 mmol, 2 eq) and Pd(dppf)Cl₂ (1.3 g, 1.7 mmol, 0.05 eq). The solution was stirred at 100° C. for 24 hrs. The solution was filtered, filtrate was diluted with water (50 mL) and extracted with EA (50 mL×2). The combined organic layers were washed with saturated brine (50 mL), concentrated under reduced pressure to give a residue. The residue was purified by column chromatography (SiO₂, Petroleum ether/Ethyl acetate=97/3 to 95/5) to give a D-2 (6.6 g, 77% yield, 90% purity) as a yellow oil. ¹H NMR (400 MHz, CD₃OD) δ ppm 7.94-8.30 (m, 1H); 7.15-7.58 (m, 5H); 6.70-7.13 (m, 2H); 5.42-5.72 (m, 1H); 5.13-5.39 (m, 3H); 1.88-2.25 (m, 3H).

Step 3: 2-(2-(benzyloxy)pyridin-4-yl)propan-1-ol (D-3

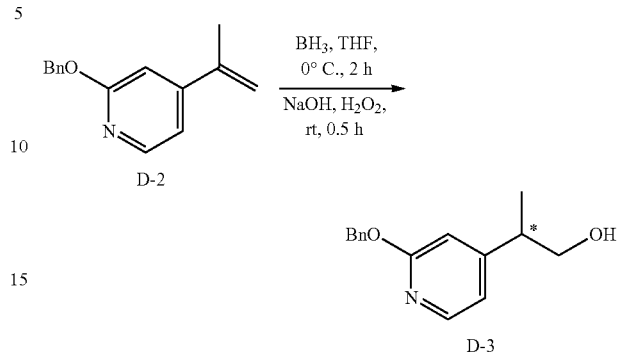

To a solution of D-2 (6.6 g, 30 mmol, 1 eq) in THF (60 mL) was added BH₃-Me₂S (10 M, 8.8 mL, 3 eq) at 0° C. and stirred at 0° C. for 2 hrs, then NaOH (6 M, 25 mL, 5 eq) was added dropwise to the mixture slowly at 0° C., and H₂O₂ (20 g, 0.2 mol, 17 mL, 30% purity, 6 eq) was added dropwise to the mixture at 0° C. The mixture was stirred at 25° C. for 0.5 hour. The reaction mixture was quenched by addition saturated Na₂SO₃ (150 mL) at 0° C., and then diluted with water (50 mL) and extracted with ethyl acetate (100 mL×3). The combined organic layers were washed with sat brine (200 mL), dried over Na₂SO₄, filtered and concentrated under reduced pressure to give a residue. The residue was purified by column chromatography (SiO₂, Petroleum ether/Ethyl acetate=30/1 to 20/1) to give D-3 (4.5 g, 63% yield) as a yellow oil. ¹H NMR (400 MHz, CD₃OD) δ ppm; 8.03 (d, J=5.6 Hz, 1H); 7.38-7.64 (m, 2H); 7.11-7.37 (m, 3H); 6.87 (dd, J=5.0, 1.4 Hz, 1H); 6.69-6.78 (m, 1H); 4.86 (s, 2H); 3.64 (qd, J=10, 6.7 Hz, 2H); 2.74-2.96 (m, 1H); 1.24 (d, J=7.2 Hz, 3H).

Enantiomeric forms of D-3, (R)-2-(2-(benzyloxy)pyridin-4-yl)propan-1-ol and (S)-2-(2-(benzyloxy)pyridin-4-yl)propan-1-ol (D-3(1) and D-3(2), stereochemistry not assigned) were isolated from D-3 (4.5 g, 19 mmol, 1 eq) by SFC column: DAICEL CHIRALPAK AD (250 mm×50 mm, 10 um); mobile phase: [0.1% NH₃H₂O MEOH]; B %: 25%-25%, 3.7; 90 min. to give D-3(1) (2 g, 44% yield, tR=1.340 min) and D-3(2) (1.73 g, 38% yield, tR=1.648 min) as a yellow gum.

Step 5: 2-(2-(benzyloxy)pyridin-4-yl)propyl 4-methylbenzenesulfonate (D-4

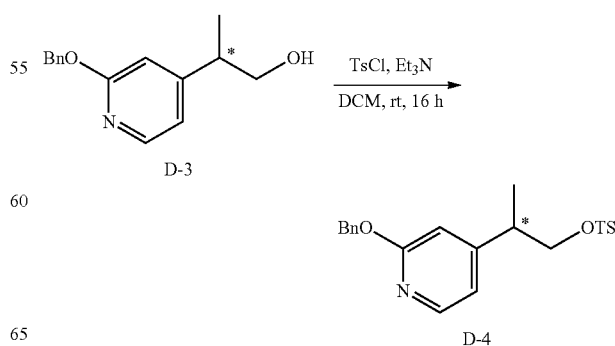

To a solution of D-3(1) (2 g, 8.2 mmol, 1 eq) in DCM (20 mL) was added Et₃N (2.5 g, 25 mmol, 3.4 mL, 3 eq) and DMAP (0.2 g, 1.2 mmol, 0.2 eq). The solution was cooled at 0° C., then TsCl (1.2 g, 16 mmol, 2 eq) was added. The solution was stirred at 25° C. for 16 hrs. The solution was diluted with H₂O (100 mL) and extracted with EA (100 mL×2). The combined organic layers were washed with brine (50 mL), concentrated under reduced pressure to give a residue. The residue was purified by column chromatography (SiO₂, Petroleum ether:Ethyl acetate=20:1 to 5:1) to give D-4(1) (3.2 g, 95% yield) as a yellow oil. LCMS: tR=0.686 min., (ES+) m/z (M+H)⁺=398.6. D-4(2) (2.5 g, 70% yield, 80% purity) was prepared from D-3(2) according to same procedure.

Step 6: ethyl (2-(2-(benzyloxy)pyridin-4-yl)propyl)(methyl)phosphinate (D-5

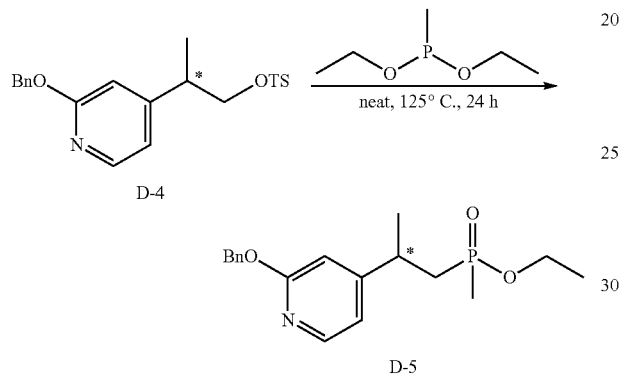

A mixture of D-4(1) (3.2 g, 8.2 mmol, 1 eq) and diethoxy(methyl)phosphane (22 g, 0.20 mol, 20 eq) were degassed and purged with N₂ for 3 times. The mixture was stirred at 125° C. for 24 hrs. The solution was diluted with H₂O (100 mL) and extracted with EA (100 mL×2). The combined organic layers were washed with brine (100 mL), concentrated under reduced pressure to give a residue. The residue was purified by column chromatography (SiO₂, Ethyl acetate:Methanol=10:1) to give D-5(1) (1.2 g, 34% yield, 75% purity) as a yellow oil. LCMS: tR=0.509 min., (ES+) m/z (M+H)⁺=334.1. D-5(2) (0.33 g, 10% yield) was prepared from D-4(2) according to same procedure.

Step 7: ethyl (2-(2-hydroxypyridin-4-yl)propyl)(methyl)phosphinate (Int-D

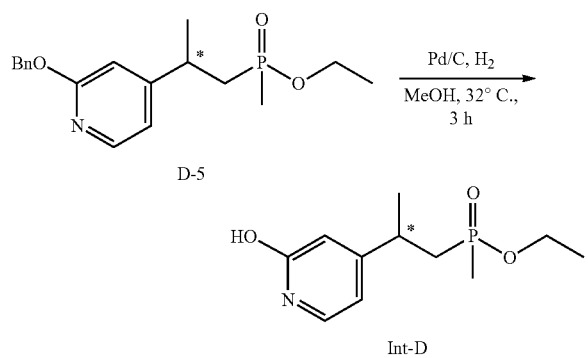

To a solution of D-5(1) (1.2 g, 3.7 mmol, 1 eq) in MeOH (150 mL) was added Pd/C (0.1 g, 66 mmol, 5% purity, 18 eq) under N₂. The suspension was degassed under vacuum and purged with H₂ several times. The mixture was stirred under H₂ (15 psi) at 32° C. for 3 hrs. The solution was filtered and concentrated under reduced pressure to give Int-D(1) (0.90 g, 50% yield, 50% purity) as a yellow oil. LCMS: tR=0.271 min., (ES+) m/z (M+H)⁺=244.1. Int-D(2) (0.20 g, 43% yield, 52% purity) was prepared from D-5(2) according to same procedure. Specific stereochemistry of enantiomers Int-D(1) and Int-D(2) were not assigned.

Example 5: Preparation of (trans)-4-(2-fluoro-5-methoxyphenyl)cyclohexyl)methyl methanesulfonate (Int-E

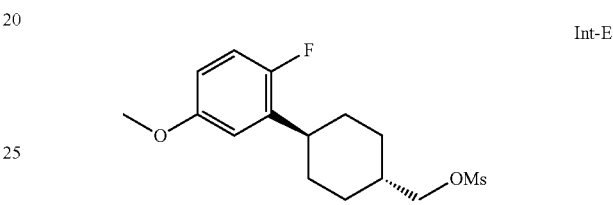

Step 1: methyl 4-(((perfluorobutyl)sulfonyl)oxy)cyclohex-3-enecarboxylate (E-1

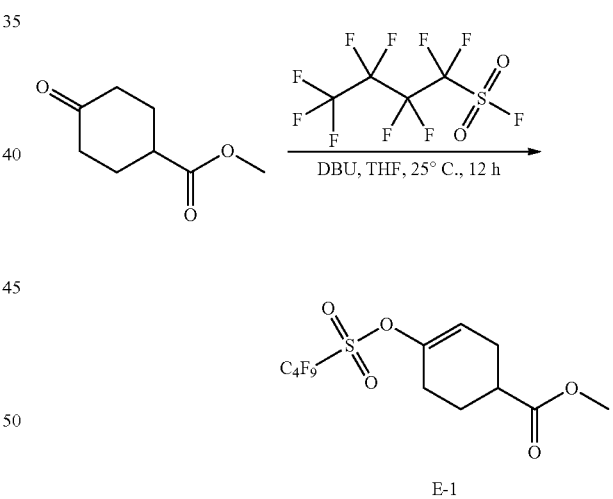

To a solution of methyl 4-oxocyclohexanecarboxylate (15 g, 96 mmol) in THF (30 mL) was added a solution of 1,1,2,2,3,3,4,4,4-nonafluorobutane-1-sulfonyl fluoride (33 g, 0.11 mol) in THF (35 mL). Then DBU (17 g, 0.11 mol, 17 mL) in THF (35 mL) was added to the mixture and an additional portion of THF (35 mL) was added to the mixture. The mixture was stirred at 25° C. for 12 hrs. Ice water (300 mL) was added to the mixture followed by NaCl (20 g) and EA (300 mL). The mixture was stirred for 0.5 hr. The organic phase was washed with saturated brine (300 mL). The organic phase was concentrated in vacuo to give E-1 (45 g) as a yellow oil, which was used for next step directly.

Step 2: methyl 2'-fluoro-5'-methoxy-2,3,4,5-tetra-hydro-[1,1'-biphenyl]-4-carboxylate (E-2

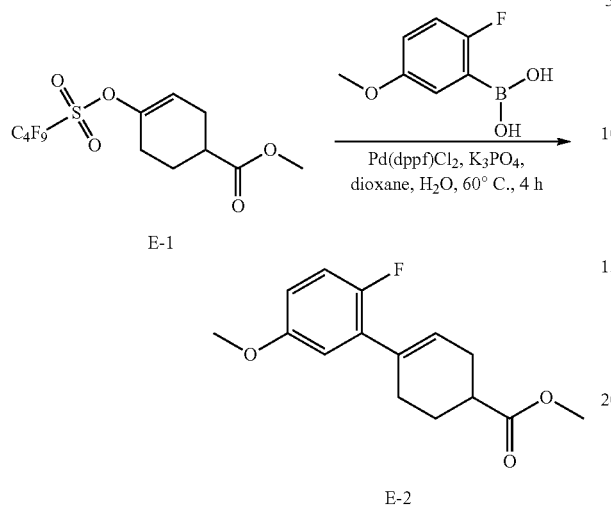

To a solution of methyl E-1 (44 g, 0.10 mol) in dioxane (150 mL) and H$_2$O (20 mL) was added (2-fluoro-5-methoxy-phenyl)boronic acid (13 g, 74 mmol), K$_3$PO$_4$ (56 g, 272 mmol) and Pd(dppf)Cl$_2$ (4.0 g, 5.0 mmol). The mixture was stirred at 60° C. for 4 hrs. The mixture was poured into H$_2$O (300 mL), then extracted with ethyl acetate (300 mL×2). The organic phase was concentrated in vacuo to give a residue. The residue was purified by column chromatography (SiO$_2$, Petroleum ether/Ethyl acetate=30/1 to 10/1) to give E-2 (14.2 g, 73% yield) as a colorless oil. LCMS: tR=0.988 min., (ES$^+$) m/z (M+H)$^+$=265.1. $^1$H NMR (400 MHz, CD$_3$OD) δ=6.98-6.90 (m, 1H), 6.80-6.72 (m, 2H), 5.60 (br d, J=2.1 Hz, 1H), 3.76 (s, 3H), 3.70 (s, 3H), 2.68 (m, 1H), 2.53-2.25 (m, 4H), 2.18-2.06 (m, 1H), 1.88-1.72 (m, 1H).

Step 3: methyl 4-(2-fluoro-5-methoxyphenyl)cyclohexanecarboxylate (E-3

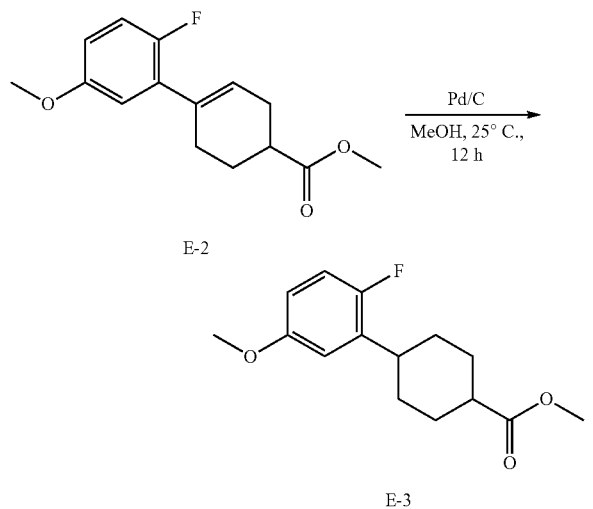

To a solution of E-2 (14 g, 54 mmol) in THF (150 mL) was added Pd/C (1.4 g, 5%). The mixture was stirred at 25° C. for 12 hrs under H$_2$ at 15 psi. The mixture was filtered to removed Pd/C. The organic phase was concentrated in vacuo to give E-3 (14.2 g, 99% yield) as a colorless oil. LCMS: (ES$^+$) m/z (M+H)$^+$=267.2.

Step 4: (trans)-methyl 4-(2-fluoro-5-methoxyphenyl)cyclohexanecarboxylate (E-4

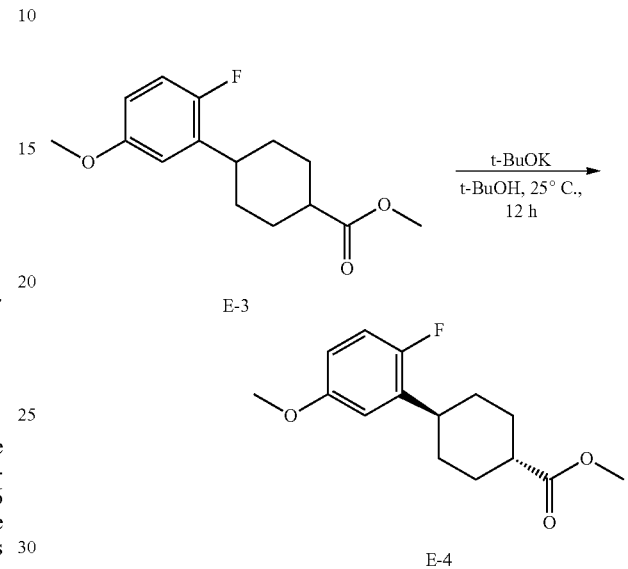

To a solution of E-3 (14 g, 53 mmol) in t-BuOH (140 mL) was added t-BuOK (12 g, 107 mmol). The mixture was stirred at 25° C. for 12 hrs, at which time the chiral purity was 97.2%. The mixture was quenched by the addition of saturated aqueous NH$_4$Cl (200 mL), then extracted with ethyl acetate (200 mL×2). The organic phase was concentrated in vacuo to give a residue. The residue was purified by column chromatography (SiO2, petroleum ether/ethyl acetate=10/1 to 1/1) to give E-4 (4.3 g, 24% yield) as a white solid. LCMS: (ES$^+$) m/z (M+H)$^+$=436.3.

Step 5: ((trans)-4-(2-fluoro-5-methoxyphenyl)cyclohexyl)methanol (E-5

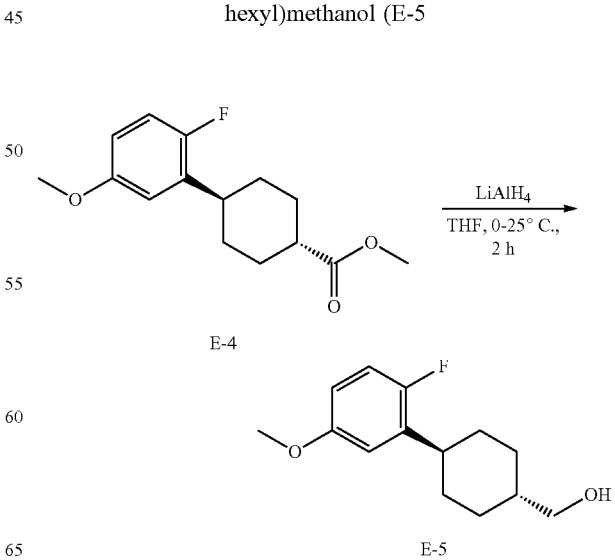

To a solution of E-4 (4.3 g, 16 mmol) in THF (50 mL) was added LiAlH₄ (1.2 g, 32 mmol) at 0° C. The mixture was stirred at 25° C. for 2 hrs. The mixture was quenched by the addition of H₂O (1.23 mL). NaOH (15% aqueous solution, 1.23 mL) and H₂O (3.7 mL) were added. Then the mixture was filtered to remove the solid, and the filtrate was concentrated in vacuo to give a residue. The residue was purified by SFC (column: DAICEL CHIRALPAK AD-H 250×30 mm×5 um; mobile phase: A: CO₂; B: 0.1% NH₄OH in EtOH; B %: 25%-25% gradient over 3.7 min) to give E-5 (2.3 g, 60% yield) as a white solid. LCMS: (ES⁺) m/z (M−OH⁻)=221.2. ¹H NMR (400 MHz, CDCl₃) δ=6.96 (dd, J=9.0, 9.8 Hz, 1H), 6.72 (dd, J=3.2, 6.0 Hz, 1H), 6.68 (td, J=3.5, 8.8 Hz, 1H), 3.80 (s, 3H), 3.52 (d, J=6.1 Hz, 2H), 2.88-2.76 (m, 1H), 1.96 (m, 4H), 1.88 (m, 1H), 1.60 (m, 1H), 1.55-1.43 (m, 2H), 1.16 (m, 2H).

Step 6: ((trans)-4-(2-fluoro-5-methoxyphenyl)cyclohexyl)methyl methanesulfonate (Int-E

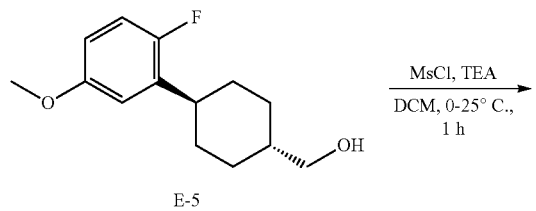

To a solution of E-5 (4.9 g, 21 mmol) and Et₃N (4 g, 41 mmol, 5.7 mL) in DCM (50 mL) was added MsCl (4.7 g, 41 mmol, 3.2 mL) at 0° C. The mixture was stirred at 25° C. for 1 hr. The mixture was poured into H₂O (50 mL), then extracted with ethyl acetate (50 mL×2). The organic phase was concentrated in vacuo to give a residue. The residue was purified by column chromatography (SiO2, Petroleum ether/Ethyl acetate=10/1 to 3/1) to give Int-E (6.2 g, 95% yield) as a white solid. ¹H NMR (400 MHz, CD₃OD) δ=6.92 (dd, J=9.0, 10.0 Hz, 1H), 6.80 (dd, J=3.2, 6.0 Hz, 1H), 6.72 (td, J=3.5, 8.8 Hz, 1H), 4.08 (d, J=6.4 Hz, 2H), 3.76 (s, 3H), 3.06 (s, 3H), 2.80 (m, 1H), 2.00-1.88 (m, 4H), 1.87-1.79 (m, 1H), 1.66-1.50 (m, 2H), 1.34-1.18 (m, 2H).

Example 6: Preparation of (1-(2-(4,4-dimethylpentyl)-5-methoxyphenyl)piperidin-4-yl)methanol (Int-F

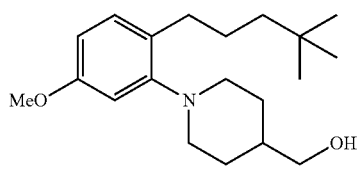

Step 1: 3,3-dimethylbutyl methanesulfonate (F-1

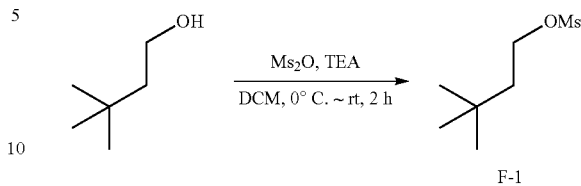

To a solution of 3,3-dimethylbutan-1-ol (5 g, 49 mmol, 6.2 mL, 1 eq) and TEA (12 g, 0.12 mol, 17 mL, 2.5 eq) in DCM (50 mL) was added methylsulfonyl methanesulfonate (11 g, 64 mmol, 1.3 eq) at 0° C. The reaction was stirred at 25° C. for 2 hrs. The reaction mixture was quenched by addition of saturated aqueous NH₄C₁ (5 mL) at 0° C., and then diluted with water (100 mL) and extracted with EA (100 mL×2). The combined organic layers were washed with sat brine (150 mL×2), dried over Na₂SO₄, filtered and concentrated under reduced pressure to give F-1 (3.1 g, crude) as a colorless oil. ¹H NMR (400 MHz, CDCl₃) δ ppm 0.96 (s, 9H) 1.69 (t, J=7.6 Hz, 2H) 3.00 (s, 3H) 4.28 (t, J=7.5 Hz, 2H).

Step 2: (3,3-dimethylbutyl)triphenylphosphonium methanesulfonate (F-2

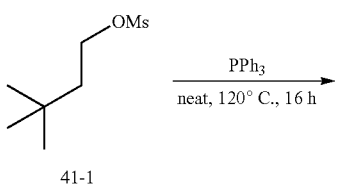

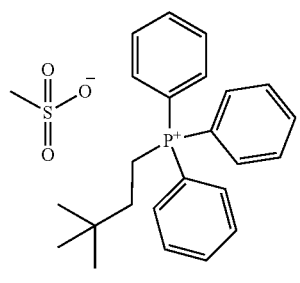

A mixture of F-1 (3.1 g, 17 mmol, 1 eq) and PPh₃ (4.5 g, 17 mmol, 1 eq) was stirred at 120° C. for 16 hr. The reaction was cooled to room temperature. The reaction mixture was purified by recrystallization from petroleum ether solvent (20 mL) to give F-2 (6 g, crude) as an off-white solid.

Step 3: methyl 1-(2-formyl-5-methoxyphenyl)piperidine-4-carboxylate (F-3)

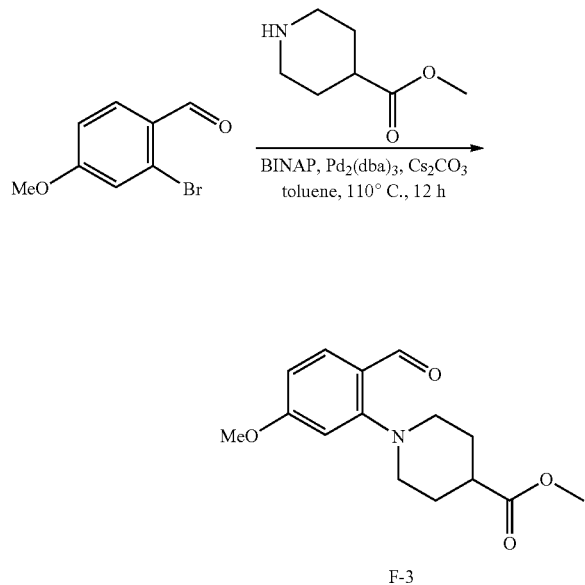

To a solution of 2-bromo-4-methoxy-benzaldehyde (2.0 g, 9.3 mmol, 1 eq) and methyl piperidine-4-carboxylate (1.3 g, 9.3 mmol, 1 eq) in toluene (20 mL) was added BINAP (0.23 g, 0.37 mmol, 0.04 eq) and $Cs_2CO_3$ (4.6 g, 14 mmol, 1.5 eq). Then $Pd_2(dba)_3$ (0.17 g, 0.19 mmol, 0.02 eq) was added under $N_2$ atmosphere. The reaction was stirred at 110° C. for 12 hrs. The reaction mixture was diluted with water (50 mL) and extracted with EA (50 mL×3). The combined organic layers were washed with sat brine (100 mL×2), dried over $Na_2SO_4$, filtered and concentrated under reduced pressure to give a residue. The residue was purified by column chromatography ($SiO_2$, Petroleum ether/Ethyl acetate=10/1 to 5/1) to give F-3 (2.4 g, 93% yield) as a yellow oil. LCMS: $(ES^+)$ m/z $(M+H)^+=278.2$

Step 4: (E)-methyl 1-(2-(4,4-dimethylpent-1-en-1-yl)-5-methoxyphenyl)piperidine-4-carboxylate (F-4)

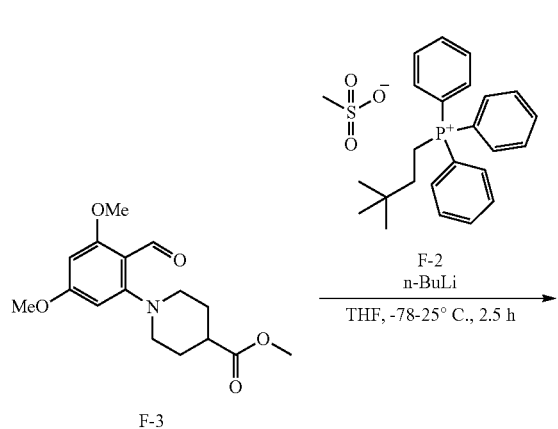

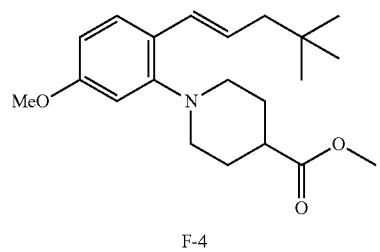

To a solution of F-2 (2.3 g, 6.5 mmol, 1.5 eq) in THF (20 mL) was added n-BuLi (2.5 M in n-hexane, 4.3 mL, 2.5 eq) at −78° C. The reaction was stirred at −78° C. for 0.5 hr, then a mixture of F-3 (1.2 g, 4.3 mmol, 1 eq) in THF (10 mL) was added dropwise. The cold bath was removed, and the reaction was stirred at 25° C. for 2 hrs. The reaction mixture was quenched by addition of saturated aqueous $NH_4Cl$ (10 mL) at 0° C., diluted with water (50 mL) and extracted with EA (50 mL×3). The combined organic layers were washed with saturated brine (150 mL×2), dried over $Na_2SO_4$, filtered and concentrated under reduced pressure to give a residue. The residue was purified by column chromatography ($SiO_2$, Petroleum ether/Ethyl acetate=I/O to 100/1) and reversed-phase HPLC (column: Welch Ultimate XB_C18 250×50 mm×40 μm; mobile phase: [A: water (0.1% FA, v/v), B: ACN]; B %: 20%-65% gradient over 40 min) to give F-4 (0.7 g, 47% yield) as a colorless oil.

Step 5: methyl 1-(2-(4,4-dimethylpentyl)-5-methoxyphenyl)piperidine-4-carboxylate (F-5)

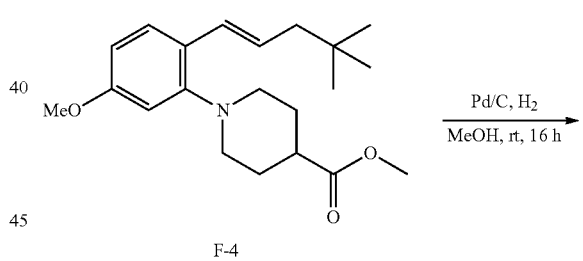

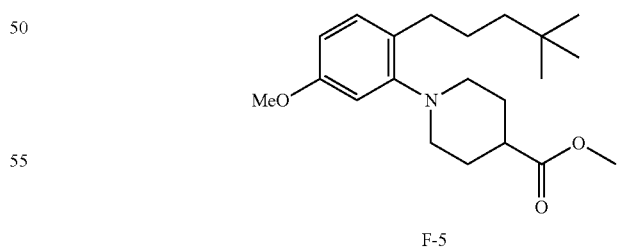

To a solution of F-4 (1.6 g, 4.6 mmol, 1 eq) in MeOH (15 mL) was added 5% Pd/C (0.4 g) under $N_2$. The suspension was degassed under vacuum and purged with $H_2$ several times. The mixture was stirred under $H_2$ (15 psi) at 25° C. for 16 hours. The reaction mixture was filtered and concentrated under reduced pressure to give F-5 (1.6 g, 99% yield) as colorless oil.

Step 6: (1-(2-(4,4-dimethylpentyl)-5-methoxyphenyl)piperidin-4-yl)methanol (Int-F

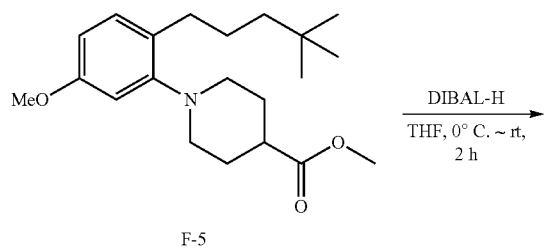

F-5

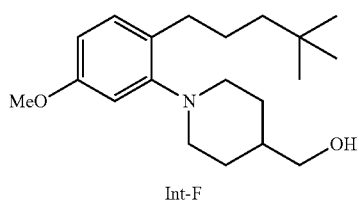

Int-F

To solution of F-5 (1.6 g, 4.6 mmol, 1 eq) in THF (20 mL) was added DIBAL-H (1 M in THF, 14 mL, 3 eq) at 0° C. under $N_2$ atmosphere. The reaction was stirred at 25° C. for 2 hrs. The reaction mixture was quenched by addition of saturated aqueous $NH_4Cl$ (10 mL) at 0° C., and then diluted with water (60 mL) and extracted with EA (60 mL×3). The combined organic layers were washed with saturated brine (100 mL×2), dried over $Na_2SO_4$, filtered and concentrated under reduced pressure to give a residue. The residue was purified by column chromatography ($SiO_2$, Petroleum ether/Ethyl acetate=5/1 to 3/1) to give Int-F (1.2 g, 81% yield) as a colorless oil. LCMS: (ES$^+$) m/z (M+H)$^+$=320.8. $^1$H NMR (400 MHz, CDCl$_3$) δ ppm 7.12 (d, J=8.4 Hz, 1H) 6.66 (d, J=2.4 Hz, 1H) 6.59 (dd, J=8.4, 2.63 Hz, 1H) 3.79 (s, 3H) 3.58 (d, J=6.4 Hz, 2H) 3.11 (br d, J=11.6 Hz, 2H) 2.60-2.73 (m, 2H) 2.48-2.58 (m, 2H) 1.83 (br dd, J=12, 1.75 Hz, 2H) 1.52-1.62 (m, 2H) 1.45 (br d, J=2.4 Hz, 3H) 1.17-1.31 (m, 2H) 0.89 (s, 9H).

Example 7: Preparation of methyl hydrogen (2-cyclopropyl-2-(3-(((trans)-4-(2-fluoro-5-methoxyphenyl)cyclohexyl)methoxy)phenyl)ethyl)phosphonate (Compound 1)

Compound 1

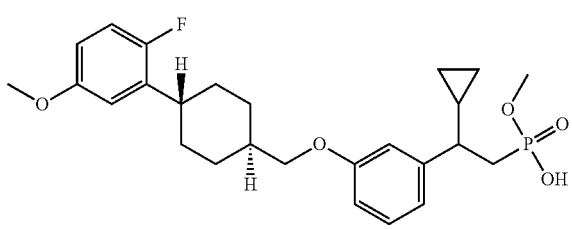

Step 1: (3-(benzyloxy)phenyl)(cyclopropyl)methanol (1-1

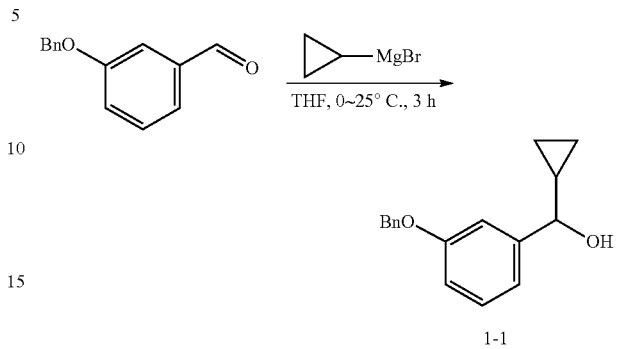

1-1

To a solution of 3-(benzyloxy)benzaldehyde (25 g, 0.12 mol, 1 eq) in THF (450 mL) was added cyclopropylmagnesium bromide (0.50 M in THF, 0.71 L, 3 eq) at 0° C. The mixture was stirred at 25° C. for 3 hours. The reaction mixture was quenched by addition of water (300 mL) at 0° C., then diluted with ethyl acetate (300 mL) and extracted with ethyl acetate (300 mL×3). The combined organic layers were washed with saturated brine (100 mL×3), dried over $Na_2SO_4$, filtered and concentrated under reduced pressure to give a residue. The residue was purified by column chromatography ($SiO_2$, Petroleum ether:Ethyl acetate=10:1 to 0:1) to give 1-1 (23 g, 68% yield, 89% purity) as a yellow oil. $^1$H-NMR (DMSO-d$_6$, 400 MHz): δ=7.49-7.42 (m, 2H), 7.39 (t, J=7.2 Hz, 2H), 7.33 (d, J=7.2 Hz, 1H), 7.22 (t, J=7.6 Hz, 1H), 7.03 (s, 1H), 6.96 (d, J=7.6 Hz, 1H), 6.87 (dd, $J_1$=2.4 Hz, $J_2$=8 Hz, 1H), 5.14 (d, J=4.4 Hz, 1H), 5.09 (s, 2H), 3.96-3.90 (m, 1H), 1.16-0.95 (m, 1H), 0.48-0.28 (d, J=7.2 Hz, 4H).

Step 2: (3-(benzyloxy)phenyl)cyclopropyl)methanone (1-2

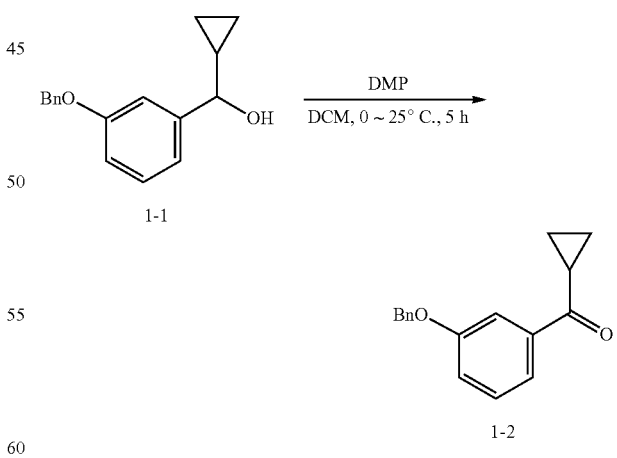

To a solution of 1-1 (23 g, 90 mmol, 1 eq) in DCM (0.23 L) was added DMP (58 g, 0.14 mol, 42 mL, 1.5 eq) at 0° C. The mixture was stirred at 25° C. for 5 hours. The reaction mixture diluted with $H_2O$ (100 mL) and extracted with DCM (100 mL×2). The combined organic layers were washed with saturated brine (100 mL×2), dried over Na₂SO₄, filtered and concentrated under reduced pressure to give a residue. The residue was purified by column chromatography (SiO₂, Petroleum ether:Ethyl acetate=20:1 to 5:1) to give 1-2 (16 g, 68.02% yield, 97% purity) as a yellow oil. ¹H-NMR (CDCl₃, 400 MHz): δ=7.50-7.45 (m, 3H), 7.45-7.38 (m, 4H), 7.37 (d, J=7.2 Hz, 1H), 7.21 (m, 1H), 5.14 (s, 2H), 2.67 (tt, J₁=4.8 Hz, J₂=8.0 Hz, 1H), 1.32-1.23 (m, 3H), 1.06 (dd, J₁=3.6 Hz, J₂=8.0 Hz, 2H).

Step 3:
1-(benzyloxy)-3-(1-cyclopropylvinyl)benzene (1-3

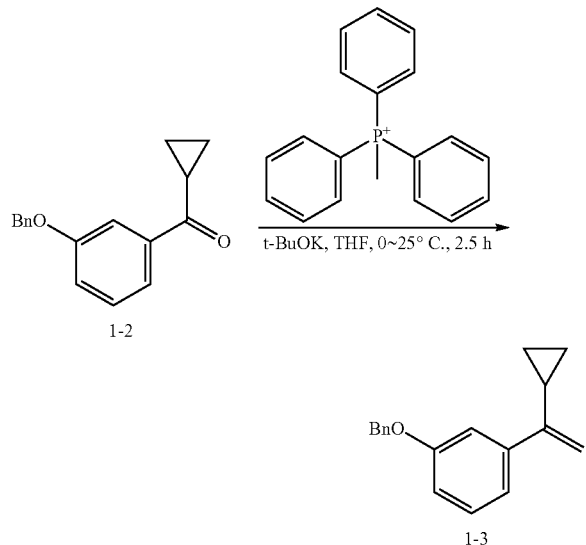

To a solution of methyltriphenylphosphoniun bromide (45 g, 0.13 mol, 2 eq) in THF (0.16 L) was added t-BuOK (1 M, 0.13 L, 2 eq) at 0° C. The reaction was stirred at 0° C. for 30 min, then 1-2 (16 g, 63 mmol, 1 eq) was added at 0° C. The reaction was stirred at 25° C. for 2 hours. The mixture was quenched by the addition of water (50 mL) and extracted with ethyl acetate (300 mL×2). The combined organic phase was washed with saturated brine (100 mL×2), dried with anhydrous Na₂SO₄, filtered and concentrated in vacuum. The residue was purified by column chromatography (SiO₂, Petroleum ether:Ethyl acetate=100:1 to 10:1) to give 1-3 (14 g, 71% yield, 80% purity) as a yellow oil. ¹H-NMR (CDCl₃, 400 MHz): δ=7.38-7.32 (m, 2H), 7.27 (s, 2H), 7.25-7.19 (m, 1H), 7.18-7.09 (m, 3H), 6.83-6.78 (m, 1H), 5.17 (d, J=0.8 Hz, 1H), 4.99 (s, 2H), 4.83 (t, J=1.2 Hz, 1H), 1.58-1.46 (m, 1H), 0.77-0.67 (m, 2H), 0.53-0.43 (m, 2H).

Step 4:
2-(3-(benzyloxy)phenyl)-2-cyclopropylethanol (1-4

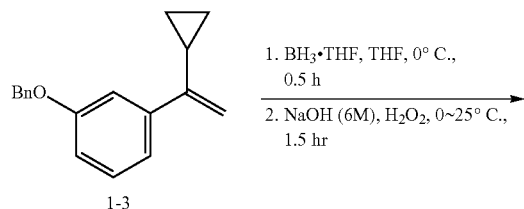

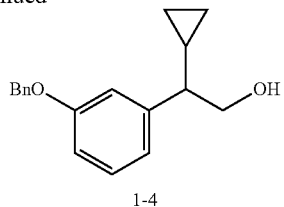

To a solution of 1-3 (14 g, 56 mmol, 1 eq) in THF (150 mL) was added BH₃·THF (1 M, 0.17 L, 3 eq) at 0° C. for 30 min. Then NaOH (6 M, 56 mL, 6 eq) and H₂O₂ (130 g, 1.1 mol, 107 mL, 30% purity, 20 eq) were added at 0° C., and the mixture was stirred at 25° C. for 1.5 hours. The mixture was quenched by the addition of water (50 mL) and extracted with ethyl acetate (200 mL×2). The combined organic phase was washed with saturated brine (50 mL×2), dried with anhydrous Na₂SO₄, filtered and concentrated in vacuum. The residue was purified by column chromatography (SiO₂, Petroleum ether:Ethyl acetate=20:1 to 3:1) to give 1-4 (11 g, 70% yield, 94% purity) as a colorless oil. ¹H-NMR (CDCl₃, 400 MHz): δ=7.35-7.30 (m, 2H), 7.27 (s, 2H), 7.24-7.18 (m, 1H), 7.14 (t, J=8 Hz, 1H), 6.81-6.78 (m, 1H), 6.77-6.73 (m, 2H), 4.94 (s, 2H), 3.86-3.63 (m, 2H), 1.91-1.84 (m, 1H), 1.44 (s, 1H), 0.93-0.82 (m, 1H), 0.56-0.45 (m, 1H), 0.38-0.28 (m, 1H), 0.22-0.15 (m, 1H), 0.02-0.05 (m, 1H).

Step 5: 1-(benzyloxy)-3-(1-cyclopropyl-2-iodoethyl)benzene (1-5

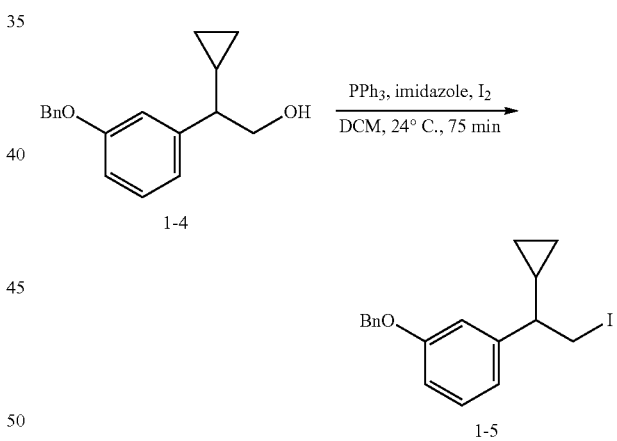

PPh₃ (7.6 g, 29 mmol, 1.5 eq) and imidazole (2.0 g, 29 mmol, 1.5 eq) were dissolved in DCM (50 mL), and the solution was stirred for 5 minutes. Then I₂ (7.4 g, 29 mmol, 5.9 mL, 1.5 eq) was added, and the mixture was stirred for 10 minutes. A DCM (170 mL) solution of 1-4 (5.2 g, 19 mmol, 1 eq) was added dropwise, and the mixture was stirred at 25° C. for 1 hour. The mixture was poured into water (50 mL) and extracted with dichloromethane (100 mL×2). The combine organic layers were washed with saturated brine (50 mL×2) and concentrated in vacuo to give a residue. The residue was purified by column chromatography (SiO₂, Petroleum ether:Ethyl acetate=1:0 to 100:1) to give 1-5 (6.5 g, 89% yield) as a white solid. ¹H-NMR (CDCl₃, 400 MHz): δ=7.27 (s, 2H), 7.25-7.19 (m, 2H), 7.18-7.13 (m, 1H), 7.11-7.03 (m, 1H), 6.73-6.65 (m, 3H), 4.90 (s, 2H), 3.41-3.37 (m, 1H), 3.31-3.27 (m, 1H), 1.94-1.88 (m, 1H), 0.93-0.90 (m, 1H), 0.52-0.40 (m, 1H), 0.34-0.12 (m, 2H), 0.03-0.05 (m, 1H).

Step 6: dimethyl (2-(3-(benzyloxy)phenyl)-2-cyclopropylethyl)phosphonate (1-6

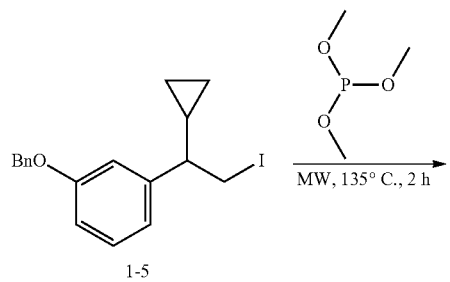

A solution of 1-5 (13 g, 34 mmol, 1 eq) in trimethyl phosphate (130 mL) was stirred at 135° C. for 2 hours in a microwave. The reaction mixture was diluted with water (50 mL) and extracted with ethyl acetate (100 mL×3). The combined organic layers were washed with saturated brine (20 mL×3), dried over $Na_2SO_4$, filtered and concentrated under reduced pressure to give a residue. The residue was purified by column chromatography ($SiO_2$, Petroleum ether/Ethyl acetate=50/1 to 5:1) to give 1-6 (3.5 g, 28% yield, 98% purity) as a colorless oil. LCMS: ($ES^+$) m/z $(M+H)^+$=361.1. $^1$H-NMR ($CD_3OD$, 400 MHz): δ=7.27 (s, 2H), 7.25-7.19 (m, 2H), 7.18-7.13 (m, 1H), 7.11-7.03 (m, 1H), 6.76-6.65 (m, 3H), 4.90 (s, 2H), 4.25-4.02 (m, 1H), 3.46-3.34 (m, 3H), 3.27 (d, J=10.8 Hz, 2H), 2.21-2.04 (m, 2H), 0.97-0.78 (m, 1H), 0.52-0.40 (m, 1H), 0.34-0.12 (m, 2H), 0.03-0.05 (m, 1H).

Step 7: dimethyl (2-cyclopropyl-2-(3-hydroxyphenyl)ethyl)phosphonate (1-7

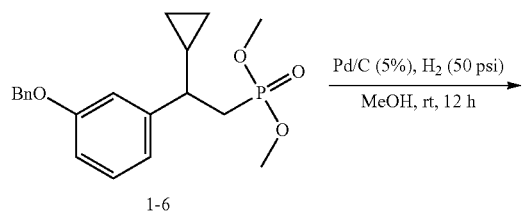

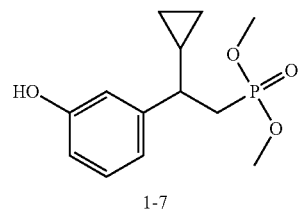

To a solution of 1-6 (0.40 g, 1.1 mmol, 1 eq) in MeOH (10 mL) was added Pd/C (0.40 g, 5%). The mixture was stirred at 25° C. for 12 hours under $H_2$ at 50 psi. The reaction mixture was filtered and concentrated under reduced pressure to give 1-7 (0.24 mg) as a colorless oil. LCMS: ($ES^+$) m/z $(M+H)^+$=271.1.

Step 8: dimethyl (2-cyclopropyl-2-(3-(((trans)-4-(2-fluoro-5 methoxyphenyl)cyclohexyl)methoxy)phenyl)ethyl)phosphonate (1-8

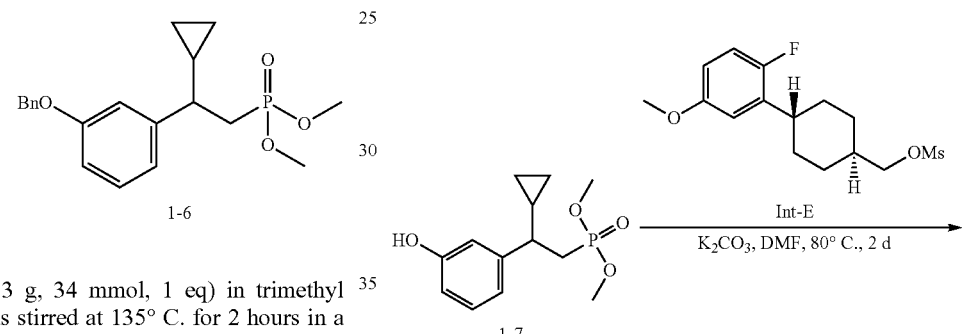

To a solution of 1-7 (0.12 g, 0.44 mmol, 1 eq) in DMF (2 mL) was added $K_2CO_3$ (61 mg, 0.44 mmol, 1 eq) and Int-E (0.14 mg, 0.44 mmol, 1 eq). The mixture was stirred at 80° C. for 48 hours. The reaction mixture was diluted with $H_2O$ (50 mL) and extracted with EA (50 mL×2). The combined organic layers were washed with saturated brine (25 mL×2), dried over $Na_2SO_4$, filtered and concentrated under reduced pressure to give a residue. The residue was purified by prep-TLC ($SiO_2$, PE:EA=1:1) to give 1-8 (60 mg, 20% yield, 71% purity) as a colorless oil. LCMS: ($ES^+$) m/z $(M+H)^+$=491.3.

Step 9: methyl hydrogen (2-cyclopropyl-2-(3-(((trans)-4-(2-fluoro-5-methoxyphenyl)cyclohexyl)methoxy)phenyl)ethyl)phosphonate (Compound 1)

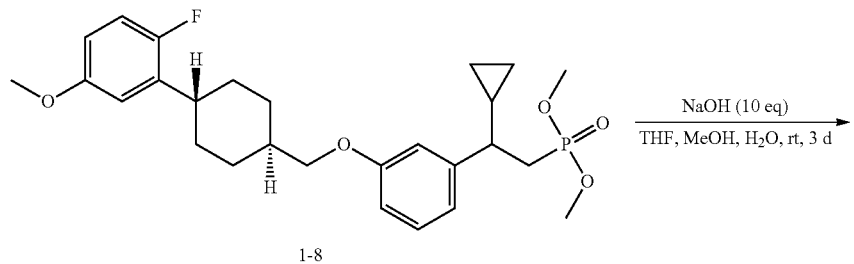

1-8

Compound 1

To a solution of 1-8 (60 mg, 120 mol, 1 eq) in THF (0.6 mL), MeOH (0.6 mL), and H$_2$O (0.6 mL) was added NaOH (50 mg, 1.2 mmol, 10 eq). The mixture was stirred at 25° C. for 12 hours. The reaction mixture was concentrated under reduced pressure to give a residue, and the pH was adjusted to 10 with 0.2 M aqueous HCl. The residue was purified by prep-HPLC (column: Phenomenex Gemini NX-C18 (75×30 mm×3 um); mobile phase: A: water (10 mM NH$_4$HCO$_3$), B: ACN; B %: 24%-54% gradient over 10 min) to give Compound 1 (2.4 mg, 4.0% yield, 98% purity) as a grey solid. LCMS: (ES$^+$) m/z (M+H)$^+$=477.2. $^1$H-NMR (CD$_3$OD, 400 MHz): δ=7.18 (t, J=8 Hz, 1H), 6.93 (t, J=9.2 Hz, 1H), 6.85-6.78 (m, 3H), 6.77-6.67 (m, 2H), 3.83 (d, J=6 Hz, 2H), 3.76 (s, 3H), 3.35 (d, J=10.8 Hz, 3H), 2.90-2.77 (m, 1H), 2.28-2.15 (m, 3H), 2.05 (d, J=12 Hz, 2H), 1.96-1.79 (m, 3H), 1.58 (m, 2H), 1.38-1.21 (m, 2H), 1.11 (m, 1H), 0.64-0.52 (m, 1H), 0.42-0.27 (m, 2H), 0.17-0.05 (m, 1H).

Example 8: Preparation of (2-cyclopropyl-2-(3-(((trans)-4-(2-fluoro-5-methoxyphenyl)cyclohexyl)methoxy)phenyl)ethyl)phosphonic acid (Compound 2)

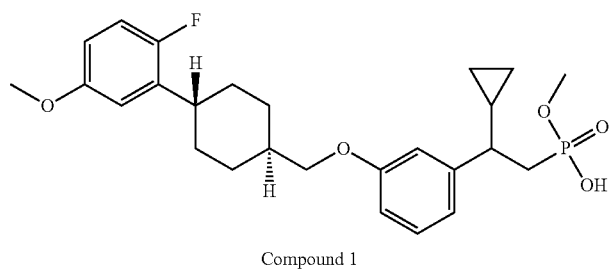

1-8

Compound 2

To a solution of 1-8 (18 mg, 0.04 mmol, 1 eq) in CHCl₃ (0.5 mL) was added TMSBr (17 mg, 0.11 mmol, 14 uL, 3 eq). The mixture was stirred at 25° C. for 2 hours. The reaction mixture diluted with H₂O (3 mL) and extracted with DCM (10 mL×2). The combined organic layers were washed with saturated brine (3 mL×2), dried over Na₂SO₄, filtered and concentrated under reduced pressure to give a residue. The residue was purified by prep-HPLC (column: 3_Phenomenex Luna C18 75×30 mm×3 um; mobile phase: A: water (0.225% FA), B: ACN; B %: 60%-90% gradient over 7 min) to give Compound 2 (4.0 mg, 23% yield, 97% purity) as a gray solid. LCMS: (ES⁺) m/z (M+H)⁺=463.2. ¹H-NMR (CD₃OD, 400 MHz): δ=7.17 (t, J=8.0 Hz, 1H), 6.96-6.89 (m, 1H), 6.85-6.78 (m, 3H), 6.76-6.68 (m, 2H), 3.83 (d, J=6.0 Hz, 2H), 3.76 (s, 3H), 2.89-2.77 (m, 1H), 2.66 (s, 1H), 2.35-2.11 (m, 3H), 2.05 (d, J=11.2 Hz, 2H), 1.96-1.80 (m, 3H), 1.65-1.50 (m, 2H), 1.36-1.23 (m, 2H), 1.13 (s, 1H), 0.65-0.52 (m, 1H), 0.43-0.31 (m, 2H), 0.15-0.05 (m, 1H).

Example 9: Preparation of 2-cyclopropyl-2-(3-(((trans)-4-(2-fluoro-5-methoxyphenyl)cyclohexyl)methoxy)phenyl)ethanesulfonic acid (Compound 3)

Compound 3

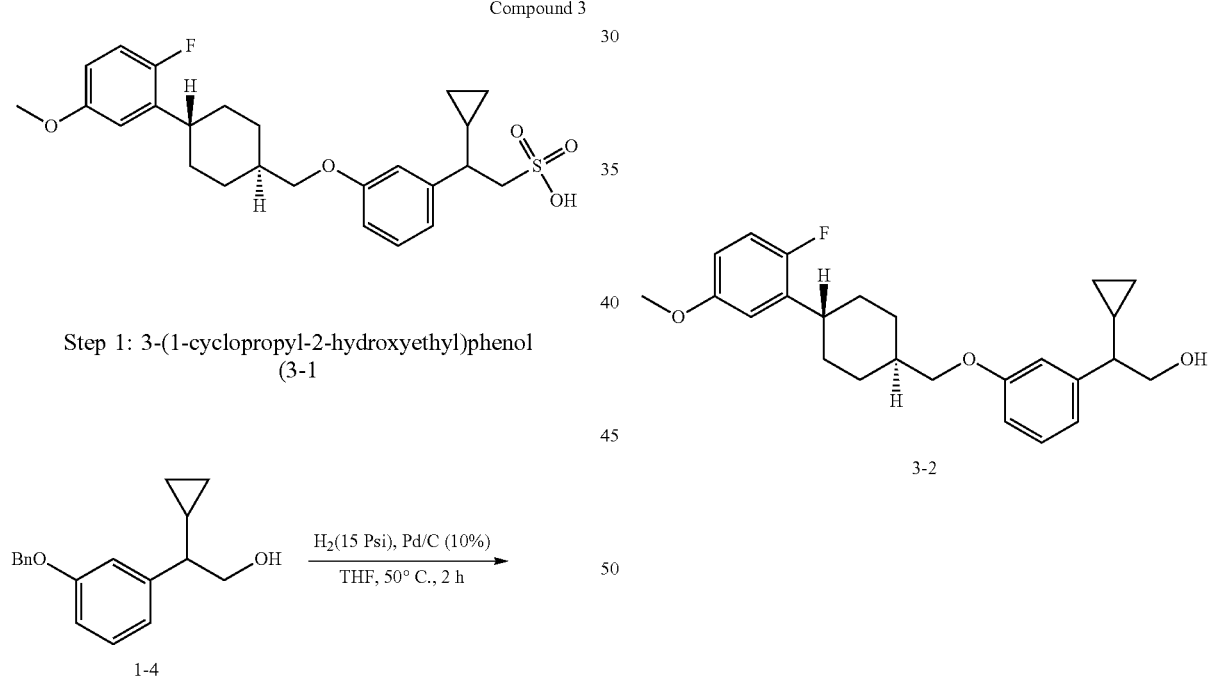

Step 1: 3-(1-cyclopropyl-2-hydroxyethyl)phenol (3-1)

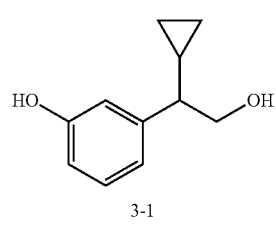

To a solution of 1-4 (1.1 g, 4.1 mmol, 1.0 eq) in THF (10 mL) was added Pd/C (0.21 g, 0.41 mmol, 10% purity, 0.10 eq) under N₂. The suspension was degassed under vacuum and purged with H₂ several times. The mixture was stirred under H₂ (15 psi) at 50° C. for 2 hrs. The mixture was filtered and concentrated and purified by prep-TLC (SiO₂, Petroleum ether:Ethyl acetate=0:1, Rf=0.3) to give 3-1 (0.70 g, 3.9 mmol, 95.81% yield) as a colorless oil.

Step 2: 2-cyclopropyl-2-(3-(((trans)-4-(2-fluoro-5-methoxyphenyl)cyclohexyl)methoxy)phenyl)ethanol (3-2

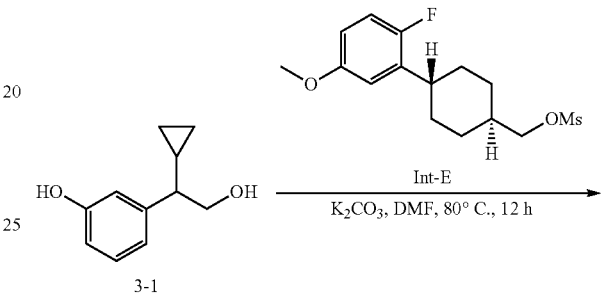

To a solution of 3-1 (0.25 g, 1.4 mmol, 1.2 eq) and Int-E (0.22 g, 1.2 mmol, 1 eq) in DMF (5 mL) was added K₂CO₃ (0.19 g, 1.4 mmol, 1.2 eq). The mixture was stirred at 80° C. for 12 hrs. The mixture was poured into water (5 mL) and extracted with ethyl acetate (10 mL×2). The combined organic phase was washed with brine (10 mL), dried with anhydrous Na₂SO₄, filtered and concentrated in vacuum. The residue was purified by column chromatography (SiO₂, Petroleum ether:Ethyl acetate=3:1) to give 3-2 (0.40 g, 1.0 mmol, 76% yield) as a colorless oil.

Step 3: 2-cyclopropyl-2-(3-(((trans)-4-(2-fluoro-5-methoxyphenyl)cyclohexyl)methoxy)phenyl)ethyl methanesulfonate (3-3

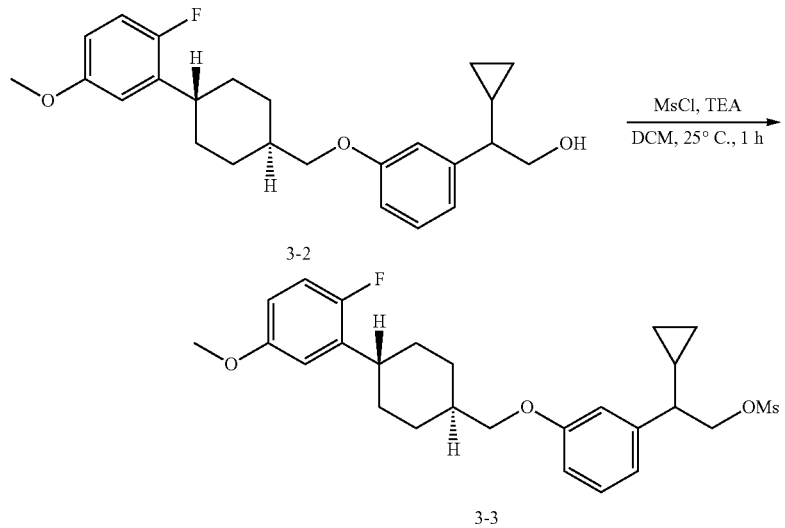

To a solution of 3-2 (0.40 g, 1.0 mmol, 1.0 eq) and TEA (0.51 g, 5.0 mmol, 0.70 mL, 5.0 eq) in DCM (5 mL) was added MsCl (0.23 g, 2.0 mmol, 2 eq) at 0° C. The mixture was stirred at 25° C. for 1 hr. The mixture was quenched by water (5 mL) and extracted with DCM (10 mL×2). The combined organic phase was washed with brine (5 mL), dried with anhydrous Na$_2$SO$_4$, filtered and concentrated in vacuum. The residue was purified by column chromatography (SiO$_2$, Petroleum ether:Ethyl acetate=3:1) to give 3-3 (0.39 g, 0.82 mol, 82% yield) as a colorless oil.

Step 4: 2-((trans)-4-((3-(1-cyclopropyl-2-iodoethyl)phenoxy)methyl)cyclohexyl)-1-fluoro-4-methoxy-benzene (3-4

To a solution of 3-3 (0.34 g, 0.71 mmol, 1.0 eq) in acetone (5.0 mL) was added NaI (0.53 g, 3.6 mmol, 5.0 eq). The mixture was stirred at 60° C. for 12 hrs. The mixture was extracted with ethyl acetate (50 mL×2). The combined organic phase was washed with brine (100 mL), dried with anhydrous Na$_2$SO$_4$, filtered and concentrated in vacuum. The residue was purified by column chromatography (SiO$_2$, Petroleum ether:Ethyl acetate=3:1) to give 3-4 (0.32 g, 88% yield) as a colorless oil. $^1$H-NMR (400 MHz, CDCl$_3$) δ 7.26-7.23 (m, 1H), 6.94 (t, J=9.2 Hz, 1H), 6.85-6.75 (m, 4H), 6.67 (td, J=3.6, 8.8 Hz, 1H), 3.83 (d, J=6.4 Hz, 2H), 3.79 (s, 3H), 3.61-3.56 (m, 1H), 3.53-3.47 (m, 1H), 2.86 (br t, J=12.4 Hz, 1H), 2.15-2.02 (m, 3H), 2.02-1.83 (m, 3H), 1.35-1.23 (m, 3H), 1.14-1.04 (m, 1H), 0.92-0.82 (m, 1H), 0.71 (m, 1H), 0.56-0.46 (m, 1H), 0.36 (m, 1H), 0.23-0.12 (m, 1H).

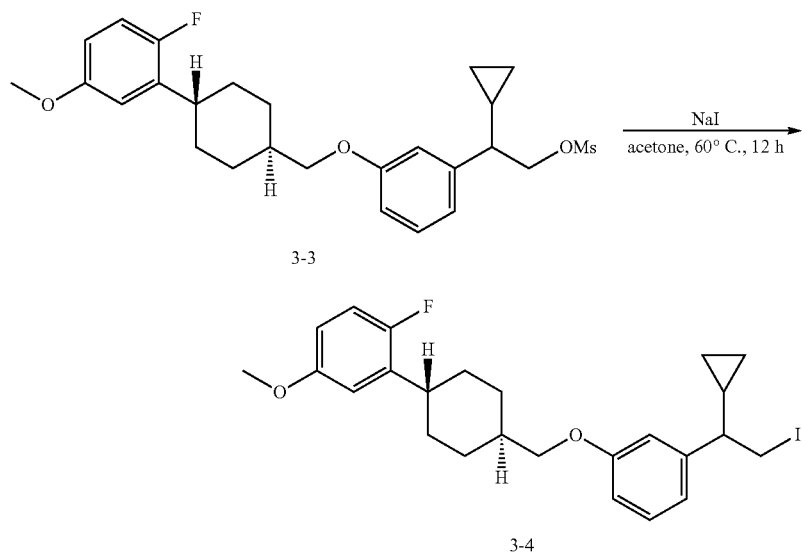

Step 5: 2-cyclopropyl-2-(3-(((trans)-4-(2-fluoro-5-methoxyphenyl)cyclohexyl)methoxy)phenyl)ethane-sulfonic acid (Compound 3)

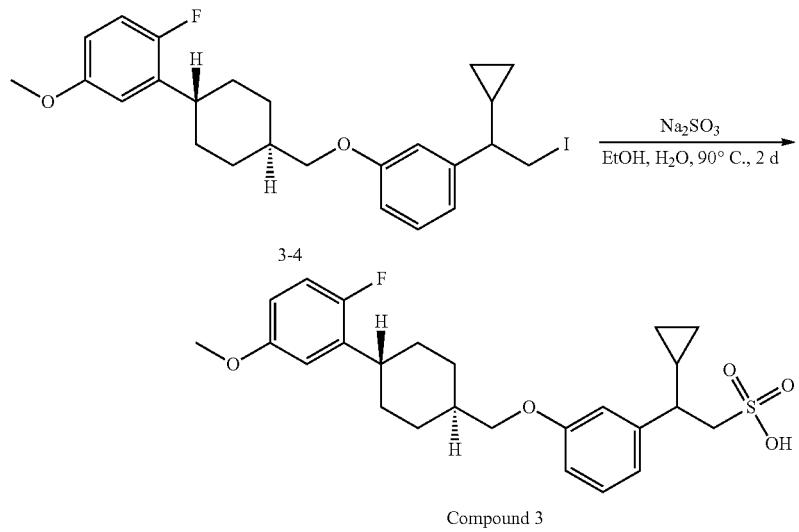

Compound 3

To a solution of 3-4 (0.16 g, 0.31 mmol, 1 eq) in H$_2$O (5.0 mL) and EtOH (50 mL) was added Na$_2$SO$_3$ (79 mg, 0.63 mmol, 2.0 eq). The mixture was stirred at 90° C. for 2 days. The mixture was concentrated to removed EtOH. The pH of the water phase was adjusted to pH=5-6 with aqueous HCl (1.0 M) and extracted with ethyl acetate (20 mL×2). The combined organic phase was washed with brine (15 mL), dried with anhydrous Na$_2$SO$_4$, filtered and concentrated in vacuum. The residue was purified by prep-TLC (SiO$_2$, Ethyl acetate:Methanol=5:1) to give Compound 3 (21 mg, 14% yield, 98% purity) as a white solid. LCMS: tR=1.335 min., (ES+) m/z (M+H)$^+$=463.1. $^1$H-NMR (400 MHz, CD$_3$OD) δ 7.16 (t, J=7.6 Hz, 1H), 6.92 (t, J=8.8 Hz, 1H), 6.87-6.76 (m, 3H), 6.76-6.67 (m, 2H), 3.83 (d, J=6.4 Hz, 2H), 3.76 (d, J=1.2 Hz, 3H), 2.89-2.79 (m, 1H), 2.54-2.44 (m, 1H), 2.05 (br d, J=13.6 Hz, 2H), 1.90 (br d, J=12.0 Hz, 3H), 1.58 (q, J=13.2 Hz, 2H), 1.37-1.23 (m, 4H), 1.20-1.09 (m, 1H), 0.63-0.53 (m, 1H), 0.44-0.32 (m, 2H), 0.18-0.07 (m, 1H).

Example 10: Preparation of (1-cyclopropyl-1-(3-(((trans)-4-(2-fluoro-5-methoxyphenyl)cyclohexyl)methoxy)phenyl)propan-2-yl)phosphonic acid (Compound 4)

Compound 4

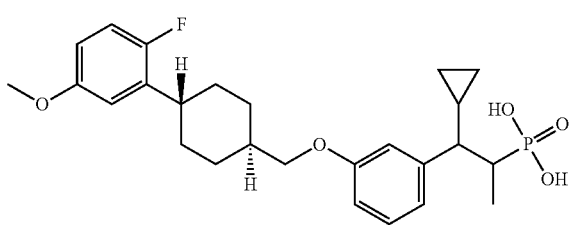

Step 1: dimethyl (1-(3-(benzyloxy)phenyl)-1-cyclopropylpropan-2-yl)phosphonate (4-1)

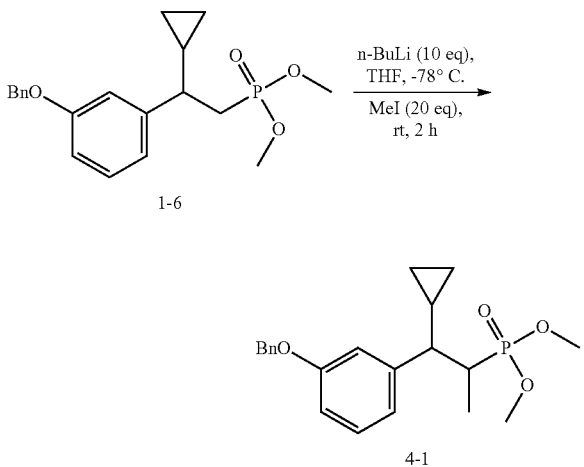

To a solution of 1-6 (3.5 g, 9.7 mmol, 1 eq) in THF (35 mL) was added n-BuLi (2.5 M in n-hexane, 39 mL, 10 eq) at −78° C. Then MeI (28 g, 190 mmol, 12 mL, 20 eq) was added slowly at the same temperature, and the mixture was stirred at 25° C. for 2 hours. The reaction mixture was quenched by addition of saturated aqueous NH$_4$Cl (20 mL) at 0° C., diluted with ethyl acetate (50 mL) and extracted with ethyl acetate (50 mL×2). The combined organic layers were washed with saturated brine (20 mL×3), dried over Na$_2$SO$_4$, filtered and concentrated under reduced pressure to give a residue. The residue was purified by column chromatography (SiO$_2$, Petroleum ether:Ethyl acetate=5:1 to 3:1) to give 4-1 (220 mg, 5.8% yield, 95% purity) as a yellow oil LCMS: tR=0.944 min, (ES$^+$) m/z (M+H)$^+$=375.1.

Step 2: dimethyl (1-cyclopropyl-1-(3-hydroxyphenyl)propan-2-yl)phosphonate (4-2)

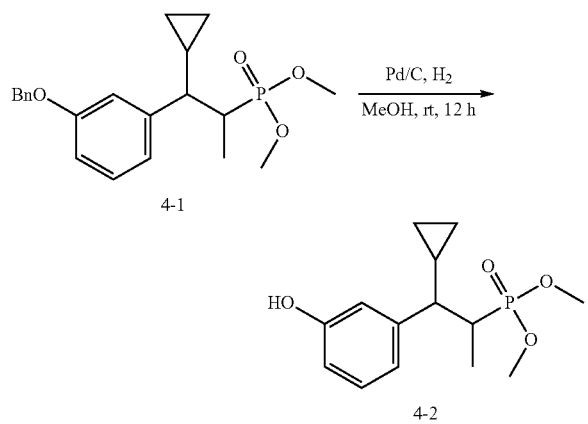

To a solution of 4-1 (0.22 g, 0.59 mmol, 1 eq) in MeOH (10 mL) was added Pd/C (0.28 g, 5%). The mixture was stirred at 25° C. for 12 hours under H$_2$ (50 psi). The reaction was filtered and concentrated under reduced pressure to give a residue. The residue was purified by column chromatography (SiO$_2$, Petroleum ether/Ethyl acetate=3:1 to 1:1) to give 4-2 (0.11 mg, 60% yield, 91% purity) as a colorless oil. LCMS: (ES$^+$) m/z (M+H)$^+$=285.1.

Step 3: dimethyl (1-cyclopropyl-1-(3-(((trans)-4-(2-fluoro-5-methoxyphenyl)cyclohexyl)methoxy)phenyl)propan-2-yl)phosphonate (4-3)

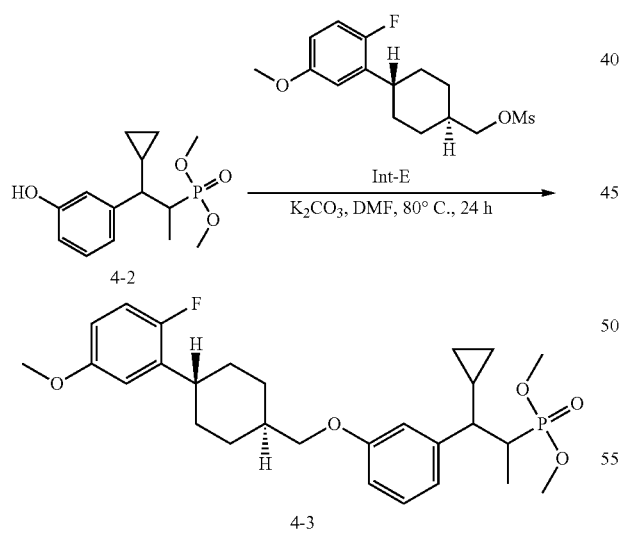

To a solution of 4-2 (55 mg, 0.19 mmol, 1 eq) and Int-E (61 mg, 0.19 mmol, 1 eq) in DMF (2 mL) was added K$_2$CO$_3$ (27 mg, 0.19 mmol, 1 eq). The mixture was stirred at 80° C. for 24 hours. The reaction mixture diluted with H$_2$O (5 mL) and extracted with EA (20 mL×2). The combined organic layers were washed with saturated brine (5 mL×2), dried over Na$_2$SO$_4$, filtered and concentrated under reduced pressure to give a residue. The residue was purified by prep-TLC (SiO$_2$, PE:EA=1:1) to give 4-3 (30 mg, 27% yield, 89% purity) as a colorless oil LCMS: tR=1.076 min, (ES$^+$) m/z (M+H)$^+$=505.2.

Step 4: (1-cyclopropyl-1-(3-(((trans)-4-(2-fluoro-5-methoxyphenyl)cyclohexyl)methoxy)phenyl)propan-2-yl)phosphonic acid (Compound 4)

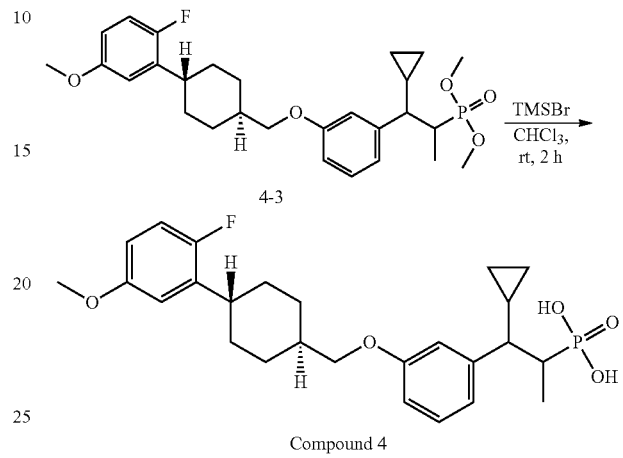

Compound 4

To a solution of 4-3 (30 mg, 60 umol, 1 eq) in CHCl$_3$ (0.5 mL) was added TMSBr (27 mg, 0.18 mmol, 3 eq). The mixture was stirred at 25° C. for 2 hours. The reaction mixture was diluted with H$_2$O (5 mL) and extracted with DCM (20 mL×2). The combined organic layers were washed with saturated brine (5 mL×2), dried over Na$_2$SO$_4$, filtered and concentrated under reduced pressure to give a residue. The residue was purified by prep-HPLC (column: Unisil 3-100 C18 Ultra 150×50 mm×3 um; mobile phase: A: water (0.225% FA), B: ACN; B %: 50%-80% gradient over 10 min) to give Compound 4 (5.5 mg, 19% yield, 98% purity) as an off-white solid. LCMS: (ES$^+$) m/z (M+H)$^+$=477.2. $^1$H-NMR (CD$_3$OD, 400 MHz): δ=7.23-7.11 (m, 1H), 6.96-6.89 (m, 1H), 6.89-6.86 (m, 1H), 6.85-6.78 (m, 2H), 6.77-6.68 (m, 2H), 3.82 (d, J=6 Hz, 2H), 3.76 (s, 3H), 2.81 (s, 1H), 2.45-2.33 (m, 1H), 2.17 (s, 1H), 2.08-1.99 (m, 1H), 2.05 (d, J=11.6 Hz, 1H), 1.91 (d, J=11.6 Hz, 2H), 1.96-1.85 (m, 1H), 1.68-1.50 (m, 2H), 1.36-1.19 (m, 5H), 1.05 (dd, J$_1$=6.8 Hz, J$_2$=17.2 Hz, 1H), 0.78-0.33 (m, 3H), 0.04-0.15 (m, 1H).

Example 11: Preparation of (2-cyclopropyl-2-(3-(((trans)-4-(2-fluoro-5-methoxyphenyl)cyclohexyl)methoxy)phenyl)ethyl)(methyl)phosphinic acid (Compounds 5, 6, 7, 8)

Compounds 5, 6, 7, 8

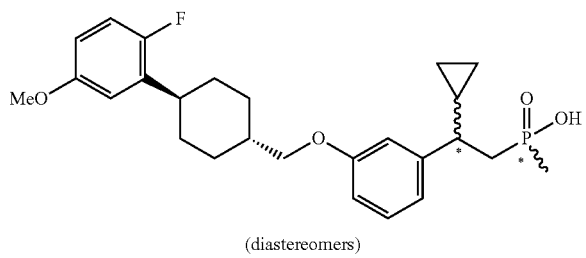

(diastereomers)

Step 7: ethyl (2-cyclopropyl-2-(3-(((trans)-4-(2-fluoro-5-methoxyphenyl)cyclohexyl)methoxy)phenyl)ethyl)(methyl)phosphinate (5-1

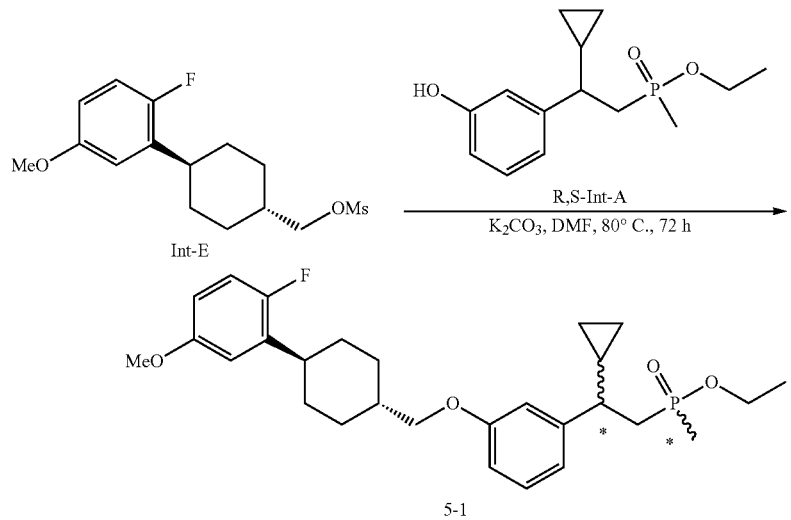

To a solution of Int-E (0.33 g, 1.2 mmol, 1 eq) in DMF (5.0 mL) was added K$_2$CO$_3$ (0.34 g, 2.5 mmol, 2 eq) and R,S-Int-A (0.39 g, 1.2 mmol, 1 eq). The mixture was stirred at 80° C. for 72 hours. The mixture was purified by reversed-phase HPLC (column: Phenomenex Luna C18 250×50 mm×10 um; mobile phase: A: water (0.1% FA), B: ACN; B %: 20%-30% gradient over 10 min) to give 5-1 (0.25 g, 41% yield) as a white oil. LCMS: (ES$^+$) m/z (M+H)$^+$=489.3.

5-1 was further separated by SFC (column: DAICEL CHIRALCEL OJ-H (250×30 mm×5 um); mobile phase: [A: CO$_2$; B: 0.1% NH$_4$OH in EtOH]; B %: 15%) to give 5-1-peak 1 (tR=0.937 min) and 5-1-peak 2 (tR=1.009 min), each as a white oil. 5-1-peak 1 was further separated by SFC (column: DAICEL CHIRALPAK AS (250×30 mm×10 um); mobile phase: A: [CO$_2$; B: 0.1% NH$_4$OH in EtOH]; B %: 50%) to give 5-1-peak 1-1 (tR=1.54 min) and 5-1-peak 1-2 (tR=1.714 min), each as a white oil. 5-1-peak 2 was further separated by SFC (column: DAICEL CHIRALPAK AS (250×30 mm×10 um); mobile phase: A: [CO$_2$; B: 0.1% NH$_4$OH in EtOH]; B %: 50%) to give 5-1-peak 2-1 (tR=1.865 min) and 5-1-peak 2-2 (tR=1.707 min), each as a white oil.

The absolute stereochemistry of each compound was not determined.

Step 8: (2-cyclopropyl-2-(3-(((trans)-4-(2-fluoro-5-methoxyphenyl)cyclohexyl)methoxy)phenyl)ethyl)(methyl)phosphinic acid (Compounds 5, 6, 7, 8

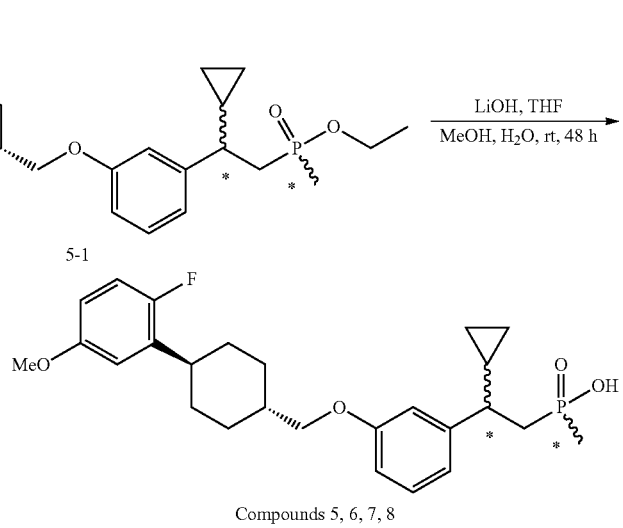

To a separate solution of each peak of 5-1 (1 eq) in MeOH, H$_2$O, THF (1:1:1)× was added LiOH (7 eq). Each mixture was stirred at 30° C. for 48 hours. Each reaction mixture was concentrated under reduced pressure to give a residue. Each residue was purified by prep-HPLC (column:

Waters Xbridge 150×25 mm×5 um; mobile phase: A: water (0.05% ammonia hydroxide v/v), B: ACN; B %: 17%-47% gradient over 10 min) and lyophilized to give Compounds 5, 6, 7, 8, each as a white solid.

Compound 5 [from 5-1-peak 1-1 (tR=1.54 min)]. LCMS: (ES$^+$) m/z (M+H)$^+$=461.2. $^1$H NMR (400 MHz, CD$_3$OD) δ 7.23-7.15 (m, 1H), 6.93 (t, J=9.6 Hz, 1H), 6.88-6.83 (m, 2H), 6.82-6.78 (m, 1H), 6.77 (d, J=8.8 Hz, 1H), 6.74-6.67 (m, 1H), 3.84 (d, J=6.0 Hz, 2H), 3.76 (s, 3H), 2.90-2.76 (m, 1H), 2.25-2.11 (m, 3H), 2.11-2.00 (m, 2H), 1.96-1.82 (m, 3H), 1.66-1.51 (m, 2H), 1.39-1.23 (m, 2H), 1.15-1.03 (m, 1H), 0.85 (d, J=14 Hz, 3H), 0.64-0.52 (m, 1H), 0.43-0.28 (m, 2H), 0.23-0.08 (m, 1H).

Compound 6 [from 5-1-peak 1-2 (tR=1.714 min)]. LCMS: (ES$^+$) m/z (M+H)$^+$=461.2. $^1$H NMR (400 MHz, CD$_3$OD) δ 7.18 (t, J=8.0 Hz, 1H), 6.92 (t, J=9.2 Hz, 1H), 6.87-6.83 (m, 2H), 6.83-6.78 (m, 1H), 6.77-6.67 (m, 2H), 3.84 (d, J=6.0 Hz, 2H), 3.76 (s, 3H), 2.90-2.75 (m, 1H), 2.26-2.16 (m, 1H), 2.15-2.09 (m, 1H), 2.09-2.00 (m, 3H), 1.95-1.84 (m, 3H), 1.67-1.49 (m, 2H), 1.38-1.22 (m, 2H), 1.14-1.00 (m, 1H), 0.76 (d, J=13.6 Hz, 3H), 0.61-0.48 (m, 1H), 0.41-0.29 (m, 2H), 0.21-0.09 (m, 1H).

Compound 7 [from 5-1-peak 2-2 (tR=1.707 min)]. LCMS: (ES$^+$) m/z (M+H)$^+$=461.2. $^1$H NMR (400 MHz, CD$_3$OD) δ=7.20 (t, J=8.0 Hz, 1H), 6.96-6.89 (m, 1H), 6.88-6.83 (m, 2H), 6.83-6.73 (m, 2H), 6.73-6.66 (m, 1H), 3.84 (d, J=6.0 Hz, 2H), 3.76 (s, 3H), 2.83 (t, J=12 Hz, 1H), 2.29-2.11 (m, 3H), 2.05 (d, J=12.8 Hz, 2H), 1.91 (m, 3H), 1.67-1.48 (m, 2H), 1.39-1.20 (m, 2H), 1.17-1.02 (m, 1H), 0.87 (d, J=14.0 Hz, 3H), 0.64-0.51 (m, 1H), 0.44-0.25 (m, 2H), 0.23-0.07 (m, 1H).

Compound 8 [from 5-1-peak 2-1 (tR=1.865 min)]. LCMS: (ES$^+$) m/z (M+H)$^+$=461.2. $^1$H NMR (400 MHz, CD$_3$OD) δ=7.20 (t, J=8.0 Hz, 1H), 6.96-6.89 (m, 1H), 6.88-6.83 (m, 2H), 6.83-6.73 (m, 2H), 6.73-6.66 (m, 1H), 3.84 (d, J=6.0 Hz, 2H), 3.76 (s, 3H), 2.83 (t, J=12 Hz, 1H), 2.29-2.11 (m, 3H), 2.05 (d, J=2.4, 12.0 Hz, 2H), 1.91 m, 3H), 1.67-1.48 (m, 2H), 1.39-1.20 (m, 2H), 1.17-1.02 (m, 1H), 0.87 (d, J=14.0 Hz, 3H), 0.64-0.51 (m, 1H), 0.44-0.25 (m, 2H), 0.23-0.07 (m, 1H).

The absolute stereochemistry of each compound was not determined.

Example 12: ((S)-2-cyclopropyl-2-(2-(((trans)-4-(2-fluoro-5-methoxyphenyl)cyclohexyl)methoxy)pyridin-4-yl)ethyl)(methyl)phosphinic acid (Compound 9)

Compound 9

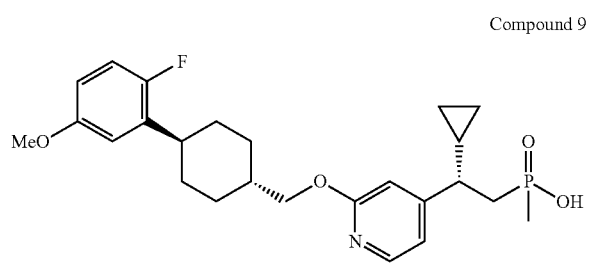 [SMILES: COc1ccc(F)c([C@H]2CC[C@H](COc3cc([C@@H](CP(C)(=O)O)C4CC4)ccn3)CC2)c1]

Step 1: 2-((trans)-4-(chloromethyl)cyclohexyl)-1-fluoro-4-methoxybenzene (9-1

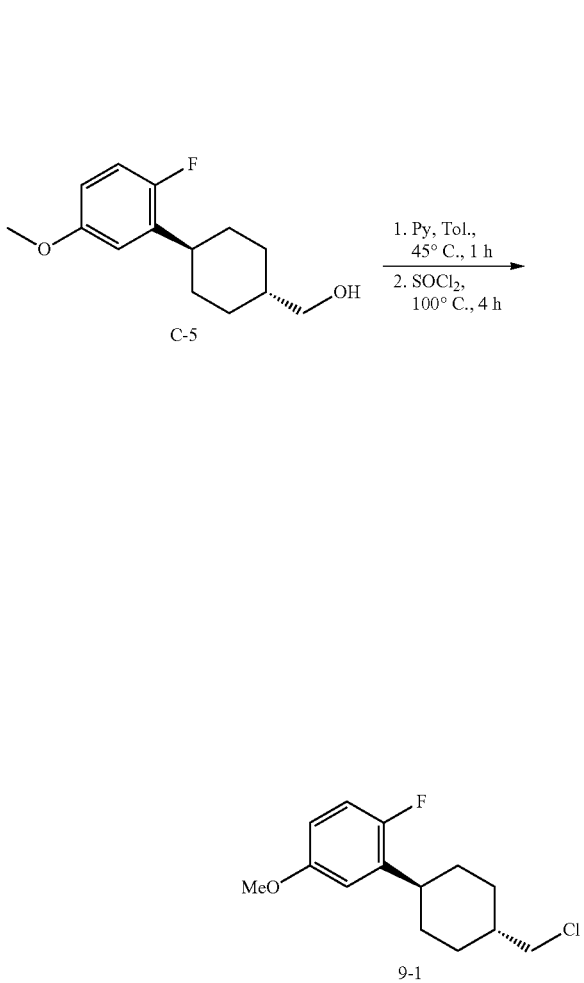

To a solution of C-5 (6.5 g, 27 mmol, 1.0 eq) in toluene (90 mL) was added pyridine (0.92 g, 11 mmol, 0.9 mL, 0.40 eq), and the mixture was stirred at 45° C. for 1 h. Then SOCl$_2$ (4.9 g, 41 mmol, 3.0 mL, 1.5 eq) was added at 45° C. The mixture was stirred at 100° C. for 4 h. The reaction mixture was diluted with H$_2$O (20 mL) and extracted with EtOAc (40 mL×2). The combined organic layers were dried over Na$_2$SO$_4$, filtered and concentrated under reduced pressure to give a residue. The residue was purified by column chromatography (SiO$_2$, Petroleum ether Ethyl acetate=10:1 to 5:1) to give 9-1 (6.6 g, 25 mmol, 95% yield) as a yellow oil. $^1$H NMR (400 MHz, CDCl$_3$-d) δ 6.92 (t, J=9.6 Hz, 1H), 6.74 (dd, J=3.2, 6.0 Hz, 1H), 6.66 (td, J=3.6, 8.8 Hz, 1H), 3.77 (s, 3H), 3.44 (d, J=6.0 Hz, 2H), 2.87-2.73 (m, 1H), 2.06-1.89 (m, 4H), 1.73 (dtd, J=2.8, 6.0, 12.0 Hz, 1H), 1.57-1.43 (m, 2H), 1.29-1.15 (m, 2H).

Step 2: ethyl ((S)-2-cyclopropyl-2-(2-(((trans)-4-(2-fluoro-5-methoxyphenyl)cyclohexyl)methoxy)pyridin-4-yl)ethyl)(methyl)phosphinate (9-2)

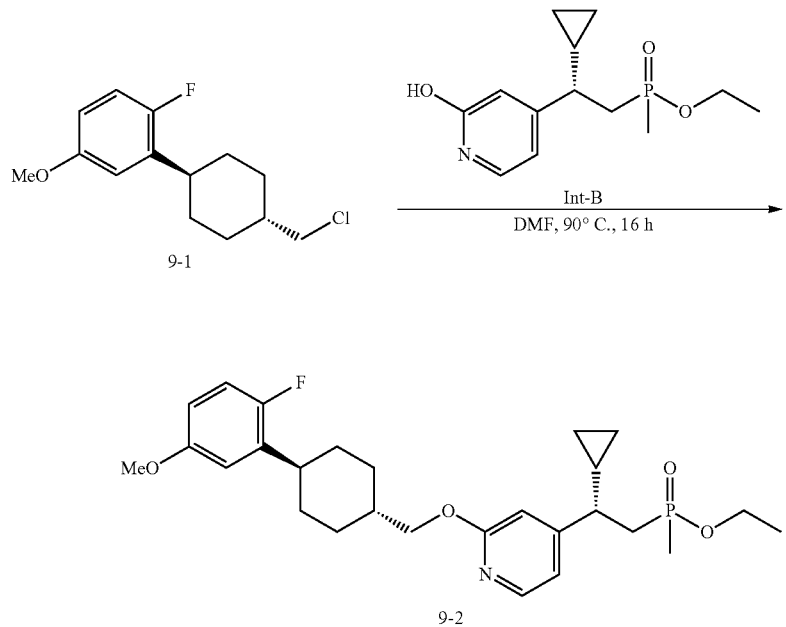

To a solution of Int-B (0.20 g, 0.74 mmol, 1.0 eq) in DMF (5 mL) was added 9-1 (0.20 g, 0.78 mmol, 1.0 eq) and $K_2CO_3$ (0.21 g, 1.5 mmol, 2.0 eq). The mixture was stirred at 90° C. for 16 hours. The reaction mixture was partitioned between water (20 mL) and ethyl acetate (50 mL). The organic phase was washed with brine (10 mL), dried with anhydrous $Na_2SO_4$, filtered and concentrated in vacuum. The residue was purified by column chromatography ($SiO_2$, Ethyl acetate:Methanol=50:1 to 5:1) to give 9-2 (0.10 g, 28% yield) as a white oil. $^1$HNMR (400 MHz, $CDCl_3$-d) δ 8.13-8.06 (m, 1H), 6.93 (t, J=9.2 Hz, 1H), 6.82-6.74 (m, 2H), 6.69-6.63 (m, 2H), 4.15 (d, J=6.4 Hz, 2H), 4.08-3.82 (m, 2H), 3.79 (s, 3H), 2.91-2.79 (m, 1H), 2.35-2.12 (m, 3H), 2.10-2.00 (m, 2H), 1.95 (br d, J=11.2 Hz, 2H), 1.91-1.82 (m, 1H), 1.53 (dq, J=2.8, 12.8 Hz, 2H), 1.37-1.13 (m, 8H), 1.12-1.00 (m, 1H), 0.70-0.60 (m, 1H), 0.53-0.35 (m, 2H), 0.25-0.15 (m, 1H).

Step 3: ((S)-2-cyclopropyl-2-(2-(((trans)-4-(2-fluoro-5-methoxyphenyl)cyclohexyl)methoxy)pyridin-4-yl)ethyl)(methyl)phosphinic acid (Compound 9)

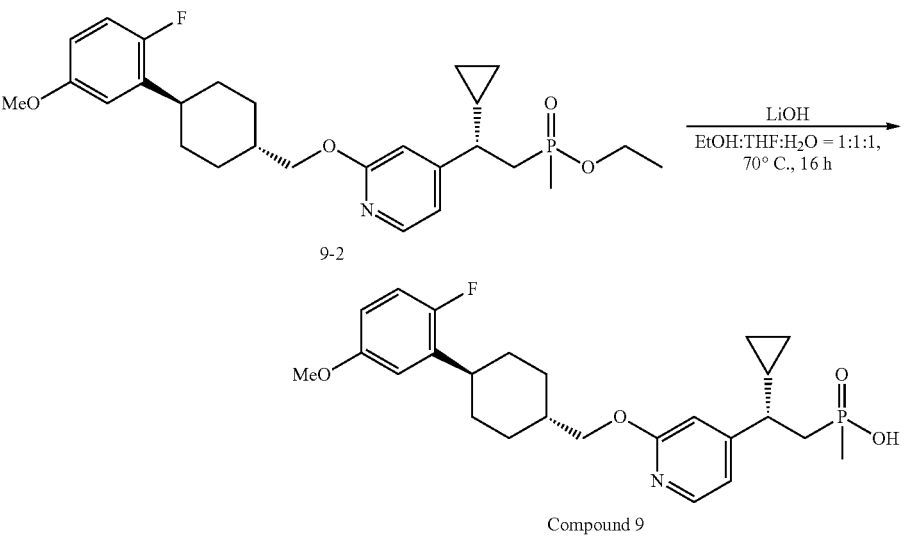

To a solution of 9-2 (80 mg, 0.16 mmol, 1.0 eq) in EtOH (1 mL), THF (1 mL) and H$_2$O (1 mL) was added LiOH H$_2$O (69 mg, 1.6 mmol, 10 eq). The mixture was stirred at 70° C. for 16 hours. The reaction mixture was acidified with 1N aqueous HCl to pH 3 and concentrated under reduced pressure to give a residue. The residue was purified by prep-HPLC (column: Waters Xbridge Prep OBD C18 150× 40 mm×10 um; mobile phase: [A: water with 0.05% NH$_4$OH+10 mM NH$_4$HCO$_3$; B: ACN]; B %: 15%-50% over 8 min) to give Compound 9 (57 mg, 72% yield, 99% purity, ammonium salt) as a white solid. LCMS: (ES$^+$) m/z (M+H)$^+$=462.1. $^1$HNMR (400 MHz, CD$_3$OD) δ 8.03-7.98 (m, 1H), 6.97-6.88 (m, 2H), 6.80 (dd, J=3.2, 6.0 Hz, 1H), 6.76 (s, 1H), 6.70 (td, J=3.6, 8.8 Hz, 1H), 4.10 (d, J=6.4 Hz, 2H), 3.76 (s, 3H), 2.83 (tt, J=3.2, 12.1 Hz, 1H), 2.28-2.11 (m, 3H), 2.09-1.99 (m, 2H), 1.96-1.81 (m, 3H), 1.58 (dq, J=2.8, 12.8 Hz, 2H), 1.30 (dq, J=3.2, 12.8 Hz, 2H), 1.15-1.05 (m, 1H), 1.01 (d, J=13.6 Hz, 3H), 0.67-0.57 (m, 1H), 0.46-0.36 (m, 2H), 0.21-0.12 (m, 1H).

Example 13: Preparation of ((S)-2-cyclopropyl-2-(3-((1-(2-(4,4-dimethylpentyl)-5-methoxyphenyl)piperidin-4-yl)methoxy)phenyl)ethyl)(methyl)phosphinic acid (Compound 10)

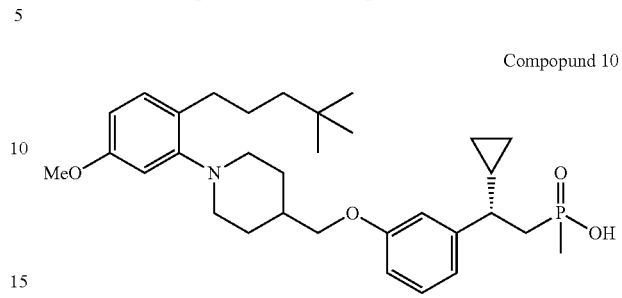

Compopund 10

Step 1: ethyl ((S)-2-cyclopropyl-2-(3-((1-(2-(4,4-dimethylpentyl)-5-methoxyphenyl)piperidin-4-yl)methoxy)phenyl)ethyl)(methyl)phosphinate (10-1

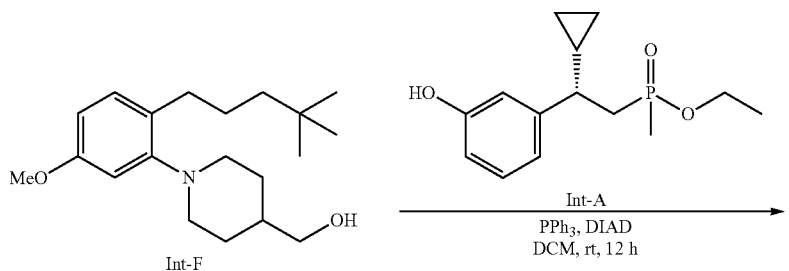

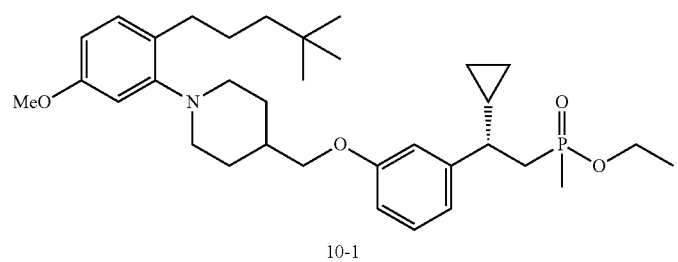

10-1

To a solution of Int-F (0.1 g, 0.31 mmol, 1 eq) and Int-A (84 mg, 0.31 mmol, 1 eq) in DCM (2 mL) was added DIAD (82 mg, 0.41 mmol, 79 uL, 1.3 eq) and PPh₃ (0.12 g, 0.47 mmol, 1.5 eq). The reaction was stirred at 25° C. for 12 hrs. The reaction mixture was diluted with water (20 mL) and extracted with EA (20 mL×3). The combined organic layers were washed with saturated brine (40 mL×2), dried over Na₂SO₄, filtered and concentrated under reduced pressure to give a residue. The residue was purified by prep-HPLC (Column: Phenomenex Luna C18 150×25 mm×10 um; mobile phase: [A: water (0.1% TFA), B: ACN]; B %: 60%-90%) to give 10-1 (0.12 g, 67% yield) as a yellow oil. LCMS: (ES⁺) m/z (M+H)⁺=570.4. ¹H NMR (400 MHz, CDCl₃) δ ppm 7.29 (s, 1H) 7.21-7.26 (m, 1H) 6.89-6.98 (m, 1H) 6.74-6.88 (m, 4H) 3.85-4.10 (m, 4H) 3.83 (s, 3H) 3.56-3.68 (m, 2H) 3.12-3.27 (m, 2H) 2.68-2.77 (m, 4H) 2.29-2.42 (m, 2H) 2.17 (brs, 2H) 2.12 (brs, 5H) 1.53-1.68 (m, 2H) 1.18-1.26 (m, 3H) 1.06 (d, J=14 Hz, 3H) 0.89 (s, 9H) 0.56-0.70 (m, 1H) 0.41-0.52 (m, 1H) 0.28-0.40 (m, 1H) 0.15-0.25 (m, 1H).

Step 2: ((S)-2-cyclopropyl-2-(3-((1-(2-(4,4-dimethylpentyl)-5-methoxyphenyl)piperidin-4-yl)methoxy)phenyl)ethyl)(methyl)phosphinic acid (Compound 10)

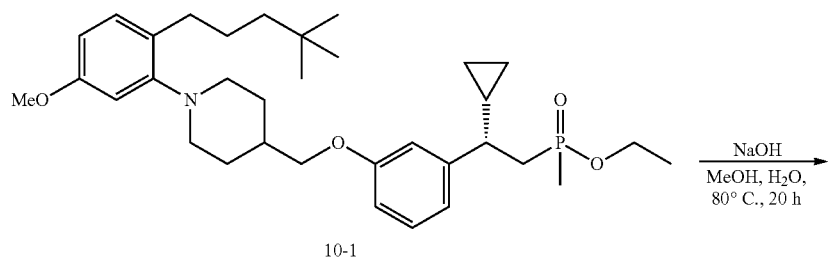

10-1

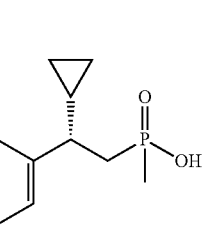

Compopund 10

To a solution of 10-1 (0.12 g, 0.21 mol, 1 eq) in MeOH (1 mL) and H₂O (1 mL) was added NaOH (84 mg, 2.1 mmol, 10 eq). The reaction was stirred at 80° C. for 20 hrs. The reaction mixture was filtered, and the filtrate was concentrated. The residue was purified by prep-HPLC (Column: Waters XBridge 150×25 mm×10 um; mobile phase: [A: water (10 mM NH₄HCO₃), B: ACN]; B %: 45%-75%) to give Compound 10 (49 mg, 43% yield) as a white solid. LCMS: (ES⁺) m/z (M+H)⁺=542.9 ¹H NMR (400 MHz, CD₃OD) δ ppm 7.18 (t, J=8.00 Hz, 1H) 7.06 (d, J=8.38 Hz, 1H) 6.81-6.92 (m, 2H) 6.75 (br d, J=7.25 Hz, 1H) 6.67 (d, J=2.50 Hz, 1H) 6.57 (dd, J=8.32, 2.56 Hz, 1H) 3.84-4.00 (m, 2H) 3.75 (s, 3H) 3.07 (br d, J=11.26 Hz, 2H) 2.70 (br t, J=11.44 Hz, 2H) 2.55 (t, J=7.82 Hz, 2H) 2.15-2.28 (m, 1H) 2.01-2.15 (m, 2H) 1.81-2.00 (m, 3H) 1.49-1.68 (m, 4H) 1.27 (s, 2H) 0.99-1.16 (m, 1H) 0.89 (s, 9H) 0.73 (br d, J=13.63 Hz, 3H) 0.48-0.64 (m, 1H) 0.34 (br s, 2H) 0.07-0.21 (m, 1H).

Example 14: Preparation of ((S)-2-cyclopropyl-2-(2-((1-(2-(4,4-dimethylpentyl)-5-methoxyphenyl)piperidin-4-yl)methoxy)pyridin-4-yl)ethyl)(methyl)phosphinic acid (Compound 11)

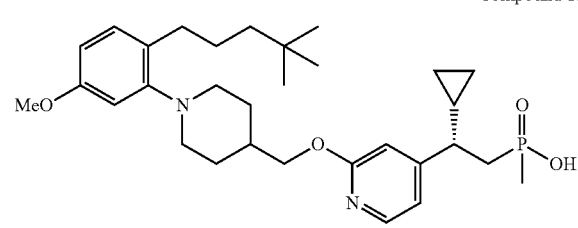

Compound 11

Step 1: 4-(bromomethyl)-1-(2-(4,4-dimethylpentyl)-5-methoxyphenyl)piperidine (11-1

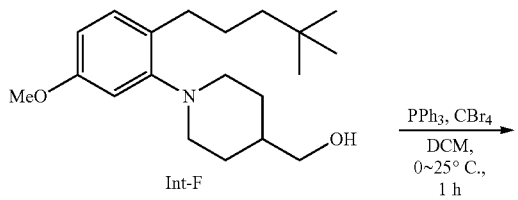

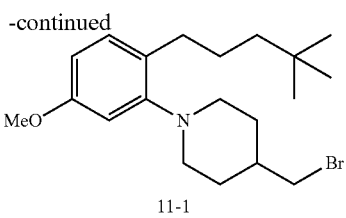

11-1

To a solution of Int-F (1.2 g, 3.9 mmol, 1 eq) in DCM (12 mL) was added CBr$_4$ (1.8 g, 5.4 mmol, 1.4 eq) and PPh$_3$ (1.4 g, 5.4 mmol, 1.4 eq) at 0° C. The reaction mixture was stirred at 25° C. for 1 hr. The combined reaction mixture was concentrated under vacuum. The residue was purified by column chromatography (SiO$_2$, Petroleum ether/Ethyl acetate=1/0 to 5/1) to give 11-1 (1.7 g, 54% yield) as a brown oil. LCMS: (ES$^+$) m/z (M+H)$^+$=382.2. $^1$H NMR (400 MHz, CDCl$_3$) S (ppm)=7.12 (d, J=8.4 Hz, 1H), 6.72-6.53 (m, 2H), 3.79 (s, 3H), 3.38 (d, J=6.4 Hz, 2H), 3.22-3.04 (m, 2H), 2.66 (br s, 2H), 2.54 (br t, J=7.2 Hz, 2H), 1.95 (br d, J=12.4 Hz, 2H), 1.86-1.73 (m, 1H), 1.60-1.43 (m, 4H), 1.28-1.24 (m, 2H), 0.89 (s, 9H).

Step 2: ethyl ((S)-2-cyclopropyl-2-(2-((1-(2-(4,4-dimethylpentyl)-5-methoxyphenyl)piperidin-4-yl)methoxy)pyridin-4-yl)ethyl)(methyl)phosphinate (11-2

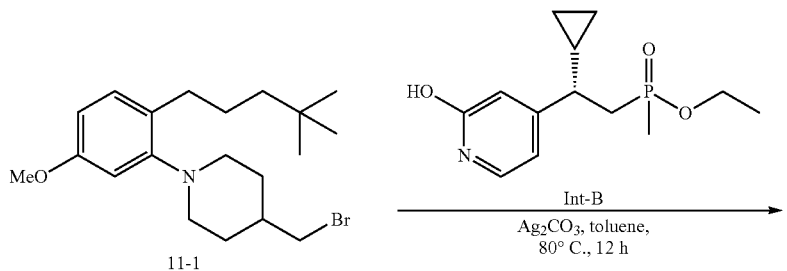

To a solution of 11-1 and Int-B (0.14 g, 0.52 mol, 2 eq) in toluene (2 mL) was added Ag$_2$CO$_3$ (0.11 g, 0.39 mol, 1.5 eq). The mixture was stirred at 80° C. for 12 hrs. The reaction mixture was filtered and concentrated under vacuum. The residue was purified by prep-TLC (SiO$_2$, EA:MeOH=10:1) to give 11-2 (39 mg, 24% yield) as yellow oil. LCMS: (ES$^+$) m/z (M+H)$^+$=571.4.

Step 3: ((S)-2-cyclopropyl-2-(2-((1-(2-(4,4-dimethylpentyl)-5-methoxyphenyl)piperidin-4-yl)methoxy)pyridin-4-yl)ethyl)(methyl)phosphinic acid (Compound 11)

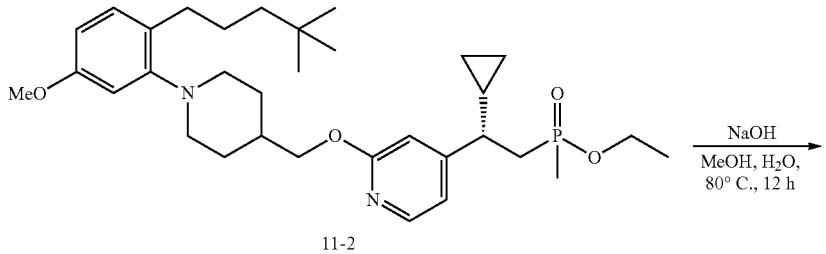

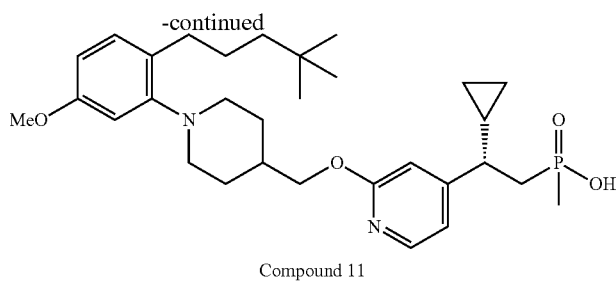

Compound 11

To a solution of 11-2 (39 mg, 68 umol, 1 eq) in MeOH (1 mL) and H$_2$O (1 mL) was added NaOH (41 mg, 1.0 mmol, 15 eq). The mixture was stirred at 80° C. for 12 hrs. The reaction mixture was filtered and concentrated under vacuum. The residue was purified by prep-HPLC (column: Phenomenex Luna C18 150×25 mm×10 um; mobile phase: [A: water (0.1% TFA), B:xs ACN]; B %: 30%-60%) to give Compound 11 (18 mg, 44% yield) as a yellow oil. LCMS: (ES$^+$) m/z (M+H)$^+$=543.3. $^1$H NMR (400 MHz, CD$_3$OD) δ (ppm)=8.28 (d, J=6 Hz, 1H), 7.60 (s, 1H), 7.55 (d, J=6.4 Hz, 1H), 7.36 (d, J=8.8 Hz, 1H), 7.21 (d, J=1.6 Hz, 1H), 7.08 (dd, J=2.4, 8.8 Hz, 1H), 4.70-4.56 (m, 2H), 4.18-3.91 (m, 3H), 3.88 (s, 3H), 3.80-3.64 (m, 1H), 3.16-2.97 (m, 1H), 2.84 (t, J=7.6 Hz, 2H), 2.65-2.35 (m, 4H), 2.31-2.14 (m, 3H), 1.73-1.57 (m, 2H), 1.45 (d, J=14 Hz, 3H), 1.39-1.31 (m, 2H), 1.26-1.20 (m, 1H), 0.91 (s, 9H), 0.80-0.69 (m, 1H), 0.55-0.44 (m, 2H), 0.36-0.26 (m, 1H).

Example 15: Preparation of ((R)-2-(2-((1-(2-(4,4-dimethylpentyl)-5-methoxyphenyl)piperidin-4-yl)methoxy)pydidin-4-yl)propyl)(methyl)phosphinic acid (Compound 12)

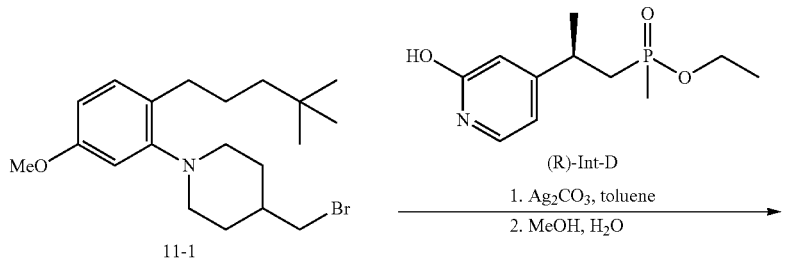

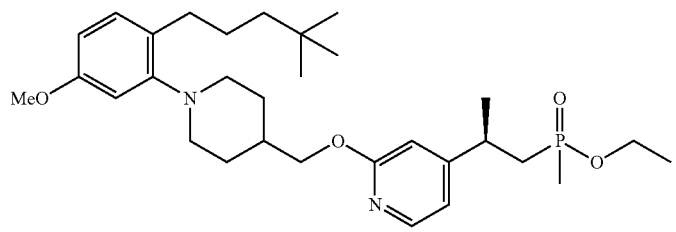

Compound 12

Compound 12 was prepared according to Example 14 from starting reagents 11-1 and (R)-Int-D. LCMS: (ES$^+$) m/z (M+H)$^+$=517.5. H NMR (400 MHz, CD$_3$OD) δ ppm 8.27 (d, J=6.0 Hz, 1H) 7.44-7.57 (m, 2H) 7.39 (d, J=8.8 Hz, 1H) 7.21 (d, J=2.0 Hz, 1H) 7.11 (dd, J=8.4, 2.4 Hz, 1H) 4.56-4.66 (m, 2H) 3.92-4.20 (m, 3H) 3.89 (s, 3H) 3.71 (br s, 1H) 3.47 (br dd, J=9.6, 7.2 Hz, 1H) 2.95-3.12 (m, 1H) 2.83 (t, J=7.6 Hz, 2H) 2.60-2.58 (m, 1H) 2.14-2.38 (m, 5H) 1.61-1.72 (m, 2H) 1.42-1.55 (m, 6H) 1.33-1.40 (m, 2H) 0.93 (s, 9H).

Example 16: Preparation of ((S)-2-(2-((1-(2-(4,4-dimethylpentyl)-5-methoxyphenyl)piperidin-4-yl)methoxy)pyridin-4-yl)propyl)(methyl)phosphinic acid (Compound 13)

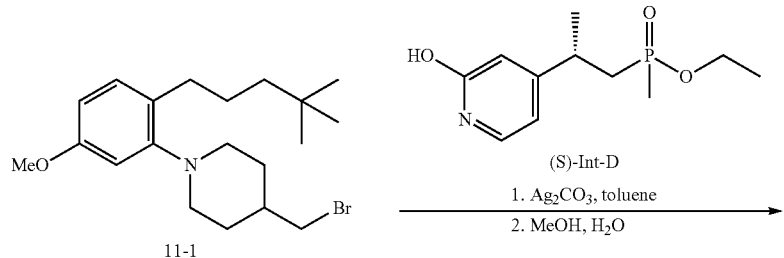

Compound 13 was prepared according to Example 14 from starting reagents 11-1 and (S)-Int-D. LCMS: (ES+) m/z (M+H)+=517.5. H NMR (400 MHz, CD$_3$OD) δ ppm 8.23 (d, J=6.0 Hz, 1H) 7.40-7.52 (m, 2H) 7.37 (d, J=8.4 Hz, 1H) 7.17 (d, J=2.0 Hz, 1H) 7.08 (dd, J=8.4, 2.4 Hz, 1H) 4.52-4.63 (m, 2H) 3.89-4.19 (m, 3H) 3.86 (s, 3H) 3.59-3.74 (m, 1H) 3.38-3.49 (m, 1H) 2.92-3.08 (m, 1H) 2.79 (t, J=7.6 Hz, 2H) 2.50-2.63 (m, 1H) 2.11-2.34 (m, 5H) 1.59-1.69 (m, 2H) 1.38-1.53 (m, 6H) 1.30-1.38 (m, 2H) 0.90 (s, 9H).

Example 17: ((R)-2-(3-((1-(2-(4,4-dimethylpentyl)-5-methoxyphenyl)piperidin-4-yl)methoxy)phenyl)propyl)(methyl)phosphinic acid (Compound 14)

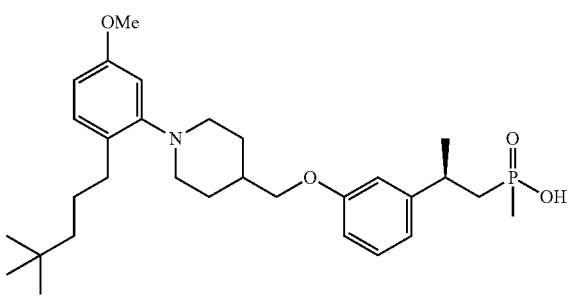

Compound 14

Step 1: ethyl ((R)-2-(3-((1-(2-(4,4-dimethylpentyl)-5-methoxyphenyl)piperidin-4-yl)methoxy)phenyl)propyl)(methyl)phosphinate (14-1)

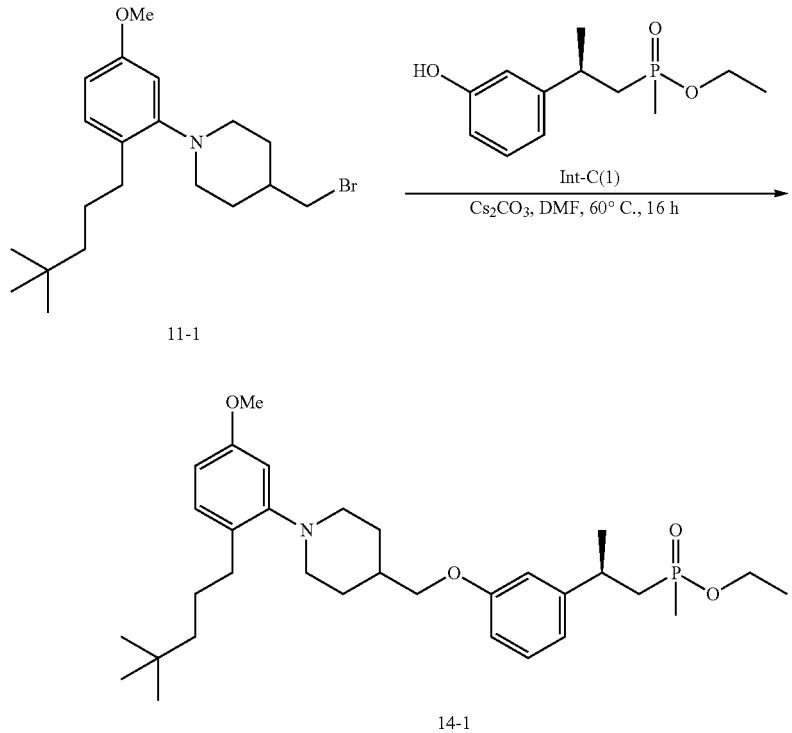

To a solution of 11-1 (0.1 g, 0.26 mol, 1 eq) and Int-C(1) (0.13 mg, 0.52 mol, 2 eq) in DMF (2 mL) was added $K_2CO_3$ (0.11 g, 0.78 mol, 3 eq). The mixture was stirred at 60° C. for 16 hrs. The reaction mixture was quenched by addition $H_2O$ (4 mL) at 25° C. and diluted with ethyl acetate (3 mL×3). The combined organic layers were washed with saturated brine (3 mL×3), dried over sodium sulfate, filtered and concentrated under reduced pressure to give a residue. The residue was purified by prep-TLC ($SiO_2$, EA:MeOH=10:1, $R^f$=0.43) to give 14-1 (55 mg, 34% yield) as a yellow oil. LCMS: (ES$^+$) m/z (M+H)$^+$=544.5.

Step 2: ((R)-2-(3-((1-(2-(4,4-dimethylpentyl)-5-methoxyphenyl)piperidin-4-yl)methoxy)phenyl)propyl)(methyl)phosphinic acid (Compound 14)

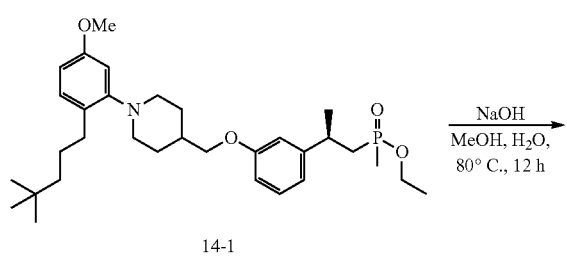

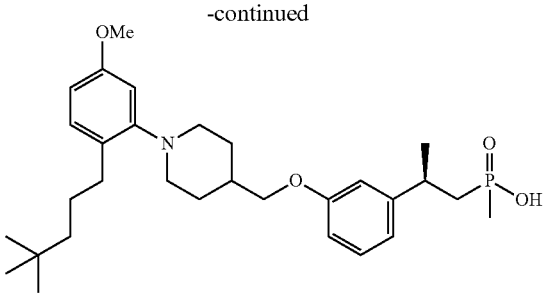

Compound 14

To a solution of 14-1 (87 mg, 0.16 mol, 1 eq) in MeOH (1 mL) and $H_2O$ (1 mL) was added NaOH (96 mg, 2.4 mmol, 15 eq). The mixture was stirred at 80° C. for 12 hrs. The reaction mixture was filtered concentrated under vacuum. The residue was purified by prep-HPLC (TFA condition, column: Phenomenex Luna C18 150×25 mm×10 um; mobile phase: [water (0.1% TFA)-ACN]; B %: 35%-65%, 10 min) to give Compound 14 (8.7 mg, 10% yield) as yellow oil. LCMS: tR=0.567 min., (ES$^+$) m/z (M+H)$^+$=516.7. $^1$H NMR (400 MHz, CD$_3$OD) δ (ppm)=7.37 (d, J=8.4 Hz, 1H), 7.22 (t, J=8 Hz, 1H), 7.16 (d, J=2 Hz, 1H), 7.08 (dd, J=2.4, 8.8 Hz, 1H), 6.91-6.83 (m, 2H), 6.78 (dd, J=2, 8 Hz, 1H), 4.18-4.08 (m, 2H), 4.08-3.88 (m, 3H), 3.86 (s, 3H), 3.67 (m, 1H), 3.15 (m, 1H), 2.96 (m, 1H), 2.76 (t, J=8 Hz, 2H), 2.54 (m, 1H), 2.20-2.01 (m, 5H), 1.71-1.54 (m, 2H), 1.41-1.29 (m, 5H), 1.11 (d, J=14 Hz, 3H), 0.90 (s, 9H).

Example 18: Preparation of ((S)-2-(3-((1-(2-(4,4-dimethylpentyl)-5-methoxyphenyl)piperidin-4-yl)methoxy)phenyl)propyl)(methyl)phosphinic acid (Compound 15)
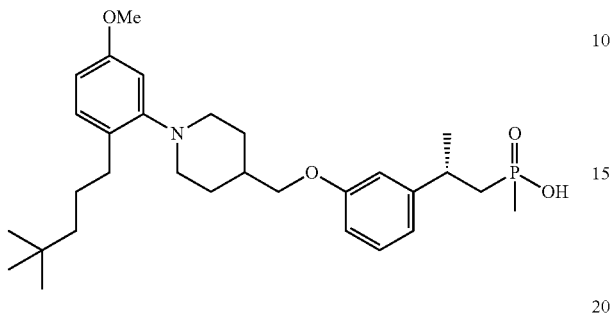
Compound 15
Step 1: ethyl ((S)-2-(3-((1-(2-(4,4-dimethylpentyl)-5-methoxyphenyl)piperidin-4-yl)methoxy)phenyl)propyl)(methyl)phosphinate (15-1):
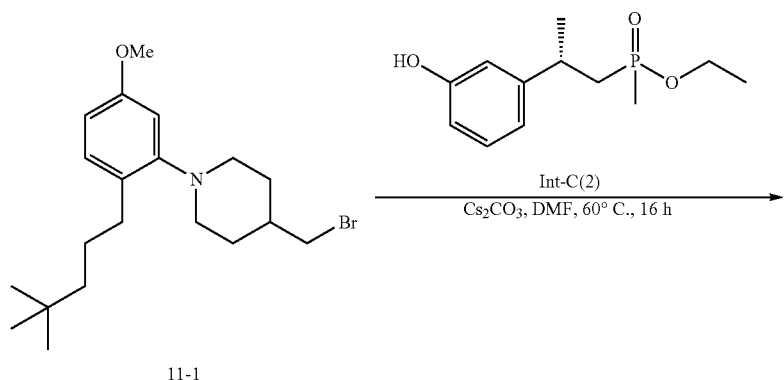
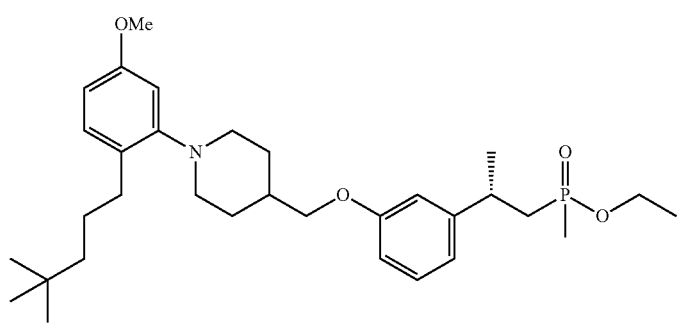
15-1
15-1 (25 mg, 16% yield) was prepared according to Example 17 from starting reagents 11-1 and Int-C(2). LCMS: (ES$^+$) m/z (M+H)$^+$=544.7.

Step 2: ((S)-2-(3-((1-(2-(4,4-dimethylpentyl)-5-methoxyphenyl)piperidin-4-yl)methoxy)phenyl)propyl)(methyl)phosphinic acid) (Compound 15)

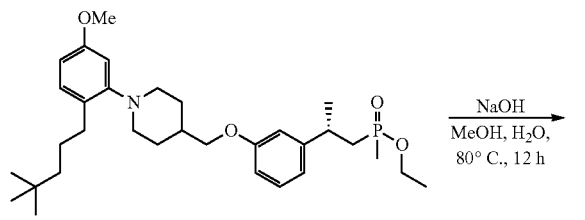

Compound 15

Compound 15 (15 mg, 21% yield) was prepared according to Example 17 from 15-1. LCMS: (ES$^+$) m/z (M+H)$^+$=516.5. $^1$H NMR (400 MHz, CD$_3$OD) δ (ppm)=7.36 (d, J=8.8 Hz, 1H), 7.22 (t, J=8 Hz, 1H), 7.16 (d, J=2.4 Hz, 1H), 7.08 (dd, J=2.4, 8.8 Hz, 1H), 6.91-6.83 (m, 2H), 6.78 (dd, J=1.6, 8 Hz, 1H), 4.18-4.07 (m, 2H), 4.06-3.90 (m, 3H), 3.86 (s, 3H), 3.67 (m, 1H), 3.15 (m, 1H), 3.03-2.90 (m, 1H), 2.77 (t, J=7.6 Hz, 2H), 2.60-2.47 (m, 1H), 2.22-2.01 (m, 5H), 1.70-1.51 (m, 2H), 1.43-1.29 (m, 5H), 1.12 (d, J=14.4 Hz, 3H), 0.90 (s, 9H).

Example 19: Preparation of (1-(3-((1-(2-(4,4-dimethylpentyl)-5-methoxyphenyl)pipeidin-4-yl)methoxy)phenyl)propan-2-yl)phosphonic acid (Compound 16)

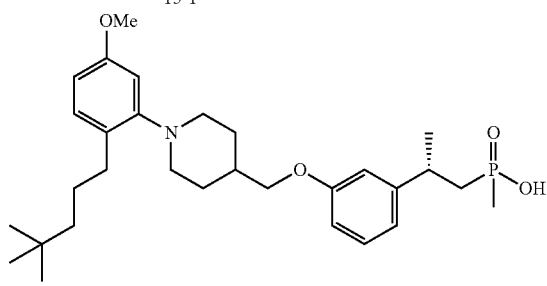

Compound 16

Step 1: 2-(3-benzyloxy)phenyl)ethan-1-ol (16-1

To a solution of 1-(benzyloxy)-3-bromobenzene (25 g, 95 mmol, 1 eq) in THF (250 mL) was added dropwise n-BuLi (2.5 M in n-hexane, 42 mL, 1.1 eq) at −78° C. under N$_2$ followed by oxirane (13 g, 0.29 mol, 14 mL, 3 eq). The mixture was warmed to 25° C. and stirred for 2 hrs. The reaction mixture was poured into saturated aqueous NH$_4$Cl solution (400 mL) in an ice bath and extracted with EA (150 mL×2). The combined organic layer was concentrated to afford a residue. The residue was purified by flash silica gel chromatography (ISCO®; 120 g SepaFlash® Silica Flash Column, Eluent of 0 to 20% Ethyl acetate/Petroleum ether gradient) to give 16-1 (10 g, 46% yield) as a colorless oil. $^1$H NMR (400 MHz, CDCl$_3$) δ 7.46-7.38 (m, 5H), 7.27-7.25 (m, 1H), 6.88-6.84 (m, 3H), 5.08 (s, 2H), 3.87 (t, J=6.8 Hz, 2H), 2.86 (t, J=6.8 Hz, 2H).

Step 2: 1-(benzyloxy)-3-(2-iodoethyl)benzene (16-2

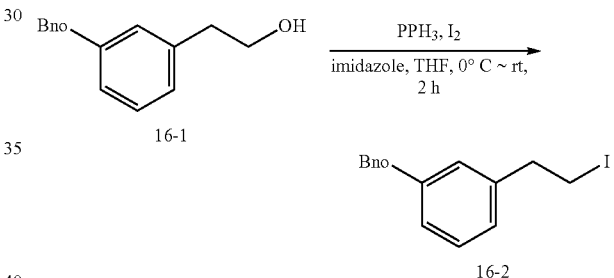

To a solution of 16-1 (9.0 g, 39 mmol, 1 eq), imidazole (3.2 g, 47 mmol, 1.2 eq) and triphenylphosphine (12 g, 47 mmol, 1.2 eq) in THF (180 mL) was added dropwise a solution of iodine (12 g, 47 mmol, 1.2 eq) in THF (90 mL) at 0° C. The reaction mixture was stirred at 25° C. for 2 hrs. The reaction mixture was filtered, and the filtrate was concentrated under reduced pressure to give a residue. The residue was purified by column chromatography (SiO$_2$, Petroleum ether/Ethyl acetate=100/1 to 60/1) to give 16-2 (12 g, 90% yield) as a yellow oil.

Step 3: diethyl (3-(benzyloxy)phenethyl)phosphonate (16-3

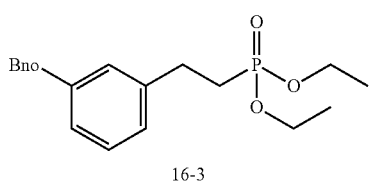

16-3

The mixture of 16-2 (7 g, 21 mmol, 1 eq) and triethyl phosphite (69 g, 0.41 mol, 71 mL, 20 eq) was stirred at 130° C. for 12 hrs. The reaction mixture was diluted with water (300 mL) and extracted with EA (200 mL×2). The combined organic layer was concentrated to give a residue. The residue was purified by reversed-phase HPLC (column: Phenomenex Luna C18 250×50 mm×10 um; mobile phase: [A: water (0.1% FA, v/v), B: can]; B %: 40%-70% gradient over 30 min) to give 16-3 (7 g, 95% yield) as colorless oil. LCMS: (ES$^+$) m/z (M+H)$^+$=349.3. $^1$H NMR (400 MHz, CDCl$_3$) δ 7.36-7.27 (m, 5H), 7.25-7.14 (m, 1H), 6.76-6.72 (m, 3H), 4.98 (s, 2H), 4.07-3.99 (m, 4H), 2.85-2.78 (m, 2H), 2.02-1.95 (m, 2H), 1.25 (t, J=6.8 Hz, 6H).

Step 4: diethyl (1-(3-(benzyloxy)phenyl)propan-2-yl)phosphonate (16-4

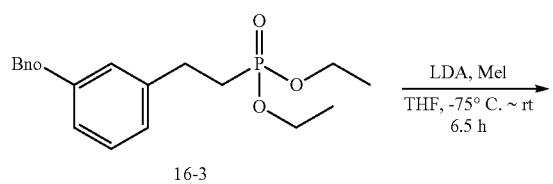

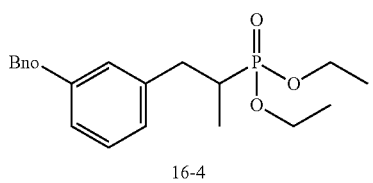

16-4

To a solution of 16-3 (1.2 g, 3.4 mmol, 1 eq) in THF (12 mL) was added dropwise LDA (2 M in THF, 6.9 mL, 4 eq) at −78° C. The mixture was stirred at −78° C. for 0.5 hr. Then MeI (4.8 g, 34 mmol, 10 eq) was added dropwise at −78° C. The mixture was stirred at −78° C. for 1 hr and 25° C. for 5 hrs. The reaction mixture was quenched with saturated aqueous NH$_4$Cl solution (80 mL) with stirring at 0° C. and extracted with ethyl acetate (30 mL×3). The combined organic layer was concentrated to give a residue that was then purified by reversed-phase HPLC (column: Phenomenex Luna C18 250×50 mm×10 um; mobile phase: [A: water (0.1% FA, v/v), B: can]; B %: 42%-72% gradient over 30 min) to give 16-4 (0.31 g, 23% yield) as a brown oil. LCMS: (ES$^+$) m/z (M+H)$^+$=363.1.

Step 5: diethyl (1-(3-hydroxyphenyl)propan-2-yl)phosphonate (16-5

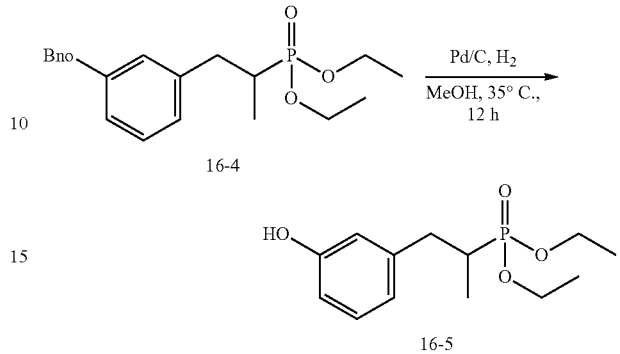

To a solution of 16-4 (0.77 g, 2.1 mmol, 1 eq) in MeOH (7 mL) was added 10% Pd/C (0.10 g, 0.21 mmol, 0.1 eq). The suspension was degassed under vacuum and purged with H$_2$ several times. The mixture was stirred at 35° C. for 12 hrs under H$_2$ (50 psi). The mixture was filtered. The filtrate was concentrated in vacuo to give 16-5 (0.47 g, crude) as a colorless oil. LCMS: (ES$^+$) m/z (M+H)$^+$=273.0.

Step 6: diethyl (1-(3-((1-(2-(4,4-dimethylpentyl)-5-methoxyphenyl)piperidin-4-yl)methoxy)phenyl)propan-2-yl)phosphonate (16-6

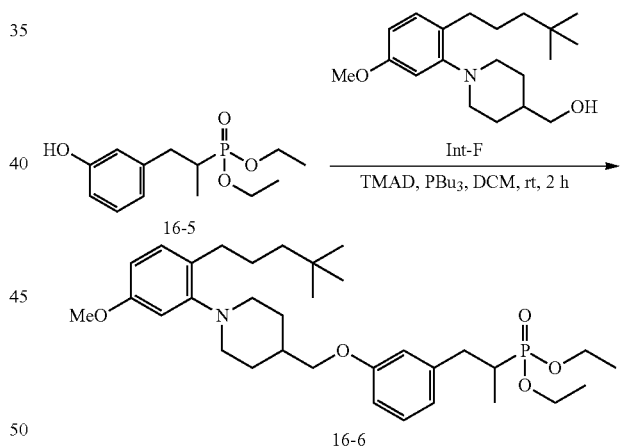

To a solution of TMAD (0.60 g, 3.5 mmol, 2.3 eq) in THF (14 mL) was added tributylphosphane (0.76 g, 3.8 mmol, 2.5 eq) dropwise at 0° C., and the mixture was stirred for 10 min. It was then added to a solution of 16-5 (0.41 g, 1.5 mmol, 1 eq) and Int-F (0.48 g, 1.5 mmol, 1 eq) in THF (9 mL) at 0° C. The mixture was stirred at 25° C. for 2 hrs. The reaction was diluted with H$_2$O (10 mL) and then extracted with EA (40 mL×2). The combined organic phase was washed with saturated brine (10 mL×2), dried over anhydrous Na$_2$SO$_4$, filtered and concentrated under pressure. The crude product was purified by reversed-phase HPLC (column: Phenomenex Luna C18 250×50 mm×10 um; mobile phase: [A: water (0.1% FA, v/v), B: can]; B %: 30%-60% gradient over 20 min) to give 16-6 (0.60 g, 68% yield) as a colorless oil. LCMS: (ES$^+$) m/z (M+H)+=574.5.

Step 7: (1-(3-((1-(2-(4,4-dimethylpentyl)-5-methoxyphenyl)piperidin-4-yl)methoxy)phenyl)propan-2-yl)phosphonic acid (Compound 16)

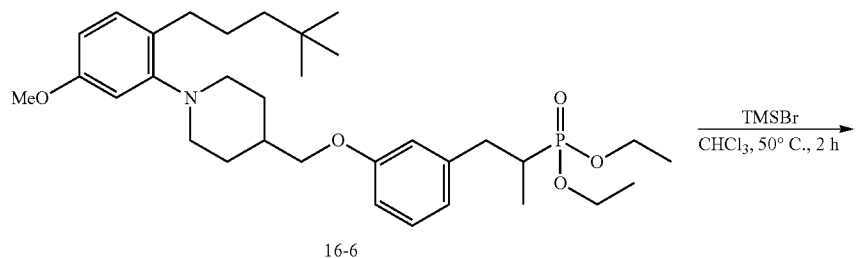

Compound 16

To a solution of 16-6 (0.16 g, 0.28 mmol, 1 eq) in CHCl$_3$ (1.5 mL) was added TMSBr (0.17 g, 1.1 mmol, 4 eq). The mixture was stirred at 50° C. for 2 hrs. The reaction mixture was concentrated under reduced pressure to give a residue. The residue was purified by prep-HPLC (column: Phenomenex Luna C18 150×25 mm×10 um; mobile phase: [A: water (0.1% TFA), B: ACN]; B %: 50%-80%) to give Compound 16 (55 mg, 31% yield) as a white solid. LCMS: (ES$^+$) m/z (M+H)$^+$=518.4. $^1$H NMR (400 MHz, CDCl$_3$) δ 7.32 (d, J=8.8 Hz, 1H), 7.19-7.08 (m, 2H), 6.95 (dd, J=2.1, 8.6 Hz, 1H), 6.79 (br s, 1H), 6.72 (br t, J=8.2 Hz, 2H), 3.98-3.89 (m, 2H), 3.83 (s, 3H), 3.73 (br d, J=11.8 Hz, 2H), 3.49-3.44 (m, 1H), 3.22 (br t, J=10.8 Hz, 1H), 2.83 (br t, J=7.8 Hz, 2H), 2.59-2.37 (m, 3H), 2.25-2.09 (m, 4H), 1.69-1.57 (m, 2H), 1.35-1.24 (m, 3H), 1.07 (br dd, J=7.0, 18.8 Hz, 3H), 0.88 (s, 9H).

Example 20: Preparation of ((R)-1-(3-((1-(2-(4,4-dimethylpentyl)-5-methoxyphenyl)piperidin-4-yl)methoxy)phenyl)butan-2-yl)methyl)phosphinic acid (Compound 17)

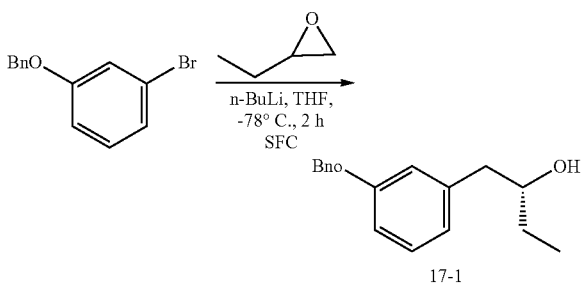

Compound 17

Step 1: (R)-1-(3-(benzyloxy)phenyl)butan-2-ol (17-1)

A solution of 1-benzyloxy-3-bromo-benzene (10 g, 38 mmol, 1 eq) in THF (200 mL) was cooled at −78° C. and n-BuLi (2.5 M in n-hexane, 17 mL, 1.1 eq) was added slowly. After the reaction mixture was stirred for 0.5 hr, 2-ethyloxirane (4.1 g, 57 mmol, 5.0 mL, 1.5 eq) and BF$_3$·Et$_2$O (8.1 g, 57 mmol, 7.0 mL, 1.5 eq) were added at −78° C. The mixture was stirred at −78° C. for 2 hrs. The reaction mixture was quenched by addition of saturated aqueous NH$_4$Cl solution (100 mL) at 0° C., then diluted with water (200 mL) and extracted with EA (300 mL×3). The combined organic layers were washed with saturated brine (500 mL×2), dried over Na$_2$SO$_4$, filtered and concentrated under reduced pressure to give a residue. The residue was purified by column chromatography (SiO$_2$, Petroleum ether/Ethyl acetate=4/1) to give racemic 17-1 (6.5 g, 65% yield) as a yellow oil. $^1$H NMR (400 MHz, CD$_3$OD) δ=7.47-7.39 (m, 2H), 7.35 (t, J=7.5 Hz, 2H), 7.30 (d, J=7.2 Hz, 1H), 7.17 (t, J=7.9 Hz, 1H), 6.89-6.76 (m, 3H), 5.05 (s, 2H), 2.69 (d, J=6.4 Hz, 2H), 0.95 (t, J=7.4 Hz, 3H). Racemic 17-1 (6.5 g, 25 mmol) was separated by SFC (column: DAICEL CHI- RALPAK AD 250 mm×50 mm, 10 um; mobile phase: [A: CO₂; B: 0.1% NH₃·H₂O in MeOH]; B %: 25%-25%) to give 17-1 (2.7 g, 41% yield, tR=1.300 min) as a yellow gum.

Step 2: (R)-1-(benzyloxy)-3-(2-iodobutyl)benzene (17-2

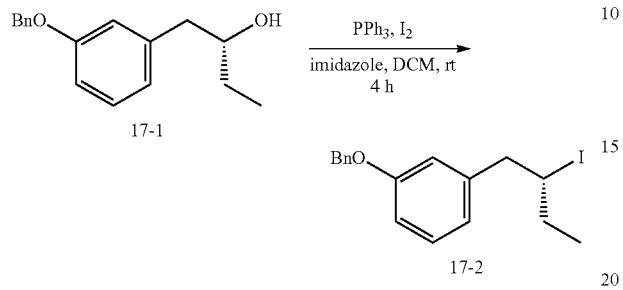

Imidazole (0.32 g, 4.7 mmol, 1.5 eq) and triphenylphosphine (1.2 g, 4.7 mmol, 1.5 eq) were dissolved in DCM (5 mL), and the solution was stirred for 5 minutes. Then I2 (1.2 g, 4.7 mmol, 1.5 eq) was added, and the mixture was stirred for 10 minutes. A solution of 17-1 (0.80 g, 3.1 mmol, 1 eq) in DCM (5 mL) was added dropwise at 0° C., and the mixture was stirred at 25° C. for 4 hrs. The solution was diluted with H₂O (100 mL) and extracted with EA (100 mL×2). The combined organic layers was washed with saturated NaHCO₃ solution (100 mL) and saturated brine (100 mL). The organic layer was dried over Na₂SO₄, filtered and concentrated under reduced pressure to give a residue. The residue was purified by column chromatography (SiO₂, Petroleum ether/Ethyl acetate=4:1) to give 17-2 (1.0 g, 23% yield) as a yellow oil.

Step 3: ethyl ((R)-1-(3-(benzyloxy)pheny)butan-2-yl)(methyl)phosphinate (17-3

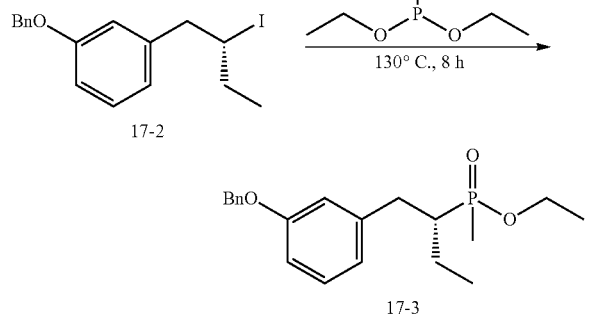

To a solution of 17-2 (1.0 g, 2.7 mmol, 1 eq) was added diethoxy(methyl)phosphane (7.4 g, 55 mmol, 20 eq). The mixture was stirred at 130° C. for 8 hrs. The solution was diluted with H₂O (20 mL) and extracted with EA (100 mL×2). The combined organic layers were washed with saturated brine (100 mL), dried over Na₂SO₄, filtered and concentrated under reduced pressure to give a residue. The residue was purified by reversed-phase HPLC (Column: 120 g Flash Column Welch Ultimate XB_C18 20-40 μm; Mobile phase: [A: 0.5% NH₃·H₂O in H₂O, B: can]; B %: 5-45%) to give 17-3 (0.13 g, 14% yield). LCMS: (ES⁺) m/z (M+H)⁺=347.5.

Step 4: ethyl ((R)-1-(3-hydroxyphenyl)butan-2-yl) methyl)phosphinate (17-4

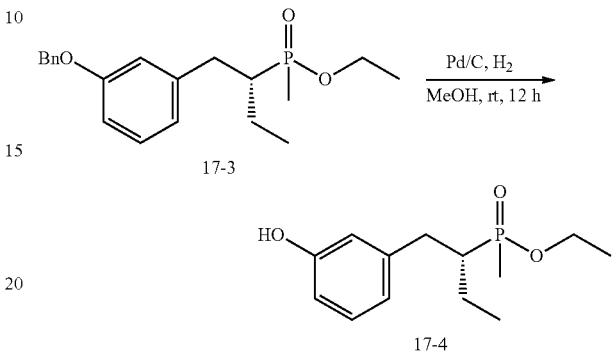

To a solution of 17-3 (0.13 g, 0.4 mol, 1 eq) in MeOH (2 mL) was added 5% Pd/C (0.1 g, 30.4 mmol, 1 eq) under N₂. The suspension was degassed under vacuum and purged with H₂ several times. The mixture was stirred at 25° C. for 12 hrs under H₂ (15 psi) atmosphere. The reaction mixture was filtered and concentrated under vacuum to give 17-4 (85 mg, 75% yield) as a yellow oil. LCMS: (ES⁺) m/z (M+H)⁺=257.2.

Step 5: ethyl ((R)-1-(3-((1-(2-(4,4-dimethylpentyl)-5-methoxyphenyl)piperidin-4-yl)methoxy)phenyl) butan-2-yl)methyl)phosphinate (17-5

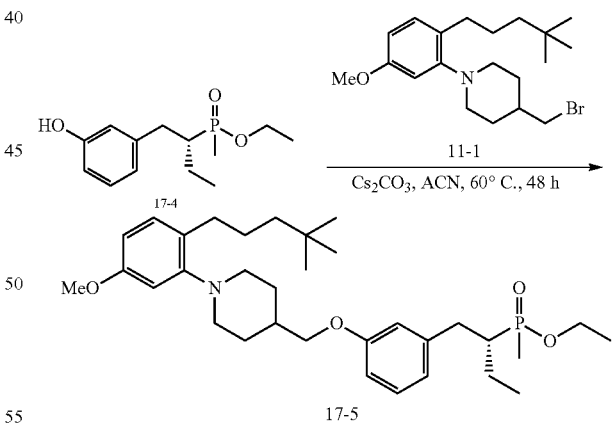

To a solution of 17-4 (85 mg, 0.3 mmol, 1.5 eq) and 11-1 (85 mg, 0.2 mmol, 1 eq) in DMF (2 mL) was added K₂CO₃ (92 mg, 0.7 mmol, 3 eq). The mixture was stirred at 60° C. for 48 hrs. The solution was diluted with H₂O (10 mL) and extracted with EA (10 mL×2). The combined organic layers were washed with brine (10 mL), dried over Na₂SO₄, filtered and concentrated under reduced pressure to give a residue. The residue was purified by prep-TLC (SiO₂, MeOH/EA=10/1) to give 17-5 (100 mg, 31% yield) as a yellow oil. LCMS: (ES⁺) m/z (M+H)⁺=558.5.

Step 6: ((R)-1-(3-((1-(2-(4,4-dimethylpentyl)-5-methoxyphenyl)piperidin-4-yl)methoxy)phenyl)butan-2-yl)methyl)phosphinic acid (Compound 17)

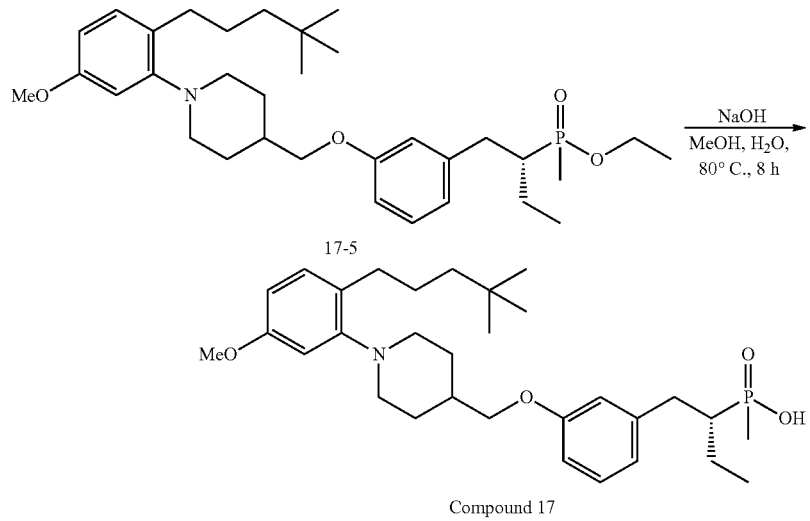

To a solution of 17-5 (100 mg, 68 umol, 1 eq) in MeOH (0.5 mL) and H$_2$O (0.5 mL) was added NaOH (29 mg, 0.7 mmol, 10 eq). The solution was stirred at 80° C. for 8 hrs. The mixture was adjusted to pH 6 with FA and then concentrated under reduced pressure to give a residue. The residue was purified by reversed-phase HPLC (column: Phenomenex Luna C18 150×25 mm×10 um; mobile phase: [A: water (0.1% TFA), B: ACN]; B %: 32%-62%) to give Compound 17 (17 mg, 44% yield, 99.8% purity) as a white powder. LCMS: (ES$^+$) m/z (M+H)$^+$=530.3. $^1$H NMR (400 MHz, CD$_3$OD) δ=7.33 (d, J=8.4 Hz, 1H), 7.20 (t, J=7.8 Hz, 1H), 7.09 (d, J=2.0 Hz, 1H), 7.02 (dd, J=2.3, 8.6 Hz, 1H), 6.88-6.81 (m, 2H), 6.78 (dd, J=2.2, 8.1 Hz, 1H), 4.18-4.04 (m, 2H), 3.94 (br dd, J=7.7, 10.9 Hz, 1H), 3.89-3.79 (m, 5H), 3.57 (br t, J=11.1 Hz, 1H), 3.05 (ddd, J=4.9, 11.7, 13.8 Hz, 1H), 2.89 (br s, 1H), 2.75-2.58 (m, 3H), 2.50 (br dd, J=6.9, 12.6 Hz, 1H), 2.15-2.01 (m, 3H), 1.99-1.85 (m, 1H), 1.73-1.46 (m, 4H), 1.33 (d, J=13.6 Hz, 5H), 0.97-0.91 (m, 3H), 0.90 (s, 9H).

Example 21: Preparation of ((S)-1-(3-((1-(2-(4,4-dimethylpentyl)-5-methoxyphenyl)piperidin-4-yl)methoxy)phenyl)butan-2-yl)methyl)phosphinic acid (Compound 18)

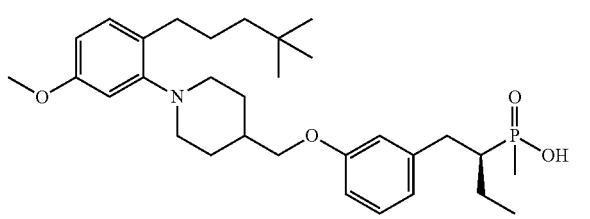

Compound 18

Step 1: (S)-1-(3-benzyloxy)phenyl)butan-2-ol (18-1

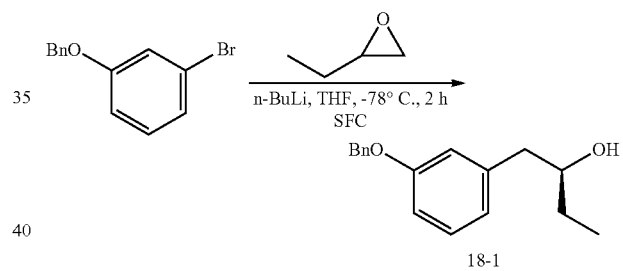

Racemic 17-1 (6.5 g, 25 mmol), prepared from 1-benzyloxy-3-bromo-benzene as described in Example 20 Step 1, was separated by SFC (column: DAICEL CHIRALPAK AD 250 mm×50 mm, 10 um; mobile phase: [A: CO$_2$; B: 0.1% NH$_3$·H$_2$O in MeOH]; B %: 25%) to give to give 18-1 (2.6 g, 39% yield, tR=1.427 min) as a yellow gum.

Step 2: (S)-1-(benzyloxy)-3-(2-iodobutyl)benzene (18-2

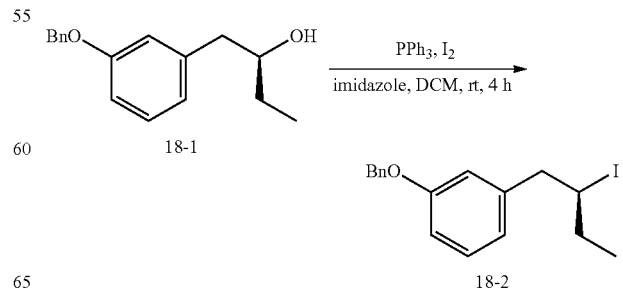

18-2 (1.3 g, 62% yield) was prepared according to Example 20 from 18-1.

Step 3: ethyl ((S)-1-(3-(benzyloxy)phenyl)butan-2-yl)(methyl)phosphinate (18-3

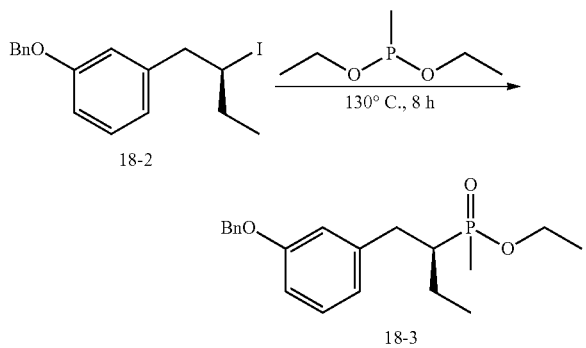

18-3 (80 mg, 83% yield) was prepared according to Example 20 from 18-2.

Step 4: ethyl ((S)-1-(3-hydroxyphenyl)butan-2-yl)(methyl)phosphinate (18-4

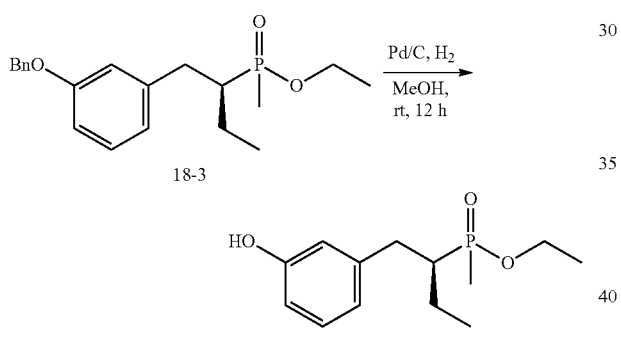

18-4 (96 mg, 65% yield) was prepared according to Example 20 from 18-3.

Step 5: ethyl ((S)-1-(3-hydroxyphenyl)butan-2-yl)(methyl)phosphinate (18-4

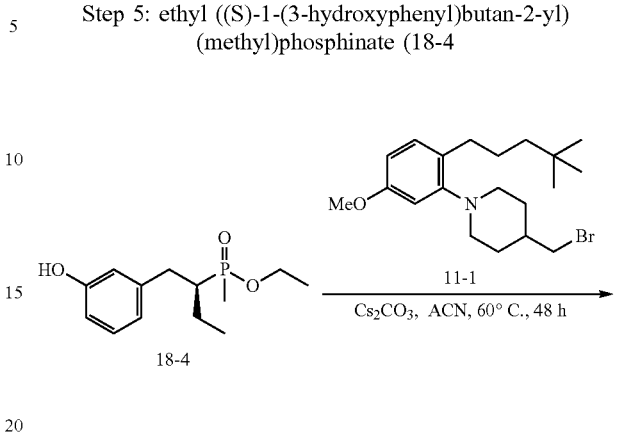

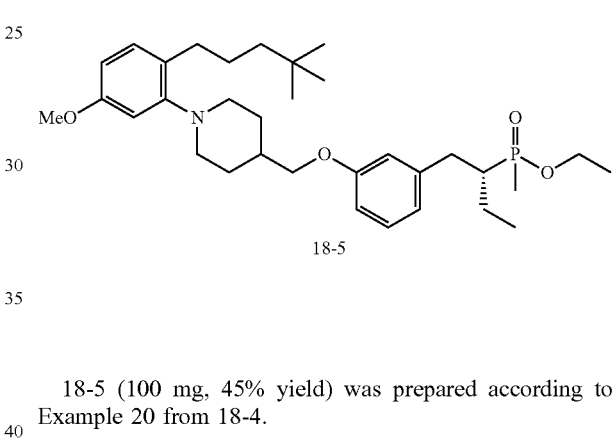

18-5 (100 mg, 45% yield) was prepared according to Example 20 from 18-4.

Step 6: ((S)-1-(3-((1-(2-(4,4-dimethylpentyl)-5-methoxyphenyl)piperidin-4-yl)methoxy)phenyl)butan-2-yl)methyl)phosphinic acid (Compound 18)

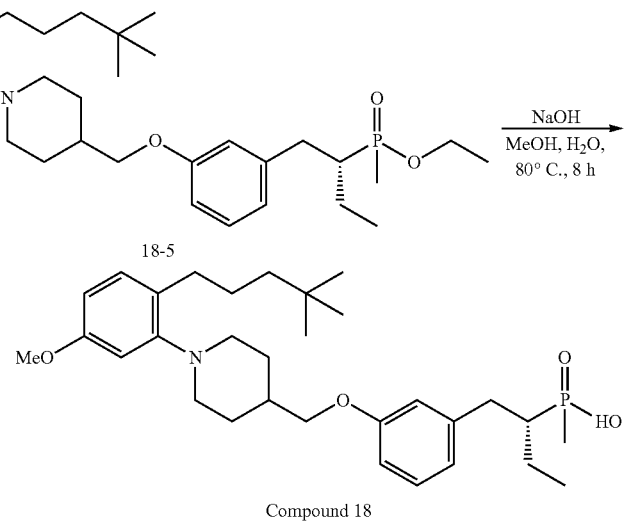

Compound 18 (18 mg, 47% yield) was prepared according to Example 20 from 18-5. LCMS: (ES+) m/z (M+H)+=530.3. ¹H NMR (400 MHz, CD₃OD) δ=7.33 (d, J=8.4 Hz, 1H), 7.24-7.14 (m, 1H), 7.09 (d, J=2.4 Hz, 1H), 7.02 (dd, J=2.4, 8.6 Hz, 1H), 6.91-6.81 (m, 2H), 6.78 (dd, J=1.9, 8.3 Hz, 1H), 4.15-4.05 (m, 2H), 3.95 (br dd, J=7.8, 11.3 Hz, 1H), 3.84 (s, 5H), 3.58 (s, 1H), 3.12-2.99 (m, 1H), 2.97-2.81 (m, 1H), 2.70 (t, J=7.8 Hz, 2H), 2.66-2.57 (m, 1H), 2.50 (br d, J=5.6 Hz, 1H), 2.18-2.01 (m, 3H), 1.99-1.85 (m, 1H), 1.76-1.42 (m, 4H), 1.33 (d, J=13.6 Hz, 3H), 1.31-1.25 (m, 2H), 0.93 (t, J=7.4 Hz, 3H), 0.89 (s, 9H).

Example 22: Preparation of (S)-(2-(3-((1-(2-(4,4-dimethylpentyl)-5-methoxyphenyl)piperidin-4-yl)methoxy)phenyl)propyl)phosphonic acid (Compound 19)

Compound 19

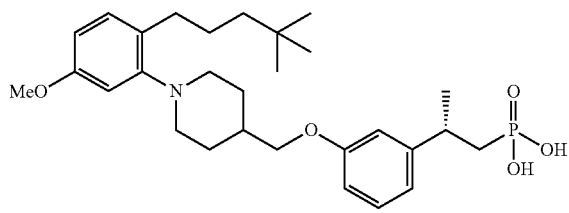

Step 1: diethyl (S)-(2-(3-(benzyloxy)phenyl)propyl) phosphonate (19-1

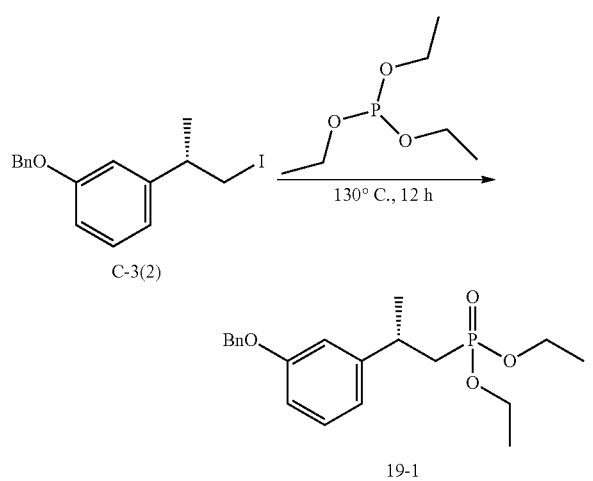

A mixture of C-3(2) (1.0 g, 2.8 mmol, 1 eq), synthesized as described in Example 3, and triethyl phosphite (9.4 g, 56 mmol, 9.7 mL, 20 eq) was stirred at 130° C. for 12 hrs. The mixture was quenched by water (80 mL), then extracted with EA (90 mL×3). The combined organic layers were washed with saturated brine (50 mL×2), dried over anhydrous Na₂SO₄, filtered and concentrated under reduced pressure to give a residue. The crude product was purified by reversed-phase HPLC (Column: 120 g Flash Column Welch Ultimate XB_C18 20-40 μm; Mobile phase: [A: 0.1% FA in H₂O, B: ACN]; B %: 30-60%) to give 19-1 (0.46 g, 44.10% yield) as a yellow oil. ¹H NMR (400 MHz, CDCl₃) δ ppm 1.14-1.32 (m, 7H) 1.36-1.41 (m, 3H) 1.85-2.24 (m, 2H) 2.98-3.33 (m, 1H) 3.81-4.09 (m, 4H) 5.03-5.11 (m, 2H) 6.80-6.89 (m, 3H) 7.19-7.25 (m, 1H) 7.30-7.36 (m, 1H) 7.37-7.42 (m, 2H) 7.42-7.48 (m, 2H).

Step 2: diethyl (S)-(2-(3-hydroxyphenyl)propyl) phosphonate (19-2

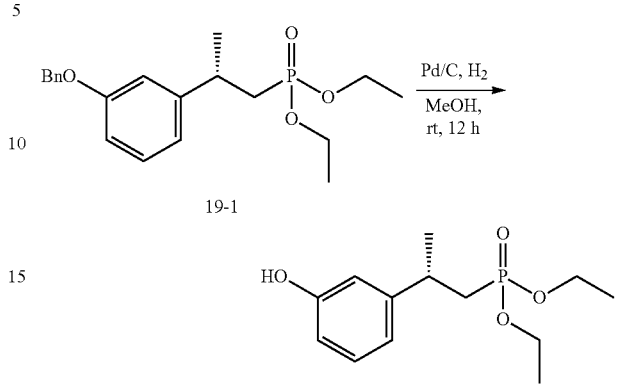

To a solution of 19-1 (0.46 g, 1.28 mmol, 1 eq) in MeOH (5 mL) was added 10% Pd/C (50 mg) under N₂. The suspension was degassed under vacuum and purged with H₂ several times. The mixture was stirred under H₂ (50 psi) at 25° C. for 12 hrs. The reaction mixture was filtered and concentrated under reduced pressure to give 19-2 (0.30 g, crude) as a colourless oil. LCMS: (ES+) m/z (M+H)+=273.3.

Step 3: diethyl (S)-(2-(3-((1-(2-(4,4-dimethylpentyl)-5-methoxyphenyl)piperidin-4-yl)methoxy)phenyl)propyl)phosphonate (19-3

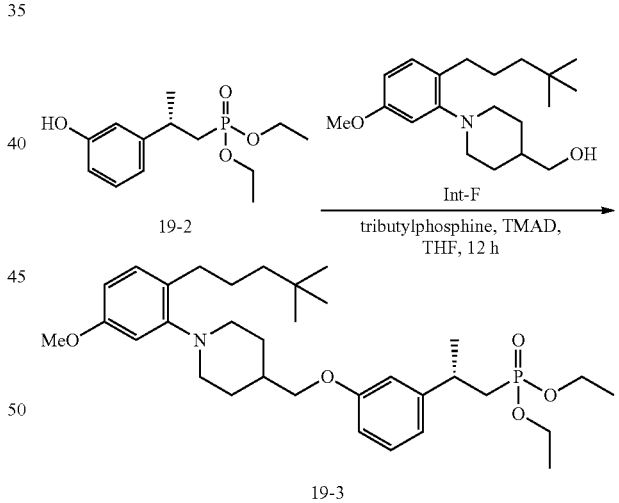

To a solution of TMAD (0.22 g, 1.3 mmol, 2.3 eq) in THF (1.5 mL) was added dropwise tributylphosphine (0.28 g, 1.4 mmol, 2.5 eq) at 0° C. under N₂. The mixture was stirred at 0° C. for 10 min and then a solution of 19-2 (0.15 g, 0.55 mmol, 1 eq) and Int-F (0.18 g, 0.55 mmol, 1 eq) in THF (3 mL) was added at 0° C. under N₂. The resulting mixture was stirred at 25° C. for 12 hrs. The reaction mixture was concentrated under reduced pressure to give a residue. The residue was purified by column chromatography (SiO₂, Petroleum ether/Ethyl acetate=10/1 to 5/1) to give 19-3 (0.13 g, 39% yield, 96% purity) as a yellow oil. LCMS: (ES+) m/z (M+H)+=574.2.

Step 4: (S)-(2-(3-((1-(2-(4,4-dimethylpentyl)-5-methoxyphenyl)piperidin-4-yl)methoxy)phenyl)propyl)phosphonic acid (Compound 19)

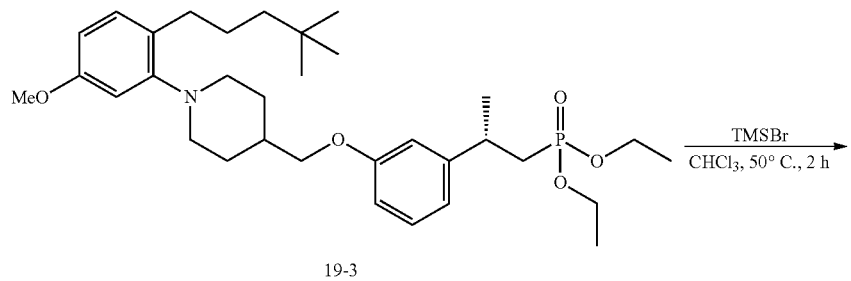

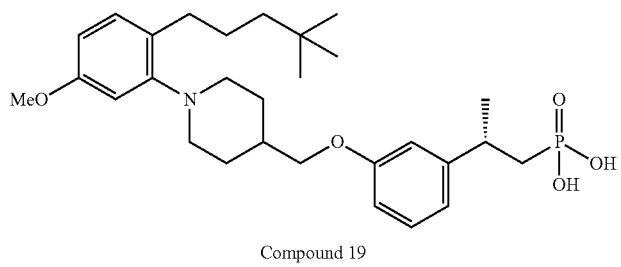

Compound 19

To a solution of 19-3 (0.13 g, 0.23 mmol, 1 eq) in CHCl$_3$ (1.5 mL) was added TMSBr (0.14 g, 0.91 mmol, 4 eq). The mixture was stirred at 50° C. for 2 hrs. The mixture was adjusted to pH 6 with FA and then purified by prep-HPLC (column: Phenomenex Luna C18 150×25 mm×10 um; mobile phase: [A: water (0.1% TFA), B: ACN]; B %: 35%-65%) to give Compound 19 (61 mg, 50% yield, 96% purity) as a white solid. LCMS: (ES$^+$) m/z (M+H)$^+$=518.5. $^1$H NMR (400 MHz, CD$_3$OD) δ ppm 0.91 (s, 8H) 1.25-1.34 (m, 2H) 1.34-1.43 (m, 3H) 1.76 (br s, 4H) 1.96-2.12 (m, 5H) 2.58-2.68 (m, 2H) 3.00-3.26 (m, 4H) 3.78-3.83 (m, 3H) 3.90-3.98 (m, 2H) 6.71-6.87 (m, 4H) 6.88-6.97 (m, 1H) 7.13-7.32 (m, 2H).

Example 23: Preparation of (R)-(2-(3-((1-(2-(4,4-dimethylpentyl)-5-methoxyphenyl)piperidin-4-yl)methoxy)phenyl)propyl)phosphonic acid (Compound 20)

Compound 20

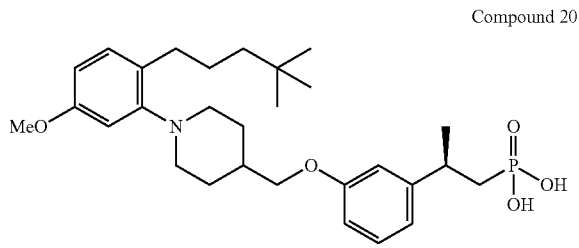 [SMILES: COc1ccc(CCCC(C)(C)C)c(N2CCC(COc3cccc([C@@H](C)CP(=O)(O)O)c3)CC2)c1]

Step 1: diethyl (R)-(2-(3-(benzyloxy)phenyl)propyl) phosphonate (20-1

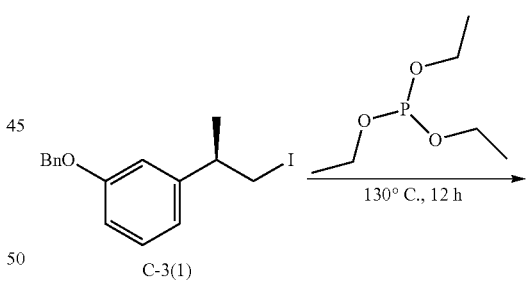

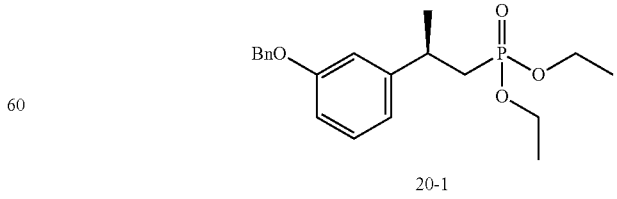

20-1 (0.88 g, 83% yield) was prepared according to Example 22 from C-3(1).

Step 2: diethyl (R)-(2-(3-hydroxyphenyl)propyl)phosphonate (20-2

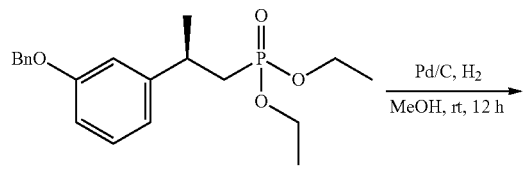

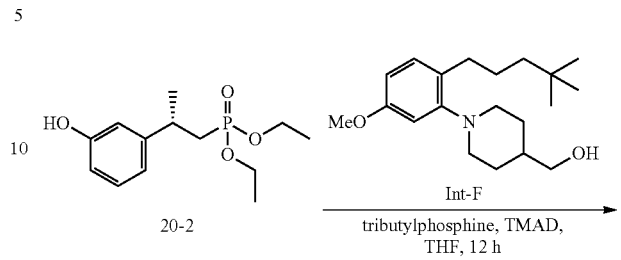

Step 3: diethyl (R)-(2-(3-((1-(2-(4,4-dimethylpentyl)-5-methoxyphenyl)piperidin-4-yl)methoxy)phenyl)propyl)phosphonate (20-3

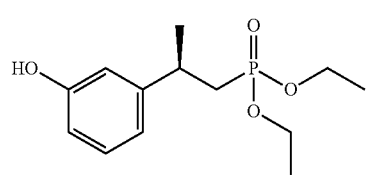

20-2

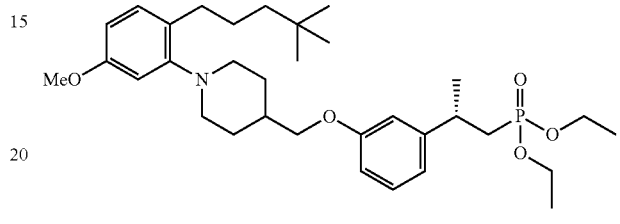

20-3

20-2 (0.78 g, crude) was prepared according to Example 22 from 20-1. LCMS: (ES+) m/z (M+H)+=273.4.

20-3 (0.20 g, 49% yield, 77% purity) was prepared according to Example 22 from 20-2.

Step 4: (R)-(2-(3-((1-(2-(4,4-dimethylpentyl)-5-methoxyphenyl)piperidin-4-yl)methoxy)phenyl)propyl)phosphonic acid (Compound 20)

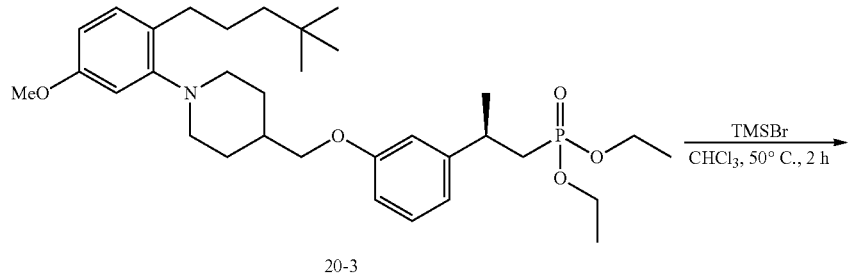

20-3

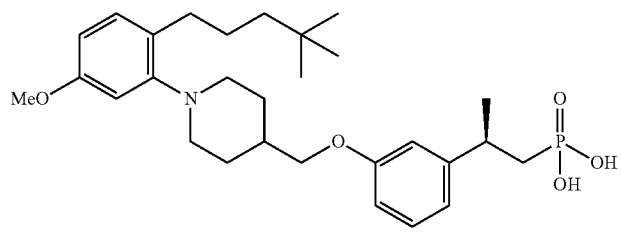

Compound 20

Compound 20 (42 mg, 23% yield, 99% purity) was prepared according to Example 22 from 20-3. LCMS: (ES+) m/z (M+H)+=518.5. $^1$H NMR (400 MHz, CD$_3$OD) δ ppm 0.85-0.92 (m, 9H) 1.21-1.32 (m, 2H) 1.37-1.42 (m, 3H) 1.54-1.70 (m, 5H) 1.89-2.09 (m, 6H) 2.54-2.61 (m, 2H) 2.77-2.89 (m, 2H) 3.10-3.20 (m, 3H) 3.74-3.78 (m, 3H) 3.87-3.93 (m, 2H) 6.61-6.66 (m, 1H) 6.72-6.79 (m, 2H) 6.80-6.86 (m, 2H) 7.08-7.13 (m, 1H) 7.16-7.23 (m, 1H).

II. Biological Evaluation

Example A-1: In Vitro Activity Assay

Cell Lines Expressing GPR40/FFAR1

CHO-K1 cells expressing human GPR40 were purchased from DiscoverX (95-1005C2). HEK293 cells expressing mouse FFAR1 were prepared using a mouse FFAR1 carrying plasmid purchased from OriGene Technologies (MR222997). The cells were transfected using Lipofectamine 2000 using manufacturer instructions and stable cell line was established from a single cell using geneticine selection. Assay ready frozen (ARF) cells were prepared and used throughout the study.

Inositol Phosphate Accumulation Assay

The assay was performed in a 384-well plate format using IP1 assay kit from Cis-Bio. ARF cells expressing FFAR1 (mouse and human) were thawed, washed and then plated in the appropriate medium (F12 based medium for CHO hFFAR1 and DMEM based medium for HEK293 mFFAR1—both were supplemented with 10% FBS and penicillin/streptomycin). 20 μL of 3.5×10$^5$ cells/mL were plated on a Poly D-Lysine coated 384-well white plate. The cells were then incubated for 16 hr at 37° C./5% CO$_2$. After 16 hr the medium was removed and 15 μL of stimulation buffer containing the test compounds was added to the cells. The plates were then incubated for 90 min at 37° C./5% CO$_2$. 5 μL of detection buffer (prepared as described in the IP-one kit) was added to each well and the plates were incubated at RT for 1 hr.

RT-FRET was measured using ClarioSTAR plate reader, calculating the ratio between emissions at 665 nm and 620 nm (HTRF ratio). HTRF ratio for positive (Max) and negative (Min) controls were used to normalize HTRF data and generate values for % activity. EC$_{50}$ and Max activity values were determined using a standard 4-parameter fit.

Results for exemplary compounds are shown in Table 1.

TABLE 1

| Compound | Human EC$_{50}$ |
|---|---|
| 1 | C |
| 2 | D |
| 3 | D |
| 4 | D |
| 5 | A |
| 6 | B |
| 7 | A |
| 8 | B |
| 9 | A |
| 10 | A |
| 11 | A |
| 12 | A |
| 13 | C |
| 14 | B |
| 15 | A |
| 16 | D |
| 17 | C |
| 18 | C |

TABLE 1-continued

| Compound | Human EC$_{50}$ |
|---|---|
| 19 | C |
| 20 | D |

A ≤ 50 nM;
50 nM < B ≤ 250 nM;
250 nM < C ≤ 1000 nM;
D > 1000 nM.

Example A-2: In Vivo Plasma Levels in Mice

Male C57BL/6J mice 10-12 weeks old were dosed with test article (30 mg/kg) or vehicle by oral gavage. Animals were euthanized with carbon dioxide at 2 h or 5 h post dose. Blood was collected for measurement of plasma concentrations of test article. Unbound exposure was calculated by multiplying the measured total exposure by the free fraction as assessed from plasma protein binding.

Plasma protein binding to isotonic phosphate buffer (PBS) containing 10% C57 BL/6 mouse plasma was determined using equilibrium dialysis of plasma spiked with test article (2 μM) against a dialysis buffer (100 mM sodium phosphate and 150 mM NaCl). At the end of the dialysis (4 hr), aliquots of the plasma and buffer were processed by protein precipitation for LC-MS/MS analysis to quantitate the test article.

Results for exemplary compounds (total exposure in plasma and unbound exposure in plasma; ratio of EC$_{50}$ to unbound exposure in plasma) are shown in Table 2.

TABLE 2

| Compound | Exposure (nM) (unbound) | Time post-dose (h) | EC$_{50}$/ unbound exposure |
|---|---|---|---|
| 5 | 8,300 (2.5) | 2 | C |
| 9 | 1,160 (2.3) | 5 | B |

A => 10;
B = 5 to 10;
C = 2 to 5;
D = 1 to 2

What is claimed is:

1. A compound of Formula (2):

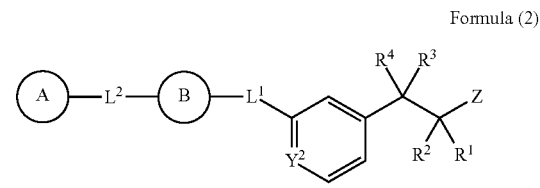

Formula (2)

or a pharmaceutically acceptable salt, solvate, or stereoisomer thereof, wherein:

Z is —P(=O)(R$^5$)OR$^6$;

R$^5$ is C$_1$-C$_6$ alkyl;

R$^6$ is hydrogen or C$_1$-C$_6$ alkyl;

R$^1$, R$^2$, and R$^3$ are each independently hydrogen, halogen, or C$_1$-C$_4$ alkyl;

R$^4$ is unsubstituted C$_3$-C$_6$ cycloalkyl;

L$^1$ is *—CH$_2$—O—;

wherein * represents the connection to Ring B;

Ring B is piperidine, which is unsubstituted or substituted with 1, 2, 3, or 4 R$^B$ substituents;

each $R^B$ is independently halogen, $C_1$-$C_6$ alkyl, or $C_1$-$C_6$ fluoroalkyl;

$L^2$ is a bond;

Ring A is aryl, which is unsubstituted or substituted with 1, 2, or 3 $R^4$ substituents;

each $R^4$ is independently halogen, $C_1$-$C_{10}$ alkyl, $C_2$-$C_{10}$ alkenyl, $C_2$-$C_{10}$ alkynyl, $C_1$-$C_{10}$ fluoroalkyl, -$L^A$-CN, -$L^A$-OH, -$L^A$-OR$^{10}$, -$L^A$-NR$^{11}$R$^{11}$, -$L^A$-C(=O)R$^{10}$, -$L^A$-C(=O)OR$^{11}$, -$L^A$-OC(=O)R$^{11}$, -$L^A$-C(=O)NR$^{11}$R$^{11}$, -$L^A$-NR$^{11}$C(=O)R$^{11}$, -$L^A$-NR$^{11}$C(=O)NR$^{11}$R$^{11}$, -$L^A$-OC(=O)NR$^{11}$R$^{11}$, -$L^A$-NR$^{11}$C(=O)OR$^{10}$, -$L^A$-OC(=O)OR$^{10}$, -$L^A$-aryl, -$L^A$-heteroaryl, -$L^A$-($C_3$-$C_{10}$ cycloalkyl), or -$L^A$-(3- to 10-membered heterocycloalkyl); wherein each alkyl, alkenyl, alkynyl, fluoroalkyl, aryl, heteroaryl, cycloalkyl, and heterocycloalkyl is independently unsubstituted or substituted with 1, 2, 3, 4, or 5 substituents selected from the group consisting of halogen, —CN, —OH, $C_1$-$C_6$ alkyl, $C_1$-$C_6$ fluoroalkyl, $C_1$-$C_6$ hydroxyalkyl, —O—($C_1$-$C_6$ alkyl), and —O—($C_1$-$C_6$ fluoroalkyl);

each $L^A$ is independently a bond or $C_1$-$C_6$ alkylene; wherein the alkylene is unsubstituted or substituted with 1, 2, or 3 substituents selected from the group consisting of halogen, —CN, —OH, —O—($C_1$-$C_6$ alkyl), and $C_1$-$C_6$ alkyl;

each $R^{10}$ is independently $C_1$-$C_6$ alkyl; wherein each alkyl is independently unsubstituted or substituted with 1, 2, 3, 4, or 5 substituents selected from the group consisting of halogen, —OH, $C_1$-$C_6$ alkyl and $C_1$-$C_6$ hydroxyalkyl; and each $R^{11}$ is independently hydrogen, $C_1$-$C_6$ alkyl, or monocyclic heteroaryl; wherein each alkyl and heteroaryl is independently unsubstituted or substituted with 1, 2, 3, 4, or 5 substituents selected from the group consisting of halogen, —OH, $C_1$-$C_6$ alkyl and $C_1$-$C_6$ hydroxyalkyl;

or two $R^{11}$ on the same nitrogen atom are taken together with the nitrogen to which they are attached to form a 3- to 6-membered N-heterocycloalkyl; wherein the heterocycloalkyl is unsubstituted or substituted with 1, 2, 3, 4, or 5 substituents selected from the group consisting of halogen, —OH, $C_1$-$C_6$ alkyl and $C_1$-$C_6$ hydroxyalkyl.

2. The compound of claim 1, having the structure of Formula (III):

Formula (III)

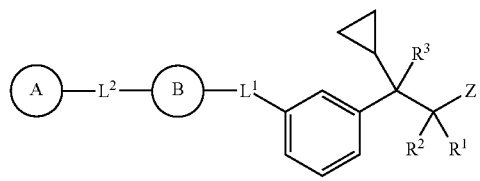

or a pharmaceutically acceptable salt, solvate, or stereoisomer thereof, wherein:

$R^1$, $R^2$, and $R^3$ are each independently hydrogen, —F, —Cl, or $C_1$-$C_4$ alkyl.

3. The compound of claim 1, having the structure of Formula (XVa-i):

Formula (XVa-i)

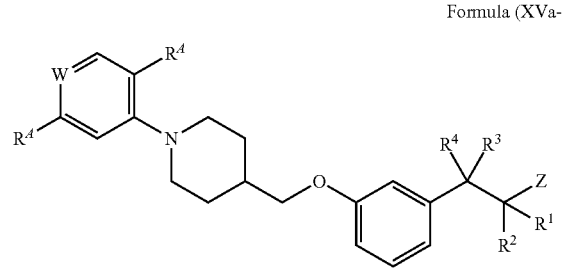

or a pharmaceutically acceptable salt, solvate, or stereoisomer thereof, wherein W is CH or CR$^A$.

4. The compound of claim 1, or a pharmaceutically acceptable salt, solvate, or stereoisomer thereof, wherein:

Z is —P(=O)(CH$_3$)OH.

5. The compound of claim 1, or a pharmaceutically acceptable salt, solvate, or stereoisomer thereof, selected from:

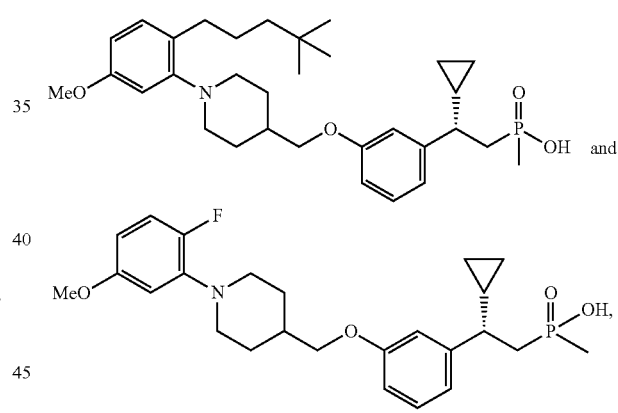

or a pharmaceutically acceptable salt, solvate, or stereoisomer thereof.

6. A pharmaceutical composition comprising a compound of claim 1, or a pharmaceutically acceptable salt, solvate, or stereoisomer thereof, and at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 12,264,171 B2 | Page 1 of 1 |
| APPLICATION NO. | : 17/745126 | |
| DATED | : April 1, 2025 | |
| INVENTOR(S) | : Iyassu Sebhat and Shuwen He | |

It is certified that error appears in the above-identified patent and that said Letters Patent is hereby corrected as shown below:

In the Claims

In Claim 1, Column 148, Line 50:
Please replace:

"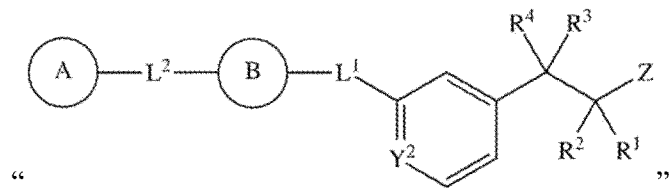"

With the following:

--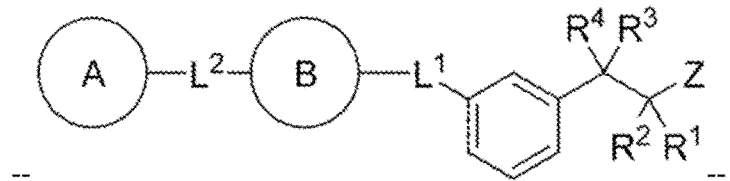--

Signed and Sealed this
Third Day of June, 2025

Coke Morgan Stewart
*Acting Director of the United States Patent and Trademark Office*